US011578336B2

(12) United States Patent
Suzuki et al.

(10) Patent No.: US 11,578,336 B2
(45) Date of Patent: Feb. 14, 2023

(54) TOBACCO PLANT AND METHOD FOR MANUFACTURING SAME

(71) Applicant: JAPAN TOBACCO INC., Tokyo (JP)

(72) Inventors: Shoichi Suzuki, Tokyo (JP); Kaori Hamano, Tokyo (JP); Seiki Sato, Tokyo (JP); Masao Arai, Tokyo (JP); Yuta Negishi, Tokyo (JP); Ayako Nomura, Tokyo (JP); Mai Tsukahara, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 248 days.

(21) Appl. No.: 16/834,608

(22) Filed: Mar. 30, 2020

(65) Prior Publication Data

US 2020/0392523 A1 Dec. 17, 2020

Related U.S. Application Data

(60) Division of application No. 16/144,479, filed on Sep. 27, 2018, now Pat. No. 10,640,780, which is a continuation of application No. PCT/JP2017/013115, filed on Mar. 29, 2017.

(30) Foreign Application Priority Data

Mar. 30, 2016 (JP) ................................ 2016-069742

(51) Int. Cl.
*C12N 15/82* (2006.01)
*A01H 1/00* (2006.01)
*C12N 15/09* (2006.01)

(52) U.S. Cl.
CPC ........... *C12N 15/8218* (2013.01); *A01H 1/00* (2013.01); *C12N 15/09* (2013.01); *C12N 15/827* (2013.01); *C12N 2310/111* (2013.01)

(58) Field of Classification Search
CPC .............................. C12N 15/8218; A01H 1/00
See application file for complete search history.

(56) References Cited

U.S. PATENT DOCUMENTS

2009/0249518 A1 10/2009 Thomas et al.
2012/0017337 A1 1/2012 Trillo et al.

FOREIGN PATENT DOCUMENTS

CN 102823449 A 12/2012
JP 6386694 B2 9/2018
WO WO 2010/081917 A1 7/2010
WO WO 2016/057515 A2 4/2016
WO WO 2017/170796 A1 10/2017
WO WO 2018/168015 A1 9/2018

OTHER PUBLICATIONS

Keller. T. et al.. The Plant Cell (Mar. 2006) vol. 18. pp. 598-611. (Year: 2006).*
India Office Action dated Jan. 28, 2021 for IN Application No. 201847040146 with English Translation.
"Nicotiana tabacum cultivar SR1 homeobox-leucine zipper protein revoulta (REV) mRNA, complete cds", Acc. JQ686937, 2014, Genbank.
Sequence Accession BCP72428, Jun. 2, 2016, attached to the office action in corresponding U.S. Appl. No. 16/569,326 dated Feb. 12, 2021.
U.S. Office Action in copending U.S. Appl. No. 16/569,326 dated Feb. 12, 2021.
Aida M, et al., "Genes Involved in Organ Separation in *Arabidopsis*: An Analysis of the cup-shaped cotyledon Mutant", The Plant Cell, (1997) 9: 841-857.
Busch BL, et al., "Shoot Branching and Leaf Dissection in Totamto are Regulated by Homologous Gene Modules", The Plant Cell (2011) vol. 23: 3595-3609.
Database GenPept, [online], Accession No. XP_009800575, Oct. 21, 2014<https://www.ncbi.nlm.nih.gov/protein/XP_009800575.1>.
Decision to Grant a Patent dated Jul. 24, 2018 in Japanese Patent Application No. 2018-505498 (with English language translation).
English translation of International Preliminary Report on Patentability and Written Opinion dated Oct. 11, 2018, in PCT/JP2017/013115 (Forms PCT/IB/338, PCT/IB/373, and PCT/ISA/237).
English translation of the International Search Report, dated Dec. 19, 2017, for International Application No. PCT/JP2017/032870.
Extended European Search Report, dated Sep. 18, 2019, for European Application No. 17775330.8.
Greb T, et al. "Molecular analysis of the Lateral Suppressor gene in *Arabidopsis* reveals a conserved control mechanism for axillary meristem formation" Genes & Development 17 (2003): 1175-1187.
Guo et al., "Genome-wide transcriptome analysis of the transition from primary to secondary stem development in tobacco", GenBank Accession, Jan. 2014, 2 pages.
Hibara K, et al. "*Arabidopsis* Cup-Shaped Cotyledon3 Regulates Postembryonic Shoot Meristem and Organ Boundary Formation" The Plant Cell (2006) vol. 18: 2946-2957.
Huh, Yeun Joo et al., "Inhibition of Chrysanthemum Axillary Buds via Transformation with the Antisense Tomato Lateral Suppressor Gene is Season Dependent" Hort. Environ. Biotechnol., 2013, vol. 54, No. 3, p. 280-287.
International Search Report dated Jul. 4, 2017 in PCT/JP2017/013115.
Japanese Journal of Phytopathology, vol. 77, No. 3, Aug. 2011, p. 258 (with partial English Translation).
Jeifetz D. et al. "CaBLIND regulates axillary meristem initiation and transition to flowering in pepper" Planta, 2011, vol. 234, p. 1227-1236.

(Continued)

*Primary Examiner* — Russell Kallis
(74) *Attorney, Agent, or Firm* — Birch, Stewart, Kolasch & Birch, LLP

(57) ABSTRACT

The present invention provides a tobacco plant which is suitable for cultivation for harvesting leaf tobaccos. The present invention includes (i) a tobacco plant in which a mutation for suppressing the development of axillary buds is introduced and (ii) a method of producing the tobacco plant.

30 Claims, 26 Drawing Sheets

Specification includes a Sequence Listing.

(56) References Cited

OTHER PUBLICATIONS

Keller, T., et al. "*Arabidopsis* Regulator of Axillary Meristems1 Controls a Leaf Axil Stem Cell Niche and Modulates Vegetative Development" The Plant Cell, (2006) vol. 18: 598-611.
Li JF, et al. "Multiplex and homologous recombination-mediated genome editing in *Arabidopsis* and Nicotiana benthamiana using guide RNA and Cas9" Nat Biotechnol. (2013), vol. 31 No. 8, 688-91.
Li, Xuevong, et al. (2003) "Control of tillering in rice" Nature, (2003) vol. 422: 618-621.
Mapelli SC, et al. "A Comparative Auxin and Cytokinin Study in Normal and to-2 Mutant Tomato Plants" Plant Cell Physiol. (1982) vol. 23(5): 751-757.
Marshallsay C. et al. "Amplification of plant U3 and U6 snRNA gene sequences using primers specific for an upstream promoter element and conserved intragenic regions" Nucleic Acids Res. 25 (1990) vol. 18, No. 12, 3459-66.
Muller D, et al. "Blind homoioaous R2R3 Myb Genes Control the Pattern of Lateral Meristem Initiation in *Arabidopsis*" The Plant Cell, (2006) vol. 18: 586-597.
Office Action dated Jun. 12, 2018 in Japanese Patent Application No. 2018-505498 (with English language translation).
Office Action dated Mar. 20, 2018 in Japanese Patent Application No. 2018-505498 (with English language translation).
Office Action dated May 15, 2018 in Japanese Patent Application No. 2018-505498 (with English language translation).
Otsuga et al., "Revoluta regulates meristem initiation at lateral positions", The Plant Journal, vol. 25, No. 2, 2001, pp. 223-236.
Raman, S. et al. "Interplay of miR164, Cup-Shaped Cotyledon genes and Lateral Suppressor controls axillary meristem formation in *Arabidopsis thaliana*" The Plant Journal (2008) 55: 65-76.
Reddy TV, et al. "Development of Tilling by sequencing platform towards enhanced leaf yield in tobacco" Industrial Crops and Products, 2012, vol. 40, p. 324-335.
Schmitz G. et al. "The tomato Blind gene encodes a MYB transcription fader that controls the formation of lateral meristems" Proc. Natl. Acad. Sci. USA, 2002, vol. 99, p. 1064-1069.
Schumacher K, et al. "The Lateral suppressor (Ls) gene of tomato encodes a new member of the VHIID protein family" Proc Natl Acad Sci USA (1999) vol. 96: 290-295.
Sun J, et al. "Inhibition of tobacco axillary bud differentiation by silencing Cup-Shaped Cotyledon 3" African Journal of Biotechnology, 2012, vol. 11, p. 3919-3927.
Takada, S. et al. "The Cup-Shaped Cotyledon1 gene of *Arabidopsis* regulates shoot apical meristem formation" Development (2001)128: 1127-1135.
Takahashi H, et al. "A method for obtaining high quality RNA from paraffin sections of plant tissues by laser microdissection" J Plant Res (2010) 123: 807-813.
Talbert, P., et al. "The Revoluta gene is necessary for apical meristem development and for limiting cell divisions in the leaves and stems of *Arabidopsis thaliana*" Development, 1995. vol. 121, p. 2723-2735.
UniProt, [online], Accession No. B5M4A5,<http://www.uniprot.org/uniprot/B5M4A5.txt?version=15>, Feb. 17, 2016 uploaded, [retrieved on Jun. 16, 2017].
UniProt, [online], Accession No. V9LXH8, <http://www.uniprot.org/uniprot/V9LXH8.txt?version=11>, Mar. 16, 2016 uploaded, [retrieved on Jun. 16, 2017].
Vroemen CW, et al. "The Cup-Shaped Cotyledon3 Gene is Required for Boundary and Shoot Meristem Formation in *Arabidopsis*" The Plant Cell (2003), 15(7): 1563-77.
Waibel F, et al. "U6 snRNA genes of *Arabidopsis* are transcribed by RNA polymerase III but contain the same two upstream promoter elements as RNA polymerase II-transcribed U-snRNA genes" Nucleic.
Wang W. et al. "Construction of RNAi Vector of NtLS Gene and its Transformation in Tobacco" Chinese Tobacco Science, 2011, vol. 32, No. 4, p. 31-35 (with English Abstract and partial English translation).
Yang et al., "Regulation of Axillary Meristem Initiation by Transcription Factors and Plant Hormones," frontiers in Plant Science, vol. 7, Feb. 18, 2016, XP55619096, (Total of 4 pages).
Yang et al., "The bHLH Protein ROX Acts in Concert with RAX1 and LAS to Modulate Axillary Meristem Formation in *Arabidopsis*," The Plant Journal, vol. 71, 2012 (Published online Apr. 26, 2012), pp. 61-70.
Zhong R, et al. "Disruption of Interfascicular Fiber Differentiation in an *Arabidopsis* Mutant" The Plant Cell(1997) vol. 9: 2159-2170.
Zhong R, et al. "IFL1, A Gene Regulating Interfascicular Fiber Differentiation in *Arabidopsis*, Encodes a Homeodomain-Leucine Zipper Protein" The Plant Cell, (1999) vol. 11: 2139-2152.
U.S. Office Action for U.S. Appl. No. 16/144,479, dated Apr. 30, 2019 (Requirement for Restriction).
U.S. Office Action for U.S. Appl. No. 16/144,479, dated Aug. 7, 2019 (Non-Final Rejection).
U.S. Office Action for U.S. Appl. No. 16/144,479, dated Jan. 8, 2020 (Notice of Allowance).

* cited by examiner

SEQUENCE LISTING

```
<160> NUMBER OF SEQ ID NOS: 317

<210> SEQ ID NO 1
<211> LENGTH: 838
<212> TYPE: PRT
<213> ORGANISM: Nicotiana tabacum
```

<400> SEQUENCE: 1

```
Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Ala Cys Gly Leu Val Ser Leu Glu Pro Thr Lys Ile Ala
    210                 215                 220

Glu Ile Leu Lys Asp Arg Pro Ser Trp Phe Arg Asp Cys Arg Asn Val
225                 230                 235                 240

Glu Val Phe Thr Met Phe Ser Ala Gly Asn Gly Thr Ile Glu Leu Leu
                245                 250                 255

Tyr Thr Gln Ile Tyr Ala Pro Thr Thr Leu Ala Pro Ala Arg Asp Phe
            260                 265                 270

Trp Thr Leu Arg Tyr Thr Thr Thr Leu Glu Asn Gly Ser Phe Val Val
        275                 280                 285

Cys Glu Arg Ser Leu Ser Gly Thr Gly Ala Gly Pro Asn Ala Ala Ser
    290                 295                 300

Ala Ser Gln Phe Val Arg Ala Gln Met Leu Pro Ser Gly Tyr Leu Ile
305                 310                 315                 320

Arg Pro Cys Asp Gly Gly Gly Ser Ile Ile His Ile Val Asp His Leu
                325                 330                 335

Asn Leu Glu Ala Trp Ser Ala Pro Glu Ile Leu Arg Pro Leu Tyr Glu
            340                 345                 350

Ser Ser Lys Val Val Ala Gln Lys Met Thr Ile Ala Ala Leu Arg Tyr
        355                 360                 365

Ala Arg Gln Ile Ala Gln Glu Thr Ser Gly Glu Val Val Tyr Gly Leu
    370                 375                 380

Gly Arg Gln Pro Ala Val Leu Arg Thr Phe Ser Gln Arg Leu Ser Arg
385                 390                 395                 400

Gly Phe Asn Asp Ala Ile Asn Gly Phe Ser Asp Asp Gly Trp Ser Leu
```

-continued

```
                405                 410                 415

Leu Ser Ser Asp Gly Gly Glu Asp Val Ile Val Ala Val Asn Ser Arg
            420                 425                 430

Lys Asn Ile Ala Thr Thr Ser Val Pro Leu Ser Pro Leu Gly Gly Ile
        435                 440                 445

Leu Cys Ala Lys Ala Ser Met Leu Leu Gln Asn Val Pro Pro Val Val
    450                 455                 460

Leu Val Arg Phe Leu Arg Glu His Arg Ser Glu Trp Ala Asp Phe Asn
465                 470                 475                 480

Val Asp Ala Tyr Val Ala Ser Ser Met Lys Ser Cys Ser Tyr Ala Tyr
                485                 490                 495

Pro Gly Met Arg Pro Thr Arg Phe Thr Gly Ser Gln Ile Ile Met Pro
            500                 505                 510

Leu Gly His Thr Ile Glu His Glu Glu Met Leu Glu Val Ile Arg Leu
        515                 520                 525

Glu Gly His Ser Ile Gly Gln Glu Asp Thr Phe Met Pro Arg Asp Val
    530                 535                 540

His Leu Leu Gln Met Cys Ser Gly Thr Asp Glu Asn Ala Val Gly Ala
545                 550                 555                 560

Cys Ser Glu Leu Val Phe Ala Ala Ile Asp Glu Met Phe Pro Asp Asp
                565                 570                 575

Ala Pro Leu Leu Pro Ser Gly Phe Arg Ile Ile Pro Leu Glu Ser Lys
            580                 585                 590

Ser Ser Asp Pro Gln Asp Thr Ser Asn Ala His Arg Thr Leu Asp Leu
        595                 600                 605

Ala Ser Ser Leu Glu Val Gly Pro Ala Thr Asn Pro Ala Thr Gly Asp
    610                 615                 620

Val Val Ser Gly Tyr Ser Ala Arg Ser Val Leu Thr Ile Ala Phe Gln
625                 630                 635                 640

Phe Pro Phe Glu Asp Asn Leu Gln Asp Asn Val Ala Thr Met Ala Arg
                645                 650                 655

Gln Tyr Val Arg Ser Val Val Ser Ser Val Gln Arg Val Ala Met Ala
            660                 665                 670

Ile Ser Pro Ala Gly Val Asn Ser Thr Phe Gly Ser Lys Leu Ser Pro
        675                 680                 685

Gly Ser Pro Glu Ala Val Thr Leu Ser His Trp Ile Cys Gln Ser Tyr
    690                 695                 700

Ser Tyr His Met Gly Thr Glu Leu Leu Gln Thr Asp Ser Arg Gly Asp
705                 710                 715                 720

Glu Ser Val Leu Lys Asn Leu Trp Gln His Gln Asp Ala Ile Leu Cys
                725                 730                 735

Cys Ser Leu Lys Ser Leu Pro Val Phe Ile Phe Ala Asn Lys Ala Gly
            740                 745                 750

Leu Asp Met Leu Glu Thr Thr Leu Val Ala Leu Gln Asp Ile Thr Leu
        755                 760                 765

Asp Lys Ile Phe Asp Glu Ser Gly Arg Lys Val Leu Phe Ala Glu Phe
    770                 775                 780

Pro Lys Ile Met Glu Gln Gly Phe Ala Tyr Leu Pro Gly Gly Ile Cys
785                 790                 795                 800

Met Ser Ala Met Gly Arg His Ile Ser Tyr Glu Gln Ala Ile Ala Trp
                805                 810                 815

Lys Val Phe Ala Ser Glu Glu Thr Val His Cys Leu Ala Phe Ser Phe
            820                 825                 830
```

-continued

Ile Asn Trp Ser Phe Val
        835

<210> SEQ ID NO 2
<211> LENGTH: 3882
<212> TYPE: DNA
<213> ORGANISM: Nicotiana tabacum

<400> SEQUENCE: 2
gaaagcttta actcaagcaa attctctctc tctctctctc tctctctctc tctctctctc 60
tcttcatttt ctttttctct tttctcaccc accactctca cacacctctt cacctcacct 120
tacacactaa aaaaacatca ctcctctctc taaaaaattc aatctttttg ctgttccaac 180
atgtctttta gagtttgttt cagtttcaga tcttaagggc gggagtgtta tgcttcttct 240
aatattttga agctcaagaa aacagagcaa atttttgctt tcttttctcc tactttttgt 300
ggggggtaat tcttgttttt gtaatctcaa agctggctgt tttatgtata tactgaaggg 360
gttgtggtga tttgtttgtc tactttaaga aggtgccatc tttttcagta atatttgggt 420
aaaagttctc tctttttttgg ccttaaacgc gaagattcag gcctctctca acgtgtcatc 480
tgttctctgt attaaacaca gctggagaat taattacata gaggtaaaaa aaggggttaa 540
agtcgccaaa gaattgaaaa aaaacagagg gctgaggtaa aaagttgatg gtttttaaaa 600
aaaaataaaa gcttaaatga tgataaagtt tggagcttta tgtgaatgga aatggtgttg 660
tgtttgtatc aaacacgagt agtttacagc ttatgtgaat ttgaaagaga gagaattttt 720
gtctgtattt atatcctttt cagccatatc tttcgttaga gcagttttgg ctgtacctta 780
atttgtaagg gtttaagcgt gaagtgtgtg tttgagcctt ctgttataag gggcacaaag 840
tatagaaaca acaaaagggg cacctaggaa tcttctggct caatcaagat cgttcattta 900
atcttgtctg agatcactag aaaaagaaaa aggaaagata aagataaagt ctttgtttca 960
gagaatctta gttctctgtg ttgatatata taataaaagc tgtttgcagg gaatatatct 1020
acttgggggt gtttttattt cttttaaggg tgtttgaaaa tttggaaatc ttgattattt 1080
ttttgtttgg gattttgggg tttgacggca aatggctatg gtggtacagc agcataggga 1140
gagtagtagt ggtagtatta caaaacatct tgacagtagt ggaaagtatg tccggtatac 1200
agctgagcaa gtggaggcat tagagagggt ttatgcagag tgccctaaac ctagctcgtt 1260
gcgccgccag caattgatcc gcgaatgccc tattctgtcg aatatcgagc ctaagcagat 1320
caaagtttgg tttcaaaaca gaaggtgtcg agagaagcaa aggaaagagt cttctagact 1380
acagactgta aatagaaagc tgtctgcaat gaataaacta ttaatggagg agaatgatcg 1440
cttgcaaaaa caggtttcac agcttgtgtg tgaaaatggc tttatgcggc aacaattgca 1500
tactgcatca gcggccacta ctgatgtaag ttgtgagtca gtggttacca cccctcagca 1560
ttccctcaga gatgctaaca accctgctgg actgctgtcg attgcagagg aaaccttagc 1620
agagttcctt tccaaggcta caggaactgc tgttgattgg gtcccgatgc ctgggatgaa 1680
gcctggtccg gattcagttg ggatttttgc catctcacac agttgtagtg gagtggcagc 1740
ccgagcatgt ggtcttgtta gtttagagcc gacaaagatt gctgagatcc tcaaagatcg 1800
accatcttgg ttccgagact gccggaacgt tgaagttttc acgatgtttt ctgcaggaaa 1860
tggaacaatt gagcttttgt acacgcagat atatgctcct accaccttgg ctcctgcacg 1920
tgatttttgg actctgagat acacaaccac cctggagaat ggtagttttg tggtttgtga 1980
aagatccctc tctggtactg gagctgggcc gaatgctgct tctgcttccc agtttgtaag 2040

-continued

```
agctcaaatg cttccgtccg gatatctaat ccgaccgtgt gacggtggag gatccattat   2100
acatattgtt gaccatctga atcttgaggc atggagtgcc cctgagattt tgcgtccact   2160
ttatgaatcg tcaaaagttg tggcacagaa aatgactatt gcggcactgc gatatgcaag   2220
gcaaatagct caggagacta gtggggaggt tgtatatggt ctgggaaggc aacctgcagt   2280
tcttcgaaca tttagccaga gattaagcag aggcttcaat gacgccatca atggattcag   2340
tgatgatggc tggtcattgt taagttctga tggtggtgaa gatgttatag ttgctgtcaa   2400
ttcaaggaag aacattgcca ccacttccgt tcctctttca ccgctgggag gcatcctttg   2460
tgccaaagca tcaatgctac tccagaatgt tcctcctgtg gtactggttc gatttctcag   2520
ggagcaccgt tcagagtggg cggactttaa tgttgatgcc tatgtagctt cgtcaatgaa   2580
atcttgttca tatgcatatc ctgggatgag gcctaccaga tttaccggaa gtcagataat   2640
aatgccactt ggccatacaa ttgaacatga agagatgctt gaggttatta gattggaagg   2700
acactctatt ggccaggaag atacttttat gccaagagat gttcaccttc tccagatgtg   2760
tagtggaact gatgagaatg ctgtcggagc ttgttctgaa ctagtttttg ctgcaattga   2820
tgagatgttt ccagatgatg caccccctgtt gccctccggg tttcgtatca ttcctctcga   2880
gtcaaaatca agcgatcccc aggatacatc gaatgctcat agaacactgg atctggcatc   2940
aagtcttgaa gttggcccag caacaaaccc tgctactgga gatgtggtct ctggctacag   3000
tgcacgatct gtgttgacaa ttgcttttca atttccattc gaggacaatc ttcaggacaa   3060
tgtagctacc atggcgcgcc agtatgttcg cagtgtggtt tcatctgtcc aacgggttgc   3120
catggcaata tctcccgcag gagtgaattc aacattcggg tccaagcttt ctccaggctc   3180
ccctgaagct gtaacgttgt cgcactggat ctgccagagc tacagttatc acatggggac   3240
agagttgctt caaactgatt cgaggggcga tgaatcagtg ctaaaaaatc tttggcaaca   3300
tcaggatgct attttgtgct gctcattgaa gtccctgccg gttttcattt ttgctaataa   3360
ggctgggctt gatatgctgg agacaacctt agttgcttta caggacatta ctctagataa   3420
gatatttgat gaatctggcc ggaaagtgtt gttcgctgaa tttcccaaga tcatggaaca   3480
gggttttgcg tacttgccgg gtggtatttg catgtcagca atgggacgac atatttcata   3540
tgaacaagct attgcatgga aagtctttgc ttctgaagaa actgtccact gcttagcctt   3600
ctcatttatt aactggtcat ttgtttaatg ttgctgtcaa atctcctttc ttttttttcc   3660
tttttgtttt ttgacatctt cctcacagag gacactgaca gccaggaaca cagttgaacg   3720
gaatgatctt tgggacggat gaaaattttg taacttgggg ggctcccgtc tgttttacct   3780
ttaatttaat tagactaaat ttgtattttg cttcctgaat tcttcatact cttatgtaaa   3840
ttttctagtg cagctttttt gagtgcagat gtttgtttcc gc                     3882
```

<210> SEQ ID NO 3
<211> LENGTH: 839
<212> TYPE: PRT
<213> ORGANISM: Nicotiana tabacum

<400> SEQUENCE: 3

```
Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45
```

```
Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Ala Cys Gly Leu Val Ser Leu Glu Pro Thr Lys Ile Ala
    210                 215                 220

Glu Ile Leu Lys Asp Arg Ser Ser Trp Phe Arg Asp Cys Arg Asn Val
225                 230                 235                 240

Glu Val Phe Thr Met Phe Ser Ala Gly Asn Gly Thr Ile Glu Leu Leu
                245                 250                 255

Tyr Thr Gln Ile Tyr Ala Pro Thr Thr Leu Ala Pro Ala Arg Asp Phe
            260                 265                 270

Trp Thr Leu Arg Tyr Thr Thr Thr Leu Glu Asn Gly Ser Phe Val Val
        275                 280                 285

Cys Glu Arg Ser Leu Ser Gly Thr Gly Ala Gly Pro Asn Ala Ala Ser
    290                 295                 300

Ala Ser Gln Phe Val Arg Ala Gln Met Leu Pro Ser Gly Tyr Leu Ile
305                 310                 315                 320

Arg Pro Cys Asp Gly Gly Gly Ser Ile Ile His Ile Val Asp His Leu
                325                 330                 335

Asn Leu Glu Ala Trp Ser Ala Pro Glu Ile Leu Arg Pro Leu Tyr Glu
            340                 345                 350

Ser Ser Lys Val Val Ala Gln Lys Met Thr Ile Ala Ala Leu Arg Tyr
        355                 360                 365

Ala Arg Gln Ile Ala Gln Glu Thr Ser Gly Glu Val Val Tyr Gly Leu
    370                 375                 380

Gly Arg Gln Pro Ala Val Leu Arg Thr Phe Ser Gln Arg Leu Ser Arg
385                 390                 395                 400

Gly Phe Asn Asp Ala Ile Asn Gly Phe Ser Asp Asp Gly Trp Ser Leu
                405                 410                 415

Leu Ser Ser Asp Gly Gly Glu Asp Val Ile Val Ala Val Asn Ser Arg
            420                 425                 430

Lys Asn Ile Ala Thr Thr Ser Val Pro Leu Ser Pro Leu Gly Gly Ile
        435                 440                 445

Leu Cys Ala Lys Ala Ser Met Leu Leu Gln Asn Val Pro Pro Ala Val
    450                 455                 460
```

-continued

```
Leu Val Arg Phe Leu Arg Glu His Arg Ser Glu Trp Ala Asp Phe Asn
465                 470                 475                 480

Val Asp Ala Tyr Val Ala Ser Ser Met Lys Ser Cys Ser Tyr Ala Tyr
                485                 490                 495

Pro Gly Val Arg Pro Thr Arg Phe Thr Gly Ser Gln Ile Ile Met Pro
            500                 505                 510

Leu Gly His Thr Ile Glu His Glu Glu Met Leu Glu Val Ile Arg Leu
        515                 520                 525

Glu Gly His Ser Ile Gly Gln Glu Asp Ala Phe Met Pro Arg Asp Ile
    530                 535                 540

His Leu Leu Gln Met Cys Ser Gly Thr Asp Glu Asn Ala Val Gly Ala
545                 550                 555                 560

Cys Ser Glu Leu Val Phe Ala Ala Ile Asp Glu Met Phe Pro Asp Asp
                565                 570                 575

Ala Pro Leu Leu Pro Ser Gly Phe Arg Ile Ile Pro Leu Glu Ser Lys
            580                 585                 590

Ser Ser Asp Pro Gln Asp Thr Ser Asn Ala His Arg Thr Leu Asp Leu
        595                 600                 605

Ala Ser Ser Leu Glu Val Gly Pro Ala Thr Asn Pro Ala Thr Gly Asp
    610                 615                 620

Val Val Ser Gly Tyr Ser Ala Arg Ser Val Leu Thr Ile Ala Phe Gln
625                 630                 635                 640

Phe Pro Phe Glu Asp Asn Leu Gln Asp Asn Val Ala Thr Met Ala Arg
                645                 650                 655

Gln Tyr Val Arg Ser Val Val Ser Ser Val Gln Arg Val Ala Met Ala
            660                 665                 670

Ile Ser Pro Ala Gly Val Asn Ser Thr Phe Gly Ser Lys Leu Ser Pro
        675                 680                 685

Gly Ser Pro Glu Ala Val Thr Leu Ser His Trp Ile Cys Gln Ser Tyr
    690                 695                 700

Ser Tyr His Met Gly Thr Glu Leu Leu Gln Ala Asp Ser Arg Gly Asp
705                 710                 715                 720

Glu Ser Val Leu Lys Asn Leu Trp Gln His Gln Asp Ala Ile Leu Cys
                725                 730                 735

Cys Ser Leu Lys Ser Leu Pro Val Phe Ile Phe Ala Asn Lys Ala Gly
            740                 745                 750

Leu Asp Met Leu Glu Thr Thr Leu Val Ala Leu Gln Asp Ile Thr Leu
        755                 760                 765

Asp Arg Ile Phe Asp Glu Ser Gly Arg Lys Val Leu Phe Ala Glu Phe
    770                 775                 780

Pro Lys Ile Met Asp Gln Gly Phe Ala Tyr Leu Pro Gly Gly Ile Cys
785                 790                 795                 800

Met Ser Ala Met Gly Arg His Ile Ser Tyr Glu Gln Ala Ile Ala Trp
                805                 810                 815

Lys Val Phe Ala Ser Glu Glu Thr Ser Val His Cys Leu Ala Phe Ser
            820                 825                 830

Phe Ile Asn Trp Ser Phe Val
        835
```

<210> SEQ ID NO 4
<211> LENGTH: 2884
<212> TYPE: DNA
<213> ORGANISM: Nicotiana tabacum

<400> SEQUENCE: 4

-continued

```
aagctgtttg cagggaatat atctacttgg gggtgttttt atttcttaaa agggtgtttg     60
aaaatttgga aatcttgatt tttttttgg tttgggattt tgaggtttga gggcaatggc    120
tatggttgca cagcagcaca gggagagtag tagtggtagt attacaaaac atcttgacag    180
tagtggaaag tatgtccggt atacagctga gcaagttgag gcattggaga gggtttatgc    240
tgagtgccct aagcctagct ccttgcgccg ccaacaattg atccgtgaat gccctattct    300
gtcgaatatc gagcctaagc agatcaaagt ttggtttcaa aacagaaggt gtcgagagaa    360
gcaaaggaaa gagtcttctc gactacagac tgtaaataga aagctgtctg caatgaataa    420
actattgatg gaggagaatg atcgcttgca aaaacaggtt tcgcagcttg tgtgtgaaaa    480
tggctttatg cggcaacagt tgcatactgc atcagcggcc actactgatg taagttgtga    540
gtctgtggta actacccctc agcattccct cagagatgct aacaaccctg ctggactgct    600
gtcgattgca gaggaaacct tagcagagtt cctttccaag gctacaggaa ctgctgttga    660
ttgggtcccg atgcctggga tgaagcctgg tccggattca gttgggattt ttgccatctc    720
acacagttgt agtggagtgg cagcccgagc atgtggtctt gttagtttag agccgacaaa    780
gattgctgag atcctcaaag atcgatcttc ttggttccga gattgccgga acgttgaagt    840
tttcacaatg ttttctgcag gaaatggaac aattgaactt ttgtacacgc agatatatgc    900
tcctaccacc ttggctcctg cacgtgattt ttggactctg agatacacaa ccaccctgga    960
gaatggtagc tttgtggttt gtgaaagatc cctctctggt actggagctg ggccgaatgc   1020
tgcttctgct tcccagtttg taagagctca aatgcttccg tctggatatc taatccgacc   1080
gtgtgacggt ggaggatcca ttatacatat tgttgaccac ctgaatcttg aggcatggag   1140
tgcccctgag attttgcgtc cactttatga atcgtcaaaa gttgtggcac agaaaatgac   1200
tattgcggca ctgcgatatg caaggcaaat agctcaggag actagtgggg aggttgtata   1260
tggtctggga aggcaacctg cagttcttcg aacatttagc cagagattaa gcagaggctt   1320
caatgatgcc atcaatggat tcagtgatga tggctggtca ttgttaagtt ctgatggtgg   1380
tgaagatgtt atagttgctg tcaattcaag gaagaacatt gccaccactt ccgttcctct   1440
ttcaccactt ggaggcatcc tttgtgccaa agcatcaatg ctactccaga atgttcctcc   1500
tgcggtactg gttcgatttc tcagggagca ccgttcagag tgggcggact ttaatgttga   1560
tgcctatgta gcttcctcaa tgaaatcttg ttcatatgca tatcctgggg tgaggcctac   1620
cagatttacc ggaagccaga taataatgcc actgggccac acaatagaac atgaagagat   1680
gcttgaagtt attagattgg aagggcactc tattggccag gaagatgctt ttatgccgag   1740
agatattcac cttctccaga tgtgtagtgg aaccgatgag aatgctgtcg gagcttgttc   1800
tgaactagtt tttgctgcaa ttgatgagat gtttccagat gatgcacccc tgttgccctc   1860
cgggtttcgt atcattcctc tcgagtcaaa atcaagcgat ccccaggata catcgaatgc   1920
tcatagaaca ctggatctgg catcaagtct tgaagttggc ccagcaacaa accctgctac   1980
tggagatgtg gtctctggct acagtgcacg atctgtattg acaattgctt ttcaatttcc   2040
attcgaggac aatcttcagg ataatgtagc taccatggcg cgccagtatg ttcgcagtgt   2100
ggtttcatct gtccaacggg ttgccatggc aatatctccc gcaggagtga attcaacatt   2160
cgggtccaag ctttctccag gctcccctga agctgtaact ttgtcgcact ggatctgcca   2220
gagctacagt tatcacatgg ggacagagtt gcttcaagct gattcgaggg gcgatgaatc   2280
agtgctaaag aatctttggc aacatcagga tgctattttg tgctgctcat tgaagtcgct   2340
```

-continued

```
gccggttttc atttttgcta ataaggctgg gcttgatatg ctggagacaa cattagttgc   2400

tttgcaagac attactctag ataggatatt tgacgaatct ggccggaaag tgttgttcgc   2460

tgaatttccc aagatcatgg atcagggttt cgcgtacctg ccgggtggta tttgcatgtc   2520

tgcaatggga cgacatattt catatgaaca agctattgca tggaaagtct ttgcttctga   2580

agaaactagt gtccactgct tagccttctc atttattaac tggtcatttg tttaatgttg   2640

ctgtcaaatc tcctcttttt tttccttttt gtttttttgac atcttcctca cagaggacac   2700

tgacagacag gaacacagtt gaacggaaag atcttgggac cgatgaaaat ttttgtaact   2760

tgtggggctc ctgtctgttt tgccttaatt taattagact aaatttgtat tttgcttccc   2820

ggattcttca tactcttgtg taaatttact agtgcagctt ttttgagtgc agatgtttgt   2880

ttcc                                                                2884


<210> SEQ ID NO 5
<211> LENGTH: 407
<212> TYPE: PRT
<213> ORGANISM: Nicotiana tabacum

<400> SEQUENCE: 5

Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met Gln Ala Leu Ala Asp Arg Tyr Pro Pro Pro Thr Leu Arg
                165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
        195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Leu His Arg Leu Leu Lys Asp Arg Glu Lys Leu Arg Ile
                245                 250                 255

Phe Leu His Arg Ile Lys Ser Met Asn Pro Lys Val Val Thr Leu Ala
            260                 265                 270
```

```
Glu Arg Glu Ala Asn His Asn His Pro Leu Phe Leu Gln Arg Phe Val
        275                 280                 285

Glu Ala Leu Asp Tyr Tyr Ala Ala Val Phe Asp Ser Leu Glu Ala Thr
    290                 295                 300

Leu Pro Pro Ser Ser Arg Glu Arg Met Thr Val Glu Gln Val Trp Phe
305                 310                 315                 320

Gly Arg Glu Ile Ile Asp Ile Val Ala Ala Glu Gly Asp Lys Arg Arg
                325                 330                 335

Glu Arg His Glu Arg Phe Arg Ser Trp Glu Val Met Leu Arg Ser Cys
            340                 345                 350

Gly Phe Ser Asn Val Ala Leu Ser Pro Phe Ala Leu Ser Gln Ala Lys
        355                 360                 365

Leu Leu Leu Arg Leu His Tyr Pro Ser Glu Gly Tyr Gln Leu Ser Val
    370                 375                 380

Ser Ser Thr Ser Asn Ser Phe Phe Leu Gly Trp Gln Asn Gln Pro Leu
385                 390                 395                 400

Phe Ser Ile Ser Ser Trp Arg
                405
```

<210> SEQ ID NO 6
<211> LENGTH: 1623
<212> TYPE: DNA
<213> ORGANISM: Nicotiana tabacum

<400> SEQUENCE: 6

```
atttcccctc ctccatcatt gaaaaccccc tctgtccttt cccctagaga gaccectttt     60

tcctctctct ctcctttctc tttttattag acgcatatat tctctcttct ttctctttct    120

agggttttca cctgaaatag ttttatttcg gtgatatgtt aggatccttt ggttcatcat    180

ctcaatctca tgatgaagaa actgatgatc aacggcggag attcagttcc acttcccctg    240

caatccaaat ccggcaacta ctcattagct gcgcggagtt aatctcgcgg tccgatttct    300

cggccgcaaa cagactcctc accattttat caactaactc ttcccctttt ggtgattcaa    360

ctgaaagatt agtccatcag ttcactcgcg cactttctct tcgcctcaac cgttatatct    420

cttcagccac taatttcttg acaccatcta atgttgttga aagttcaaat gattcagctc    480

tacttcagtc atcctatctt tccctaaacc aagtgactcc tttcattaga tttagtcagc    540

taactgctaa tcaagcgatt ttggaagcta ttaacgataa ccaacaagcg atccacatcg    600

ttgattttga tattaatcac ggtgttcaat ggccaccgtt aatgcaagca ctagctgatc    660

gttaccctcc tccaactctt cggattaccg gtactggaaa tgaccttgat acccttcgta    720

gaaccggaga tcgtttagct aaatttgctc actctttagg ccttagattt cagtttcacc    780

ctcttttgat taccaataat aatgacaatg atcatgaccc ttcaataatt tcttctattg    840

ttcttctccc tgatgagaca ttagctatca actgtgtatt ttatcttcac aggctcttga    900

aagaccgcga aaagttaagg atttttttgc ataggattaa atccatgaac cctaaagttg    960

taacgctggc cgagagagaa gcaaatcata atcacccact ttttttgcaa agatttgtgg   1020

aggctttgga ttattatgca gctgtgtttg attcattgga agcaactttg ccaccgagca   1080

gtagagagag gatgacagtg gaacaagttt ggttcgggag agaaataatt gatatagtag   1140

cagcagaagg agataagaga agagaaagac acgagagatt cagatcatgg gaagtaatgt   1200

tgaggagctg tggatttagc aatgttgctt taagcccttt tgcactctca caagctaaac   1260

ttctcttgag acttcattac ccatctgaag gataccagct tagtgtttcg agtacgagta   1320
```

-continued

```
attctttctt cttgggttgg caaaatcaac cccttttttc catatcttct tggcgttaaa   1380

tttaaaaccc taaaaaacaa gatttttatc tatctgcatg gtgaaggaca aagaggtctt   1440

caatctcagg ttcttttttt tttttttttt ttatatatat atcttgtttg ggtttaaggt   1500

tattgggctg atgaatgttt taattttaac ataggtctac ttacgtagta gttataggtt   1560

gataatgaga tataattaac taagtctttg tataatgcag atcctgaact taatctttat   1620

ttg                                                                 1623
```

```
<210> SEQ ID NO 7
<211> LENGTH: 410
<212> TYPE: PRT
<213> ORGANISM: Nicotiana tabacum

<400> SEQUENCE: 7

Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
    210                 215                 220

Pro Ser Ile Ile Ser Ser Ile Val Leu Leu Pro Asp Glu Thr Leu Ala
225                 230                 235                 240

Ile Asn Cys Val Phe Tyr Leu His Arg Leu Leu Lys Asp Arg Glu Met
                245                 250                 255

Leu Arg Ile Phe Leu His Arg Ile Lys Ser Met Asn Pro Lys Val Val
            260                 265                 270

Thr Leu Ala Glu Arg Glu Ala Asn His Asn His Pro Leu Phe Leu Gln
        275                 280                 285

Arg Phe Val Glu Ala Leu Asp Tyr Tyr Ala Ala Val Phe Asp Ser Leu
    290                 295                 300

Glu Ala Thr Leu Pro Pro Ser Ser Arg Glu Arg Met Thr Val Glu Gln
305                 310                 315                 320
```

```
Val Trp Phe Gly Arg Glu Ile Ile Asp Ile Val Ala Ala Glu Gly Asp
                325                 330                 335

Lys Arg Arg Glu Arg His Glu Arg Phe Arg Ser Trp Glu Val Met Leu
            340                 345                 350

Arg Ser Cys Gly Phe Ser Asn Val Ala Leu Ser Pro Phe Ala Leu Ser
        355                 360                 365

Gln Ala Lys Leu Leu Leu Arg Leu His Tyr Pro Ser Glu Gly Tyr Gln
    370                 375                 380

Leu Ser Val Ser Ser Thr Ser Asn Ser Phe Phe Leu Gly Trp Gln Asn
385                 390                 395                 400

Gln Pro Leu Phe Ser Ile Ser Ser Trp Arg
                405                 410


<210> SEQ ID NO 8
<211> LENGTH: 1827
<212> TYPE: DNA
<213> ORGANISM: Nicotiana tabacum

<400> SEQUENCE: 8

aggttcttct tccttaatat tgagtcaaga ttagtactac tactatagcc aagaaaatgt      60

gaaatcatat agtactaact ttcccttctc cctagctact gataactcta attaatttca     120

gatgccaaaa ccataaattt cccctcctcc atcattgaaa accccttttgt cctttccccc    180

cagacccccct tttcctctct ctctctctcc tttctctttt tattagacgc atattctctc    240

ttctttctct ttctagggtt ttcacctgaa atagttttat ttcgttgata tgttaggatc     300

ctttggttca tcatctcaat ctcatgatga agaagctgat gatcaacggc ggagatgcag     360

ttccacttcc cctgcaatcc aaatccggca actactcatt agctgcgcgg agttaatctc     420

acggtccgat ttctcggcgg caaacagact cctcaccatt ttatcaacta actcttcccc     480

ttttggtgat tcaactgaaa gattagtcca tcagttcact cgcgcacttt ccattcgcct     540

caaccgctat atctcttcag ccactaattt cttgacacct aatgcatcat ctaatgttgt     600

tgaaagttca aatgattcag ctctacttca gtcatcctat ctttccctaa accaagtgac     660

cccttttatt agatttagtc agctaactgc taatcaagcg attttagaag ctattaacga     720

taaccaacaa gcgatccaca tcgttgattt tgatattaat cacggtgttc aatggccacc     780

gttaatgcaa gcactagctg atcgttaccc tcctccaact cttcggatta ccggtactgg     840

aaatgacctc gataccccttc gtagaaccgg agatcgttta gctaaatttg ctcactcttt    900

aggccttaga tttcagtttc accctctttt gatcaccaat aataatgaca atgatcatga     960

cccttcaatc atttcttcta ttgttcttct ccctgatgag acattagcaa tcaactgtgt    1020

attttatctt cacaggctct taaaagaccg cgaaatgtta aggatttttt tgcataggat    1080

taaatccatg aaccctaaag ttgtaacact ggccgagaga gaagcaaatc ataatcaccc    1140

actttttttg caaagatttg tggaggcttt ggattattat gcagctgtct ttgattcatt    1200

ggaagcaact ttgccgccga gcagtagaga gaggatgaca gtggagcaag tttggttcgg    1260

aagagaaatt atagatatag tagcagcaga aggagataag agaagagaaa gacacgagag    1320

attcagatca tgggaagtaa tgttgaggag ctgtggattt agcaatgttg ctttaagtcc    1380

ttttgcactt tcacaagcta aacttctctt gagacttcat tacccttctg aaggatacca    1440

gcttagtgtt tcgagtacga gtaattcttt cttcttgggt tggcaaaatc aacccctttt    1500

ttccatatct tcttggcgtt aaattataag ggaaattaaa accctaaaaa caagatttta    1560
```

-continued

```
tctatctgca tggtgaagga caaagaggtc ttcaatctca ggttcttttt gttttttaa   1620

cttgtttgga tatgaggtta ttgagctgat gaatgtttta attttaacat aggcctactt   1680

acgtagtagt tataggttga taatgatata tatttaacta agtctttgta taatgcagat   1740

cctgaactta atttttattt ttattatttt gttgttaatg aaagattctg ttaccaaatt   1800

ttatcagtct atttaattag aggccaa                                       1827
```

<210> SEQ ID NO 9
<211> LENGTH: 337
<212> TYPE: PRT
<213> ORGANISM: Nicotiana tabacum

<400> SEQUENCE: 9

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Pro Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Thr Pro Asn Asn Arg Pro
145                 150                 155                 160

Asn Ile Thr Gly Leu Asn His Gln Ser Ile Ser Ser Ala His Gln Thr
                165                 170                 175

Asn Phe Leu Tyr Thr Asn Asn Asn Met Asn Phe Pro Asn Leu Gly Ala
            180                 185                 190

Thr Asn Asn Gln Tyr Pro Tyr Asn Ile Gln Ser His Asn Leu Leu Met
        195                 200                 205

Phe Gly Glu Ala Ser Cys Ser Ser Ser Asp Gly Ser Cys Ser Gln Met
    210                 215                 220

Ser Phe Gly Lys Glu Ile Lys Arg Glu Glu Ile Met Ser Asn Ser Leu
225                 230                 235                 240

Gln Gln Gly Gln Ile Ser Ser Val Asn Ala Phe Glu Glu Asn His Gln
                245                 250                 255

Asn Phe Thr Leu Asp Tyr Gly Asn Ser Ser Ser Asn Trp Val Asp Gln
            260                 265                 270

Lys Pro Asn Val Tyr Phe Gly Thr Thr Thr Thr Gln Val Leu Gln Tyr
        275                 280                 285

Asp Asn Val Glu Glu Val Lys Gln Gln Leu Thr Ser Cys Thr Asn Gly
    290                 295                 300

Asn Asn Gly Ser Thr Ile Gly Cys Asn Asn Asn Asn Ser Met Phe Val
305                 310                 315                 320

Phe Asn Asp Glu Asn Tyr Asn Lys Ser Asn Glu Ile Glu Met Phe Tyr
```

-continued 325 330 335

Tyr

<210> SEQ ID NO 10
<211> LENGTH: 1239
<212> TYPE: DNA
<213> ORGANISM: Nicotiana tabacum

<400> SEQUENCE: 10

```
gtccatctgt ctatataggt agaatgagag taaaggagaa aacatatcct cctctccatt     60

tctgtagaca aagattctca aagagaaaca aattaaacac tagagagtga gagagtgcta    120

taagaaaaag aatatgggga gagctccatg ttgtgataaa gcaaatgtga agagagggcc    180

atggtctcct gaagaagatg ctaaactcaa agatttcatt cacaaatatg gaactggtgg    240

aaattggatt gctcttcctc aaaaagctgg actaaagaga tgtgggaaga gttgtagatt    300

gagatggcta aattatttaa ggcctaacat taaacatggt gatttttctg aggaagaaga    360

tagagttatt tgcaccttgt attccaccat tggaagcagg tggtcaataa tagcagctca    420

attaccggga agaactgaca atgatatcaa gaattactgg aatactaagc tcaagaaaaa    480

acctatggga ttaatgcaat caactaacca aagaaaatca ccatattttc cagctactaa    540

ttctcttcaa acccaacccc agataaattc aagtcttttt agagacttat attacacccc    600

aaataatagg cctaatatta caggcctaaa tcatcagtcc atttcttctg cccaccagac    660

aaattttctc tacactaata ataacatgaa ctttcctaat ttgggtgcta caaataatca    720

atatccttat aatatccaaa gtcataattt acttatgttt ggagaagcaa gttgttcttc    780

atcagatgga agttgcagcc aaatgagttt tggtaaagaa atcaagagag aagaaattat    840

gagtaatagt ttacaacaag gtcaaatttc aagtgttaat gcttttgaag aaaaccacca    900

gaattttact cttgattatg gcaatagtag tagtaattgg gtggatcaaa aaccaaatgt    960

gtattttggt actactacta ctcaagtact tcagtatgat aatgttgaag aagttaagca   1020

gcagctaaca agttgtacca atggcaacaa tggtagtact attggatgta acaacaacaa   1080

cagtatgttc gtgttcaatg atgagaatta taacaagtca aatgagatag agatgttcta   1140

ttactaaaga agaaatgact gttgaaaaga aaacaaatgc aagtaccatt aggaagattt   1200

gaaagggcgt ttgggtatgg gggttgccaa gaagattca                           1239
```

<210> SEQ ID NO 11
<211> LENGTH: 336
<212> TYPE: PRT
<213> ORGANISM: Nicotiana tabacum

<400> SEQUENCE: 11

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95
```

```
Leu Pro Gly Arg Thr Asp Asn Asp Ile Lys Asn Tyr Trp Asn Thr Lys
            100                 105                 110

Leu Lys Lys Lys Leu Met Gly Leu Met Gln Ser Thr Asn Gln Arg Lys
        115                 120                 125

Ser Pro Tyr Phe Pro Ala Thr Asn Ser Leu Gln Ala Gln Pro Gln Ile
    130                 135                 140

Asn Ser Ser Leu Phe Arg Asp Leu Tyr Tyr Asn Pro Asn Asn Arg Pro
145                 150                 155                 160

Ile Ile Thr Gly Leu Asn Gln Ser Ile Ser Ser Ala His Gln Pro Asn
                165                 170                 175

Phe Leu Tyr Thr Asn Ser Asn Met Asn Phe Pro Asn Leu Gly Ala Thr
            180                 185                 190

Asn Ser Gln Tyr Pro Tyr Asn Ile Gln Ser His Asn Leu Leu Met Phe
        195                 200                 205

Gly Glu Ala Ser Cys Ser Ser Ser Asp Gly Ser Cys Ser Gln Met Ser
    210                 215                 220

Phe Gly Lys Glu Ile Lys Arg Glu Glu Ile Met Ser Asn Cys Leu Gln
225                 230                 235                 240

Gln Gly Gln Ile Ser Ser Val Asn Ala Phe Glu Glu Asn Gln Asn Phe
                245                 250                 255

Thr Leu Asp Tyr Gly Asn Ser Ser Ser Asn Trp Val Asp Gln Lys Pro
            260                 265                 270

Asn Val Tyr Phe Gly Asn Thr Thr Thr Thr Thr Gln Val Leu Gln Tyr
        275                 280                 285

Asp Val Glu Glu Val Lys Gln Gln Leu Thr Ser Cys Thr Asn Gly Asn
    290                 295                 300

Asn Gly Ser Thr Ile Gly Cys Asn Asn Asn Asn Ser Met Phe Val Phe
305                 310                 315                 320

Asn Asp Glu Asn Tyr Asn Lys Ser Asn Glu Ile Gly Met Phe Tyr Tyr
                325                 330                 335
```

<210> SEQ ID NO 12
<211> LENGTH: 1343
<212> TYPE: DNA
<213> ORGANISM: Nicotiana tabacum

<400> SEQUENCE: 12

```
gtccacttgt ctatatagca agaaagagag taaaggagaa aacatattct cctctccatt      60

tctgtagaca agattctcaa aaagaaacaa attaaacact agagagtgag agagaactat     120

aagaaaaaga atatggggag agctccatgt tgtgataaag caaatgtgaa gagagggcca     180

tggtctcctg aagaagatgc taaactcaaa gatttcattc acaaatatgg aactggtgga     240

aattggattg ctcttcccca aaaagcagga ctaaagagat gtgggaagag ttgtagattg     300

agatggctaa attatctaag gcctaatatc aaacatggtg atttttcgga ggaagaagat     360

agagttattt gcagcttgta ttccaccatt ggaagcaggt ggtcaataat agcagctcaa     420

ttaccaggaa ggactgacaa tgatatcaag aattactgga atactaaact caagaaaaag     480

cttatgggat taatgcaatc aacaaaccaa agaaaatcac catattttcc agctactaat     540

tctcttcaag cccaacccca gataaattca agtcttttta gagacttata ttacaaccca     600

aataataggc ctattattac aggcctaaat cagtccattt cttctgccca ccagccaaat     660

tttctctaca ctaatagtaa catgaatttt cctaatttgg gtgctacaaa tagtcaatat     720

ccttataata ttcaaagtca taatttactt atgtttggag aagcaagttg ttcttcatca     780
```

```
gatggaagtt gtagccaaat gagttttggc aaagaaatca agagagagga aattatgagt    840

aattgtttac aacaaggtca aatttcaagt gttaatgctt ttgaagaaaa tcagaatttc    900

actcttgatt atggtaacag tagtagtaat tgggtggatc aaaaaccaaa tgtgtatttt    960

ggaaatacta ctactactac tcaagtactt cagtatgatg ttgaagaagt taagcagcag   1020

ctaacaagtt gtaccaatgg caacaatggc agtactattg gatgtaacaa caacaacagt   1080

atgttcgtgt tcaatgatga gaattataac aagtcaaatg agatagggat gttctattac   1140

tgaagaagaa atgactagct gttgaaaaga gaaaacaaat gtaagtacac cattaggaag   1200

atttgaaagg gcgtttgggt atgggggttg gcaagaagat tcaaactttt tctggggttt   1260

tgtgtaattg tggtggaatt attattattg aaacttcttt acttcaattt aaatcgtcgg   1320

tacatattac gtagttgtag tac                                           1343
```

<210> SEQ ID NO 13
<211> LENGTH: 168
<212> TYPE: PRT
<213> ORGANISM: Nicotiana tabacum

<400> SEQUENCE: 13

```
Met Asp Gln Gln His Ser Thr Cys Phe Ser Ser Ser Ser Lys Ile Asn
1               5                   10                  15

Asp Lys Glu Lys Lys Lys Lys Arg Ser Val Val Lys Leu Ser Thr Asp
            20                  25                  30

Pro Gln Ser Val Ala Ala Arg Glu Arg Arg His Arg Ile Ser Asp Arg
        35                  40                  45

Phe Lys Ile Leu Gln Ser Leu Ile Pro Gly Gly Ser Lys Met Asp Thr
    50                  55                  60

Val Thr Met Leu Glu Glu Ala Ile His Tyr Val Lys Phe Leu Lys Thr
65                  70                  75                  80

Gln Ile Trp Leu His Gln Thr Val Ile Asn Ile Val Asp Asp Tyr Asp
                85                  90                  95

Asn Pro Asn Tyr His Asp Gln Leu Leu Met Ala His Asp Ser Asn Phe
            100                 105                 110

Ala Asn Tyr Tyr Pro His Glu Met Val Glu Tyr Cys Pro Ala Pro Val
        115                 120                 125

Glu Asn Ala Gln Ile Asn Tyr Asn Leu Asp Gln Leu Gln Leu Pro Gly
    130                 135                 140

Tyr Ala Phe Ser Asp Gly Asp Gln Phe Gln Gly Glu Glu Thr Asn Ile
145                 150                 155                 160

Thr Gly Asp Ser Phe Met Tyr Tyr
                165
```

<210> SEQ ID NO 14
<211> LENGTH: 594
<212> TYPE: DNA
<213> ORGANISM: Nicotiana tabacum

<400> SEQUENCE: 14

```
aaaatagagg taattagttg tatcaatgga tcaacaacat tccacttgtt tttcttcttc     60

aagtaaaatt aatgacaaag aaaagaagaa aaaaagatca gttgtgaaac tatcaactga    120

tccacaaagt gtagcagctc gtgaaagaag gcatagaatc agtgatcgtt tcaagatttt    180

gcagagttta atccctggtg gttcaaaaat ggatacagtt actatgttag aagaagcaat    240

tcactatgtc aaatttctta agactcaaat atggctgcat caaaccgtga ttaatattgt    300
```

-continued

```
agatgattat gataatccaa attatcatga tcagttgcta atggctcatg actctaattt    360

tgctaattat tatcctcatg aaatggtgga atattgccca gctcctgttg agaatgcaca    420

aataaattat aacttggacc agctgcagct tccaggttat gcattttcag atggggatca    480

attccaagga gaagaaacta atattactgg tgattctttt atgtactatt agttagttaa    540

ttatgttgcc taagtttaat tagaatacgt agtgtgtggt agtatggtat gttg          594


<210> SEQ ID NO 15
<211> LENGTH: 165
<212> TYPE: PRT
<213> ORGANISM: Nicotiana tabacum

<400> SEQUENCE: 15

Met Asp Gln Gln His Ser Thr Cys Phe Ser Ser Ser Ser Lys Ile Asn
1               5                   10                  15

Asp Lys Glu Lys Lys Lys Lys Gly Ser Val Val Lys Leu Ser Thr Asp
            20                  25                  30

Pro Gln Ser Val Ala Ala Arg Glu Arg Arg His Arg Ile Ser Asp Arg
        35                  40                  45

Phe Lys Ile Leu Gln Ser Leu Val Pro Gly Gly Ser Lys Met Asp Thr
    50                  55                  60

Val Thr Met Leu Glu Glu Ala Ile His Tyr Val Lys Phe Leu Lys Met
65                  70                  75                  80

Gln Ile Trp Leu His Gln Thr Met Ile Asn Ile Val Asp Asp Tyr Asp
                85                  90                  95

Asn Pro Asn Tyr His His Gln Leu Leu Met Ala His Asp Ser Asn Phe
            100                 105                 110

Ala Asn Tyr Tyr Pro His Glu Asn Asn Ser Thr Pro Val Glu Asn Ala
        115                 120                 125

Gln Ile Asn Tyr Asn Leu Asp Gln Leu Gln Leu Pro Gly Tyr Ala Phe
    130                 135                 140

Ser Asp Gly Asp Gln Phe Gln Gly Glu Glu Thr Asn Ile Ser Gly Asp
145                 150                 155                 160

Ala Phe Met Tyr Tyr
                165


<210> SEQ ID NO 16
<211> LENGTH: 660
<212> TYPE: DNA
<213> ORGANISM: Nicotiana tabacum

<400> SEQUENCE: 16

tgcatggaca atctcctctt ctcaaacttc ataaagatat tatattaaaa aaaataaaga     60

agaagagaag atagaggtaa ttagctatag caatggatca acaacattcc acttgttttt    120

cttcttcaag caaaattaat gacaaagaaa agaagaaaaa aggatcagtt gtgaaactat    180

caactgatcc acaaagtgta gcagctcgtg aaagaaggca tagaatcagt gatcgtttca    240

agattttgca gagtttagtc cctggtggtt ctaaaatgga cacagttaca atgttagaag    300

aagcaattca ctatgtcaaa tttctcaaga tgcaaatatg gctgcatcaa accatgatta    360

atattgtaga tgattatgat aatccaaatt atcatcatca gttgctaatg gctcatgact    420

ctaattttgc taattattat cctcatgaga ataactcaac tcctgttgag aatgcacaaa    480

taaattataa cttggaccag ctgcagcttc caggttatgc attttcagat ggagatcaat    540

tccaaggaga agaaactaat atttctggtg atgcttttat gtactattaa ttagtaatta    600
```

gttaattatg ttgcctaagt ttaattagaa tacgtagtgt gtggtagtat ggtatgttgt 660

<210> SEQ ID NO 17
<211> LENGTH: 400
<212> TYPE: PRT
<213> ORGANISM: Nicotiana tabacum

<400> SEQUENCE: 17

```
Met Leu Ser Met Glu Glu Ile Leu Cys Glu Leu Ser Arg Glu Asp Met
1               5                   10                  15

Asn Asn Glu Lys Gly Leu Pro Pro Gly Phe Arg Phe His Pro Thr Asp
            20                  25                  30

Glu Glu Leu Ile Thr Phe Tyr Leu Ala Ser Lys Val Phe Asn Gly Thr
        35                  40                  45

Phe Cys Gly Ile Gln Ile Ala Glu Val Asp Leu Asn Arg Cys Glu Pro
    50                  55                  60

Trp Glu Leu Pro Glu Val Ala Lys Met Gly Glu Arg Glu Trp Tyr Phe
65                  70                  75                  80

Phe Ser Leu Arg Asp Arg Lys Tyr Pro Thr Gly Leu Arg Thr Asn Arg
                85                  90                  95

Ala Thr Gly Ala Gly Tyr Trp Lys Ala Thr Gly Lys Asp Arg Glu Val
            100                 105                 110

Tyr Ser Ala Thr Asn Gly Ala Leu Leu Gly Met Lys Lys Thr Leu Val
        115                 120                 125

Phe Tyr Lys Gly Arg Ala Pro Lys Gly Glu Lys Thr Lys Trp Val Met
    130                 135                 140

His Glu Tyr Arg Leu Asp Gly Asp Phe Ser Tyr Arg Tyr Ser Ser Lys
145                 150                 155                 160

Glu Glu Trp Val Ile Cys Arg Ile Leu His Lys Ile Gly Glu Lys Lys
                165                 170                 175

Asn Pro Ile Tyr Gln Ala Ala Gly Gln Asn Tyr Gly Tyr Pro Thr Ser
            180                 185                 190

Leu Lys Thr Trp Pro Ser Ser Ser Phe Leu Asn Thr Ala Thr Ser Ala
        195                 200                 205

Glu Ala Ala Pro Asn Pro Ile Leu Ala Glu Thr Pro Asn Pro Lys Thr
    210                 215                 220

Thr Thr Thr Thr His Trp Gln Glu Ser Phe Gln Ile Ser Gln Asn Ser
225                 230                 235                 240

Met Gln Ser Leu His Asn Phe Tyr Leu Phe His His Gln Glu Asn Asp
                245                 250                 255

Leu Met Lys Ser Leu Phe Asn Pro Ile Asn Val Ser Gln Thr Asn Leu
            260                 265                 270

Phe Pro Ile Asn Asn Ser Val Leu Ser Ser Ala Thr Ser Phe Ser Thr
        275                 280                 285

Ser Gln Ser Thr Lys Lys Tyr Lys Glu Asp Ile Asn Lys Asn Ser Ser
    290                 295                 300

Leu Ser Ser Phe Leu Val Ser Asn Ser Lys Lys Asn Glu Lys His Gln
305                 310                 315                 320

Val Pro Leu Met Gln Ala Asn Thr Thr Met Lys Thr Glu Ala Ser Phe
                325                 330                 335

Ser Pro Tyr Ser Gly Cys Tyr Asn Asp Gln Asn Pro Met Ala Thr Asn
            340                 345                 350

Phe Gly Met Asn Asn Ser Thr Asp Trp Ser Leu Val Gly Ile Glu Gly
        355                 360                 365
```

-continued

```
Met His Phe Asn Gly Gly Cys Thr Gln Ser Gln Met Val Leu Asp His
    370                 375                 380

Met His Cys Pro Ile Lys Ile Ala Ala Glu Ser Trp Pro Leu Asp Leu
385                 390                 395                 400
```

<210> SEQ ID NO 18
<211> LENGTH: 1461
<212> TYPE: DNA
<213> ORGANISM: Nicotiana tabacum

<400> SEQUENCE: 18

```
tactatcact taataccatc attcatcatg ttgtcaatgg aagaaatatt gtgtgaacta      60

agtagagaag acatgaataa tgagaaaggt ctaccacctg gttttaggtt tcatcctact     120

gatgaagagc ttatcacttt ctaccttgcc tctaaggttt ttaacggcac cttttgtggt     180

attcagattg ctgaagttga tctcaacaga tgtgagccct gggaacttcc agaagtggca     240

aagatggggg aaagagaatg gtatttcttt agcttaaggg acagaaaata cccaaccgga     300

ctaagaacaa accgggcaac aggagctggt tattggaaag ctacaggaaa agatagagaa     360

gtgtacagtg caacaaatgg agcactcctt gggatgaaga aaacattggt tttttacaaa     420

ggaagagcac caaagggtga gaaaaccaaa tgggttatgc atgaatatcg tcttgacggc     480

gatttttcct accgttactc ttctaaggag gaatgggtga tatgcagaat actacacaaa     540

atagggggaga agaaaaatcc aatataccaa gctgcaggac aaaactatgg ctaccctaca     600

agcttgaaaa catggccatc atcatctttt cttaacacag caacatcagc agaagcagct     660

ccaaatccta tattggctga aacaccaaat ccaaaaacca caacaactac acattggcaa     720

gaatcattcc aaatatcaca aaactcaatg caatcactgc acaactttta tctatttcac     780

caccaagaaa acgaccttat gaaatccctc ttcaacccca ttaatgtttc ccaaacaaac     840

ctcttcccaa taaataatag tgtcctttct tctgctacct ccttttctac atcccaaagc     900

acaaaaaaat acaaagaaga cataaacaaa aactcgtcac tatcatcttt cctcgttagc     960

aattcaaaga aaaatgaaaa acatcaagtc ccactcatgc aggctaacac aacaatgaaa    1020

acagaagcca gtttttcacc atattctggt tgttacaatg atcaaaaccc tatggctacg    1080

aattttggta tgaataattc aacagattgg agtttagtag gcatagaagg gatgcatttt    1140

aatggtggat gtactcagtc tcagatggtg ttggatcaca tgcattgtcc catcaaaata    1200

gctgcagaat cttggcctct tgatctctaa aaatagaaga ttttgttttt aataaattct    1260

actgtaggat gatatggtaa ttaattatta ctcctgttat atcatcctta tctatgaata    1320

gctatcctct aagtatataa aagtaattca ggctgctctt tatattctga aacatgttgc    1380

ttgctcctta agcatctagg taataccgct atgtaagata tatcttcctt ttctcgacta    1440

aagttgtgat ctattgatgg g                                               1461
```

<210> SEQ ID NO 19
<211> LENGTH: 399
<212> TYPE: PRT
<213> ORGANISM: Nicotiana tabacum

<400> SEQUENCE: 19

```
Met Leu Ser Met Glu Glu Ile Leu Cys Glu Leu Ser Arg Asp Asp Met
1               5                   10                  15

Asn Asn Glu Lys Gly Leu Pro Pro Gly Phe Arg Phe His Pro Thr Asp
            20                  25                  30
```

```
Glu Glu Leu Ile Thr Phe Tyr Leu Ala Ser Lys Val Phe Asn Gly Thr
        35                  40                  45

Phe Cys Gly Ile Gln Ile Ala Glu Val Asp Leu Asn Arg Cys Glu Pro
    50                  55                  60

Trp Glu Leu Pro Glu Val Ala Lys Met Gly Glu Arg Glu Trp Tyr Phe
65                  70                  75                  80

Phe Ser Leu Arg Asp Arg Lys Tyr Pro Thr Gly Leu Arg Thr Asn Arg
                85                  90                  95

Ala Thr Gly Ala Gly Tyr Trp Lys Ala Thr Gly Lys Asp Arg Glu Val
            100                 105                 110

Tyr Ser Ala Thr Asn Gly Ala Leu Leu Gly Met Lys Lys Thr Leu Val
        115                 120                 125

Phe Tyr Lys Gly Arg Ala Pro Lys Gly Glu Lys Thr Lys Trp Val Met
    130                 135                 140

His Glu Tyr Arg Leu Asp Gly Asp Phe Ser Tyr Arg Tyr Ser Ser Lys
145                 150                 155                 160

Glu Glu Trp Val Ile Cys Arg Ile Leu His Lys Ile Gly Glu Lys Lys
                165                 170                 175

Asn Pro Ile Tyr Gln Ala Ala Gly Gln Asn Tyr Gly Tyr Pro Thr Ser
            180                 185                 190

Leu Lys Thr Trp Pro Ser Ser Ser Phe Leu Asn Thr Ala Ala Pro Asn
        195                 200                 205

Pro Ile Leu Ala Glu Thr Pro Asn Pro Lys Thr Thr Thr Thr Thr His
    210                 215                 220

Trp Gln Glu Ser Phe Gln Ile Ser Gln Asn Ser Val Gln Ser Leu His
225                 230                 235                 240

Asn Leu Tyr Leu Phe His His Gln Glu Asn Asp Leu Met Lys Ser Leu
                245                 250                 255

Phe Ser Pro Ile Asn Val Ser Gln Thr Asn Leu Phe Pro Ile Asn Asn
            260                 265                 270

Ser Asp Leu Ser Ser Ala Ala Ser Phe Ser Thr Ser Gln Ser Thr Lys
        275                 280                 285

Lys Tyr Lys Glu Asp Ile Asn Lys Asn Ser Ser Ile Ser Ser Phe Leu
    290                 295                 300

Phe Ser Asn Ser Phe Cys Thr Ser Lys Lys Asn Glu Lys Gln Gln Val
305                 310                 315                 320

Pro Leu Met Gln Ala Asn Thr Thr Met Lys Thr Glu Ala Ser Phe Ser
                325                 330                 335

Pro Tyr Ser Gly Cys Tyr Asn Asp Gln Asn Pro Met Ala Ser Thr Phe
            340                 345                 350

Gly Met Asn Asn Ser Ser Asp Trp Ser Leu Val Gly Ile Glu Gly Met
        355                 360                 365

His Phe Asn Gly Gly Cys Thr Gln Ser Gln Met Val Leu Asp His Met
    370                 375                 380

Asn Cys Pro Ile Lys Ile Thr Ala Glu Ser Trp Pro Leu Asp Leu
385                 390                 395
```

<210> SEQ ID NO 20
<211> LENGTH: 1465
<212> TYPE: DNA
<213> ORGANISM: Nicotiana tabacum

<400> SEQUENCE: 20

```
ctactacatc acttaatatc attcattatg ttgtcaatgg aagaaatatt gtgtgaactt      60
```

agtagagatg acatgaataa tgagaaaggt ctaccacctg gttttaggtt tcatcctact 120
gatgaagagc ttatcacttt ctaccttgcc tctaaggttt ttaacggcac cttttgtggt 180
attcagattg ctgaagttga cctcaacaga tgtgagccct gggaacttcc agaagtggca 240
aagatggggg agagagaatg gtatttcttt agcttaaggg acagaaaata cccaaccggg 300
ctaagaacaa accgggcaac aggagcaggt tattggaaag ctacaggaaa agatagggaa 360
gtgtacagtg caaccaatgg agcactcctt gggatgaaga aaacactggt tttttacaaa 420
ggaagagcac caaagggtga gaaaaccaag tgggttatgc acgaatatcg tcttgacggt 480
gatttttctt accgctactc ttctaaggag gaatgggtga tatgcagaat actacacaaa 540
ataggggaga agaaaaatcc aatataccaa gctgcaggac aaaactatgg ctaccctaca 600
agcttgaaaa catggccatc atcatctttt ctcaacacag cagctccaaa tcccatattg 660
gctgaaacac caaatccaaa aaccacaact actacacatt ggcaagaatc attccaaata 720
tcacaaaact cagtgcaatc actgcacaac ctttatctat ttcaccacca agaaaacgac 780
cttatgaaat ccctcttcag tcccattaat gtttcccaaa caaacctctt cccaataaat 840
aatagtgacc tttcttctgc tgcctccttt tctacatccc aaagcaccaa aaaatacaaa 900
gaagacataa acaaaaactc gtcaatatca tctttcctct ttagcaattc cttttgcact 960
tcaaagaaaa atgaaaaaca gcaagttcca ctaatgcagg ctaacacaac aatgaaaaca 1020
gaagctagtt tttcaccata ttctggttgt tacaatgatc aaaaccctat ggcttcgact 1080
tttgggatga ataattcatc agattggagt ttagtaggca tagaagggat gcattttaat 1140
ggtggatgta ctcagtctca gatggtgttg gatcacatga attgtcccat caaaatcact 1200
gcagaatctt ggcctctcga tctctaaaaa tagaagagtt gtttttccat aatttctata 1260
gtaggatgat atggtaatta attatgacta ctgttatgtc atcctctata tatagctatc 1320
cgctctagta tatgtaatct ttgtaattaa tttaggctgc tttattctga aagatgttgc 1380
tttctcctta aggatatatc tagctagtac cgctatgtaa gatatatctt tcttttctcg 1440
actaatgtaa agttgcaatc tattg 1465

<210> SEQ ID NO 21
<211> LENGTH: 7032
<212> TYPE: DNA
<213> ORGANISM: Nicotiana tabacum

<400> SEQUENCE: 21
tctcaaagct ggctgtttta tgtatatact gaaggggttg tggtgatttg tttgtctact 60
ttaagaaggt gccatctttt tcagtaatat ttgggtaaaa gttctctctt ttttggcctt 120
aaacgcgaag attcaggcct ctctcaacgt gtcatctgtt ctctgtatta aacacagctg 180
gagaattaat tacatagagg taaaaaaagg ggttaaagtc gccaaagaat tgaaaaaaaa 240
cagagggctg aggtaaaaag ttgatggttt ttaaaaaaaa ataaaagctt aaatgatgat 300
aaagtttgga gctttatgtg aatggaaatg gtgttgtgtt tgtatcaaac acgagtagtt 360
tacagcttat gtgaatttga aagagagaga atttttgtct gtatttatat ccttttcagc 420
catatctttc gttagagcag ttttggctgt accttaattt gtaagggttt aagcgtgaag 480
tgtgtgtttg agccttctgt tataaggggc acaaagtata gaaacaacaa aaggggcacc 540
taggaatctt ctggctcaat caagatcgtt catttaatct tgtctgagat cactagaaaa 600
agaaaaagga aagataaaga taaagtcttt gtttcagaga atcttagttc tctgtgttga 660
tatatataat aaaagctgtt tgcagggaat atatctactt gggggtgttt ttatttcttt 720

-continued

```
taagggtgtt tgaaaatttg gaaatcttga ttattttttt gtttgggatt ttggggtttg    780
agggcaaatg gctatggtgg tacagcagca tagggagagt agtagtggta gtattacaaa    840
acatcttgac agtagtggaa agtatgtccg gtatacagct gagcaagtgg aggcattaga    900
gagggtttat gcagagtgcc ctaaacctag ctcgttgcgc cgccagcaat tgatccgcga    960
atgccctatt ctgtcgaata tcgagcctaa gcagatcaaa gtttggtttc aaaacagaag   1020
gtacactgcc cgctgttcaa ttttgattgc tccaatttgg tttctttttt gttcttaaat   1080
gcatatattt aggtgtcgtg cacttgtgat cttggactga aatatgggat aagttagatg   1140
agtgatggtt aaattggaat atatcactgt gcttctagtt tcctaggctt gtcgattggg   1200
ttgtatggat taatcggggg gggggggcat taagtgaatc gtgaattgga tgtgtagttt   1260
gatttctgtc tgtcgggtag ttgagcttag attttggaat tgagggtgaa cattgtgcca   1320
tttcaggtgt cgagagaagc aaaggaaaga gtcttctaga ctacagactg taaatagaaa   1380
gctgtctgca atgaataaac tattaatgga ggagaatgat cgcttgcaaa aacaggtttc   1440
acagcttgtg tgtgaaaatg gctttatgcg gcaacaattg catactgtaa gttaacataa   1500
tttttccttt atacttgtgg taaaaagctt tatttttttgc ttactgtaga cgaatggtaa   1560
cgtatatctt gtcttttgtt tctgatgaaa tggctaagca ctatgaattt taagatttct   1620
gatattccac agcttatggt aacatatttt aaacagtgta aataaacttt attctgatga   1680
cactgtttta ggacattctt atagttatgg aatgcatggc tttagatatg ggactaaatt   1740
ttatgttcat cgtgtttttg cattctatat tcttctactc gcccttgttt tgctgtgaag   1800
ttgaaccaat aaacaagaaa cagatgatgg atatctccgg tgatcttttg ttccatagga   1860
ttaattagac tgtatttgtg ttttctgcag gcatcagcgg ccactactga tgtaagttgt   1920
gagtcagtgg ttaccacccc tcagcattcc ctcagagatg ctaacaaccc tgctgggtaa   1980
ttaatttcaa acacctattt ctcccatcct ttccgtctat ggtgtccatt ctccaacata   2040
tttatgttat ttattcaatg gcatatacaa cattttgagg ggctaatttg tttatctcta   2100
agtcaagttt gttctctatg cagactgctg tcgattgcag aggaaacctt agcagagttc   2160
ctttccaagg ctacaggaac tgctgttgat tgggtcccga tgcctgggat gaaggtttga   2220
actttagtca atcctcttta ttttttgaaa attcagtatt gccatgtctc tttgactgga   2280
tagctaaaaa actaaatttt cattctattg ccagcctggt ccggattcag ttgggatttt   2340
tgccatctca cacagttgta gtggagtggc agcccgagca tgtggtcttg ttagtttaga   2400
gccgacaaag gtaagcagtc atgtggaaaa ttaatttaaa tgtagtgctg ttgctctatt   2460
actagttttg gtcctttgac gggtgtacta gatgttgcca gtttcttctt agtaaatata   2520
tttttgtcaa atatttacag attgctgaga tcctcaaaga tcgaccatct tggttccgag   2580
actgccggaa cgttgaagtt ttcacgatgt tttctgcagg aaatggaaca attgagcttt   2640
tgtacacgca ggtaattaat taccttctca tcaatcttca cgtaggcttc tgattggaga   2700
agctacagca ttgaggggat ttttgaaatc atttcttttc agatatatgc tcctaccacc   2760
ttggctcctg cacgtgattt ttggactctg agatacacaa ccaccctgga gaatggtagt   2820
tttgtggtat gcacatcctc cgcattagcg tgtcttagga taagcaatct ggccactttt   2880
gtacttagtt atgaatattt tgctgatagt ttgttgtatg tgccatcaat tcctcctccc   2940
ctcaaggttt gtgaaagatc cctctctggt actggagctg ggccgaatgc tgcttctgct   3000
tcccagtttg taagagctca aatgcttccg tccggatatc taatccgacc gtgtgacggt   3060
```

-continued ggaggatcca ttatacatat tgttgaccat ctgaatcttg aggtcagatt gcacactgta 3120
ctaccacttc cctttctttt taacttgttc tgtcttgcag ctggacttca cggcataatg 3180
tttttcttca ggcatggagt gcccctgaga ttttgcgtcc actttatgaa tcgtcaaaag 3240
ttgtggcaca gaaaatgact attgcggtga gttgaaccgt tgattgtcat taaatactgg 3300
atgtgtaaca acctttttag tcttcacaac tagatctcaa tttttgttga gctctgaagt 3360
cgaaagggtt gtaatttctg gacgagcagt tagatatagc ctgatatttt tgtttattca 3420
gttagaagtt cccagcttta aaaatataga acacctgaca aatccttagt ctcttaatgc 3480
acgttattga ggatttcttt gttttttcga gttttctaag gttcattatt gttttcctca 3540
tggggttgcc ataaaagtct gcatgtgaaa catatagtat tgaagaactg taggctgtga 3600
agcgcaccat actcttaact gcattagttg ttgctttaat tccatatgtt gctctgagaa 3660
tacttgcagc attttttatg tttcaagtac ttgagcaatt accgtagctt accatcacaa 3720
caaaagaaat actaattata gtatgttttt gctgtaaagg cactgcgata tgcaaggcaa 3780
atagctcagg agactagtgg ggaggttgta tatggtctgg gaaggcaacc tgcagttctt 3840
cgaacattta gccagagatt aagcaggtgc tgtttattgc tctgattgtt ctgtgctatg 3900
agatatgata tgccataaaa gtagacatac gaattctgaa gcacaagtat cataattaag 3960
ctattttcta tattgcagag gcttcaatga cgccatcaat ggattcagtg atgatggctg 4020
gtcattgtta agttctgatg gtggtgaaga tgttatagtt gctgtcaatt caaggaagaa 4080
cattgccacc acttccgttc ctctttcacc gctgggaggc atcctttgtg ccaaagcatc 4140
aatgctactc caggtgaata gattaccttt taactgacta gaaattttca ttggccaact 4200
acctttgcct tgttagataa aattgttcca gactgttgca gattttgatg atgctttcaa 4260
tttctaaact cttggaatga atcgggattc ctggaatata agagaatatt actcagtgtt 4320
ctataaagct atttgtttaa tgcaccatgt ggggcatctt gttgctatta aatggaagaa 4380
tgagaattga cttttaactc ttctgtatgg tggcagaatg ttcctcctgt ggtactggtt 4440
cgatttctca gggagcaccg ttcagagtgg gcggacttta atgttgatgc ctatgtagct 4500
tcgtcaatga aatcttgttc atatgcatat cctgggatga ggcctaccag atttaccgga 4560
agtcagataa taatgccact tggccataca attgaacatg aagaggtaag cactttgcac 4620
ttgccccagt tccatccatc ccatgtgttg gagtgtgctt atacagcacc agtatttttt 4680
ataatcagaa agttagcact ctttgaattg ctaggcttgt tacctaatat tgctaatatt 4740
atactttaga cttcctctca tttttttttt attttgtttt gctttgcaga tgcttgaggt 4800
tattagattg gaaggacact ctattggcca ggaagatact tttatgccaa gagatgttca 4860
ccttctccag gtaccttttg cctatgcatt gatgtttcgg tgtgttatct acgtacagac 4920
attgttgaag caatagctaa caaacggtta tttctagatg tgtagtggaa ctgatgagaa 4980
tgctgtcgga gcttgttctg aactagtttt tgctgcaatt gatgagatgt ttccagatga 5040
tgcacccctg ttgccctccg ggtttcgtat cattcctctc gagtcaaaat cagttgagta 5100
aaaatatttc attttcaact ttaagcattg aatttggcca atctattgtt tacatggatt 5160
atttttcatt ttgcttgatt ttggagcata accggtgatt ctattttcag agcgatcccc 5220
aggatacatc gaatgctcat agaacactgg atctggcatc aagtcttgaa gttggcccag 5280
caacaaaccc tgctactgga gatgtggtct ctggctacag tgcacgatct gtgttgacaa 5340
ttgcttttca atttccattc gaggacaatc ttcaggacaa tgtagctacc atggcgcgcc 5400
agtatgttcg cagtgtggtt tcatctgtcc aacgggttgc catggcaata tctcccgcag 5460

```
gagtgaattc aacattcggg tccaagcttt ctccaggctc ccctgaagct gtaacgttgt   5520
cgcactggat ctgccagagc tacaggtaaa atgatttctc aactatggtg aaaccttgtt   5580
ctcttcgttt cagctcaata tggggtttat tgctttacat gttcatactg tcgtgcttac   5640
aagtcactcg ttgcaaatct catttaccac caagagccaa agtagtgtca agtgtgcatg   5700
ttgagatctt caattatttt atgagaattt ttcctttctc aacatattga gaaaaagcag   5760
acggtcttag aagtactttt ctgattgtta acataccgtt ttcttctttt gcatttaata   5820
tccagttatc acatggggac agagttgctt caaactgatt cgaggggcga tgaatcagtg   5880
ctaaaaaatc tttggcaaca tcaggatgct attttgtgct gctcattgaa ggtatgaatt   5940
ctcttatcat gtaaacagca tgttacggtt agtaaaaaaa tattgtatgt tgtgttgcgg   6000
tgaaacatga acatatacgt aaagaaaaaa tgtattaacc tagtaaatcc acgatgaagg   6060
cagatttgtt caaaagttaa tctcatgacc ctaattaata ttagaatacg aaagagctgg   6120
acaaggatat tagaaataag tccgacttaa attatacttg tgatggtgat attttatggt   6180
gaaaatgcca tatcatgggt gtatatttga actacttgtg attggcattt tgattgtcct   6240
cattttggtc cctagcatgc ttttgacatg tcaacatgga aatgagttgc taagaaattg   6300
gaaggactga cctattcgtt cacgttcctt ttatcttgtt aaaagaatgt gtttagtaag   6360
ttaaatttct ttctctgctg ttgcagtccc tgccggtttt catttttgct aataaggctg   6420
ggcttgatat gctggagaca accttagttg ctttacagga cattactcta gataagatat   6480
ttgatgaatc tggccggaaa gtgttgttcg ctgaatttcc caagatcatg gaacaggtat   6540
ttacagctga ctctggtctt ttgcagaacc tagaaaacaa aagttgaggt cttaactgtt   6600
actttttcc gcgatgttga ttcttgatca tagggttttg cgtacttgcc gggtggtatt   6660
tgcatgtcag caatgggacg acatatttca tatgaacaag ctattgcatg gaaagtcttt   6720
gcttctgaag aaactgtcca ctgcttagcc ttctcattta ttaactggtc atttgtttaa   6780
tgttgctgtc aaatctcctt tcttttttt cctttttgtt ttttgacatc ttcctcacag   6840
aggacactga cagccaggaa cacagttgaa cggaatgatc tttgggacgg atgaaaattt   6900
tgtaacttgg ggggctcccg tctgttttac ctttaattta attagactaa atttgtattt   6960
tgcttcctga attcttcata ctcttatgta aattttctag tgcagctttt ttgagtgcag   7020
atgtttgttt cc                                                       7032
```

<210> SEQ ID NO 22
<211> LENGTH: 7155
<212> TYPE: DNA
<213> ORGANISM: Nicotiana tabacum

<400> SEQUENCE: 22

```
tctcaaagct ggctgtttta tgtatatact gaaggggttg tggtgatttg tttgtctact     60
ttaagaaggt gccatctttt tcagtaatat ttgggtaaag gttctctttt tttggcctta    120
cacgcgaaga ttcaggcctc tctgaacgtg tcatttgttc tctgtattaa acacagctgg    180
agaagtaatt acatcaaggt agaaaaaggg gttaaagatt ccaaagaatt gagtgtttga    240
aaaaaaaaac agagggctga ggtaaaaagt tgatggtttt aaaaaaaata aattaaatga    300
tgatagagtt tggagcttta tgtgaatgga aatggtgttg tgtttttatc aaacacgagt    360
agtttacagc ttatgtgaat ttgaaagaga gagagaattt ttgtctgtat ttatatcctt    420
ttcagccata tctttcgtta gagcagtttt ggctgtacct taatttgtaa gtttttaagc    480
```

```
gtgaagtgtg tgtttgagcc ttctgttata aggggcacaa agtatagaaa caacaaaagg    540
gggcacctag gaatcttctg gctcaatcaa gatcgttcat ttaatcttgt ctgagatcac    600
tagaaaaaga aaaaaaaaag agataaagat aaagtctttg tttcagagaa tcttagttct    660
ctgtgttgat atatataata aaagctgttt gcagggaata tatctacttg gggtgtttt    720
tatttcttaa aagggtgttt gaaaatttgg aaatcttgat ttttttttg gtttgggatt    780
ttgaggtttg agggcaatgg ctatggttgc acagcagcac agggagagta gtagtggtag    840
tattacaaaa catcttgaca gtagtggaaa gtatgtccgg tatacagctg agcaagttga    900
ggcattggag agggtttatg ctgagtgccc taagcctagc tccttgcgcc gccaacaatt    960
gatccgtgaa tgccctattc tgtcgaatat cgagcctaag cagatcaaag tttggtttca   1020
aaacagaagg tacactgccc attgttcaat ttggattact ccaatttggt ttcttttttg   1080
ttcttaaatg catatattta ggtgtgtact gcacttgtga tcttgggctc tagtttgttt   1140
ggtactgctc aaatcttgga ttagttagat cagtgatgga tgaagtggaa tatatcactg   1200
tccttctagt ttcctaggct tgtcgattgg gttgtatgag ttaaccgtgg ggcattaagt   1260
gaatcatgaa ttgcatatgt agtttgattt ctgtctgttg ggtagttgag cttagatttt   1320
ggaatagagg gtgaatattg tatcatttca ggtgtcgaga gaagcaaagg aaagagtctt   1380
ctcgactaca gactgtaaat agaaagctgt ctgcaatgaa taaactattg atggaggaga   1440
atgatcgctt gcaaaaacag gtttcgcagc ttgtgtgtga aaatggcttt atgcggcaac   1500
agttgcatac tgtaagttaa cataattttt cctttattat ttatggtaaa aaaccttttt   1560
tttcacttaa cgtatcttgt cttttgtttc tgataagcac tatggatttt aagattcctg   1620
atattccaca gcttatggta acatatttta aacagtgtaa attgtcttta ttttgatgac   1680
aggttttagg tcattcttat agttacgaaa tgcatgacta aattttgaat tcatcgtgtt   1740
tttgctttct atattcttct acccgccctt cttgttttgc tgtgatattg aaccaatgga   1800
caagaaacgg atggcagata tctccggtga tcttttgttc tgtaggaatt aattagactg   1860
tatttgtgtt ttctgcaggc atcagcggcc actactgatg taagttgtga gtctgtggta   1920
actacccctc agcattccct cagagatgct aacaaccctg ctgggtaatt aatttcaaac   1980
tcctatttct cccacccctt ctgtctatgg tgtttataca tatttatgtt atttattaaa   2040
tggcatagac cacattttga ggggctaatt tgtttatctc taagtcaagt ttgttctctc   2100
cgcagactgc tgtcgattgc agaggaaacc ttagcagagt tcctttccaa ggctacagga   2160
actgctgttg attgggtccc gatgcctggg atgaaggttt gaactttagt caatcctttt   2220
ttgttttaaa aaaaaattca gtattgccac gtgcctcttt gactggatag ctaaaaaact   2280
aaattttcat tctattgtca gcctggtccg gattcagttg ggatttttgc catctcacac   2340
agttgtagtg gagtggcagc ccgagcatgt ggtcttgtta gtttagagcc gacaaaggta   2400
agcagtcttg tggaaaatta atttaaatgt agtgctgctg ctctattact agttttggtc   2460
ccttgatgag tgtactagat tatgccagtt tcttctaagt acatatattt ttgtctaata   2520
tttacagatt gctgagatcc tcaaagatcg atcttcttgg ttccgagatt gccggaacgt   2580
tgaagttttc acaatgtttt ctgcaggaaa tggaacaatt gaacttttgt acacgcaggt   2640
aattaattac tttctcatca atcttcacgt aggcttctga ttggagaagc tacagcattg   2700
aggggattgt tgaaatcatt ttttttccag atatatgctc ctaccacctt ggctcctgca   2760
cgtgattttt ggactctgag atacacaacc accctggaga atggtagctt tgtggtaagc   2820
acatccttca cattagtgtg tcttaggatt agcaatctgg ccacttttgt acttagttat   2880
```

```
gaatattttg ctgatagttt gttgtatgtg cccatcaatt cctcctcccc gtaaggtttg   2940
tgaaagatcc ctctctggta ctggagctgg gccgaatgct gcttctgctt cccagtttgt   3000
aagagctcaa atgcttccgt ctggatatct aatccgaccg tgtgacggtg gaggatccat   3060
tatacatatt gttgaccacc tgaatcttga ggtcagatta cacgctgtac taccacttct   3120
ctttcttatt agcttgttct gtcttgcagc tggacttcac tgcataatat tgtttttcag   3180
gcatggagtg cccctgagat tttgcgtcca ctttatgaat cgtcaaaagt tgtggcacag   3240
aaaatgacta ttgcggtgag ttgaaccctt ggtttttatt aactactgga tgtttaacaa   3300
ccttttttggt cttcacaact agatctcaat ttttgttcag ctctgaagta gataggattg   3360
tactttctgg acgagcagtt agatatagcc tgatattttt gtttattctg ttagaagttc   3420
ccagctttaa aaatatagaa cacctgacaa atccttagtc tcttaatgca cgttatcgag   3480
gatttcttcg ttattcgagt tttcaaaggt tcattattgt tttcctcatt gtgttgccat   3540
aaaagtctgc atgtgaaaca tataagtaat gaagaacctt atgctgtgaa gcacagcata   3600
ctgttaactg cattcgatgt tgcttaattc cagaagttgc tctgagaata cttacagcct   3660
tttttatat tttaagtact tgagcaatta ccgttactta ccacaacagc aaaagaaata   3720
ctaattatgg ttagttttg ctgtaaaggc actgcgatat gcaaggcaaa tagctcagga   3780
gactagtggg gaggttgtat atggtctggg aaggcaacct gcagttcttc gaacatttag   3840
ccagagatta agcaggtgct ggttattgct ctgattgttc tgtgcttcga gatatgatat   3900
gccataaaag tagacatacg aatcctgaag cgcaagtatc ataattaggc tattttctat   3960
attgcagagg cttcaatgat gccatcaatg gattcagtga tgatggctgg tcattgttaa   4020
gttctgatgg tggtgaagat gttatagttg ctgtcaattc aaggaagaac attgccacca   4080
cttccgttcc tctttcacca cttggaggca tcctttgtgc caaagcatca atgctactcc   4140
aggtcaacag attaagcttt cttgaactaa ctacagattt tcattggcca actacctttg   4200
ccttgttaat tcactgaata ggtcaagtaa ttctaaagac aagttttgca gtgctcttgt   4260
tgccttgtta gttcatagca aacagagttg cagctgttca aagtaggatc atatattgtg   4320
atacctattc agtatctgta ttagatctag tatcacaaga caagttttct ttactgctct   4380
tgtttcttag aaattggctc tatactctta ctaaaaaaga gcgataatgg tagattttga   4440
agtcgaggaa aaattaaaat cgttccggat tgttgcagat ttttattatg ctttcaattt   4500
ctaattctag gaaagaatca ggattcctgg aatattagag aatattactc agtgttttat   4560
aaagctattt gtttaatgct ctgagtaggg catcttgcta ttaattggaa gaatgagaat   4620
tgacttttaa ctcttttgtt cggtggcaga atgttcctcc tgcggtactg gttcgatttc   4680
tcagggagca ccgttcagag tgggcggact ttaatgttga tgcctatgta gcttcctcaa   4740
tgaaatcttg ttcatatgca tatcctgggg tgaggcctac cagatttacc ggaagccaga   4800
taataatgcc actgggccac acaatagaac atgaagaggt aagcggtttg caattgcccc   4860
agttctcact tatgtgttat ggggaatgcc tcgacataca tgagcaagaa tttgagactt   4920
gagacttcct ctcactttat tttggtttgc agatgcttga agttattaga ttggaagggc   4980
actctattgg ccaggaagat gcttttatgc cgagagatat tcaccttctc caggtacttt   5040
tgcttataca ttgatgtttc ggtgtgttgt atgtacatac attgttgaag gataatgcta   5100
acaaacagtt atttctagat gtgtagtgga accgatgaga atgctgtcgg agcttgttct   5160
gaactagttt ttgctgcaat tgatgagatg tttccagatg atgcacccct gttgccctcc   5220
```

gggtttcgta tcattcctct cgagtcaaaa tcagttgagt aaaatatttt gattttcaac 5280
ttcaagcatt gaatttggca aatctattgt ttacatggat ttttttttt cttttcattt 5340 tgctcgattt tggagcataa ccggtgattc tattttcaga gcgatcccca ggatacatcg 5400
aatgctcata gaacactgga tctggcatca agtcttgaag ttggcccagc aacaaaccct 5460
gctactggag atgtggtctc tggctacagt gcacgatctg tattgacaat tgcttttcaa 5520
tttccattcg aggacaatct tcaggataat gtagctacca tggcgcgcca gtatgttcgc 5580
agtgtggttt catctgtcca acgggttgcc atggcaatat ctcccgcagg agtgaattca 5640
acattcgggt ccaagctttc tccaggctcc cctgaagctg taactttgtc gcactggatc 5700
tgccagagct acaggtaaaa tgatttctca actatggtga aaccttattc tctgcatttc 5760
agctcaatat ggggtttatt gctttacatg ttcatactgt cgtgcttaca agtcgattca 5820
ttgcaaatct catttaccac caagagcgga agcagtgtcg agtgtgcatg ttgatcttca 5880
attatttttt gagaattttt cctttctcaa catattgaga aaaatcagat ggtcttagaa 5940
gtacttttct gattgttaac ataccgtttt cttcttttgc atataatatc cagttatcac 6000
atggggacag agttgcttca agctgattcg aggggcgatg aatcagtgct aaagaatctt 6060
tggcaacatc aggatgctat tttgtgctgc tcattgaagg tatgaattct cttatgaact 6120
catgtaaaca gcatattacg gtttgttagt aaaaaaattg taggttgtgt tgcggtgaaa 6180
catgaacata tgcataaaga aaaatgtatt aacctagtag tgtcatgacc ctaattaata 6240
ttagaatatg aaggagctgg acaatgatat taagaaataa gctcgactta aattatattt 6300
gtgatggtga ttttttatgg tgaaaatgtc atatcatggg tgcatatttg aactacttgt 6360
gattggcatt ttgattgtcc tcattttggt ccctagcatg cttttgacat gtcaacatgc 6420
attgcttttg acctattcat ccgccttcta gtcttttatc ttgttaaatg aatggcgtta 6480
gtaagttgaa tttctttctc tgctgttgca gtcgctgccg gttttcattt ttgctaataa 6540
ggctgggctt gatatgctgg agacaacatt agttgctttg caagacatta ctctagatag 6600
gatatttgac gaatctggcc ggaaagtgtt gttcgctgaa tttcccaaga tcatggatca 6660
ggtatttaca gccgactctt agtctttgca gaaccgagaa accaaagttg aggtcttaac 6720
tcttactttc ttcgattctg tttattcttg atcatagggt ttcgcgtacc tgccgggtgg 6780
tatttgcatg tctgcaatgg gacgacatat ttcatatgaa caagctattg catggaaagt 6840
ctttgcttct gaagaaacta gtgtccactg cttagccttc tcatttatta actggtcatt 6900
tgtttaatgt tgctgtcaaa tctcctcttt ttttcctttt tgttttttga catcttcctc 6960
acagaggaca ctgacagaca ggaacacagt tgaacggaaa gatcttggga ccgatgaaaa 7020
tttttgtaac ttgtggggct cctgtctgtt ttgccttaat ttaattagac taaatttgta 7080
ttttgcttcc cggattcttc atactcttgt gtaaatttac tagtgcagct tttttgagtg 7140
cagatgtttg tttcc 7155

<210> SEQ ID NO 23
<211> LENGTH: 1457
<212> TYPE: DNA
<213> ORGANISM: Nicotiana tabacum

<400> SEQUENCE: 23
atttcccctc ctccatcatt gaaaacccct ttgtcctttc cccccagacc ccttttcct 60 ctctctctct ctcctttctc tttttattag acgcatattc tctcttcttt ctctttctag 120
ggttttcacc tgaaatagtt ttatttcgtt gatatgttag gatcctttgg ttcatcatct 180

```
caatctcatg atgaagaagc tgatgatcaa cggcggagat gcagttccac ttcccctgca    240
atccaaatcc ggcaactact cattagctgc gcggagttaa tctcacggtc cgatttctcg    300
gcggcaaaca gactcctcac cattttatca actaactctt cccctttggg tgattcaact    360
gaaagattag tccatcagtt cactcgcgca ctttccattc gcctcaaccg ctatatctct    420
tcagccacta atttcttgac acctaatgca tcatctaatg ttgttgaaag ttcaaatgat    480
tcagctctac ttcagtcatc ctatctttcc ctaaaccaag tgaccccttt tattagattt    540
agtcagctaa ctgctaatca agcgatttta gaagctatta acgataacca acaagcgatc    600
cacatcgttg attttgatat taatcacggt gttcaatggc caccgttaat gcaagcacta    660
gctgatcgtt accctcctcc aactcttcgg attaccggta ctggaaatga cctcgatacc    720
cttcgtagaa ccggagatcg tttagctaaa tttgctcact ctttaggcct tagatttcag    780
tttcaccctc ttttgatcac caataataat gacaatgatc atgacccttc aatcatttct    840
tctattgttc ttctccctga tgagacatta gcaatcaact gtgtatttta tcttcacagg    900
ctcttaaaag accgcgaaat gttaaggatt tttttgcata ggattaaatc catgaaccct    960
aaagttgtaa cactggccga gagagaagca aatcataatc acccactttt tttgcaaaga   1020
tttgtggagg ctttggatta ttatgcagct gtctttgatt cattggaagc aactttgccg   1080
ccgagcagta gagagaggat gacagtggag caagtttggt tcggaagaga aattatagat   1140
atagtagcag cagaaggaga taagagaaga gaaagacacg agagattcag atcatgggaa   1200
gtaatgttga ggagctgtgg atttagcaat gttgctttaa gtccttttgc actttcacaa   1260
gctaaacttc tcttgagact tcattaccct tctgaaggat accagcttag tgtttcgagt   1320
acgagtaatt ctttcttctt gggttggcaa aatcaacccc ttttttccat atcttcttgg   1380
cgttaaatta taagggaaat taaaacccta aaaacaagat tttatctatc tgcatggtga   1440
aggacaaaga ggtcttc                                                  1457
```

<210> SEQ ID NO 24
<211> LENGTH: 1548
<212> TYPE: DNA
<213> ORGANISM: Nicotiana tabacum

<400> SEQUENCE: 24

```
aggttcttct tccttaatat tgagtcacag attagtacca ctactatagc caagaaaatg     60
tgaaatcata tagtactaaa tattaatttc agatgccaaa accataaatt tcccctcctc    120
catcattgaa aaccccctct gtcctttccc ctagagagac cccttttttcc tctctctctc   180
ctttctcttt ttattagacg catatattct ctcttctttc tctttctagg gttttcacct    240
gaaatagttt tatttcggtg atatgttagg atcctttggt tcatcatctc aatctcatga    300
tgaagaaact gatgatcaac ggcggagatt cagttccact tcccctgcaa tccaaatccg    360
gcaactactc attagctgcg cggagttaat ctcgcggtcc gatttctcgg ccgcaaacag    420
actcctcacc attttatcaa ctaactcttc cccttttggt gattcaactg aaagattagt    480
ccatcagttc actcgcgcac tttctcttcg cctcaaccgt tatatctctt cagccactaa    540
tttcttgaca ccatctaatg ttgttgaaag ttcaaatgat tcagctctac ttcagtcatc    600
ctatctttcc ctaaaccaag tgactccttt cattagattt agtcagctaa ctgctaatca    660
agcgattttg gaagctatta acgataacca acaagcgatc cacatcgttg attttgatat    720
taatcacggt gttcaatggc caccgttaat gcaagcacta gctgatcgtt accctcctcc    780
```

-continued

```
aactcttcgg attaccggta ctggaaatga ccttgatacc cttcgtagaa ccggagatcg    840

tttagctaaa tttgctcact ctttaggcct tagatttcag tttcaccctc ttttgattac    900

caataataat gacaatgatc atgacccttc aataatttct tctattgttc ttctccctga    960

tgagacatta gctatcaact gtgtatttta tcttcacagg ctcttgaaag accgcgaaaa   1020

gttaaggatt tttttgcata ggattaaatc catgaaccct aaagttgtaa cgctggccga   1080

gagagaagca aatcataatc acccactttt tttgcaaaga tttgtggagg ctttggatta   1140

ttatgcagct gtgtttgatt cattggaagc aactttgcca ccgagcagta gagagaggat   1200

gacagtggaa caagtttggt tcgggagaga aataattgat atagtagcag cagaaggaga   1260

taagagaaga gaaagacacg agagattcag atcatgggaa gtaatgttga ggagctgtgg   1320

atttagcaat gttgctttaa gccctttttgc actctcacaa gctaaacttc tcttgagact   1380

tcattaccca tctgaaggat accagcttag tgtttcgagt acgagtaatt ctttcttctt   1440

gggttggcaa aatcaacccc ttttttccat atcttcttgg cgttaaattt aaaaccctaa   1500

aaaacaagat ttttatctat ctgcatggtg aaggacaaag aggtcttc               1548
```

<210> SEQ ID NO 25
<211> LENGTH: 1936
<212> TYPE: DNA
<213> ORGANISM: Nicotiana tabacum

<400> SEQUENCE: 25

```
gtccatctgt ctatataggt agaatgagag taaaggagaa aacatatcct cctctccatt     60

tctgtagaca aagattctca aagagaaaca aattaaacac tagagagtga gagagtgcta    120

taagaaaaag aatatgggga gagctccatg ttgtgataaa gcaaatgtga agagagggcc    180

atggtctcct gaagaagatg ctaaactcaa agatttcatt cacaaatatg gaactggtgg    240

aaattggatt gctcttcctc aaaaagctgg taacaacaac ttctactcca ctagtcctct    300

atgtgtatgt attttattat tattattatt attattatta ttattattat tattattatt    360

attcatgaat cgaagggaca aaggtctaaa tctcagtggg tcgtggtagc aaggccattc    420

cgccatttat aatatcttct tgcaaattcc accagtttca tatgtgtatg tttttttctt    480

attagtcata aatcaaagcg acgaagggtt aaatttcagt tgattgtgat agcaaggtca    540

cactctaccg cttataatat ctcgtggcgt atttaacatt gtttgtatgt atatgtttga    600

gtataaaggg aggaaagctt atatttatat ttgagtggat tgagtttttt tccttgttgc    660

tgcattattt atgatttgat gagatttatg ttgggaactg caggactaaa gagatgtggg    720

aagagttgta gattgagatg gctaaattat ttaaggccta acattaaaca tggtgatttt    780

tctgaggaag aagatagagt tatttgcacc ttgtattcca ccattggaag caggtaatat    840

atatatacct ttttttggtc gtaatttttt tttcattttt tatcatcttt ctgatgaatt    900

tgagactgaa acaaaaactg ttcccactaa aaatggaaaa gtaaaacctc aataagtaag    960

aaaagggaaa aaacaatgag ggctcagaaa gaaatgcaaa tagtcagttg gatttttaat   1020

taaagattct gccatttatg gacatatttt tctgcatgca tgccaggttt agatctaaga   1080

tcaagtcttt atttactcac ttacagatgt ttaattatta agacaaagtt ccaatttttc   1140

ttctttcttc tctttctttt tgtggaaatt ttttctctag taaaccaatt aatttttgtt   1200

ataacatgtg caatataata tgttaacagg tggtcaataa tagcagctca attaccggga   1260

agaactgaca atgatatcaa gaattactgg aatactaagc tcaagaaaaa acctatggga   1320

ttaatgcaat caactaacca aagaaaatca ccatattttc cagctactaa ttctcttcaa   1380
```

acccaacccc agataaattc aagtcttttt agagacttat attacacccc aaataatagg 1440
cctaatatta caggcctaaa tcatcagtcc atttcttctg cccaccagac aaattttctc 1500
tacactaata ataacatgaa ctttcctaat ttgggtgcta caaataatca atatccttat 1560
aatatccaaa gtcataattt acttatgttt ggagaagcaa gttgttcttc atcagatgga 1620
agttgcagcc aaatgagttt tggtaaagaa atcaagagag aagaaattat gagtaatagt 1680
ttacaacaag gtcaaatttc aagtgttaat gcttttgaag aaaaccacca gaattttact 1740
cttgattatg gcaatagtag tagtaattgg gtggatcaaa aaccaaatgt gtattttggt 1800
actactacta ctcaagtact tcagtatgat aatgttgaag aagttaagca gcagctaaca 1860
agttgtacca atggcaacaa tggtagtact attggatgta acaacaacaa cagtatgttc 1920
gtgttcaatg atgaga 1936

<210> SEQ ID NO 26
<211> LENGTH: 1752
<212> TYPE: DNA
<213> ORGANISM: Nicotiana tabacum

<400> SEQUENCE: 26
ccacttgtct atatagcaag aaagagagta aaggagaaaa catattctcc tctccatttc 60
tgtagacaag attctcaaaa agaaacaaat taaacactag agagtgagag agaactataa 120
gaaaaagaat atggggagag ctccatgttg tgataaagca aatgtgaaga gagggccatg 180
gtctcctgaa gaagatgcta aactcaaaga tttcattcac aaatatggaa ctggtggaaa 240
ttggattgct cttccccaaa aagcaggtaa caacaacttc tactccctta ttcccagaat 300
cgaagcgaca aagggttaaa tctcagtgga ttgtggtagc aagatcatat tctatcgctt 360
acaatatctc gtcgcgtatt taacactttc gtatgtatat gtttgaatat agggggaggg 420
aagcttacat taatatttat actttgagtg gattaagttt ttttttggtt gcttcattat 480
ttatgatttt gatgagatat atgtttggaa ctgcaggact aaagagatgt gggaagagtt 540
gtagattgag atggctaaat tatctaaggc ctaatatcaa acatggtgat ttttcggagg 600
aagaagatag agttatttgc agcttgtatt ccaccattgg aagcaggtac aatatacctt 660
tttttagtct taaattgttt tccatttttt atcatctttc tgatgaattt gagactgaaa 720
caaaaactgt tcccactaaa aatggaaaag aagaacctta ataaataaga aaagggaaaa 780
aacaatgagg gctcagaaag aaatgcaaat agtctgttgg atttttaatt aaagattctg 840
ccatttatgg acattttttt ctgcatgcat gccaggttta gatctaagat caagtcttta 900
tttactcact tacagctgtt taagtattac tactacaaaa ttccaacgtt tcttcttttc 960
tctctttttt tttttttttt tggaaaactt ttccttttgt aaaccaatta aattttgtta 1020
taacatatgc aatatattat gttaacaggt ggtcaataat agcagctcaa ttaccaggaa 1080
ggactgacaa tgatatcaag aattactgga atactaaact caagaaaaag cttatgggat 1140
taatgcaatc aacaaaccaa agaaaatcac catattttcc agctactaat tctcttcaag 1200
cccaacccca gataaattca agtcttttta gagacttata ttacaaccca aataataggc 1260
ctattattac aggcctaaat cagtccattt cttctgccca ccagccaaat tttctctaca 1320
ctaatagtaa catgaatttt cctaatttgg gtgctacaaa tagtcaatat ccttataata 1380
ttcaaagtca taatttactt atgtttggag aagcaagttg ttcttcatca gatggaagtt 1440
gtagccaaat gagttttggc aaagaaatca agagagagga aattatgagt aattgtttac 1500

```
aacaaggtca aatttcaagt gttaatgctt ttgaagaaaa tcagaatttc actcttgatt   1560

atggtaacag tagtagtaat tgggtggatc aaaaaccaaa tgtgtatttt ggaaatacta   1620

ctactactac tcaagtactt cagtatgatg ttgaagaagt taagcagcag ctaacaagtt   1680

gtaccaatgg caacaatggc agtactattg gatgtaacaa caacaacagt atgttcgtgt   1740

tcaatgatga ga                                                       1752
```

<210> SEQ ID NO 27
<211> LENGTH: 648
<212> TYPE: DNA
<213> ORGANISM: Nicotiana tabacum

<400> SEQUENCE: 27

```
gcatggacaa tctcatcttc tcaaacttca taaagatatc tttaaaaaaa agagaaaata     60

gaggtaatta gttgtatcaa tggatcaaca acattccact tgtttttctt cttcaagtaa    120

aattaatgac aaagaaaaga agaaaaaaag atcagttgtg aaactatcaa ctgatccaca    180

aagtgtagca gctcgtgaaa gaaggcatag aatcagtgat cgtttcaaga ttttgcagag    240

tttaatccct ggtggttcaa aaatggatac agttactatg ttagaagaag caattcacta    300

tgtcaaattt cttaagactc aaatatggct gcatcaaacc gtgattaata ttgtagatga    360

ttatgataat ccaaattatc atgatcagtt gctaatggct catgactcta attttgctaa    420

ttattatcct catgaaatgg tggaatattg cccagctcct gttgagaatg cacaaataaa    480

ttataacttg gaccagctgc agcttccagg ttatgcattt tcagatgggg atcaattcca    540

aggagaagaa actaatatta ctggtgattc ttttatgtac tattagttag ttaattatgt    600

tgcctaagtt taattagaat acgtagtgtg tggtagtatg gtatgttg                 648
```

<210> SEQ ID NO 28
<211> LENGTH: 773
<212> TYPE: DNA
<213> ORGANISM: Nicotiana tabacum

<400> SEQUENCE: 28

```
atataaacca tgcatggaca atctcctctt ctcaaacttc ataaagatat tatattaaaa     60

aaaataaaga agaagagaag atagaggtaa ttagctatag caatggatca acaacattcc    120

acttgttttt cttcttcaag caaaattaat gacaaagaaa agaagaaaaa aggatcagtt    180

gtgaaactat caactgatcc acaaagtgta gcagctcgtg aaagaaggca tagaatcagt    240

gatcgtttca agattttgca gagtttagtc cctggtggtt ctaaaatgga cacagttaca    300

atgttagaag aagcaattca ctatgtcaaa tttctcaaga tgcaaatatg gctgcatcaa    360

accatgatta atattgtaga tgattatgat aatccaaatt atcatcatca gttgctaatg    420

gctcatgact ctaattttgc taattattat cctcatgaga ataactcaac tcctgttgag    480

aatgcacaaa taaattataa cttggaccag ctgcagcttc caggttatgc attttcagat    540

ggagatcaat tccaaggaga agaaactaat atttctggtg atgcttttat gtactattaa    600

ttagtaatta gttaattatg ttgcctaagt ttaattagaa tacgtagtgt gtggtagtat    660

ggtatgttgt tttctctctt tctatctagc agcctaatga tgggtttgtg ttaattaatt    720

agatgtagta aattgtaagt gttggttagt tgattaagta tgttgcaagt ttg           773
```

<210> SEQ ID NO 29
<211> LENGTH: 3335
<212> TYPE: DNA
<213> ORGANISM: Nicotiana tabacum

<400> SEQUENCE: 29
tactatcact taataccatc attcatcatg ttgtcaatgg aagaaatatt gtgtgaacta 60
agtagagaag acatgaataa tgagaaaggt ctaccacctg gttttaggtt tcatcctact 120
gatgaagagc ttatcacttt ctaccttgcc tctaaggttt ttaacggcac cttttgtggt 180
attcagattg ctgaagttga tctcaacaga tgtgagccct gggaacttcc aggtaacaca 240
cacacacaca cacattccct tcattaaatt cttcttttgt tcatgtccca aaaagtacaa 300
ggaaaaaata gtagtaactc aaaaggaagc tgatgaaaag tctttttctt atttttttat 360
ttttaactcc ttgtcttgaa catggtttta aagttttgga atttgtctgt tgtaaacaca 420
tgtgatggaa tgtagtcgta gtatatatgg cagacgtact actgttttaa gatattcttc 480
attgctttgt cacgagaaat atttactact agtaatattt aaaattatat aatgagaata 540
tgagaagatt ctagtctaaa atacattaat aattggagat tcttgtctaa aatactttag 600
tcttcttctt ttgcatgtgc atatgatatc tcacaaagaa agtttttttgt gaaattccac 660
tattaatacg tacctcacgt catttatgat ttaccagcta cgttaagttc ttaataatac 720
atgtcctact ttggacctat aaatttcaga catctctctc ttttgttacc tgtcatttat 780
gatttaccag cttcggtaag ttcttaacag tagtaagaca tgtacttgaa atatgttgtc 840
cactgattct taaccctttc ctagccatag aatatagtag taggcaggag cggatttagg 900
ggcgcaaggg tgttcaccca aattatacta tatatatata aggcaaaatc tgttttttat 960
ctctatatat taagttttga atgctctcaa cacaatccaa aagtatagtt tagtggtcaa 1020
agggattcaa aatctacata aggtcatggg ttcaatttca actagctaca aaaaaaaaat 1080
ttgaacccct tcgtagagat cccgcctatg catctcctgt tgttgcagaa agcaattaat 1140
atgtgtcaaa tctacttcta tgattattca ttgaaactaa aaaatacagt agaaaatatg 1200
tgtaccagct agttattatt gcgcacatta tatgaatgcg actattatag taatttaatg 1260
gtatgtttta gtaattttga aagtgaaaat tgcagaagtg gcaaagatgg gggaaagaga 1320
atggtatttc tttagcttaa gggacagaaa atacccaacc ggactaagaa caaaccgggc 1380
aacaggagct ggttattgga aagctacagg aaaagataga gaagtgtaca gtgcaacaaa 1440
tggagcactc cttgggatga agaaaacatt ggttttttac aaaggaagag caccaaaggg 1500
tgagaaaacc aaatgggtta tgcatgaata tcgtcttgac ggcgattttt cctaccgtta 1560
ctcttctaag gtaaatttct aatcctatct atcgatttga aaatagcacg ctcatctcgc 1620
ttttcgttca taataaataa ccaatttatt tttaattttt gttcaaaata tgtgacatat 1680
tatcttattt cagtttagac gatgacatat ttcgattatc gtgagagtaa tagttgatta 1740
cttgtagggc tatattgtac gtatctatag ggtttgtcct ttttagggtt gacttgttta 1800
gtaagtctcg tgatattaat tgatgtgatg ttgacttgat tgatggatag atggatatga 1860
gaaggtgttg ttatagtacc ctaaagataa ttgccgactc ttttcacttt gctgattctt 1920
aagaaaacat agtgaaaatt aaaaattatc ttggaatttt atgtacaaat tttaatggtt 1980
atttaatttc atgttcaagg gtattcccta accaatgtca cttaaaatat gtactgtaga 2040
gttattaggt gctttgacta aaaagattag tatactatca cttgacatat gtggttatta 2100
gtgttatcac tactaaaaac gggaattaac cactgacacg ttctgtagct aaacataaat 2160
tagcaatgat tataaataaa ttatgttagc tacgagtgaa ttaaagagta gtataacccg 2220
tcacttaggt gctttgatta aaaagagtag tataatataa tgtcgcttga aatatgtggt 2280

```
tattaagtcc tttcactatt aaaatcagaa attagcgaca tgcaaatttt gtaactaaac   2340
ggaaattagc gacaaattat aaagaaatta tgttttctat gagtgattta gcgacagatt   2400
aacgatgaag ttcctagtta attctagttc tttttgtaga gtaatttgtt aaaaagttgt   2460
aataaaattg gcaggaggaa tgggtgatat gcagaatact acacaaaata ggggagaaga   2520
aaaatccaat ataccaagct gcaggacaaa actatggcta ccctacaagc ttgaaaacat   2580
ggccatcatc atcttttctt aacacagcaa catcagcaga agcagctcca aatcctatat   2640
tggctgaaac accaaatcca aaaaccacaa caactacaca ttggcaagaa tcattccaaa   2700
tatcacaaaa ctcaatgcaa tcactgcaca acttttatct atttcaccac caagaaaacg   2760
accttatgaa atccctcttc aaccccatta atgtttccca aacaaacctc ttcccaataa   2820
ataatagtgt cctttcttct gctacctcct tttctacatc ccaaagcaca aaaaaataca   2880
aagaagacat aaacaaaaac tcgtcactat catctttcct cgttagcaat tcaaagaaaa   2940
atgaaaaaca tcaagtccca ctcatgcagg ctaacacaac aatgaaaaca gaagccagtt   3000
tttcaccata ttctggttgt tacaatgatc aaaaccctat ggctacgaat tttggtatga   3060
ataattcaac agattggagt ttagtaggca tagaagggat gcattttaat ggtggatgta   3120
ctcagtctca gatggtgttg gatcacatgc attgtcccat caaaatagct gcagaatctt   3180
ggcctcttga tctctaaaaa tagaagattt tgtttttaat aaattctact gtaggatgat   3240
atggtaatta attattactc ctgttatatc atccttatct atgaatagct atcctctaag   3300
tatataaaag taattcaggc tgctctttat attct                              3335
```

<210> SEQ ID NO 30
<211> LENGTH: 3339
<212> TYPE: DNA
<213> ORGANISM: Nicotiana tabacum

<400> SEQUENCE: 30

```
tacttccctt tctccctttg gtttcagtgc ctaatttgtt ttcttttctt ttctcttttg     60
tatatatata taatcctcca ctttctaacc agctactaca tcacttaata tcattcatta    120
tgttgtcaat ggaagaaata ttgtgtgaac ttagtagaga tgacatgaat aatgagaaag    180
gtctaccacc tggttttagg tttcatccta ctgatgaaga gcttatcact ttctaccttg    240
cctctaaggt ttttaacggc accttttgtg gtattcagat tgctgaagtt gacctcaaca    300
gatgtgagcc ctgggaactt ccaggtaaca cacacacaca cattgccttc attatattct    360
tcttttgttc atgtcccaaa gtacagggaa aaaatagtag taactcaaaa ggaagctgat    420
gagagtcttt ttttaccccc tttgtcttga aaatatatgg ttttaaagtt ttggaatttg    480
tctgttgtaa atacatgtaa tggaatgtag tagtatggca gacgtactag ctgttttaag    540
atattcttca ttgctttatc atcagaaata tttattcata tctaaaacaa ataatgagag    600
tatgagaaga ttcttgtcta aaatacatta aatgggatat tcttgtctaa aatactttag    660
tcattcttct tttgcatgtg catatgatat ctcaccaaga aagtttttct gtgaagttcc    720
actattgata cgtaccctca cgtcattaat tagttattta ccagcttcgc taagttctta    780
ataatacatg tccttgaatt ataatgccct ttcgacctat aaatttcaga catatctttc    840
ttttgttacc tcatgtcatt tatgatttac cagcttcgct aagttcttaa tagtagtaag    900
acatgtacat gaaatatgtt gtccactgac tcataaccct ttcctagcca tagaatatag    960
taggagtact attttcttct ttccttacat ttttaaaaat gaaaatgtat gcatctccct   1020
gttgttgcag aaagaaatta atatgggtca aatctacctc tatgattact tattaaaaca   1080
```

```
agcaaaatac agtagaaaat atgtgtacca gctagttgtt attattgcgc acatgcatta   1140
acatgaatgc gactattata gtaatttaat ggtatgttct agtaattttg aaagtgaaaa   1200
ttgcagaagt ggcaaagatg ggggagagag aatggtattt ctttagctta agggacagaa   1260
aatacccaac cgggctaaga acaaaccggg caacaggagc aggttattgg aaagctacag   1320
gaaaagatag ggaagtgtac agtgcaacca atggagcact ccttgggatg aagaaaacac   1380
tggtttttta caaaggaaga gcaccaaagg gtgagaaaac caagtgggtt atgcacgaat   1440
atcgtcttga cggtgatttt tcttaccgct actcttctaa ggtaaatttc tcatccttat   1500
tactcgctat ttagatgata tagttaatta ctcggagatt gagaaaatta aagggagtaa   1560
ttaattgtag agctttattg tatgtagggt ctataggttt tgtccttttt agggttgact   1620
tgtttagtaa gtctcgtgat attaattgac gtgatgtgga cttgattgat ggatatgagg   1680
tgttgttata gtactctaaa gatacttgcc aaatcttttc actttgctga ttcttaagaa   1740
aacatagcga aaatcatctt ggaatttcat gtactaaaat taaagattat ttcatgttca   1800
agggtattcc ctaaacctaa tgtcacatta aaaagttatt atagagttct taggtgcttt   1860
gattaaaaag agtactagtg taatgtcact cgacatgtct ttattaggtg ctttcactag   1920
tgtaatgtca cttgacatgt ctttattccc taaacctaat gtcacgttaa aaagatatta   1980
tagagttctt aggtgcttta aataaaaaga gtactagtgt aatgtcactt gacatgtctt   2040
tattaggtgc tttcactaat aaaaacaaaa attatatagc aatgattata aaaaaaaaat   2100
tgttagctac gagcgattac ccgtcactta ggtgctttga ttaaaagaga agtataatgt   2160
cgcttgaaat atgtggttat taggtgcttt tactattaaa aatatgaatt ggcgatggac   2220
aaattctgta gttaattata aagcagacac attataaaga aattatgtta gctacgagtg   2280
atttagtgac agatttagga caaagtttgt agctaattct aatttttttt gtaatgtttg   2340
ttaaaaaatt gtaataaact tggcaggagg aatgggtgat atgcagaata ctacacaaaa   2400
taggggagaa gaaaaatcca atataccaag ctgcaggaca aaactatggc taccctacaa   2460
gcttgaaaac atggccatca tcatcttttc tcaacacagc agctccaaat cccatattgg   2520
ctgaaacacc aaatccaaaa accacaacta ctacacattg gcaagaatca ttccaaatat   2580
cacaaaactc agtgcaatca ctgcacaacc tttatctatt tcaccaccaa gaaaacgacc   2640
ttatgaaatc cctcttcagt cccattaatg tttcccaaac aaacctcttc ccaataaata   2700
atagtgacct ttcttctgct gcctcctttt ctacatccca aagcaccaaa aaatacaaag   2760
aagacataaa caaaaactcg tcaatatcat ctttcctctt tagcaattcc ttttgcactt   2820
caaagaaaaa tgaaaaacag caagttccac taatgcaggc taacacaaca atgaaaacag   2880
aagctagttt ttcaccatat tctggttgtt acaatgatca aaaccctatg gcttcgactt   2940
ttgggatgaa taattcatca gattggagtt tagtaggcat agaagggatg cattttaatg   3000
gtggatgtac tcagtctcag atggtgttgg atcacatgaa ttgtcccatc aaaatcactg   3060
cagaatcttg gcctctcgat ctctaaaaat agaagagttg tttttccata atttctatag   3120
taggatgata tggtaattaa ttatgactac tgttatgtca tcctctatat atagctatcc   3180
gctctagtat atgtaatctt tgtaattaat ttaggctgct ttattctgaa agatgttgct   3240
ttctccttaa ggatatatct agctagtacc gctatgtaag atatatcttt cttttctcga   3300
ctaatgtaaa gttgcaatct attgatggga gtatttata                          3339
```

<210> SEQ ID NO 31

-continued

<211> LENGTH: 445
<212> TYPE: DNA
<213> ORGANISM: Artificial sequence
<220> FEATURE:
<223> OTHER INFORMATION: Synthetic: RNAi trigger sequence derived from Nicotiana tabacum

<400> SEQUENCE: 31
gcctatgtag cttcgtcaat gaaatcttgt tcatatgcat atcctgggat gaggcctacc 60
agatttaccg gaagtcagat aataatgcca cttggccata caattgaaca tgaagagatg 120
cttgaggtta ttagattgga aggacactct attggccagg aagatacttt tatgccaaga 180
gatgttcacc ttctccagat gtgtagtgga actgatgaga atgctgtcgg agcttgttct 240
gaactagttt ttgctgcaat tgatgagatg tttccagatg atgcacccct gttgccctcc 300
gggtttcgta tcattcctct cgagtcaaaa tcaagcgatc cccaggatac atcgaatgct 360
catagaacac tggatctggc atcaagtctt gaagttggcc cagcaacaaa ccctgctact 420
ggagatgtgg tctctggcta cagtg 445

<210> SEQ ID NO 32
<211> LENGTH: 565
<212> TYPE: DNA
<213> ORGANISM: Artificial sequence
<220> FEATURE:
<223> OTHER INFORMATION: Synthetic: RNAi trigger sequence derived from Nicotiana tabacum

<400> SEQUENCE: 32
ctcaagaaaa agcttatggg attaatgcaa tcaacaaacc aaagaaaatc accatatttt 60
ccagctacta attctcttca agcccaaccc cagataaatt caagtctttt tagagactta 120
tattacaacc caaataatag gcctattatt acaggcctaa atcagtccat ttcttctgcc 180
caccagccaa attttctcta cactaatagt aacatgaatt ttcctaattt gggtgctaca 240
aatagtcaat atccttataa tattcaaagt cataatttac ttatgtttgg agaagcaagt 300
tgttcttcat cagatggaag ttgtagccaa atgagttttg gcaaagaaat caagagagag 360
gaaattatga gtaattgttt acaacaaggt caaatttcaa gtgttaatgc ttttgaagaa 420
aatcagaatt tcactcttga ttatggtaac agtagtagta attgggtgga tcaaaaacca 480
aatgtgtatt ttggaaatac tactactact actcaagtac ttcagtatga tgttgaagaa 540
gttaagcagc agctaacaag ttgta 565

<210> SEQ ID NO 33
<211> LENGTH: 364
<212> TYPE: DNA
<213> ORGANISM: Artificial sequence
<220> FEATURE:
<223> OTHER INFORMATION: Synthetic: RNAi trigger sequence derived from Nicotiana tabacum

<400> SEQUENCE: 33
gaagaaactg atgatcaacg gcggagattc agttccactt cccctgcaat ccaaatccgg 60
caactactca ttagctgcgc ggagttaatc tcgcggtccg atttctcggc cgcaaacaga 120
ctcctcacca ttttatcaac taactcttcc ccttttggtg attcaactga aagattagtc 180
catcagttca ctcgcgcact ttctcttcgc ctcaaccgtt atatctcttc agccactaat 240
ttcttgacac catctaatgt tgttgaaagt tcaaatgatt cagctctact tcagtcatcc 300
tatctttccc taaaccaagt gactcctttc attagattta gtcagctgac tgctaatcaa 360
gcga 364

<210> SEQ ID NO 34
<211> LENGTH: 304
<212> TYPE: DNA
<213> ORGANISM: Artificial sequence
<220> FEATURE:
<223> OTHER INFORMATION: Synthetic: RNAi trigger sequence derived from Nicotiana tabacum

<400> SEQUENCE: 34
ttcttcaagc aaaattaatg acaaagaaaa gaagaaaaaa ggatcagttg tgaaactatc 60
aactgatcca caaagtgtag cagctcgtga aagaaggcat agaatcagtg atcgtttcaa 120
gattttgcag agtttagtcc ctggtggttc taaaatggac acagttacaa tgttagaaga 180
agcaattcac tatgtcaaat ttctcaagat gcaaatatgg ctgcatcaaa ccatgattaa 240
tattgtagat gattatgata atccaaatta tcatcatcag ttgctaatgg ctcatgactc 300
taat 304

<210> SEQ ID NO 35
<211> LENGTH: 437
<212> TYPE: DNA
<213> ORGANISM: Artificial sequence
<220> FEATURE:
<223> OTHER INFORMATION: Synthetic: RNAi trigger sequence derived from Nicotiana tabacum

<400> SEQUENCE: 35
acctggtttt aggtttcatc ctactgatga agagcttatc actttctacc ttgcctctaa 60
ggtttttaac ggcacctttt gtggtattca gattgctgaa gttgatctca acagatgtga 120
gccctgggaa cttccagaag tggcaaagat gggggaaaga gaatggtatt tctttagctt 180
aagggacaga aaatacccaa ccggactaag aacaaaccgg gcaacaggag ctggttattg 240
gaaagctaca ggaaaagata gagaagtgta cagtgcaaca aatggagcac tccttgggat 300
gaagaaaaca ttggtttttt acaaaggaag agcaccaaag ggtgagaaaa ccaaatgggt 360
tatgcatgaa tatcgtcttg acggcgattt ttcctaccgt tactcttcta aggaggaatg 420
ggtgatatgc agaatac 437

<210> SEQ ID NO 36
<211> LENGTH: 111
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by EMS treatment, derived from Nicotiana tabacum

<400> SEQUENCE: 36

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

```
Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu
            100                 105                 110


<210> SEQ ID NO 37
<211> LENGTH: 116
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by EMS treatment,
      derived from Nicotiana tabacum

<400> SEQUENCE: 37

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser
        115


<210> SEQ ID NO 38
<211> LENGTH: 68
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by EMS treatment,
      derived from Nicotiana tabacum

<400> SEQUENCE: 38

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys
65


<210> SEQ ID NO 39
<211> LENGTH: 398
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by EMS treatment,
      derived from Nicotiana tabacum
```

-continued

<400> SEQUENCE: 39

```
Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
    210                 215                 220

Pro Ser Ile Ile Ser Ser Ile Val Leu Leu Pro Asp Glu Thr Leu Ala
225                 230                 235                 240

Ile Asn Cys Val Phe Tyr Leu His Arg Leu Leu Lys Asp Arg Glu Met
                245                 250                 255

Leu Arg Ile Phe Leu His Arg Ile Lys Ser Met Asn Pro Lys Val Val
            260                 265                 270

Thr Leu Ala Glu Arg Glu Ala Asn His Asn His Pro Leu Phe Leu Gln
        275                 280                 285

Arg Phe Val Glu Ala Leu Asp Tyr Tyr Ala Ala Val Phe Asp Ser Leu
    290                 295                 300

Glu Ala Thr Leu Pro Pro Ser Ser Arg Glu Arg Met Thr Val Glu Gln
305                 310                 315                 320

Val Trp Phe Gly Arg Glu Ile Ile Asp Ile Val Ala Ala Glu Gly Asp
                325                 330                 335

Lys Arg Arg Glu Arg His Glu Arg Phe Arg Ser Trp Glu Val Met Leu
            340                 345                 350

Arg Ser Cys Gly Phe Ser Asn Val Ala Leu Ser Pro Phe Ala Leu Ser
        355                 360                 365

Gln Ala Lys Leu Leu Leu Arg Leu His Tyr Pro Ser Glu Gly Tyr Gln
    370                 375                 380

Leu Ser Val Ser Ser Thr Ser Asn Ser Phe Phe Leu Gly Trp
385                 390                 395
```

<210> SEQ ID NO 40

<211> LENGTH: 145
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by EMS treatment, derived from Nicotiana tabacum

<400> SEQUENCE: 40

```
Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn
145
```

<210> SEQ ID NO 41
<211> LENGTH: 163
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by EMS treatment, derived from Nicotiana tabacum

<400> SEQUENCE: 41

```
Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140
```

Ala Ile His Ile Val Asp Phe Asp Ile Asn His Gly Val Gln Trp Pro
145 150 155 160

Pro Leu Met

<210> SEQ ID NO 42
<211> LENGTH: 838
<212> TYPE: PRT
<213> ORGANISM: Nicotiana tabacum

<400> SEQUENCE: 42

Met Ala Met Val Val Gln Gln His Arg Glu Ser Ser Ser Gly Ser Ile
1 5 10 15

Thr Lys His Leu Asp Ser Ser Gly Lys Tyr Val Arg Tyr Thr Ala Glu
20 25 30

Gln Val Glu Ala Leu Glu Arg Val Tyr Ala Glu Cys Pro Lys Pro Ser
35 40 45

Ser Leu Arg Arg Gln Gln Leu Ile Arg Glu Cys Pro Ile Leu Ser Asn
50 55 60

Ile Glu Pro Lys Gln Ile Lys Val Trp Phe Gln Asn Arg Arg Cys Arg
65 70 75 80

Glu Lys Gln Arg Lys Glu Ser Ser Arg Leu Gln Thr Val Asn Arg Lys
85 90 95

Leu Ser Ala Met Asn Lys Leu Leu Met Glu Glu Asn Asp Arg Leu Gln
100 105 110

Lys Gln Val Ser Gln Leu Val Cys Glu Asn Gly Phe Met Arg Gln Gln
115 120 125

Leu His Thr Ala Ser Ala Ala Thr Thr Asp Val Ser Cys Glu Ser Val
130 135 140

Val Thr Thr Pro Gln His Ser Leu Arg Asp Ala Asn Asn Pro Ala Gly
145 150 155 160

Leu Leu Ser Ile Ala Glu Glu Thr Leu Ala Glu Phe Leu Ser Lys Ala
165 170 175

Thr Gly Thr Ala Val Asp Trp Val Pro Met Pro Gly Met Lys Pro Gly
180 185 190

Pro Asp Ser Val Gly Ile Phe Ala Ile Ser His Ser Cys Ser Gly Val
195 200 205

Ala Ala Arg Ala Cys Gly Leu Val Ser Leu Glu Pro Thr Lys Ile Ala
210 215 220

Glu Ile Leu Lys Asp Arg Pro Ser Trp Phe Arg Asp Cys Arg Asn Val
225 230 235 240

Glu Val Phe Thr Met Phe Ser Ala Gly Asn Gly Thr Ile Glu Leu Leu
245 250 255

Tyr Thr Gln Ile Tyr Ala Pro Thr Thr Leu Ala Pro Ala Arg Asp Phe
260 265 270

Trp Thr Leu Arg Tyr Thr Thr Thr Leu Glu Asn Gly Ser Phe Val Val
275 280 285

Cys Glu Arg Ser Leu Ser Gly Thr Gly Ala Gly Pro Asn Ala Ala Ser
290 295 300

Ala Ser Gln Phe Val Arg Ala Gln Met Leu Pro Ser Gly Tyr Leu Ile
305 310 315 320

Arg Pro Cys Asp Gly Gly Gly Ser Ile Ile His Ile Val Asp His Leu
325 330 335

Asn Leu Glu Ala Trp Ser Ala Pro Glu Ile Leu Arg Pro Leu Tyr Glu
340 345 350

```
Ser Ser Lys Val Val Ala Gln Lys Met Thr Ile Ala Ala Leu Arg Tyr
        355                 360                 365

Ala Arg Gln Ile Ala Gln Glu Thr Ser Gly Glu Val Val Tyr Gly Leu
    370                 375                 380

Gly Arg Gln Pro Ala Val Leu Arg Thr Phe Ser Gln Arg Leu Ser Arg
385                 390                 395                 400

Gly Phe Asn Asp Ala Ile Asn Gly Phe Ser Asp Asp Gly Trp Ser Leu
                405                 410                 415

Leu Ser Ser Asp Gly Gly Glu Asp Val Ile Val Ala Val Asn Ser Arg
            420                 425                 430

Lys Asn Ile Ala Thr Thr Ser Val Pro Leu Ser Pro Leu Gly Gly Ile
        435                 440                 445

Leu Cys Ala Lys Ala Ser Met Leu Leu Gln Asn Val Pro Pro Val Val
    450                 455                 460

Leu Val Arg Phe Leu Arg Glu His Arg Ser Glu Trp Ala Asp Phe Asn
465                 470                 475                 480

Val Asp Ala Tyr Val Ala Ser Ser Met Lys Ser Cys Ser Tyr Ala Tyr
                485                 490                 495

Pro Gly Met Arg Pro Thr Arg Phe Thr Gly Ser Gln Ile Ile Met Pro
            500                 505                 510

Leu Gly His Thr Ile Glu His Glu Glu Met Leu Glu Val Ile Arg Leu
        515                 520                 525

Glu Gly His Ser Ile Gly Gln Glu Asp Thr Phe Met Pro Arg Asp Val
    530                 535                 540

His Leu Leu Gln Met Cys Ser Gly Thr Asp Glu Asn Ala Val Gly Ala
545                 550                 555                 560

Cys Ser Glu Leu Val Phe Ala Ala Ile Asp Glu Met Phe Pro Asp Asp
                565                 570                 575

Ala Pro Leu Leu Pro Ser Gly Phe Arg Ile Ile Pro Leu Glu Ser Lys
            580                 585                 590

Ser Ser Asp Pro Gln Asp Thr Ser Asn Ala His Arg Thr Leu Asp Leu
        595                 600                 605

Ala Ser Ser Leu Glu Val Gly Pro Ala Thr Asn Pro Ala Thr Gly Asp
    610                 615                 620

Val Val Ser Gly Tyr Ser Ala Arg Ser Val Leu Thr Ile Ala Phe Gln
625                 630                 635                 640

Phe Pro Phe Glu Asp Asn Leu Gln Asp Asn Val Ala Thr Met Ala Arg
                645                 650                 655

Gln Tyr Val Arg Ser Val Val Ser Ser Val Gln Arg Val Ala Met Ala
            660                 665                 670

Ile Ser Pro Ala Gly Val Asn Ser Thr Phe Gly Ser Lys Leu Ser Pro
        675                 680                 685

Gly Ser Pro Glu Ala Val Thr Leu Ser His Trp Ile Cys Gln Ser Tyr
    690                 695                 700

Ser Tyr His Met Gly Thr Glu Leu Leu Gln Thr Asp Ser Arg Gly Asp
705                 710                 715                 720

Glu Ser Val Leu Lys Asn Leu Trp Gln His Gln Asp Ala Ile Leu Cys
                725                 730                 735

Cys Ser Leu Lys Ser Leu Pro Val Phe Ile Phe Ala Asn Lys Ala Gly
            740                 745                 750

Leu Asp Met Leu Glu Thr Thr Leu Val Ala Leu Gln Asp Ile Thr Leu
        755                 760                 765

Asp Lys Ile Phe Asp Glu Ser Gly Arg Lys Val Leu Phe Ala Glu Phe
```

```
    770                 775                 780

Pro Lys Ile Met Glu Gln Gly Phe Ala Tyr Leu Pro Gly Gly Ile Cys
785                 790                 795                 800

Met Ser Ala Met Gly Arg His Ile Ser Tyr Glu Gln Ala Ile Ala Trp
                805                 810                 815

Lys Val Phe Ala Ser Glu Glu Thr Val His Cys Leu Ala Phe Ser Phe
            820                 825                 830

Ile Asn Trp Ser Phe Val
        835


<210> SEQ ID NO 43
<211> LENGTH: 839
<212> TYPE: PRT
<213> ORGANISM: Nicotiana tabacum

<400> SEQUENCE: 43

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Ala Cys Gly Leu Val Ser Leu Glu Pro Thr Lys Ile Ala
    210                 215                 220

Glu Ile Leu Lys Asp Arg Ser Ser Trp Phe Arg Asp Cys Arg Asn Val
225                 230                 235                 240

Glu Val Phe Thr Met Phe Ser Ala Gly Asn Gly Thr Ile Glu Leu Leu
                245                 250                 255

Tyr Thr Gln Ile Tyr Ala Pro Thr Thr Leu Ala Pro Ala Arg Asp Phe
            260                 265                 270

Trp Thr Leu Arg Tyr Thr Thr Thr Leu Glu Asn Gly Ser Phe Val Val
        275                 280                 285

Cys Glu Arg Ser Leu Ser Gly Thr Gly Ala Gly Pro Asn Ala Ala Ser
    290                 295                 300
```

-continued

```
Ala Ser Gln Phe Val Arg Ala Gln Met Leu Pro Ser Gly Tyr Leu Ile
305                 310                 315                 320

Arg Pro Cys Asp Gly Gly Gly Ser Ile Ile His Ile Val Asp His Leu
                325                 330                 335

Asn Leu Glu Ala Trp Ser Ala Pro Glu Ile Leu Arg Pro Leu Tyr Glu
            340                 345                 350

Ser Ser Lys Val Val Ala Gln Lys Met Thr Ile Ala Ala Leu Arg Tyr
        355                 360                 365

Ala Arg Gln Ile Ala Gln Glu Thr Ser Gly Glu Val Val Tyr Gly Leu
    370                 375                 380

Gly Arg Gln Pro Ala Val Leu Arg Thr Phe Ser Gln Arg Leu Ser Arg
385                 390                 395                 400

Gly Phe Asn Asp Ala Ile Asn Gly Phe Ser Asp Asp Gly Trp Ser Leu
                405                 410                 415

Leu Ser Ser Asp Gly Gly Glu Asp Val Ile Val Ala Val Asn Ser Arg
            420                 425                 430

Lys Asn Ile Ala Thr Thr Ser Val Pro Leu Ser Pro Leu Gly Gly Ile
        435                 440                 445

Leu Cys Ala Lys Ala Ser Met Leu Leu Gln Asn Val Pro Pro Ala Val
    450                 455                 460

Leu Val Arg Phe Leu Arg Glu His Arg Ser Glu Trp Ala Asp Phe Asn
465                 470                 475                 480

Val Asp Ala Tyr Val Ala Ser Ser Met Lys Ser Cys Ser Tyr Ala Tyr
                485                 490                 495

Pro Gly Val Arg Pro Thr Arg Phe Thr Gly Ser Gln Ile Ile Met Pro
            500                 505                 510

Leu Gly His Thr Ile Glu His Glu Glu Met Leu Glu Val Ile Arg Leu
        515                 520                 525

Glu Gly His Ser Ile Gly Gln Glu Asp Ala Phe Met Pro Arg Asp Ile
    530                 535                 540

His Leu Leu Gln Met Cys Ser Gly Thr Asp Glu Asn Ala Val Gly Ala
545                 550                 555                 560

Cys Ser Glu Leu Val Phe Ala Ala Ile Asp Glu Met Phe Pro Asp Asp
                565                 570                 575

Ala Pro Leu Leu Pro Ser Gly Phe Arg Ile Ile Pro Leu Glu Ser Lys
            580                 585                 590

Ser Ser Asp Pro Gln Asp Thr Ser Asn Ala His Arg Thr Leu Asp Leu
        595                 600                 605

Ala Ser Ser Leu Glu Val Gly Pro Ala Thr Asn Pro Ala Thr Gly Asp
    610                 615                 620

Val Val Ser Gly Tyr Ser Ala Arg Ser Val Leu Thr Ile Ala Phe Gln
625                 630                 635                 640

Phe Pro Phe Glu Asp Asn Leu Gln Asp Asn Val Ala Thr Met Ala Arg
                645                 650                 655

Gln Tyr Val Arg Ser Val Val Ser Ser Val Gln Arg Val Ala Met Ala
            660                 665                 670

Ile Ser Pro Ala Gly Val Asn Ser Thr Phe Gly Ser Lys Leu Ser Pro
        675                 680                 685

Gly Ser Pro Glu Ala Val Thr Leu Ser His Trp Ile Cys Gln Ser Tyr
    690                 695                 700

Ser Tyr His Met Gly Thr Glu Leu Leu Gln Ala Asp Ser Arg Gly Asp
705                 710                 715                 720

Glu Ser Val Leu Lys Asn Leu Trp Gln His Gln Asp Ala Ile Leu Cys
```

```
                725                 730                 735

Cys Ser Leu Lys Ser Leu Pro Val Phe Ile Phe Ala Asn Lys Ala Gly
            740                 745                 750

Leu Asp Met Leu Glu Thr Thr Leu Val Ala Leu Gln Asp Ile Thr Leu
        755                 760                 765

Asp Arg Ile Phe Asp Glu Ser Gly Arg Lys Val Leu Phe Ala Glu Phe
    770                 775                 780

Pro Lys Ile Met Asp Gln Gly Phe Ala Tyr Leu Pro Gly Gly Ile Cys
785                 790                 795                 800

Met Ser Ala Met Gly Arg His Ile Ser Tyr Glu Gln Ala Ile Ala Trp
                805                 810                 815

Lys Val Phe Ala Ser Glu Glu Thr Ser Val His Cys Leu Ala Phe Ser
            820                 825                 830

Phe Ile Asn Trp Ser Phe Val
        835


<210> SEQ ID NO 44
<211> LENGTH: 407
<212> TYPE: PRT
<213> ORGANISM: Nicotiana tabacum

<400> SEQUENCE: 44

Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met Gln Ala Leu Ala Asp Arg Tyr Pro Pro Pro Thr Leu Arg
                165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
        195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Leu His Arg Leu Leu Lys Asp Arg Glu Lys Leu Arg Ile
                245                 250                 255
```

```
Phe Leu His Arg Ile Lys Ser Met Asn Pro Lys Val Val Thr Leu Ala
            260                 265                 270

Glu Arg Glu Ala Asn His Asn His Pro Leu Phe Leu Gln Arg Phe Val
        275                 280                 285

Glu Ala Leu Asp Tyr Tyr Ala Ala Val Phe Asp Ser Leu Glu Ala Thr
    290                 295                 300

Leu Pro Pro Ser Ser Arg Glu Arg Met Thr Val Glu Gln Val Trp Phe
305                 310                 315                 320

Gly Arg Glu Ile Ile Asp Ile Val Ala Ala Glu Gly Asp Lys Arg Arg
                325                 330                 335

Glu Arg His Glu Arg Phe Arg Ser Trp Glu Val Met Leu Arg Ser Cys
            340                 345                 350

Gly Phe Ser Asn Val Ala Leu Ser Pro Phe Ala Leu Ser Gln Ala Lys
        355                 360                 365

Leu Leu Leu Arg Leu His Tyr Pro Ser Glu Gly Tyr Gln Leu Ser Val
    370                 375                 380

Ser Ser Thr Ser Asn Ser Phe Phe Leu Gly Trp Gln Asn Gln Pro Leu
385                 390                 395                 400

Phe Ser Ile Ser Ser Trp Arg
                405


<210> SEQ ID NO 45
<211> LENGTH: 410
<212> TYPE: PRT
<213> ORGANISM: Nicotiana tabacum

<400> SEQUENCE: 45

Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
    210                 215                 220
```

```
Pro Ser Ile Ile Ser Ser Ile Val Leu Leu Pro Asp Glu Thr Leu Ala
225                 230                 235                 240

Ile Asn Cys Val Phe Tyr Leu His Arg Leu Leu Lys Asp Arg Glu Met
                245                 250                 255

Leu Arg Ile Phe Leu His Arg Ile Lys Ser Met Asn Pro Lys Val Val
            260                 265                 270

Thr Leu Ala Glu Arg Glu Ala Asn His Asn His Pro Leu Phe Leu Gln
        275                 280                 285

Arg Phe Val Glu Ala Leu Asp Tyr Tyr Ala Ala Val Phe Asp Ser Leu
    290                 295                 300

Glu Ala Thr Leu Pro Pro Ser Ser Arg Glu Arg Met Thr Val Glu Gln
305                 310                 315                 320

Val Trp Phe Gly Arg Glu Ile Ile Asp Ile Val Ala Ala Glu Gly Asp
                325                 330                 335

Lys Arg Arg Glu Arg His Glu Arg Phe Arg Ser Trp Glu Val Met Leu
            340                 345                 350

Arg Ser Cys Gly Phe Ser Asn Val Ala Leu Ser Pro Phe Ala Leu Ser
        355                 360                 365

Gln Ala Lys Leu Leu Leu Arg Leu His Tyr Pro Ser Glu Gly Tyr Gln
    370                 375                 380

Leu Ser Val Ser Ser Thr Ser Asn Ser Phe Phe Leu Gly Trp Gln Asn
385                 390                 395                 400

Gln Pro Leu Phe Ser Ile Ser Ser Trp Arg
                405                 410


<210> SEQ ID NO 46
<211> LENGTH: 167
<212> TYPE: PRT
<213> ORGANISM: Nicotiana tabacum

<400> SEQUENCE: 46

Asp Gln Gln His Ser Thr Cys Phe Ser Ser Ser Ser Lys Ile Asn Asp
1               5                   10                  15

Lys Glu Lys Lys Lys Lys Arg Ser Val Val Lys Leu Ser Thr Asp Pro
            20                  25                  30

Gln Ser Val Ala Ala Arg Glu Arg Arg His Arg Ile Ser Asp Arg Phe
        35                  40                  45

Lys Ile Leu Gln Ser Leu Ile Pro Gly Gly Ser Lys Met Asp Thr Val
    50                  55                  60

Thr Met Leu Glu Glu Ala Ile His Tyr Val Lys Phe Leu Lys Thr Gln
65                  70                  75                  80

Ile Trp Leu His Gln Thr Val Ile Asn Ile Val Asp Asp Tyr Asp Asn
                85                  90                  95

Pro Asn Tyr His Asp Gln Leu Leu Met Ala His Asp Ser Asn Phe Ala
            100                 105                 110

Asn Tyr Tyr Pro His Glu Met Val Glu Tyr Cys Pro Ala Pro Val Glu
        115                 120                 125

Asn Ala Gln Ile Asn Tyr Asn Leu Asp Gln Leu Gln Leu Pro Gly Tyr
    130                 135                 140

Ala Phe Ser Asp Gly Asp Gln Phe Gln Gly Glu Glu Thr Asn Ile Thr
145                 150                 155                 160

Gly Asp Ser Phe Met Tyr Tyr
                165
```

<210> SEQ ID NO 47
<211> LENGTH: 165
<212> TYPE: PRT
<213> ORGANISM: Nicotiana tabacum

<400> SEQUENCE: 47

```
Met Asp Gln Gln His Ser Thr Cys Phe Ser Ser Ser Ser Lys Ile Asn
1               5                   10                  15

Asp Lys Glu Lys Lys Lys Lys Gly Ser Val Val Lys Leu Ser Thr Asp
            20                  25                  30

Pro Gln Ser Val Ala Ala Arg Glu Arg Arg His Arg Ile Ser Asp Arg
        35                  40                  45

Phe Lys Ile Leu Gln Ser Leu Val Pro Gly Gly Ser Lys Met Asp Thr
    50                  55                  60

Val Thr Met Leu Glu Glu Ala Ile His Tyr Val Lys Phe Leu Lys Met
65                  70                  75                  80

Gln Ile Trp Leu His Gln Thr Met Ile Asn Ile Val Asp Asp Tyr Asp
                85                  90                  95

Asn Pro Asn Tyr His His Gln Leu Leu Met Ala His Asp Ser Asn Phe
            100                 105                 110

Ala Asn Tyr Tyr Pro His Glu Asn Asn Ser Thr Pro Val Glu Asn Ala
        115                 120                 125

Gln Ile Asn Tyr Asn Leu Asp Gln Leu Gln Leu Pro Gly Tyr Ala Phe
    130                 135                 140

Ser Asp Gly Asp Gln Phe Gln Gly Glu Glu Thr Asn Ile Ser Gly Asp
145                 150                 155                 160

Ala Phe Met Tyr Tyr
                165
```

<210> SEQ ID NO 48
<211> LENGTH: 2640
<212> TYPE: DNA
<213> ORGANISM: Nicotiana tabacum

<400> SEQUENCE: 48

```
ttgtttggga ttttggggtt tgagggcaaa tggctatggt ggtacagcag catagggaga     60

gtagtagtgg tagtattaca aaacatcttg acagtagtgg aaagtatgtc cggtatacag    120

ctgagcaagt ggaggcatta gagagggttt atgcagagtg ccctaaacct agctcgttgc    180

gccgccagca attgatccgc gaatgcccta ttctgtcgaa tatcgagcct aagcagatca    240

aagtttggtt tcaaaacaga aggtgtcgag agaagcaaag gaaagagtct tctagactac    300

agactgtaaa tagaaagctg tctgcaatga ataaactatt aatggaggag aatgatcgct    360

tgcaaaaaca ggtttcacag cttgtgtgtg aaaatggctt tatgcggcaa caattgcata    420

ctgcatcagc ggccactact gatgtaagtt gtgagtcagt ggttaccacc cctcagcatt    480

ccctcagaga tgctaacaac cctgctggac tgctgtcgat tgcagaggaa accttagcag    540

agttcctttc caaggctaca ggaactgctg ttgattgggt cccgatgcct gggatgaagc    600

ctggtccgga ttcagttggg atttttgcca tctcacacag ttgtagtgga gtggcagccc    660

gagcatgtgg tcttgttagt ttagagccga caaagattgc tgagatcctc aaagatcgac    720

catcttggtt ccgagactgc cggaacgttg aagttttcac gatgttttct gcaggaaatg    780

gaacaattga gcttttgtac acgcagatat atgctcctac caccttggct cctgcacgtg    840

atttttggac tctgagatac acaaccaccc tggagaatgg tagttttgtg gtttgtgaaa    900

gatccctctc tggtactgga gctgggccga atgctgcttc tgcttcccag tttgtaagag    960
```

ctcaaatgct tccgtccgga tatctaatcc gaccgtgtga cggtggagga tccattatac 1020
atattgttga ccatctgaat cttgaggcat ggagtgcccc tgagattttg cgtccacttt 1080
atgaatcgtc aaaagttgtg gcacagaaaa tgactattgc ggcactgcga tatgcaaggc 1140
aaatagctca ggagactagt ggggaggttg tatatggtct gggaaggcaa cctgcagttc 1200
ttcgaacatt tagccagaga ttaagcagag gcttcaatga cgccatcaat ggattcagtg 1260
atgatggctg gtcattgtta agttctgatg gtggtgaaga tgttatagtt gctgtcaatt 1320
caaggaagaa cattgccacc acttccgttc ctctttcacc gctgggaggc atcctttgtg 1380
ccaaagcatc aatgctactc cagaatgttc ctcctgtggt actggttcga tttctcaggg 1440
agcaccgttc agagtgggcg gactttaatg ttgatgccta tgtagcttcg tcaatgaaat 1500
cttgttcata tgcatatcct gggatgaggc ctaccagatt taccggaagt cagataataa 1560
tgccacttgg ccatacaatt gaacatgaag agatgcttga ggttattaga ttggaaggac 1620
actctattgg ccaggaagat acttttatgc caagagatgt tcaccttctc cagatgtgta 1680
gtggaactga tgagaatgct gtcggagctt gttctgaact agtttttgct gcaattgatg 1740
agatgtttcc agatgatgca cccctgttgc cctccgggtt tcgtatcatt cctctcgagt 1800
caaaatcaag cgatccccag gatacatcga atgctcatag aacactggat ctggcatcaa 1860
gtcttgaagt tggcccagca acaaaccctg ctactggaga tgtggtctct ggctacagtg 1920
cacgatctgt gttgacaatt gcttttcaat ttccattcga ggacaatctt caggacaatg 1980
tagctaccat ggcgcgccag tatgttcgca gtgtggtttc atctgtccaa cgggttgcca 2040
tggcaatatc tcccgcagga gtgaattcaa cattcgggtc caagctttct ccaggctccc 2100
ctgaagctgt aacgttgtcg cactggatct gccagagcta cagttatcac atggggacag 2160
agttgcttca aactgattcg aggggcgatg aatcagtgct aaaaaatctt tggcaacatc 2220
aggatgctat tttgtgctgc tcattgaagt ccctgccggt tttcattttt gctaataagg 2280
ctgggcttga tatgctggag acaaccttag ttgctttaca ggacattact ctagataaga 2340
tatttgatga atctggccgg aaagtgttgt tcgctgaatt tcccaagatc atggaacagg 2400
gttttgcgta cttgccgggt ggtatttgca tgtcagcaat gggacgacat atttcatatg 2460
aacaagctat tgcatggaaa gtctttgctt ctgaagaaac tgtccactgc ttagccttct 2520
catttattaa ctggtcattt gtttaatgtt gctgtcaaat ctcctttctt ttttttcctt 2580
tttgtttttt gacatcttcc tcacagagga cactgacagc caggaacaca gttgaacgga 2640

<210> SEQ ID NO 49
<211> LENGTH: 2726
<212> TYPE: DNA
<213> ORGANISM: Nicotiana tabacum

<400> SEQUENCE: 49
aagctgtttg cagggaatat atctacttgg gggtgttttt atttcttaaa agggtgtttg 60
aaaatttgga aatcttgatt ttttttttgg tttgggattt tgaggtttga gggcaatggc 120
tatggttgca cagcagcaca gggagagtag tagtggtagt attacaaaac atcttgacag 180
tagtggaaag tatgtccggt atacagctga gcaagttgag gcattggaga gggtttatgc 240
tgagtgccct aagcctagct ccttgcgccg ccaacaattg atccgtgaat gccctattct 300
gtcgaatatc gagcctaagc agatcaaagt ttggtttcaa aacagaaggt gtcgagagaa 360
gcaaaggaaa gagtcttctc gactacagac tgtaaataga aagctgtctg caatgaataa 420

-continued

```
actattgatg gaggagaatg atcgcttgca aaaacaggtt tcgcagcttg tgtgtgaaaa    480
tggctttatg cggcaacagt tgcatactgc atcagcggcc actactgatg taagttgtga    540
gtctgtggta actacccctc agcattccct cagagatgct aacaaccctg ctggactgct    600
gtcgattgca gaggaaacct tagcagagtt cctttccaag gctacaggaa ctgctgttga    660
ttgggtcccg atgcctggga tgaagcctgg tccggattca gttgggattt ttgccatctc    720
acacagttgt agtggagtgg cagcccgagc atgtggtctt gttagtttag agccgacaaa    780
gattgctgag atcctcaaag atcgatcttc ttggttccga gattgccgga acgttgaagt    840
tttcacaatg ttttctgcag gaaatggaac aattgaactt ttgtacacgc agatatatgc    900
tcctaccacc ttggctcctg cacgtgattt ttggactctg agatacacaa ccaccctgga    960
gaatggtagc tttgtggttt gtgaaagatc cctctctggt actggagctg ggccgaatgc   1020
tgcttctgct tcccagtttg taagagctca aatgcttccg tctggatatc taatccgacc   1080
gtgtgacggt ggaggatcca ttatacatat tgttgaccac ctgaatcttg aggcatggag   1140
tgcccctgag attttgcgtc cactttatga atcgtcaaaa gttgtggcac agaaaatgac   1200
tattgcggca ctgcgatatg caaggcaaat agctcaggag actagtgggg aggttgtata   1260
tggtctggga aggcaacctg cagttcttcg aacatttagc cagagattaa gcagaggctt   1320
caatgatgcc atcaatggat tcagtgatga tggctggtca ttgttaagtt ctgatggtgg   1380
tgaagatgtt atagttgctg tcaattcaag gaagaacatt gccaccactt ccgttcctct   1440
ttcaccactt ggaggcatcc tttgtgccaa agcatcaatg ctactccaga atgttcctcc   1500
tgcggtactg gttcgatttc tcagggagca ccgttcagag tgggcggact ttaatgttga   1560
tgcctatgta gcttcctcaa tgaaatcttg ttcatatgca tatcctgggg tgaggcctac   1620
cagatttacc ggaagccaga taataatgcc actgggccac acaatagaac atgaagagat   1680
gcttgaagtt attagattgg aagggcactc tattggccag gaagatgctt ttatgccgag   1740
agatattcac cttctccaga tgtgtagtgg aaccgatgag aatgctgtcg gagcttgttc   1800
tgaactagtt tttgctgcaa ttgatgagat gtttccagat gatgcacccc tgttgccctc   1860
cgggtttcgt atcattcctc tcgagtcaaa atcaagcgat ccccaggata catcgaatgc   1920
tcatagaaca ctggatctgg catcaagtct tgaagttggc ccagcaacaa accctgctac   1980
tggagatgtg gtctctggct acagtgcacg atctgtattg acaattgctt ttcaatttcc   2040
attcgaggac aatcttcagg ataatgtagc taccatggcg cgccagtatg ttcgcagtgt   2100
ggtttcatct gtccaacggg ttgccatggc aatatctccc gcaggagtga attcaacatt   2160
cgggtccaag ctttctccag gctcccctga agctgtaact ttgtcgcact ggatctgcca   2220
gagctacagt tatcacatgg ggacagagtt gcttcaagct gattcgaggg gcgatgaatc   2280
agtgctaaag aatctttggc aacatcagga tgctattttg tgctgctcat tgaagtcgct   2340
gccggttttc atttttgcta ataaggctgg gcttgatatg ctggagacaa cattagttgc   2400
tttgcaagac attactctag ataggatatt tgacgaatct ggccggaaag tgttgttcgc   2460
tgaatttccc aagatcatgg atcagggttt cgcgtacctg ccgggtggta tttgcatgtc   2520
tgcaatggga cgacatattt catatgaaca agctattgca tggaaagtct ttgcttctga   2580
agaaactagt gtccactgct tagccttctc atttattaac tggtcatttg tttaatgttg   2640
ctgtcaaatc tcctcttttt ttccttttttg ttttttgaca tcttcctcac agaggacact   2700
gacagacagg aacacagttg aacgga                                        2726
```

<210> SEQ ID NO 50
<211> LENGTH: 1730
<212> TYPE: DNA
<213> ORGANISM: Nicotiana tabacum

<400> SEQUENCE: 50
aggttcttct tccttaatat tgagtcacag attagtacca ctactatagc caagaaaatg 60
tgaaatcata tagtactaaa tattaatttc agatgccaaa accataaatt tcccctcctc 120
catcattgaa aaccccctct gtcctttccc ctagagagac cccttttcc tctctctctc 180 ctttctcttt ttattagacg catatattct ctcttctttc tctttctagg gttttcacct 240
gaaatagttt tatttcggtg atatgttagg atcctttggt tcatcatctc aatctcatga 300
tgaagaaact gatgatcaac ggcggagatt cagttccact tcccctgcaa tccaaatccg 360
gcaactactc attagctgcg cggagttaat ctcgcggtcc gatttctcgg ccgcaaacag 420
actcctcacc attttatcaa ctaactcttc cccttttggt gattcaactg aaagattagt 480
ccatcagttc actcgcgcac tttctcttcg cctcaaccgt tatatctctt cagccactaa 540
tttcttgaca ccatctaatg ttgttgaaag ttcaaatgat tcagctctac ttcagtcatc 600
ctatctttcc ctaaaccaag tgactccttt cattagattt agtcagctaa ctgctaatca 660
agcgattttg gaagctatta acgataacca acaagcgatc cacatcgttg attttgatat 720
taatcacggt gttcaatggc caccgttaat gcaagcacta gctgatcgtt accctcctcc 780
aactcttcgg attaccggta ctggaaatga ccttgatacc cttcgtagaa ccggagatcg 840
tttagctaaa tttgctcact ctttaggcct tagatttcag tttcaccctc ttttgattac 900
caataataat gacaatgatc atgacccttc aataatttct tctattgttc ttctccctga 960
tgagacatta gctatcaact gtgtatttta tcttcacagg ctcttgaaag accgcgaaaa 1020
gttaaggatt tttttgcata ggattaaatc catgaaccct aaagttgtaa cgctggccga 1080
gagagaagca aatcataatc acccactttt tttgcaaaga tttgtggagg ctttggatta 1140
ttatgcagct gtgtttgatt cattggaagc aactttgcca ccgagcagta gagagaggat 1200
gacagtggaa caagtttggt tcgggagaga aataattgat atagtagcag cagaaggaga 1260
taagagaaga gaaagacacg agagattcag atcatgggaa gtaatgttga ggagctgtgg 1320
atttagcaat gttgctttaa gcccttttgc actctcacaa gctaaacttc tcttgagact 1380
tcattaccca tctgaaggat accagcttag tgtttcgagt acgagtaatt ctttcttctt 1440
gggttggcaa aatcaacccc ttttttccat atcttcttgg cgttaaattt aaaaccctaa 1500
aaaacaagat ttttatctat ctgcatggtg aaggacaaag aggtcttcaa tctcaggttc 1560 ttttttttt ttttttttta tatatatatc ttgtttgggt ttaaggttat tgggctgatg 1620
aatgttttaa ttttaacata ggtctactta cgtagtagtt ataggttgat aatgagatat 1680
aattaactaa gtctttgtat aatgcagatc ctgaacttaa tctttatttg 1730

<210> SEQ ID NO 51
<211> LENGTH: 1827
<212> TYPE: DNA
<213> ORGANISM: Nicotiana tabacum

<400> SEQUENCE: 51
aggttcttct tccttaatat tgagtcaaga ttagtactac tactatagcc aagaaaatgt 60
gaaatcatat agtactaact ttcccttctc cctagctact gataactcta attaatttca 120
gatgccaaaa ccataaattt cccctcctcc atcattgaaa acccctttgt cctttccccc 180

-continued

```
cagaccccct tttcctctct ctctctctcc tttctctttt tattagacgc atattctctc    240

ttctttctct ttctagggtt ttcacctgaa atagttttat ttcgttgata tgttaggatc    300

ctttggttca tcatctcaat ctcatgatga agaagctgat gatcaacggc ggagatgcag    360

ttccacttcc cctgcaatcc aaatccggca actactcatt agctgcgcgg agttaatctc    420

acggtccgat ttctcggcgg caaacagact cctcaccatt ttatcaacta actcttcccc    480

ttttggtgat tcaactgaaa gattagtcca tcagttcact cgcgcacttt ccattcgcct    540

caaccgctat atctcttcag ccactaattt cttgacacct aatgcatcat ctaatgttgt    600

tgaaagttca aatgattcag ctctacttca gtcatcctat ctttccctaa accaagtgac    660

ccctttttatt agatttagtc agctaactgc taatcaagcg attttagaag ctattaacga   720

taaccaacaa gcgatccaca tcgttgattt tgatattaat cacggtgttc aatggccacc    780

gttaatgcaa gcactagctg atcgttaccc tcctccaact cttcggatta ccggtactgg    840

aaatgacctc gataccccttc gtagaaccgg agatcgttta gctaaatttg ctcactcttt   900

aggccttaga tttcagtttc accctctttt gatcaccaat aataatgaca atgatcatga    960

cccttcaatc atttcttcta ttgttcttct ccctgatgag acattagcaa tcaactgtgt   1020

attttatctt cacaggctct taaaagaccg cgaaatgtta aggatttttt tgcataggat   1080

taaatccatg aaccctaaag ttgtaacact ggccgagaga gaagcaaatc ataatcaccc   1140

actttttttg caaagatttg tggaggcttt ggattattat gcagctgtct ttgattcatt   1200

ggaagcaact ttgccgccga gcagtagaga gaggatgaca gtggagcaag tttggttcgg   1260

aagagaaatt atagatatag tagcagcaga aggagataag agaagagaaa gacacgagag   1320

attcagatca tgggaagtaa tgttgaggag ctgtggattt agcaatgttg ctttaagtcc   1380

ttttgcactt tcacaagcta aacttctctt gagacttcat taccccttctg aaggatacca  1440

gcttagtgtt tcgagtacga gtaattcttt cttcttgggt tggcaaaatc aacccctttt   1500

ttccatatct tcttggcgtt aaattataag ggaaattaaa accctaaaaa caagatttta   1560

tctatctgca tggtgaagga caaagaggtc ttcaatctca ggttcttttt gttttttttaa  1620

cttgtttgga tatgaggtta ttgagctgat gaatgtttta attttaacat aggcctactt   1680

acgtagtagt tataggttga taatgatata tatttaacta agtctttgta taatgcagat   1740

cctgaactta atttttattt ttattatttt gttgttaatg aaagattctg ttaccaaatt   1800

ttatcagtct atttaattag aggccaa                                       1827
```

<210> SEQ ID NO 52
<211> LENGTH: 649
<212> TYPE: DNA
<213> ORGANISM: Nicotiana tabacum

<400> SEQUENCE: 52

```
gcatggacaa tctcatcttc tcaaacttca taaagatatc tttaaaaaaa agagaaaata     60

gaggtaatta gttgtatcaa tggatcaaca acattccact tgtttttctt cttcaagtaa    120

aattaatgac aaagaaaaga agaaaaaaag atcagttgtg aaactatcaa ctgatccaca    180

aagtgtagca gctcgtgaaa gaaggcatag aatcagtgat cgtttcaaga ttttgcagag    240

tttaatccct ggtggttcaa aaatggatac agttactatg ttagaagaag caattcacta    300

tgtcaaattt cttaagactc aaatatggct gcatcaaacc gtgattaata ttgtagatga    360

ttatgataat ccaaattatc atgatcagtt gctaatggct catgactcta attttgctaa    420

ttattatcct catgaaatgg tggaatattg cccagctcct gttgagaatg cacaaataaa    480
```

ttataacttg gaccagctgc agcttccagg ttatgcattt tcagatgggg atcaattcca 540
aggagaagaa actaatatta ctggtgattc ttttatgtac tattagttag ttaattatgt 600
tgcctaagtt taattagaat acgtagtgtg tggtagtatg gtatgttgt 649

<210> SEQ ID NO 53
<211> LENGTH: 740
<212> TYPE: DNA
<213> ORGANISM: Nicotiana tabacum

<400> SEQUENCE: 53
aaacttcata aagatattat attaaaaaaa ataaagaaga agagaagata gaggtaatta 60
gctatagcaa tggatcaaca acattccact tgtttttctt cttcaagcaa aattaatgac 120
aaagaaaaga agaaaaaagg atcagttgtg aaactatcaa ctgatccaca aagtgtagca 180
gctcgtgaaa gaaggcatag aatcagtgat cgtttcaaga ttttgcagag tttagtccct 240
ggtggttcta aaatggacac agttacaatg ttagaagaag caattcacta tgtcaaattt 300
ctcaagatgc aaatatggct gcatcaaacc atgattaata ttgtagatga ttatgataat 360
ccaaattatc atcatcagtt gctaatggct catgactcta attttgctaa ttattatcct 420
catgagaata actcaactcc tgttgagaat gcacaaataa attataactt ggaccagctg 480
cagcttccag gttatgcatt ttcagatgga gatcaattcc aaggagaaga aactaatatt 540
tctggtgatg cttttatgta ctattaatta gtaattagtt aattatgttg cctaagttta 600
attagaatac gtagtgtgtg gtagtatggt atgttgtttt ctctctttct atctagcagc 660
ctaatgatgg gtttgtgtta attaattaga tgtagtaaat tgtaagtgtt ggttagttga 720
ttaagtatgt tgcaagtttg 740

<210> SEQ ID NO 54
<211> LENGTH: 15103
<212> TYPE: DNA
<213> ORGANISM: Nicotiana tabacum

<400> SEQUENCE: 54
ttctagggat tacggaaatt catttacgta catttagttt gaataacttc ttaacaaaat 60
ggtaattgtt tttaaattct aaaaataaag gatagagaag gaaaatgtca cgacccgaaa 120
ttctcacctt cgggatcgtg acggtatcta acattttact tgctaggcaa gtcaacgttt 180
gagtaaatta tatgttattt caacaactca agtaattaaa ctcatttaaa ctgaaatgaa 240
actaaaaaga agtgtgaggt gacataataa cccaaaatat ttaagtacaa tccggacctg 300
gagttacaag tacatgagct actagaaatt ctacaaacag agtctgcaat aaatgtaatc 360
gtctcgaata aaatgaacag taactaagga aagaggaagc ggacttcaag gtctgcggac 420
gccatcagat ctaccccgag tctccgagta tgtcaatccg agccgataca gctcacgtag 480
tgctgggact agttctaaaa tctgcacaag aagtttagag tagtatgagt acaaccgacc 540
caatgtccat aagtgtcgag cctaacctca acgaggtagt gacgaggcta taacaggaca 600
ctcacgtaat tcaacatgta cgaactaaga catatacaca atatagtaac aataaagaat 660
taatctatga aattgggagg ggacatgcaa acggggaaca agatacgata attacaacat 720
aaataacaac ataagacagt caaataaatc atcaaccaag aaaagggata aacatgatga 780
ataaagatgg cacaacattg cccatcgtgc ttttactctc aaccttgcca tgaaataata 840
ataatagcac gacatcaccc ttcgtgtttt tactctcaat ctctccatga acaataaata 900
cggcacgaca tcactcttcg tgctttaact ctctttctca ccatgtatta atcagtaatt 960
gaaacaaata ataacacgac atcacccttc gtgctttaac actctccctt accatgtagt 1020
aatgaatata aaaataaaca agaataaacc ttacgtcaat aatgatttcg aaacacaaat 1080
cctcaatttc aaagaaatac tcaactatca caacttaatt cataaatgca gggagaacaa 1140
tcaaataaga aataaactaa tctaagcatg gacatcatga gtaaagaagg caataaatta 1200
caagcagcaa gtatcactcg catgttttaa cccaataata acacataagt actcgtcacc 1260
tcacttatat gttataccca aacatttaaa catatagcaa ataggcaaac aagtcctaat 1320
cactcaagtc aaggttagcg acgacactta cccacttcat agtccactca gagctctatc 1380
gaggcatttc ctctagaatc cgcctccaac ccactcgtat ctaaccacaa tcgactcgat 1440
aacgtcaaat aatgttaaga aaatcaatta cattacataa agaaaggatt tttacacctt 1500
ttcccaaaag taaaaaaaag tcaacctcga gctcgcttag tcaaaatccg agagtccgac 1560
caaaactcat ttatccattc accccgagtc cgattatgta attaattttg aaattcgaac 1620
tcaaattaag gtctaaatcc cgtatttgca aaaatccaaa attcttccta aatccctagt 1680
tttctactat ggaagaacaa agtttagggc tagaaattaa tgggcgatgt tacaaattga 1740
agaaaatgag ttaaagtgta caaacctatg aattggtatt gggttttcca ttcaaaattg 1800
catctaggcc gagctctaat ggagagtttt atgaaaaagg gtgaaatcct gtttttgaaa 1860
catttaaatc actgggcgtc aggtgttcat cacgatcgcg tgaaacttga cgcgttcgcg 1920
gagagcattg cctaactggc ttatacgatc gcgagtatct ccacacgttc gtgaaggttt 1980
agcctgcctc tcctccgcat tcgcgagcct aggttcgctt tcgcatagag taacctcaac 2040
tcctagccca gcctatctaa cactacgcgt tcgcgaagag cagacccccc agtgctccgc 2100
gttggcaacc aaggtctcgc gttcgggtag aataaaatcc tccccaatcc cagattccct 2160
ttcgcgaccg cgagaaaggc ttcgctgtct cgaagcacaa tacactagat gacagctgaa 2220
cctcgaaacc catatttttc taagttcaaa tggtccgtag gctatccaaa attcacccaa 2280
gccctagggg ctccaaacca aatatgcacg caagtacaaa aatattatac gaactcgctc 2340
gcacgatcaa agctccaaat aatacttaga actacgaatc aaacaccaaa tcgaatgaaa 2400
ttttcaataa agcttaagaa cattcaattt ttcaatcgga cgtccgaatc acgtcaaatc 2460
atttccgttt tgcaccaaat tttacagaca agtcataaat atagtaatga acatatacca 2520
agtttcggaa ctaagatccg gacccggtat caacaaagtc aaacatcggt caaatttata 2580
aagtctttaa acctttaaat ttcaaattct cgacaaattg cgataactcg agctagggat 2640
atccgaattc aattccgggc atacgctcaa gtcccaaatc acgatacaaa ctatcgggat 2700
cgtcaaaata cgaatccggt tctgtttcct taaaatattg gccgaaatca attcaaatga 2760
attttaaagc acgaattcac attttaatta atttttcaca tataagcctt cgggaagtat 2820
gaacttaaca cgcaaatcga cctgtcgggt tatcacagaa aaaaccatga gtaccaccag 2880
tagagttctc ttttaacttc tttttcctta gagtttagct ctgagttaaa aaaaatcttc 2940
ttgataatag taaccatata tagaataaaa atgtcctata atttcaaggg cagatatagg 3000
atacatgaat tatgaattca atcaaataca ataatatgtt caaatatcca attatcattg 3060
aattcagcgt tattactatc cacaaaattc gaactttaaa tatacttttg cataatttag 3120
attcaactaa acaaagatca tataagaaca aagatgtcct gtgatttcag ggcagatatg 3180
cgacataagg tatgaattca gtcaaattca atatttttag tatcagatgt acaaatatta 3240
aattctaatc tagtaactca aatggtcatt aaaatttagt ggtagtccaa ccacaaaatt 3300

```
gaaattctaa atctcctttt atataatgta gatcaagtta agaaatttca tctagacaat   3360
attgaccata tttggacaaa gatgtccttt gaacttttcc ttttatgttt atagctagaa   3420
aaaataatcc aaacagcggt gatcacatat tttattaaaa agaaaaagaa aaagaagttg   3480
tattattata ctctatcgga ttactgaata ttttatattc gtacattata atttcaatta   3540
aatagttgaa gagaaaggac ataaaagaaa acagaaaaac acaaaggcaa gagcaacaac   3600
agcagcataa aaacactggc attttcgatt tgcgagctca taaagcttta actcaagcaa   3660
attctctctc tctctctctc tctctctctc tctctctctc tctctccatt ttctttttct   3720
cttttctcac ccaccactct cacacacctc ttcacctcac cttacacact aaaaaaacat   3780
cactcctctc tctaaaaaat tcaatctttt tgctgttcca acatgtcttt tagagtttgt   3840
ttcagtttca gatcttaagg gcgggagtgt tatgcttctt ctaatatttt gaagctcaag   3900
aaaacagagc aaatttttgc tttcttttct cctacttttt gtggggggta attcttgttt   3960
ttgtaatctc aaagctggct gttttatgta tatactgaag ggttgtggt gatttgtttg    4020
tctactttaa gaaggtgcca tctttttcag taatatttgg gtaaaagttc tctctttttt   4080
ggccttaaac gcgaagattc aggcctctct caacgtgtca tttgttctct gtattaaaca   4140
cagctggaga attaattaca tagaggtaaa aaaaggggtt aaagattcca aagaattgaa   4200
aaaaaacaga gggctgaggt aaaaagttga tggtttttaa aaaaaaataa aagcttaaat   4260
gatgataaag tttggagctt tatgtgaatg gaaatggtgt tgtgtttgta tcaaacacga   4320
gtagtttaca gcttatgtga atttgaaaga gagagaattt ttgtctgtat ttatatcctt   4380
ttcagccata tctttcgtta gagcagtttt ggctgtacct taatttgtaa gggtttaagc   4440
gtgaagtgtg tgtttgagcc ttctgttata aggggcacaa agtatagaaa caacaaaagg   4500
ggcacctagg aatcttctgg ctcaatcaag atcgttcatt taatcttgtc tgagatcact   4560
agaaaaagaa aaaggaaaga taaagataaa gtctttgttt cagagaatct tagttctctg   4620
tgttgatata tataataaaa gctgtttgca gggaatatat ctacttgggg gtgtttttat   4680
ttcttttaag ggtgtttgaa aatttggaaa tcttgattat tttttgttt gggattttgg    4740
ggtttgaggg caaatggcta tggtggtaca gcagcatagg gagagtagta gtggtagtat   4800
tacaaaacat cttgacagta gtggaaagta tgtccggtat acagctgagc aagtggaggc   4860
attagagagg gtttatgcag agtgccctaa acctagctcg ttgcgccgcc agcaattgat   4920
ccgcgaatgc cctattctgt cgaatatcga gcctaagcag atcaaagttt ggtttcaaaa   4980
cagaaggtac actgcccgct gttcaatttt gattgctcca atttggtttc tttttgttc    5040
ttaaatgcat atatttaggt gtcgtgcact tgtgatcttg gactgaaata tgggataagt   5100
tagatgagtg atggttaaat tggaatatat cactgtgctt ctagtttcct aggcttgtcg   5160
attgggttgt atggattaat cggggggggg gggcattaag tgaatcgtga attggatgtg   5220
tagtttgatt tctgtctgtc gggtagttga gcttagattt tggaattgag ggtgaacatt   5280
gtgccatttc aggtgtcgag agaagcaaag gaaagagtct tctagactac agactgtaaa   5340
tagaaagctg tctgcaatga ataaactatt aatggaggag aatgatcgct tgcaaaaaca   5400
ggtttcacag cttgtgtgtg aaaatggctt tatgcggcaa caattgcata ctgtaagtta   5460
acataatttt tcctttatac ttgtggtaaa aagctttatt ttttgcttac tgtagacgaa   5520
tggtaacgta tatcttgtct tttgtttctg atgaaatggc taagcactat gaattttaag   5580
atttctgata ttccacagct tatggtaaca tattttaaac agtgtaaata aactttattc   5640
```

```
tgatgacact gttttaggac attcttatag ttatggaatg catggcttta gatatgggac   5700
taaattttat gttcatcgtg tttttgcatt ctatattctt ctactcgccc ttgttttgct   5760
gtgaagttga accaataaac aagaaacaga tgatggatat ctccggtgat cttttgttcc   5820
ataggattaa ttagactgta tttgtgtttt ctgcaggcat cagcggccac tactgatgta   5880
agttgtgagt cagtggttac caccccctcag cattccctca gagatgctaa caaccctgct   5940
gggtaattaa tttcaaacac ctatttctcc catcctttcc gtctatggtg tccattctcc   6000
aacatattta tgttatttat tcaatggcat atacaacatt ttgaggggct aatttgttta   6060
tctctaagtc aagtttgttc tctatgcaga ctgctgtcga ttgcagagga aaccttagca   6120
gagttccttt ccaaggctac aggaactgct gttgattggg tcccgatgcc tgggatgaag   6180
gtttgaactt tagtcaatcc tctttatttt ttgaaaattc agtattgcca tgtctctttg   6240
actggatagc taaaaaacta aattttcatt ctattgccag cctggtccgg attcagttgg   6300
gatttttgcc atctcacaca gttgtagtgg agtggcagcc cgagcatgtg gtcttgttag   6360
tttagagccg acaaaggtaa gcagtcatgt ggaaaattaa tttaaatgta gtgctgttgc   6420
tctattacta gttttggtcc tttgacgggt gtactagatg ttgccagttt cttcttagta   6480
aatatatttt tgtcaaatat ttacagattg ctgagatcct caaagatcga ccatcttggt   6540
tccgagactg ccggaacgtt gaagttttca cgatgttttc tgcaggaaat ggaacaattg   6600
agcttttgta cacgcaggta attaattacc ttctcatcaa tcttcacgta ggcttctgat   6660
tggagaagct acagcattga ggggattttt gaaatcattt cttttcagat atatgctcct   6720
accaccttgg ctcctgcacg tgatttttgg actctgagat acacaaccac cctggagaat   6780
ggtagttttg tggtatgcac atcctccgca ttagcgtgtc ttaggataag caatctggcc   6840
acttttgtac ttagttatga atattttgct gatagtttgt tgtatgtgcc atcaattcct   6900
cctcccctca aggtttgtga aagatccctc tctggtactg gagctgggcc gaatgctgct   6960
tctgcttccc agtttgtaag agctcaaatg cttccgtccg gatatctaat ccgaccgtgt   7020
gacggtggag gatccattat acatattgtt gaccatctga atcttgaggt cagattgcac   7080
actgtactac cacttccctt tctttttaac ttgttctgtc ttgcagctgg acttcacggc   7140
ataatgtttt tcttcaggca tggagtgccc ctgagatttt gcgtccactt tatgaatcgt   7200
caaaagttgt ggcacagaaa atgactattg cggtgagttg aaccgttgat tgtcattaaa   7260
tactggatgt gtaacaacct ttttagtctt cacaactaga tctcaatttt tgttgagctc   7320
tgaagtcgaa agggttgtaa tttctggacg agcagttaga tatagcctga tatttttgtt   7380
tattcagtta gaagttccca gctttaaaaa tatagaacac ctgacaaatc cttagtctct   7440
taatgcacgt tattgaggat ttctttgttt tttcgagttt tctaaggttc attattgttt   7500
tcctcatggg gttgccataa aagtctgcat gtgaaacata tagtattgaa gaactgtagg   7560
ctgtgaagcg caccatactc ttaactgcat tagttgttgc tttaattcca tatgttgctc   7620
tgagaatact tgcagcattt tttatgtttc aagtacttga gcaattaccg tagcttacca   7680
tcacaacaaa agaaatacta attatagtat gtttttgctg taaaggcact gcgatatgca   7740
aggcaaatag ctcaggagac tagtggggag gttgtatatg gtctgggaag gcaacctgca   7800
gttcttcgaa catttagcca gagattaagc aggtgctgtt tattgctctg attgttctgt   7860
gctatgagat atgatatgcc ataaaagtag acatacgaat tctgaagcac aagtatcata   7920
attaagctat tttctatatt gcagaggctt caatgacgcc atcaatggat tcagtgatga   7980
tggctggtca ttgttaagtt ctgatggtgg tgaagatgtt atagttgctg tcaattcaag   8040
```

gaagaacatt gccaccactt ccgttcctct ttcaccgctg ggaggcatcc tttgtgccaa 8100
agcatcaatg ctactccagg tgaatagatt accttttaac tgactagaaa ttttcattgg 8160
ccaactacct ttgccttgtt agataaaatt gttccagact gttgcagatt ttgatgatgc 8220
tttcaatttc taaactcttg gaatgaatcg ggattcctgg aatataagag aatattactc 8280
agtgttctat aaagctattt gtttaatgca ccatgtgggg catcttgttg ctattaaatg 8340
gaagaatgag aattgacttt taactcttct gtatggtggc agaatgttcc tcctgtggta 8400
ctggttcgat ttctcaggga gcaccgttca gagtgggcgg actttaatgt tgatgcctat 8460
gtagcttcgt caatgaaatc ttgttcatat gcatatcctg ggatgaggcc taccagattt 8520
accggaagtc agataataat gccacttggc catacaattg aacatgaaga ggtaagcact 8580
ttgcacttgc cccagttcca tccatcccat gtgttggagt gtgcttatac agcaccagta 8640
tttttataa tcagaaagtt agcactcttt gaattgctag gcttgttacc taatattgct 8700
aatattatac tttagacttc ctctcatttt ttttttattt tgttttgctt tgcagatgct 8760
tgaggttatt agattggaag gacactctat tggccaggaa gatactttta tgccaagaga 8820
tgttcacctt ctccaggtac cttttgccta tgcattgatg tttcggtgtg ttatctacgt 8880
acagacattg ttgaagcaat agctaacaaa cggttatttc tagatgtgta gtggaactga 8940
tgagaatgct gtcggagctt gttctgaact agtttttgct gcaattgatg agatgtttcc 9000
agatgatgca cccctgttgc cctccgggtt tcgtatcatt cctctcgagt caaaatcagt 9060
tgagtaaaaa tatttcattt tcaactttaa gcattgaatt tggccaatct attgtttaca 9120
tggattattt ttcattttgc ttgattttgg agcataaccg gtgattctat tttcagagcg 9180
atccccagga tacatcgaat gctcatagaa cactggatct ggcatcaagt cttgaagttg 9240
gcccagcaac aaaccctgct actggagatg tggtctctgg ctacagtgca cgatctgtgt 9300
tgacaattgc ttttcaattt ccattcgagg acaatcttca ggacaatgta gctaccatgg 9360
cgcgccagta tgttcgcagt gtggtttcat ctgtccaacg ggttgccatg gcaatatctc 9420
ccgcaggagt gaattcaaca ttcgggtcca agctttctcc aggctcccct gaagctgtaa 9480
cgttgtcgca ctggatctgc cagagctaca ggtaaaatga tttctcaact atggtgaaac 9540
cttgttctct tcgtttcagc tcaatatggg gtttattgct ttacatgttc atactgtcgt 9600
gcttacaagt cactcgttgc aaatctcatt taccaccaag agccaaagta gtgtcaagtg 9660
tgcatgttga gatcttcaat tattttatga gaatttttcc tttctcaaca tattgagaaa 9720
aagcagacgg tcttagaagt acttttctga ttgttaacat accgttttct tcttttgcat 9780
ttaatatcca gttatcacat ggggacagag ttgcttcaaa ctgattcgag gggcgatgaa 9840
tcagtgctaa aaaatctttg gcaacatcag gatgctattt tgtgctgctc attgaaggta 9900
tgaattctct tatcatgtaa acagcatgtt acggttagta aaaaaatatt gtatgttgtg 9960
ttgcggtgaa acatgaacat atacgtaaag aaaaaatgta ttaacctagt aaatccacga 10020
tgaaggcaga tttgttcaaa agttaatctc atgaccctaa ttaatattag aatacgaaag 10080
agctggacaa ggatattaga aataagtccg acttaaatta tacttgtgat ggtgatattt 10140
tatggtgaaa atgccatatc atgggtgtat atttgaacta cttgtgattg gcattttgat 10200
tgtcctcatt ttggtcccta gcatgctttt gacatgtcaa catggaaatg agttgctaag 10260
aaattggaag gactgaccta ttcgttcacg ttccttttat cttgttaaaa gaatgtgttt 10320
agtaagttaa atttctttct ctgctgttgc agtccctgcc ggttttcatt tttgctaata 10380

-continued

```
aggctgggct tgatatgctg gagacaacct tagttgcttt acaggacatt actctagata  10440
agatatttga tgaatctggc cggaaagtgt tgttcgctga atttcccaag atcatggaac  10500
aggtatttac agctgactct ggtcttttgc agaacctaga aaacaaaagt tgaggtctta  10560
actgttactt ttttccgcga tgttgattct tgatcatagg gttttgcgta cttgccgggt  10620
ggtatttgca tgtcagcaat gggacgacat atttcatatg aacaagctat tgcatggaaa  10680
gtctttgctt ctgaagaaac tgtccactgc ttagccttct catttattaa ctggtcattt  10740
gtttaatgtt gctgtcaaat ctcctttctt ttttttcctt tttgtttttt gacatcttcc  10800
tcacagagga cactgacagc caggaacaca gttgaacgga atgatctttg ggacggatga  10860
aaattttgta acttgggggg ctcccgtctg ttttaccttt aatttaatta gactaaattt  10920
gtattttgct tcctgaattc ttcatactct tatgtaaatt ttctagtgca gcttttttga  10980
gtgcagatgt ttgtttccgc atattctacc actgattcat tttatattta gctttagtat  11040
ttgcagtgat attcaagatg ctgcaatgtt gctaagctta tgtgatattt ttttcttata  11100
acaactgaga aaacttattt cgacaactta acttgaacgg aaatcctaca ttattaaaca  11160
aagagtagat aaaggttagt cgtgaatgga agataaatta ttataatata tacaacaaag  11220
ataagtacaa aataatgatg gtctcgattg ttattttaaa ataaatttta ggtttaatgt  11280
gtgcttttgg acttgaataa caagctcaag atgtgctagg gagattgcct ccaatgaata  11340
agacctgtct tatcatccat tatatgctat gtaatgtcaa agattcaagg gtgcccacta  11400
tacttttgca caatcctgca catatagcaa cagccaacaa gcatagcaca actcaagttt  11460
gcgcattgac ctgctttaca caatttgtat ttacacactg cagcggcaat tgtatgtttt  11520
ttggacatgg atcatccaga caaacatctg caatatcaga acaaaaatca gttctttaca  11580
aaaatgtttg gatattgttt gagtatttcc tgagaaccat tcttcctctt caccgagatg  11640
caagtgacca aaagtttaag agaaatgatg gcatagcaca gaaccagcta agaaaggcca  11700
tggcagtagc agtctcaaac tctgtgcagt gattctgaga gcagacacca aggtcattgc  11760
caatcagtac agtaatgcca gcagaagcac aggctgcagc aaacgtgagg gtagaagtga  11820
cctgcaagaa agatagtatt tataaggaga tgaatggaaa ggagtcatgt agctactcag  11880
atgcttcagg atgagcttat atacaacttg tgttaaatgc tcaaagcgga atgtggtgca  11940
cgcatagccc gaaaagttta taataatgga gtaaaaggaa gagaccaatt caagaagtgc  12000
aaaatggaga taggtacggg ggatttgctg ttataataaa ttacaaatct ggttatcaag  12060
aaacaataaa ctattaactc cagactatga gatatttaaa agataataga gcttttctac  12120
ctacaaggta atttctacat catattagaa gggttgagga accaggttaa aaaaaccaat  12180
tttatgtctg acctcacaga ccttgaggga tcagcgatgg atcagaaatg cccaagaata  12240
catcaaaaag tagcaaaatc tcctacaaaa tgaacagact gaggaagaag ttcccaccag  12300
acgggtaact gggctaagag ggctcaaaat ctgtttcagt tattgcacgg aagttgtcca  12360
actgtgacta agtcttacat aaactgtgtc actctcttcc atcattaggg acgaatgatc  12420
tggatcccca gccattcata tcataactct ttcatgcaag agtttatcac tctattcata  12480
attaattttg cagtcaattt tattccgaaa agaaacatag caagactata ttaatattaa  12540
ccaatttaaa gtcccaaatg agccatgaca tatatcaata ggcatattaa acttggagag  12600
aacgaaagag ggcatgctgc caaagtttat atcaataggc atattaaact tggagcgaaa  12660
acgaaaaaag ggaatgttgc caaagtttac ttgcaaagag gaaattttag gggaaaagtc  12720
atatttacta attctctaat accatttcaa ttcactttta aacaattact atgagtagcc  12780
```

```
caaatcattg attatgttta actgcgcatc tttcatatct ttctgagctc cttaaataaa  12840
tggctattgc ctattgcaaa attcatatac cacaagtata cgaccaactt tactggtgca  12900
gtaaaatact gcttatccgg ctcttaaatg taaaaaaggc atgttgctta taaggcaacc  12960
aagagaatgt gaccatctta aacgtaaagg gtacctaatt ttaatatttc attgctgagt  13020
atacaataaa aaaattaggc aactcaactt ctctattttt tttttctgta taaactctat  13080
ggatacacca tcttactccc ttcttccact atccttttta gtgcaccccc aaaagattga  13140
aacatttcta tttatgaaaa ctacctccca acactatcct tttcactaaa aaagaaaatt  13200
ttaatgctca tttctaccaa gagcgagcca tcagcattca tgatgaagta tatcatgata  13260
gaaaggccat tttcgcaact tgtgtttgtt ttacttatgt gtgtatacat ttctaaaatt  13320
cactttccaa taaaaccacc tcataaatatg gaacggacgg agtactaaaa gtcataagtt  13380
tataggaatt ccaagttcat gaaacaccct taacagctag ccaagttatc aaaggctatg  13440
ccctacttct tgagttgtca cccgcgtttt atgagtttct catagttgca tcatcgcggt  13500
gcctagaggg gatatgtacc aacttaatct taccaattag tctaaagaaa ataatttgat  13560
atgtatttgt gcaagacgtt gaagcaagct ggtagaggtt gtattcaacg gcacaaaaac  13620
caatgaagcc ccttaatttt ttgaatccaa tataatactt ttagaatcct tataaaaaaa  13680
atgtttagaa tgccattact agaatttagt aagcatacca tgaggtctct aagaaattaa  13740
tcatctctct catggcatta tatattacac aaccttccct taaattttgg tacctatacg  13800
agaccctctg gatgggtcaa aaactgaata actaaagaaa caacaaagaa ataggcatta  13860
ctttttctta ttttacctta taaaatagaa ataattaatt ttcaaacttt atgccataga  13920
ggatgcccta tccatcactg gtaactactc gtgagaccaa gcaagtggaa taatccgaag  13980
aaagaggggt gagggagact cctaattgtt tcccccattt agatcctgta aatgcaattt  14040
aattccctca tcctatttgt ttgctccatt aagatattat taataaacac attttaataa  14100
aattagtaga gatgcatatt tccaagtgat tgttttgtat taaccaaacg taataaataa  14160
ggatatttac aaaaactcta gtacatattg caagatccat tcaatgggat ggaagaagca  14220
tgcagatcac ttcacaaact attgacatag tttttttatta tctggattga tcatatttgc  14280
aaatagttta caaagtttta agattaaatg cattaaattg gtataaatata taggatctaa  14340
agtcattcaa ttcactagaa aactcgtgaa attgtgacct tggaccttaa atagcaacag  14400
aagaatgaaa ggccagcgga aattctgtta aatacatggt cattatggac aagagaaaat  14460
gggtatggtc attgcacaga attactccat gagtagatgt gaatattgac aatattgaat  14520
tgtgtttaat ccagcacaag ctgccccact cttgagctag tcaattttcc ggcacttctt  14580
ccacatacat aagagttgaa aaccaaaaat tggccctgga taacttatat ccaagcttca  14640
tatttcaaag actactaggt aggcaattag ggcataatat ctctggaaac ctagccaatt  14700
tctttgttaa aaagaaaaat gggtaaataa aaataatcaa acattctaaa caactgaaga  14760
gtagttaaac aaaggtcatt ttgcataaac aggaagttag tgcatgcata atatacaagc  14820
tatctcaatt aaaactggat aagacataaa gaaaaatcat atcgatccaa gtatatatgt  14880
attaaaattt tcagtgcaat tgcaaggtgg aactaaacca gaaacacata agcaaaagtc  14940
atatctttcc atgccaatcg caagctggaa agttttttaa ttccatatta tacttatcaa  15000
acgaaagaaa gtcacgacac tcatctattt gatcaattgc aatagctatc ttttgtatca  15060
agtccttgca cgtctgattg tatcagtctc tattcaaaag cta                   15103
```

<210> SEQ ID NO 55
<211> LENGTH: 14465
<212> TYPE: DNA
<213> ORGANISM: Nicotiana tabacum

<400> SEQUENCE: 55
agattttggc tattcttttt tgaaaatatt gtttgttcat gaaatatgat cacttttgat 60
tcaatttcaa gttgcagttt ttgggtgaaa attttctttc actcacaaaa atttaactct 120
ttttcaaatt aaatgcatat caaacacaac ttcaacttcc aaaagttatt ttcaccataa 180
cttcaaaaac tattttatca agttttgaca aaatctatat ccaaacgcta gcgaattgtt 240
tttacccaag aactgtccta cataagtttt tgaaaactcg aaatttctct tcaatttttt 300
tttaaaattg atcatattcc atgaatatac aatattttta attttttttt taaatagcca 360
aaagtatatg accaaccggg agctaaagtt taggttaaac aatcaaatgg ttaaaagact 420
agcataacaa tttagtcatg taggtgattt gctagtcatt ttcaaaatgt tacatttcct 480
agactggagc aggagcaaag attcaagaaa ttaatcctaa tactgacaca aatattagat 540
gactagtgtg aattgatctc atagggggat catccattca cttgctacct tactagccat 600
cagttaaaac aacgaaaaga ttgatacaga ttctcacaaa tgaagaaaaa aagaagtaaa 660
ctacaaggac aaaaaacaaa gatttaaagc ccatttggat ggtcttaaag atttgactgt 720
tatttttggt tcgttttaag taattttcaa cttatttcaa actctttata attttgagcc 780
cgttaggatt aactgattta aactagctga taagcattta gtgctgaaaa atatttttaa 840
gtgttgaaac tgatttaata aataagcagt tacatgtttg attacaagtg ctgaaattga 900
taataagttg ctgcaatatt tgataaaaaa aatgccgata aattcctttt ttgttaaaat 960
gacttaaata accttagaag tgtttacact tataaggacg taatttcttc aaaattttaa 1020
attccaaatc gatccaaata caaaatattc tatttgtcat tttttaaaa tacaactgtg 1080 cttagataag ataactttta tgataaatat aatttatttt atgctaagta tataatcata 1140
agttataata attaataaat tgataaaaaa ttttcaataa aaaataaacc taaataggac 1200
aaaatatttg aagagaaaca aacactgtgt ttatcaccac aacacttaga aagcaacaca 1260
cgtcctcatt tattacatac aattcaaaga ttaatacaca atcaatagat ataaatatgc 1320
aaaggaataa ataatttgct tatcttaaat agtcaatgag cattgtaggc ttgaagaggc 1380
gggggagggg ggtttaggtt gaaatagtac ttgagtcagt gagtatccat gtaagagttt 1440
tgttctaaaa aaaaatattt taaggataaa atagtaaaat ttttgatcaa atttaaagtg 1500
cttataagct aaaaatttat aagctgaggg tgaccgactt atgatttatt tttgacttat 1560
aagcacttga cttataaaca cttttaactt taccaaacgc gtaaatatac cgataaatgc 1620
ttataagcta gtttgacgag cttataaact taaccgaaca ccctcttact tatataaaaa 1680
taaaagaaaa tattaaaagt aataaatctt tttgcagaga gtagagtaga ggggtgaaac 1740
cctaatagtc agagagacag agtatagacc acaaaggggc acagtagcca taggtattgg 1800
cagaagaaaa gattatgatt tgaccaaagc atttatatcc acagtacatg gcgtgggtct 1860
tatatgtcat ttcatatact gtacattgga ctagcttgta aatgcgccga atgggtaata 1920
ttaaattttt tgtttttata ataataatgg ctaaatcaat ttattattta tcaactaatt 1980
tcacggtata tatatgttat cacaaaataa ataactttat attgacactt catagttttt 2040
gataattatt aatttttaat tatcaactag aaatattact gagaaaagaa tccagacagt 2100
agagatcata aatattaaca aagttctatt agtatcttat aaatgaggct taaatctaag 2160

```
tcaaaacaca agagacgttt gcaaatgtgc caacttatca aattatgaat cacatttcac   2220
aatctgcctg ataatccctt tgaatttaca ttaatacatg ctccaaaaaa tttaacttta   2280
ctcactttaa cttaagaaca ttggctttat tcctctaatt tgtgaatata caagcagctt   2340
gttctagaca ttactgaaat tcatttacgt acatttagtt tgaataacta tttaacaaat   2400
ggtaattgtt tttaaattct aaaaataaag gatagagaag gaaaaaacca tgagtaccac   2460
ccgtagagtt ctcttttaac ttctttttcc ttagagttta gctctgagtt aaaaaaattc   2520
atcttgataa tagtaaccat atatggaata aaaatgtcct ataatttcaa gggcagatat   2580
acgatatata taaattatga attcaatcaa atccaattgt atgttcaaat attcaattat   2640
cattgaattt agcattattg ctatccacaa aattcaaact ctagatatgc tttgatataa   2700
tttagattca tctagacaat agagaccata tagaaaaaaa aaatcctgta atttgaggga   2760
cagatatgcc atgtaagtta cgaattcagt caaattcaat aatttagtat cagatgtaca   2820
tatattaaat tctaatttag taactcaaat gatcattaaa tttagtggta ttccaaccac   2880
aaaatttaaa ttctaaatct ccttttatat ataatgtaga tcaagttaaa acattcatca   2940
agacaatatt gaccatatat ggacaaaaat gtcctttgaa cttttccctt ttatgtttat   3000
agctagaatt catgtttata gctagaaaaa atcatccaaa cagtggtgat cacatatttt   3060
attttattaa aaggaaaaag aaaaagaaaa agaagttgta ttattatact ctagcagata   3120
actgaatatt tatattcgta cgtaccatat tgcaatttta attaaattat tagtgaagaa   3180
aaaggacata aaataaaaga aaacagaaaa acacaaaggc aagagcaaca gcagcagcat   3240
aaaaacactg gcattttcga tttgcgagct cataaagctt taagtcaagc aaattcccac   3300
atcacagtct ctctctctct ctccattttc ttttgccctt ttctcaccca ccactctcac   3360
acacctcttc acctcacctt acacacacta aaaaaacatc acttctctct gtctctctct   3420
ctaaaaaaaa ttctatcttt ttgctgttcc aacatgtctt ttagagtttg tttcagtttc   3480
agatcttaag tgggaggtgt tatgcttctt cttatatatt gaagctcaag aaaactaaga   3540
aaacagagca aatttttgct ttcttttctc ctacttttg tgggggtaat tcttgttttt   3600
gtaatctcaa agctggctat tttatgtata tactgaaggg gttgtggtga tttgtttgtc   3660
tactttaaga aggtgccatc tttttcagta atatttgggt aaaggttctc ttttttggc   3720
cttacacgcg aagattcagg cctctctgaa cgtgtcattt gttctctgta ttaaacacag   3780
ctggagaagt aattacatca aggtagaaaa aggggttaaa gattccaaag aattgagtgt   3840
ttgaaaaaaa aaacagaggg ctgaggtaaa aagttgatgg ttttaaaaaa aataaattaa   3900
atgatgatag agtttggagc tttatgtgaa tggaaatggt gttgtgtttt tatcaaacac   3960
gagtagttta cagcttatgt gaatttgaaa gagagagaga atttttgtct gtatttatat   4020
ccttttcagc catatctttc gttagagcag ttttggctgt accttaattt gtaagttttt   4080
aagcgtgaag tgtgtgtttg agccttctgt tataaggggc acaaagtata gaaacaacaa   4140
aagggggcac ctaggaatct tctggctcaa tcaagatcgt tcatttaatc ttgtctgaga   4200
tcactagaaa aagaaaaaaa aaagagataa agataaagtc tttgtttcag agaatcttag   4260
ttctctgtgt tgatatatat aataaaagct gtttgcaggg aatatatcta cttgggggtg   4320
tttttatttc ttaaaagggt gtttgaaaat ttggaaatct tgattttttt tttggtttgg   4380
gattttgagg tttgagggca atggctatgg ttgcacagca gcacagggag agtagtagtg   4440
gtagtattac aaaacatctt gacagtagtg gaaagtatgt ccggtataca gctgagcaag   4500
```

ttgaggcatt ggagagggtt tatgctgagt gccctaagcc tagctccttg cgccgccaac 4560
aattgatccg tgaatgccct attctgtcga atatcgagcc taagcagatc aaagtttggt 4620
ttcaaaacag aaggtacact gcccattgtt caatttggat tactccaatt tggtttcttt 4680
tttgttctta aatgcatata tttaggtgtg tactgcactt gtgatcttgg gctctagttt 4740
gtttggtact gctcaaatct tggattagtt agatcagtga tggatgaagt ggaatatatc 4800
actgtccttc tagtttccta ggcttgtcga ttgggttgta tgagttaacc gtggggcatt 4860
aagtgaatca tgaattgcat atgtagtttg atttctgtct gttgggtagt tgagcttaga 4920
ttttggaata gagggtgaat attgtatcat ttcaggtgtc gagagaagca aaggaaagag 4980
tcttctcgac tacagactgt aaatagaaag ctgtctgcaa tgaataaact attgatggag 5040
gagaatgatc gcttgcaaaa acaggtttcg cagcttgtgt gtgaaaatgg ctttatgcgg 5100
caacagttgc atactgtaag ttaacataat ttttccttta ttatttatgg taaaaaacct 5160
ttttttcac ttaacgtatc ttgtcttttg tttctgataa gcactatgga ttttaagatt 5220
cctgatattc cacagcttat ggtaacatat tttaaacagt gtaaattgtc tttattttga 5280
tgacaggttt taggtcattc ttatagttac gaaatgcatg actaaatttt gaattcatcg 5340
tgtttttgct ttctatattc ttctacccgc ccttcttgtt ttgctgtgat attgaaccaa 5400
tggacaagaa acggatggca gatatctccg gtgatctttt gttctgtagg aattaattag 5460
actgtatttg tgttttctgc aggcatcagc ggccactact gatgtaagtt gtgagtctgt 5520
ggtaactacc cctcagcatt ccctcagaga tgctaacaac cctgctgggt aattaatttc 5580
aaactcctat ttctcccacc ccttctgtct atggtgttta tacatattta tgttatttat 5640
taaatggcat agaccacatt ttgaggggct aatttgttta tctctaagtc aagtttgttc 5700
tctccgcaga ctgctgtcga ttgcagagga aaccttagca gagttccttt ccaaggctac 5760
aggaactgct gttgattggg tcccgatgcc tgggatgaag gtttgaactt tagtcaatcc 5820
tttttgttt taaaaaaaaa ttcagtattg ccacgtgcct ctttgactgg atagctaaaa 5880
aactaaattt tcattctatt gtcagcctgg tccggattca gttgggattt ttgccatctc 5940
acacagttgt agtggagtgg cagcccgagc atgtggtctt gttagtttag agccgacaaa 6000
ggtaagcagt cttgtggaaa attaatttaa atgtagtgct gctgctctat tactagtttt 6060
ggtcccttga tgagtgtact agattatgcc agtttcttct aagtacatat atttttgtct 6120
aatatttaca gattgctgag atcctcaaag atcgatcttc ttggttccga gattgccgga 6180
acgttgaagt tttcacaatg ttttctgcag gaaatggaac aattgaactt ttgtacacgc 6240
aggtaattaa ttactttctc atcaatcttc acgtaggctt ctgattggag aagctacagc 6300
attgagggga ttgttgaaat catttttttt ccagatatat gctcctacca ccttggctcc 6360
tgcacgtgat ttttggactc tgagatacac aaccaccctg gagaatggta gctttgtggt 6420
aagcacatcc ttcacattag tgtgtcttag gattagcaat ctggccactt ttgtacttag 6480
ttatgaatat tttgctgata gtttgttgta tgtgcccatc aattcctcct ccccgtaagg 6540
tttgtgaaag atccctctct ggtactggag ctgggccgaa tgctgcttct gcttcccagt 6600
ttgtaagagc tcaaatgctt ccgtctggat atctaatccg accgtgtgac ggtggaggat 6660
ccattataca tattgttgac cacctgaatc ttgaggtcag attacacgct gtactaccac 6720
ttctctttct tattagcttg ttctgtcttg cagctggact tcactgcata atattgtttt 6780
tcaggcatgg agtgcccctg agattttgcg tccactttat gaatcgtcaa aagttgtggc 6840
acagaaaatg actattgcgg tgagttgaac ccttggtttt tattaactac tggatgttta 6900

-continued

```
acaacctttt tggtcttcac aactagatct caatttttgt tcagctctga agtagatagg   6960
attgtacttt ctggacgagc agttagatat agcctgatat ttttgtttat tctgttagaa   7020
gttcccagct ttaaaaatat agaacacctg acaaatcctt agtctcttaa tgcacgttat   7080
cgaggatttc ttcgttattc gagttttcaa aggttcatta ttgttttcct cattgtgttg   7140
ccataaaagt ctgcatgtga aacatataag taatgaagaa ccttatgctg tgaagcacag   7200
catactgtta actgcattcg atgttgctta attccagaag ttgctctgag aatacttaca   7260
gccttttttt atattttaag tacttgagca attaccgtta cttaccacaa cagcaaaaga   7320
aatactaatt atggttagtt tttgctgtaa aggcactgcg atatgcaagg caaatagctc   7380
aggagactag tggggaggtt gtatatggtc tgggaaggca acctgcagtt cttcgaacat   7440
ttagccagag attaagcagg tgctggttat tgctctgatt gttctgtgct tcgagatatg   7500
atatgccata aaagtagaca tacgaatcct gaagcgcaag tatcataatt aggctatttt   7560
ctatattgca gaggcttcaa tgatgccatc aatggattca gtgatgatgg ctggtcattg   7620
ttaagttctg atggtggtga agatgttata gttgctgtca attcaaggaa gaacattgcc   7680
accacttccg ttcctctttc accacttgga ggcatccttt gtgccaaagc atcaatgcta   7740
ctccaggtca acagattaag ctttcttgaa ctaactacag attttcattg gccaactacc   7800
tttgccttgt taattcactg aataggtcaa gtaattctaa agacaagttt tgcagtgctc   7860
ttgttgcctt gttagttcat agcaaacaga gttgcagctg ttcaaagtag gatcatatat   7920
tgtgatacct attcagtatc tgtattagat ctagtatcac aagacaagtt ttctttactg   7980
ctcttgtttc ttagaaattg gctctatact cttactaaaa aagagcgata atggtagatt   8040
ttgaagtcga ggaaaaatta aaatcgttcc ggattgttgc agatttttat tatgctttca   8100
atttctaatt ctaggaaaga atcaggattc ctggaatatt agagaatatt actcagtgtt   8160
ttataaagct atttgtttaa tgctctgagt agggcatctt gctattaatt ggaagaatga   8220
gaattgactt ttaactcttt tgttcggtgg cagaatgttc ctcctgcggt actggttcga   8280
tttctcaggg agcaccgttc agagtgggcg gactttaatg ttgatgccta tgtagcttcc   8340
tcaatgaaat cttgttcata tgcatatcct ggggtgaggc ctaccagatt taccggaagc   8400
cagataataa tgccactggg ccacacaata gaacatgaag aggtaagcgg tttgcaattg   8460
ccccagttct cacttatgtg ttatggggaa tgcctcgaca tacatgagca agaatttgag   8520
acttgagact tcctctcact ttattttggt ttgcagatgc ttgaagttat tagattggaa   8580
gggcactcta ttggccagga agatgctttt atgccgagag atattcacct tctccaggta   8640
cttttgctta tacattgatg tttcggtgtg ttgtatgtac atacattgtt gaaggataat   8700
gctaacaaac agttatttct agatgtgtag tggaaccgat gagaatgctg tcggagcttg   8760
ttctgaacta gtttttgctg caattgatga gatgtttcca gatgatgcac ccctgttgcc   8820
ctccgggttt cgtatcattc ctctcgagtc aaaatcagtt gagtaaaata ttttgatttt   8880
caacttcaag cattgaattt ggcaaatcta ttgtttacat ggattttttt ttttcttttc   8940
attttgctcg attttggagc ataaccggtg attctatttt cagagcgatc cccaggatac   9000
atcgaatgct catagaacac tggatctggc atcaagtctt gaagttggcc cagcaacaaa   9060
ccctgctact ggagatgtgg tctctggcta cagtgcacga tctgtattga caattgcttt   9120
tcaatttcca ttcgaggaca atcttcagga taatgtagct accatggcgc gccagtatgt   9180
tcgcagtgtg gtttcatctg tccaacgggt tgccatggca atatctcccg caggagtgaa   9240
```

-continued

```
ttcaacattc gggtccaagc tttctccagg ctcccctgaa gctgtaactt tgtcgcactg   9300
gatctgccag agctacaggt aaaatgattt ctcaactatg gtgaaacctt attctctgca   9360
tttcagctca atatggggtt tattgcttta catgttcata ctgtcgtgct tacaagtcga   9420
ttcattgcaa atctcattta ccaccaagag cggaagcagt gtcgagtgtg catgttgatc   9480
ttcaattatt ttttgagaat ttttcctttc tcaacatatt gagaaaaatc agatggtctt   9540
agaagtactt ttctgattgt taacataccg ttttcttctt ttgcatataa tatccagtta   9600
tcacatgggg acagagttgc ttcaagctga ttcgaggggc gatgaatcag tgctaaagaa   9660
tctttggcaa catcaggatg ctattttgtg ctgctcattg aaggtatgaa ttctcttatg   9720
aactcatgta aacagcatat tacggtttgt tagtaaaaaa attgtaggtt gtgttgcggt   9780
gaaacatgaa catatgcata aagaaaaatg tattaaccta gtagtgtcat gaccctaatt   9840
aatattagaa tatgaaggag ctggacaatg atattaagaa ataagctcga cttaaattat   9900
atttgtgatg gtgatttttt atggtgaaaa tgtcatatca tgggtgcata tttgaactac   9960
ttgtgattgg cattttgatt gtcctcattt tggtccctag catgcttttg acatgtcaac  10020
atgcattgct tttgacctat tcatccgcct tctagtcttt tatcttgtta aatgaatggc  10080
gttagtaagt tgaatttctt tctctgctgt tgcagtcgct gccggttttc atttttgcta  10140
ataaggctgg gcttgatatg ctggagacaa cattagttgc tttgcaagac attactctag  10200
ataggatatt tgacgaatct ggccggaaag tgttgttcgc tgaatttccc aagatcatgg  10260
atcaggtatt tacagccgac tcttagtctt tgcagaaccg agaaaccaaa gttgaggtct  10320
taactcttac tttcttcgat tctgtttatt cttgatcata gggtttcgcg tacctgccgg  10380
gtggtatttg catgtctgca atgggacgac atatttcata tgaacaagct attgcatgga  10440
aagtctttgc ttctgaagaa actagtgtcc actgcttagc cttctcattt attaactggt  10500
catttgttta atgttgctgt caaatctcct cttttttcc tttttgtttt ttgacatctt   10560
cctcacagag gacactgaca gacaggaaca cagttgaacg gaaagatctt gggaccgatg  10620
aaaattttg taacttgtgg ggctcctgtc tgttttgcct taatttaatt agactaaatt   10680
tgtattttgc ttcccggatt cttcatactc ttgtgtaaat ttactagtgc agctttttg   10740
agtgcagatg tttgtttcca aatattcgtt cactgaatca tttcaattta gctctagtat  10800
ttgcagtgag aatcaaaagt ttgtgatact tttttggtat atcagcagag aaaacttctt  10860
tcagcaactt atcaatttga ttggcaatcc tatacgacta aatagactcg ataaaggctg  10920
gttgtgtgaa tgtaagataa taaattatat atactacagc aagagttaag gatgaagtac  10980
aaaataatga cagcctcttc gattgttatt ttgaaacaag ttttaggtga aatatgtgtg  11040
cttttggact tgaatctaaa tgttacgttt gaataacgtc ggaacaaact ccaaatgtgc  11100
taggaagagt gcccacgtga tgtcaaagat tcaagagtgc ctactatagt ttttgcacaa  11160
tcctgcacat ataatagcag caagcatatc acaacacaag tttgcgcatt gacctgcttt  11220
acacaatttg tatttacaca ctgcagcagc aattgtatgt ttcttggaca ttgatcatct  11280
agacaaacat ttgcaatatc agaacaaaaa gcagttcttt ccaaaaatgt tcggacattg  11340
tttgagtatt tccttgagaa ccattcttct tcctcttcac cgggatgcaa gtgaccaaaa  11400
atttatgaga aatgatggca tagcacagaa ccagctaaga aaagccatgg cagtagctgt  11460
ctcaaactct atgcagtgat tctgagagca gacaccaagg tcattgccaa tcagtacagt  11520
aatgccagca gaagcacagg ctgcagcaaa cgtgagggta gaagtgacct gcaagaaagc  11580
tgatattttt acaaggagat gaatggaaag gagtcgtgaa gctattcaga tgcttcagga  11640
```

-continued

```
tgagcttata tacaccttgc gttaaatgca caaagttgaa tgtggcgcac acatattccg  11700
aaaaagttta taataatgga gtaaaaggaa gagacaaaat caagaagtgc aaaatggaga  11760
taggtacatg ggatttgctg ttataataaa caccaactct ggttatcaag aaataataaa  11820
ctcttaactc cagattatga gatatttaaa agatgataga gctttttttaa ctttgctaca  11880
aggtaatttc cacatcaaat tataagggtt gtggagacca ggttaaaaac accaatttca  11940
tgtctgacct cacagacctt gagggatcag cgatggatca gaaatgccca agaatacatc  12000
aaaaagtagc aaaatctcct acaaaatgaa cagaatgagg atgaaagttc ccgggtaacc  12060
gagctaaaag ggctcaaaaa actgtttcag ttattgcact gaagttgtcc aagctgtgat  12120
taagtcttac ataagctgtg tcactctctt tagggacaag tgatttactt ctggatccct  12180
agccatttct atcataactc tttcatgcaa gagtttatca ctctattcat aaataatttt  12240
gcagtcaatt ttattccgaa tagaaacata gcgagactat atttacatta gccaatttaa  12300
agtcccaaat gagccatgac atatatcaat aagcatatta aacttggaga gagaacgaaa  12360
gagggcctgc tgccaaagtt tacttgcaaa gaggaaattt tagaggaaaa gtcatattta  12420
ctaattctct aataccattt aaattcactt ttaaacaatt accatgagta gcccaaatca  12480
ttgattacgt ttaactgcgc atcttccata tctttttgag ctccttaatt ggctattgcc  12540
tattgaaaaa ttcatatacc acaagtatac gaccaacttt actgttgcag ttaaatactt  12600
gcttatgcag ctctccagga tatgcatcct agattctaat ttatctatat ctcccaaatg  12660
gaaaggcaac caagagaatg tgaccatctt aaacgtaaag ggtaactaat tttaatattt  12720
ccttgctgag tttacagtaa aaaagttagg caactgaact tctctatttt ttttttctgt  12780
aaatactcta tggatagacc atcttactcc cttcttccac tatccttttt agtgcacccc  12840
caaaagattg aaacatttct atttacaaaa actacctccc aacactatcc ttttccttaa  12900
ttaatgctca tttctgccaa gagtgagcca tcagcattca tgatgaagta tatcatgata  12960
gaaagacaat gctggcaact tgcatttgtt ttacttatgc gtctatacac aggggcggat  13020
gtagttcatt accgacgggt tcaattgaac ccataacttt tgacgcagag taaaaatcat  13080
aactttaaaa atataatagg ttcaatgcta aaaactttaa aagttgaacc cataggattt  13140
aaatcctgga tccgcctctg tctatacatt tcaaaaattc actttccaat aaaactacct  13200
cataatatgg aagtgaccga gtactaaagg tcataagttt atatgaattc aagttcatga  13260
aatactctta acagctagcc aagttagcaa aggctatgcc ctacttcttg agttgtcacc  13320
cacgttttat gagtttctca tagttgcatc atcacagtgc ctagagggga tatgtaccaa  13380
cttaatctta ccaattagtc taaagaaaat aatttgacat gtatttgtgc aagacgttga  13440
agcaagctga tagaggttgt ataatggcac aaaaaccaat gaaggccatt aatttttttaa  13500
tccaatatat atttttagaa tccctaaaaa aaatgcttgg aatggcattt cttaaagtat  13560
ttagtaagca tacaatgagg tttctaagaa attaatcatc tctctcatgg cattatatat  13620
tacacaacct tccctaaaat tttgatacct atacgagacc ctctgaatgg gtcaaaaact  13680
gaataactcg agaaacaaca aagaaatagg tagtactttt tcttatcgta ccttataaaa  13740
aagaaataat taattttcaa actttatgcc ataaaggatg ccctatccat cactggttta  13800
ctcatgagac caagcaagtg gaataatcca aagaaagagg ggtgagggag actcctaatt  13860
ttttgctcca tttagatttg taaatgcatt ttaattccct catcctaatt gtttgcttca  13920
ttacgatata gttaataaac gcattttaat aaaattagta gaaatgcata tttccaggtg  13980
```

-continued

```
attgttttgt attaaccaaa cataataaat aaggatatta acaaaatctc tagtacatat  14040
tgcaagatcc attaaattgg atggaggaag tatgccgatc acttcacaaa ctattgacag  14100
tcttttacta tttggaagga ccaaatttgc acatagtgta caaagttttg tgattaaatg  14160
cattaaattg gtataatata tttggatctt aagtcattca attcactgca aaactcgtga  14220
aattgtgacc ttggacctta aataggaaca gaaggacgaa aggccagcgg aaattctgtt  14280
aaatacatgg tcattatgga caagagaaaa taggtatggt cattgcacag aattactcca  14340
tgagtagatg tgaatattga cagttaatat gcaaggaatt gtgttaaatc cagcacaagc  14400
ttccccactt ttgagctagt caattttccg gcacttcttc catactagtg gaggtaacgc  14460
ccgtg                                                              14465
```

<210> SEQ ID NO 56
<211> LENGTH: 9831
<212> TYPE: DNA
<213> ORGANISM: Nicotiana tabacum

<400> SEQUENCE: 56

```
acaagtgttt attgcccaga caggagagaa gtcacattgc caattacatg gatctagttc     60
ttatagagtg cctggagaga ggaaagcaaa tcaattgtct gccttcatta tcaagctgct    120
cgacagggtt ataaatggct ccaaggctca tgctactctt tatggcttta ttctaaccac    180
agttctggat agtctcaatg tgcctctaaa gaaatgggaa atgatctcga gaaaggatca    240
ctttggcatc aatactcttc ttgcttgtga ctatgcagtc aatgacatcc caaatgaacc    300
tggtacatcc tagaagacac ccatcaacag caaagtcagg actctggttc aggaatatgt    360
agccaaggat gctgaaatag ctaggctttt ggctcgtgtg attgaagtga aatttgagag    420
ggatggtctc agaactgagc ttgacaaaga aaaggagaaa aatgatggaa ttcttcataa    480
catgctgaac cttctccaag cccaaaccca accatatagt tcttccaagc cttaggactc    540
ctagcttttg tctcctgaac ttgtttagta cctcagtgac ccagattagg gatttttcta    600
tcttttattt ttgctcatga tttggatgtt tttctttctt tttgtggatt gttggtggca    660
acatatctct gtcaatgata actactattt tgctcttgtt taatgttaat ttgtccttga    720
tattttaaat atattttctt gattactgat gattactcca tgattacatt tgcagttgcc    780
gcagtggcca tgggtactta ttaaaatctg ggaatcacac tttgtatgta acatttcgat    840
gatgccaaaa gggagaagag agttgtgctt tacacacatt ctgaaataag taatatttat    900
aacctaatta acctggtcct tgatgttaag tgaattttct aagtttagta ttgatggtta    960
agctgagttc ttacaggtcc caaataagta aaaagcacag agtttgtcat catcaaaaag   1020
ggatatttgt tggcccaaga acaggtgaag ttttgaagat tgacaaaaga actcagacat   1080
ggaccaggtc catcttgtga agcacagtca tgatcaacct atacatgtga gatgcacgtg   1140
aaagagataa gtcttactga ttaagcaaca atatctcttg atctgatcga aaaggatgaa   1200
gatagtgtta gagtttgaga tcatcatgaa ctcttccacg atagaagagc agcaattgag   1260
tcacaatcaa actctgatta ctaacctatt aaatgtcagt ttgttctctt ttacaggaaa   1320
tacacatacg caaaagttaa actaaattga gagcaaaaga gcaaggcgat tttgcaagca   1380
atttatgtgt gatttgagtg tgcactcctg aagctacttg aacgagatag aagaaccagt   1440
tccatcgtgt ctatctttta ttctagttca attgtagtag gtggtttaaa attatacctt   1500
tcagctttca tagaagcaat tgtattagat acctagagtg ttcaagttat agctaacttg   1560
aagttgtcgc aacagttgag gttgtgtgcc acaacgggat tagagttaat ccttaggttt   1620
```

```
ataaagagtt tttgtaaaag ctattttggc tcagtgattt tagtggaagt ttgggaaaat   1680
cctactgagt tgtaggtcat ggttttttca ccttttgagc caggtgtttt ccacgtaaaa   1740
atctccgtgt tctttatttt ctgtatttat tattccgcaa ttagtagtag ttggaacacc   1800
tagaaaacca agttcttcta tagagtagtt aagcgaaaat tgggtgccac acaaatcacc   1860
cctctagtgt ggtattgacg cttaaaacat caattagtta atttctggag caactagcta   1920
ctagttgtta ttaaaatagt tagtttcttt gttagctaat atgttgtttt ggttgtaaat   1980
tagttccggt gtgtagtttg gactttggaa gaagacttgt accagattgt agtttgttat   2040
tttctttggt cttatgaatg ctcacactaa acatcaagtt ggtactttga ttttgcattt   2100
gaattagaag tagtagttga gacgtgttgt tgctatgcat aagtagtaaa agattggttt   2160
gagcttagtt ggtttcgtga taagattgga aataaaagaa atgtgtcaaa gttatgtaaa   2220
aatcagtaaa ataggctgct accttttaat attaccacaa gtccacattt attttagttt   2280
taaacaatat aaatttgtta aggtaatctt cttacaatag tctcatcttt taatttagta   2340
acagataatt gcaaagtcaa tccaactaat catacactac ccatatgtaa aaaaaaaaaa   2400
aaaaaaaaaa aaaaaaaaaa aaaaaaagtg aacaatcaat gcacaaaaag aaaaaaaaat   2460
atttttcttc tttaattaat tccataacat agtccttaaa attagttaat tctttgtttt   2520
agaaaaattg taacagtcta gttaattctc caaaatgaag caaaagattt tttttcttaa   2580
gtattacgtc acttttttta ttaatccacc aaataaatta aattagattt agttcactaa   2640
ataaactcaa taagatcaga tgttttattt atttataaaa ataactcaat tacttaatca   2700
caaatgatca tgactaactc aaaagtaatt tgttttaaca aaaataatta atttcgtctt   2760
aaccgatgtc gggacgactc attttggaat aaatacataa ataaaatggc caggtcgcga   2820
ggacacgtca tattccaatt ctttcaaata agcttgttat ttattaactt tgagtaggct   2880
ccaattttag gtgcggcgca cgaactaagg tcggagatat tcatcttggt tagcgtaagc   2940
tagggttggg gatattcgtc ctagtttgag attaattaag tcatcaacag taaaagtgga   3000
cataggcaaa acatgaaaac cgaataaagc acaatttatc cataattaat tcatgccaaa   3060
tttaagttaa taaagcaact gtgctagaac cacggactcg gagaatgctt tacaccttct   3120
ccccgatcaa caaaaatctt tattcggact ttatttttgc agaccgataa taatagagtc   3180
aaatcttcct ttgactaggg attcaaataa aaagtgactt ggaacatgca aaaatcaatt   3240
ccaagcgggc gaatctgtaa acaaaataat ccttattcaa atttgtcact ttaattgaaa   3300
aactctttaa cccactattc ataacatata tatttttggg gtagaaaagg ggtgtgacag   3360
ttatgaccta ctttatgcat cagtgttcga atttattttg atcaacaccc ttttggaaga   3420
gcgtttgata gaaatggttg gcttaataaa caatcatatt atcatcacct gcggaatcat   3480
atcattaact tttgaaaatt aaaatggttt tcaaagacgt tttgataaaa gaattcctat   3540
tgtcgcagtt ggaatctaca agaccaagat gttgatctag tgctatattt ggagaaagtg   3600
ccttaattaa aaaaaaattg ttcattagtt gtcttaagat tttttattat ttaaaaaaaa   3660
attaagacac aaagaaacac atttacgagt atatgtcggc cgactaatgt gaagttcccc   3720
acggacaacc cacacatatt gtggtcaaga tggattctat cataatcaaa agtcatcatc   3780
aattcaattc tcatatttgg catctcaagt acatgcacaa aagcaactta ggatgtaagt   3840
ttatatgcac attcttgaaa tagaacctat ttagtacgta gtacttaatt agttacagta   3900
gtattattta ttctctgcta cagagctatg gtttatcaaa tatatcagat tatcatttgt   3960
```

-continued

```
tgtgtaggcc atttccttat ttgtacttgg tattaattct ggcaaaagca caaaactggg   4020
aaatgaggtt cttcttcctt aatattgagt cacagattag taccactact atagccaaga   4080
aaatgtgaaa tcatatagta ctaaatatta atttcagatg ccaaaaccat aaatttcccc   4140
tcctccatca ttgaaaaccc cctctgtcct ttcccctaga gagacccctt tttcctctct   4200
ctctcctttc tctttttatt agacgcatat attctctctt ctttctcttt ctagggtttt   4260
cacctgaaat agttttattt cggtgatatg ttaggatcct ttggttcatc atctcaatct   4320
catgatgaag aaactgatga tcaacggcgg agattcagtt ccacttcccc tgcaatccaa   4380
atccggcaac tactcattag ctgcgcggag ttaatctcgc ggtccgattt ctcggccgca   4440
aacagactcc tcaccatttt atcaactaac tcttcccctt ttggtgattc aactgaaaga   4500
ttagtccatc agttcactcg cgcactttct cttcgcctca accgttatat ctcttcagcc   4560
actaatttct tgacaccatc taatgttgtt gaaagttcaa atgattcagc tctacttcag   4620
tcatcctatc tttccctaaa ccaagtgact cctttcatta gatttagtca gctaactgct   4680
aatcaagcga ttttggaagc tattaacgat aaccaacaag cgatccacat cgttgatttt   4740
gatattaatc acggtgttca atggccaccg ttaatgcaag cactagctga tcgttaccct   4800
cctccaactc ttcggattac cggtactgga aatgaccttg ataccctt cg tagaaccgga   4860
gatcgtttag ctaaatttgc tcactcttta ggccttagat ttcagtttca ccctcttttg   4920
attaccaata ataatgacaa tgatcatgac ccttcaataa tttcttctat tgttcttctc   4980
cctgatgaga cattagctat caactgtgta ttttatcttc acaggctctt gaaagaccgc   5040
gaaaagttaa ggattttttt gcataggatt aaatccatga accctaaagt tgtaacgctg   5100
gccgagagag aagcaaatca taatcaccca cttttttttgc aaagatttgt ggaggctttg   5160
gattattatg cagctgtgtt tgattcattg gaagcaactt tgccaccgag cagtagagag   5220
aggatgacag tggaacaagt ttggttcggg agagaaataa ttgatatagt agcagcagaa   5280
ggagataaga gaagagaaag acacgagaga ttcagatcat gggaagtaat gttgaggagc   5340
tgtggattta gcaatgttgc tttaagccct tttgcactct cacaagctaa acttctcttg   5400
agacttcatt acccatctga aggataccag cttagtgttt cgagtacgag taattctttc   5460
ttcttgggtt ggcaaaatca accccttttt tccatatctt cttggcgtta aatttaaaac   5520
cctaaaaaac aagattttta tctatctgca tggtgaagga caaagaggtc ttcaatctca   5580
ggttcttttt ttttttttt ttttatatat atatcttgtt tgggtttaag gttattgggc   5640
tgatgaatgt tttaatttta acataggtct acttacgtag tagttatagg ttgataatga   5700
gatataatta actaagtctt tgtataatgc agatcctgaa cttaatcttt atttgtatta   5760
tttttttttg ttactgaaag attctgttac caaattttat cagtctattt aattagaggc   5820
caacgattgt taggtatgtg gcacttcgag tgggaaatga tatattccca ttaaaggtgt   5880
taattaacca ccaaattgtt ctttaggtct gtttgtcatt ttgtattaag gtggatggtt   5940
tattatatat atcttctctt taatgctaat catgcttaac tttttcattt agtaccagca   6000
agcatatttg tttactttat tggttattcc ttatcaaagt cttcatcttg ttgctttttt   6060
ttattgtact ttacaaaaga tttctagtat taatggaaag tgctcatatt tggaaaaaga   6120
catggccaac aagaaatgtc tatataccccc atttcttctt cttcttcttt ttttccgaaa   6180
atttcttatt tttgttttta tttctgtttc ttgttgagtg ctttcatggt agaagaagaa   6240
gtaggagatt cttggacatg gctgcatgag aattgttaaa taaccccgta tacatacaca   6300
agtagtgttg gctgtctttg atatcaaacc atttattgcc ctaatttctg ccttttgtcc   6360
```

```
cctcaacaaa accatcaaag ttctcaaaga gggtttattc ttgtttccca ctttgccccc   6420
cacctattag ggccacccca ccaaagggat ctctctcgtg tctagtgttt tttcccaagg   6480
accaccactc cttttttttt ctctaccata acttcgtcca caccatctta ttgtgatatt   6540
ttcgtttaat gaatttgcag ccatgccttc attcatcatc agaactcagt cataagcaca   6600
gattctgaga gagtaattaa tgaatgaatc agtggtgatt tgacgtaaag tatacatgat   6660
tatggttttt agctgaataa gcagagggag aaaatatata catatataaa caagtagagt   6720
aaaagaatga cgcaagatta gtaccaaaag agtgaaggaa gagatttaat attataggga   6780
aaagggaagt agtaggtgat acttgacagg ttgataagat ggttattact acaagttgat   6840
gtattgacgc taactcacgc aagagagacc tactcactgt acaatatttt tacaagaata   6900
agcgattctt tctctcttta cttgcaagaa ttgtgtgttg tgtgagttgt atggcgcatt   6960
ttctaggagc ctgtggtagt gatggatgta ttcatataat acaatacaat acatatggaa   7020
tagatagata gataagatgg tgcacgcatg agaggcaatt atgcaactta cgtcaactac   7080
ttccatccat ccatcttttc ttccttctgt ttctgtctga tatagtgagt atatgcttgt   7140
gctggtgttg tgtgcttttc tggcctggga ttttcctaac actttagata atttaggttc   7200
ccatcaataa taatgtcttt ttagaggagc atcatcgata gatattcaaa tattaaacct   7260
ggcctagcta ctatctaggg cgtctgctag gtttttccat taccctttgt atatctctta   7320
tgtgggacct tttgtttatg gaagaatatg gagtactttt attcatctcg tagggtcttg   7380
aatacaagat tttatatata tcactcttta aaaatgacca tcctaaaatt cttcctcttt   7440
catttgcatt taccagaatt gatattagta cctaaactag tactcttcac tgaggccttt   7500
tgtatttagt cctattatat ttgaatttgg cactatttaa attaaaaaaa taatctacaa   7560
taaaaaattc ttccctaaac attacccatc aaatactcac cacctaaggt aactctacca   7620
tgtattaatt ttttggatca aatctagtga ggattaattc tccacttatg ttctttcgga   7680
actggctaag taatcttcaa aagctagggc atctccgcag tcatatcgtg ccctcccaag   7740
tatagcgacc gcttctatat tttccctgaa tttcatctgt gctagggctt gttttcacgt   7800
tgatttcaaa caaaggctaa caatttcatt gagtaacttt ttctcatttc aggactcgaa   7860
ccttaaacct ctgttcaaat aacttctaag aagtatatat gtatacaatg tttgtattca   7920
ttgtgacaaa gtattatgag ttgtacaact ttcttgtgaa gatagagcat aatgttaaac   7980
aaggatctat atagagcata atgtcaacaa aacaacaaca tcaacccagt aatcatccta   8040
ctaataggat ttggggaggg tagagtgtac gtaaacctta cccatacagg ggagggggta   8100
aagaggttat tttcgggaga ccctcggctc agagacaaaa aaatctataa taacaacaga   8160
aaccagacaa ataatatcag catcataaga gacaacaaat aagtggaatg acaataatta   8220
tgccaataat aacattgaaa aaaataaaat taaaaattaa aaataaaaat agtgtgatga   8280
acaaaaatcg ctagcagtct tagacaaaac actatcagac tagctggaac aacgaggaaa   8340
aacgctgaag tacccccta a cctacaaccc taatgctcga catccacacc tccctatcca   8400
gggtcatgtc ctcggaaatc tcaaatcgcg tcatgtcctg cctgatcacc tcgccccatt   8460
acttcttagg tcgccctcta cctcttctca tacctgtcaa agccaaccgt cacacctcct   8520
aactggggca tctaggcttc tcggggccgg ccagcccgta gatctaaaag gatccatcca   8580
tagcgcccga accatccacg cctcgctttc cgcatcttgt cgtccatggg agccacgccc   8640
accttatcca gccttatcca gcctagtgtg cccccacatc atctcaacat cctcatttcg   8700
```

```
actactttca tcttctggat acaagaattc ttgactggcc aacattcagc tccatacaac   8760
atggtcgatc taaccaccac tctataaaac ttgcctttaa atttcagtgg catgttagta   8820
tgtttacttt agatacaatg ttttttagag tcttatagtc ttgttagaat actatatatt   8880
ataaaatatg gagacttctg ggcacttttg ttttatttta tataagatag gattggaatg   8940
aattcaattg gagggacatg catgataaat gaatattcat gtagccgata tatgtttggg   9000
actgaaacga cattattatt gtgaaatatt ttacaattgc atttcacact cactgaagtg   9060
aaactttgat tccacgtcgg tcaatactta ggtgttacgg tttggctgcg aggggaatcg   9120
aagagagcaa attaattaaa gtatttaatg aggaatcatg agttagttgg tggaattata   9180
atagtcaaat gaatgagtta ttcgcctgat aatatagttg atagtagtat atactatata   9240
tgttgatact agttattggt ggtgacctaa ttaagtaaag agaagagaag agtggttatg   9300
taaaggaatc taggtatagt gggggatggg gggaggcaag gttaaaagaa aggtggaaaa   9360
tccaagaatc ctgcttcctc tagtaacata gcatatcctg caattcgtgc ttttgtttcc   9420
tctcacaaga taactacttt tttgattaat tattacattt gacacataca tacaaaccta   9480
taaaattaga catccttatg gaatcttacg actccgaact tgtcatatat cctttaatta   9540
tgcttagctt tttgctaaaa acaaaaagga tatccttatt ccaaaatgca actaggagca   9600
tcttcccaca tttctttttt atgcctctgc atcatcaaat cccataatgc cgcacaacaa   9660
tttcttttta cttgagtata ttctagctta gctatttcat acgaataatg ggtatacaaa   9720
tttgcttatt ttaggtttta aataccgatt taaatatatt ggatgggttc aacttttaaa   9780
attcttacac tgatatacat gcatagaata tgtggaaaac tttaatatta a            9831
```

<210> SEQ ID NO 57
<211> LENGTH: 10589
<212> TYPE: DNA
<213> ORGANISM: Nicotiana tabacum

<400> SEQUENCE: 57

```
gacgtcttac ccggttcaat gcctattgca cctcgttgaa gaggctctac gtgcctactt     60
cattcatctt tgcctaatcc ttatcggtca ccaggcaacg aaggtagctg gctatgccga    120
ccggagcgga cagggctcgg gcgtccatcg ggatagtaag aatgaccatt ctcttacggt    180
cggggtcaac acccgggggg agggaacttc ttcactagtt tcgggctcaa gctcgagctc    240
ggcttgctcg ctcccgatga cacatccttt tttgggacct ccaggtgacc aagcctggag    300
aagtcctcca atgcgaccat gtccatgcca tcaaagaacg tgttgagggc attatctgga    360
cccgacgcta tctcatttaa tttctcttta ttagcttgaa cctcttcgag catggactca    420
gtataggacg gcgtctctgc gatgtcaatg atactagcta catccttcgg gacaggagcg    480
gcttctcgat aggccatgga ctccgtctct ccctctggtt ctcgagctag agggggatcg    540
acctcttggt cacctttcct ggttgccacc ttctccctct cgttgagggt cgactcatga    600
gcaatgaact caaggtcgtc atcctcagga taatccctaa gccggtagag ggaatcagat    660
ttcggtaccc tcgacttggt gctctttttg tttttctgga cctggacgac caccctcttc    720
ttcttcacct cgacatccgg ggagcctgtg gatttccttt tattcttctt tttctcttcc    780
cttacggcgg cctcgggctg tcccgaagcg gagggttcag cgagcgagga cggatcctcg    840
tcctcatcca atggcttgag ctcggtggtc atgggtgaac ctgtgagaag aaagaagact    900
tagcgatata ttcatcaagt atatgaatgt aatcattcgg gagagagact cactatggga    960
acgagcctcc catttgccct tcgagagctt gcgccatacg ctcgaagtag gacatctatt   1020
```

```
tgcacatccc ctcgattcac tccttgaagc aggggaatgt attaggaacc tgggcaactg   1080
ctacataatg gcaaatacag gcaattagaa aaaagaataa aaggaaatgc cagatactcg   1140
agagggaaaa gacttacggg atgcgtttca ctttttgagg aatggtagaa attcggagag   1200
gatgaggtct tcggttttca cccgaacgaa cctcccctac caacctcgat ctcggtcctc   1260
gtcgatgctc gagaacggag ccttgcttgc tcggcgaacg atcttaatca acccctctcg   1320
gaagattcga ggactgtata gatgaagtag atgttcgagg gtgaactgag gtgcttcagt   1380
tttgtttaca aagtgttgga ggaggattac gatcctccaa aaggacaggt gaaggcagac   1440
cttgcacctt ttatagatgt cgaggactat ggggtccacc gggacgagcg tgaaggagta   1500
agtgtaaaca cttaggtacc cctccacgtg agtggtgatg tctttgttgg gcccggggac   1560
gaccacctcc tttccctccc agttacactc tacccgaact atgggtagtg tctcctcagt   1620
aacagagcat atgtacctcc atgctccctc gtctcggtcc tgttgactgg aggctttctc   1680
gacgttgaag tcattctcga tagagcagcc cccgagtacg aagctcttca agggaggctc   1740
atgggctacc tcaggaatgg ccacctcggc atttatggcc agattggaaa ataaaggagc   1800
ggtttgttga ggaacgaatt tgaaagtttt tgctatcggg ttctgaaaaa tatgaaggtt   1860
tgaagaaaaa atatgaagat ttgaagatag aatggaaata tgaaggtctg ggttgaagat   1920
tgaaagagaa tgtatgaaga ttgaggatga aggtatgaaa atctaaggag caatctatga   1980
agatttgaag gagttaaagg tatgtaaaga attcaagggt aaatcaagga gctctagaat   2040
cgaaaagtgg agaagtgaaa aaggggtcgg agcttttata gaggaaggac aatcaatgca   2100
tgacgtttca cattcgagga cagtcaatca acggccgata cgtgtccgat gttagaacga   2160
tgcgactaat gggacgtttc attgatccgt catctcggtt gtaacgtacg aagaaaggaa   2220
tcggggttca tttatcgctt cccgtcgttt cgataaatct atcctccgaa aaacaagggg   2280
actatctgta tacgggtaaa atcaggcaat gtctaccctg attctcctat aagagaataa   2340
agggggagcg cggatccgcg agattgtaat cgaggacaga gacccatcgt atcaagatcc   2400
aagaagagtg aacgatatat ctaacatcag acacggcaaa gcgatgtacc ccggaccgaa   2460
tataactcct agacctcggg agaagcgggg gacggttatg catgacagat aggagactgt   2520
atactcgccc tcaatcggat attacgacgc gaatctcgtc agtaacaatt atggatcaat   2580
aattactgga aaaagaagat ttttaccttt tttagactta tactaggact gaaattctcg   2640
tactatataa aggtaaagtt tttctttgat ctgacacatt gtaacacgca attcaaagaa   2700
ataaaaattt gtttttgcct tctaactaat gttaaaaatt ttgctcactt gttctgttct   2760
tcattcacga ctggactcga accgagggtc caatcgagta cgaggtcact gttcaatcta   2820
agatcatgct tggtcataac attgcgattg gtttgatcat ttatttcgtc tttaattcat   2880
ttatctgtta tttttaatta ttcgtgttga attaaatcac gtatcattta aaccgcgtac   2940
aaatttaatt gttacccatt tttaaggtaa acaactatag acgaaaaaaa aaatataaat   3000
attaaatatt atgtttcgaa agatacacaa tagacaagaa aagaaaagaa aaatcccctta   3060
taaaatttgg atttagccca ccagttttat tgagacgtct ttgtgtgtta gttacccggc   3120
aaaggttatg aacctacttt atgcgtcaat gtccgaattt atttttatca acatcctttt   3180
ggaagagctt ttgatagaaa tggttggctt aattagcaat catattatca tcacctgcgc   3240
tttggtgtta tatcattcgg aatcatatca ttaccttttg aaatttaaaa tggttttcaa   3300
agacgtttcg ataaaaaaat tcctattgtc gcagttggaa tctacaagac gaagatgttg   3360
```

-continued atctagtgct atatttggag aaagtgcctt aattaaaaat aaaaaattgt tgatcagttg 3420
tcttaagatt ttttattatt aaaaaaaaaa aattaagata caaagaaaca catttacgag 3480
tatatgtcgg ccgactaatt aatgtgaagt tccacacggt caacccacac atattgtggt 3540
caagatagat tctatcataa tcaaaagtca ttatcgactc aattttcata tttggcatct 3600
taagtacatg cacaaaagct acttaggatg taagtttata atcattcatt cttgaaatag 3660
aacctattta atagtactta attagttaca gtagtataat ttattctctg ctaaagagct 3720
attgttcatc aaatatatca gattatcctt tgtggtgtag accatttcct tatttgtact 3780
tagtattaat tctggcaaaa gcacaaaact gggaaatgag gttcttcttc attaatgttg 3840
agtcaagatt agtactacta ctatagccaa gaaaatgtga aatcatatag tactaacttt 3900
cccttctccc tagctactga taactctaat taatttcaga tgccaaaacc ataaatttcc 3960
cctcctccat cattgaaaac ccctttgtcc tttcccccca gacccccttt tcctctctct 4020
ctctctcctt tctcttttta ttagacgcat attctctctt ctttctcttt ctagggtttt 4080
cacctgaaat agttttattt cgttgatatg ttaggatcct ttggttcatc atctcaatct 4140
catgatgaag aagctgatga tcaacggcgg agatgcagtt ccacttcccc tgcaatccaa 4200
atccggcaac tactcattag ctgcgcggag ttaatctcac ggtccgattt ctcggcggca 4260
aacagactcc tcaccatttt atcaactaac tcttcccctt ttggtgattc aactgaaaga 4320
ttagtccatc agttcactcg cgcactttcc attcgcctca accgctatat ctcttcagcc 4380
actaatttct tgacacctaa tgcatcatct aatgttgttg aaagttcaaa tgattcagct 4440
ctacttcagt catcctatct ttccctaaac caagtgaccc cttttattag atttagtcag 4500
ctaactgcta atcaagcgat tttagaagct attaacgata accaacaagc gatccacatc 4560
gttgattttg atattaatca cggtgttcaa tggccaccgt taatgcaagc actagctgat 4620
cgttaccctc ctccaactct tcggattacc ggtactggaa atgacctcga tacccttcgt 4680
agaaccggag atcgtttagc taaatttgct cactctttag gccttagatt tcagtttcac 4740
cctcttttga tcaccaataa taatgacaat gatcatgacc cttcaatcat ttcttctatt 4800
gttcttctcc ctgatgagac attagcaatc aactgtgtat tttatcttca caggctctta 4860
aaagaccgcg aaatgttaag gattttttttg cataggatta aatccatgaa ccctaaagtt 4920
gtaacactgg ccgagagaga agcaaatcat aatcacccac tttttttgca aagatttgtg 4980
gaggctttgg attattatgc agctgtcttt gattcattgg aagcaacttt gccgccgagc 5040
agtagagaga ggatgacagt ggagcaagtt tggttcggaa gagaaattat agatatagta 5100
gcagcagaag gagataagag aagagaaaga cacgagagat tcagatcatg ggaagtaatg 5160
ttgaggagct gtggatttag caatgttgct ttaagtcctt ttgcactttc acaagctaaa 5220
cttctcttga gacttcatta cccttctgaa ggataccagc ttagtgtttc gagtacgagt 5280
aattctttct tcttgggttg gcaaaatcaa cccctttttt ccatatcttc ttggcgttaa 5340
attataaggg aaattaaaac cctaaaaaca agattttatc tatctgcatg gtgaaggaca 5400
aagaggtctt caatctcagg ttctttttgt ttttttaact tgtttggata tgaggttatt 5460
gagctgatga atgttttaat tttaacatag gcctacttac gtagtagtta taggttgata 5520
atgatatata tttaactaag tctttgtata atgcagatcc tgaacttaat ttttattttt 5580
attattttgt tgttaatgaa agattctgtt accaaatttt atcagtctat ttaattagag 5640
gccaaagatt gttaggtatg tggcacttgg agtgggaaat gatatattcc cattaaaggt 5700
gttaattaac caccaaattg ttctttaggt ctgtttgtca ttttgtatta aggtggatgg 5760

```
ttcattatct tctctttaat gctaatcatg cttcaccttt tcatttagta ctagcaagca   5820
tatttgttta ctttattggt tattccttat caaagtcttt atcttgttgc tttttttttt   5880
tattgtactt tacaaaagat ttctggtatt aatggaaagt gctcatattt ggaaaaagac   5940
atggccaaca agaaaggtgt ataccccatt tctttttctt tttctccaaa tttttttttt   6000
tttttttctg tttcttgttg agttctttca tggaagaaga agaagagtag gagattcttg   6060
gacatggctg catgagaatt gttattgttt tgtgcactta aataaccccg tatacataca   6120
caagtagtgt tggctgtctt tgatattgca ccatttattg ccctaatttc tgccttttgt   6180
cccctcaaca aaaccatcaa agttctcaaa tagggtttat tcttgtttcc cactttgccc   6240
cccacccatt agggccaccc caccaaaggg atctctctcg tgtctagtgt tttttcccaa   6300
ggaccaccac tacttttttt tttttctcta ccataacttc cacaccatct tgtgatcttt   6360
cgtttaataa tgattttgca gccatgcctt cgttcatcag aactcggtca taagcacaga   6420
ttctgagaga gtaattaatg aatgaatcag tggtgatttg acttatacat gattatggtt   6480
tttagctcaa taagcagagg gagaaaatat atataaacaa gtaaatctag tagaagaagt   6540
agaagtttta tagctagagt agtgggaaag aatgacgcaa gattagtacc aaaagagtga   6600
aggaagagct ttaatatagg gaaaagggaa gtagtaggtg atacttgaca ggttgataag   6660
atggttacta ctacaagttg atgtattgac gctaactcac gcaagagacc tactcactgt   6720
gcaatattta caagaagcga ttctttctct ctttacttgc aagagttgtg tgttccgagt   6780
tgtatggcgc atatgaacct tttttcatac aatacaatac atatggaata gatagataag   6840
acggtgcacg catgaggcaa ttatgcaact taacatcaac tacttccatc atcttttctt   6900
ccctctgttt ctgtttctgt ttctgtttct gtctgatata ctatatgctt ctctggcctg   6960
gattttccta actcttttga taatttaggt tcccatcaat aatgtctttt tagaggagca   7020
tcatatcgat agatattcaa atattaaacc tggcctaggg ctagggcgtc tgctaggttt   7080
ttgcattact ctttgtatat ctcatctgtg ggacctttttg tttatggaag aatatacttt   7140
tattcatctt gttgggtctt aaattcaaga tttaatatta ctctttaaaa attaatgact   7200
atcctaaaat tcttcctctt ttatttgcat ttacaagaat tgatattagt acctaaaact   7260
cttctctggg gccttttgta tttagtcctt ttatgtttga aattgacact atttaaataa   7320
aacataatct acaataagat gttcttcacc cttcgggttg cccggttggt ttggatggga   7380
tcgattcccc cgatatcttc tgggttgagc atatcgcaca gggcttgtct agtgcggttt   7440
gcattcccta tgtggtttgc attccctatg tggtttgcat gctattatac atgggtttac   7500
ccagtggaca caaagtattc aatacagagt gttcacccga agaacagagg ctgtggcaaa   7560
gattgtaacg gccgcgggtt tcccctctta caaaaaaaaa aaatgttctt ccttaaacat   7620
tacccatcaa agactcacca aagatagctc taccaagtat tatttttgga tcaaatggca   7680
tttccacggt catatctcct cccccccccc cctccccccc ccccccaaag ctagtgatca   7740
cttccatatt ttttcctgat ttcatcggtg ctcaaatact tgttcattca tcttcattcc   7800
aaacaaaggc gaaaaacttc actattgagt gcttttttcc tattccaagt gtcaaaccct   7860
aaacttctag tcaaataata tctaagatgt atactcttat actatgtttg tattcattat   7920
gacaaagtat gatgagttgt acaattttct tgcggactta gtgaaaatag agcataatgt   7980
taaaaaaata tttacatgat attaattagc cggattaagt ttataacgtt agtatatatg   8040
tctactttag gtacaataca agtcttatac tcttgtcaga atttatatgt cacaaaatat   8100
```

-continued

```
agaaacttct agctactttt ttttaatttt atataatata atattggaat gaatttaagt   8160
ggagcaaaag tgaatattca tgtagtcgat atattctaat ctgtttgggg ctgagatgac   8220
atgattgtag tgaaatattg taccattgca tttcacactc actgaactga aactttggtt   8280
ccacgtcggt gatcatttgc atgtttcatt agtcaatact gtggctgtta tgatttggct   8340
gcgagggga tcgaagagag cacattaaag tatttaatca ggatttatga gttgaatgct   8400
gttagttggc ggaattaata gtcaaataat gaatgagtta ctcgctgata tagttaatag   8460
tactccgtat atatgttgat tctagttatt ggtggtgacc taagtaaaga gaatagatga   8520
gaggagtggt ggtatgtaaa ggaatctagg taaaggggtg ggggtggggg gaggcaaagt   8580
tgaaaagaaa ggtggaaaat ccaagaatcc tgcttcctct agtaacatag catatcctgc   8640
tattcgtgct tttgtttcct ctcacaagat aactactttt tgattaatta ttacatttga   8700
cgcatacaaa cctataaaat taaactaatc aacgacatcc ttatggaatc ttacgagtcc   8760
gaacttgtca tatatataac tttaaagtac tttgtcactt cttaatatgc tcctttaatt   8820
gtgcttagct ttttgctaaa aaacaaaaag gatatcctta ttccaaaatg caactgggag   8880
catcttctca cttttctttt ttatgcctct gcatcatcaa atcccacaat gccgcacaac   8940
aaactcttgt tacttaagta tatattctac ttcataagaa taatgggtat aaaaatttgc   9000
ttattttatg ttttaaatac caccgaaaat tcataagcaa attcaggatt taaatatatt   9060
aaatgaattc aacttttaaa attgttgcac ttatatatat atatatatat atatatgcat   9120
atccaagttg agggatacgg gttcacatga actcatatta ctttctctaa accatgtata   9180
acaatgttat attttttcaa aattatttaa atatatgtgt gtgaacccat tctcaaaatc   9240
tcttatggtg caattattat tgggtgcaca tctacaagtg aaatttgcag ctcaaaacct   9300
catctgggcg gtcttgtttt ccgcatggag tataactata tatgtgaaaa ttactagaat   9360
ttcaaaatga atataatttt gaaatgttgt gggttcctgg taagagacta aagttaaact   9420
cgtcaaatat aaattctaga tccacctctt cacaatagtg cacccattct tttgaaattc   9480
tggatctgcc tctgttaata atatatatat atatatatat atatatatat atatatgaac   9540
acaaaataat atgtggaaaa ctttactatt aataccactg ctaaacattt gaatggattc   9600
ttcatgccgt gtgctccttt gttgaagaac acgtacttgg gagggcgaga tttcgaataa   9660
aaaagttata ctaataacaa acagcaacaa ttataagaaa atgaaaataa aagggaaaga   9720
gcactcacat aaactagaaa ctgtagagtt ggcaagtacc aggtatatat gtccttgaat   9780
gttttttacg aggaattgag taaaacgcta gctatttcaa cacatatata aaaagcatca   9840
ataccaattt tatggtttct cttaggtgtt gatagattct cttttgtcag caaagttctt   9900
gcattaacta tatgaaattt ataataaaaa tgctgctctt ttaattgagt atacatgcag   9960
tctcctaaca tatacattct ccgtcccgat atatacttga tttgatgcat ttcaaaaatt  10020
aaatgtttga gtgttttggt gaattgtgct tgatatagaa gtatttaaaa taagaaagaa  10080
atgtaacggc agaatcttaa gtcgaaagtc aaattaaatt tgaaaaataa aaaataatac  10140
tcttgatact tactagtact agtcaatggg cagctctttc gggactaacc aaaagcatta  10200
ttcttattgt ttccggcata gtattaaaat gtaacaatgc ttaattatgt tacaaaatta  10260
atgtttttgt ggacttcgga ataatttatt tctgaattcg ccggtgttat cgaaaacatg  10320
gggacagtcc ccccaaaatc cacgggttat tgtgcaaaga cgaacataca agtttatttt  10380
tgataattta atcccaagca tcaactttct catacttctc taatcccttt gcatccaaaa  10440
ttatcaaaaa tagagaatat taaatgatag ggggaaaatg atcattaaat gcttcccttc  10500
```

cgggacatcc ggtttaaggg gggaaaagga gatattagat gcatgcaaaa taataaattc 10560
ttggaagtaa ttaatccgaa gttctgacg 10589

<210> SEQ ID NO 58
<211> LENGTH: 9770
<212> TYPE: DNA
<213> ORGANISM: Nicotiana tabacum

<400> SEQUENCE: 58
gtctacaaga aaatatgcat ccggatattc aaaaatccaa aagaaaagaa aagttgaaaa 60
tttaataaaa tctcaaaaag gagttctcga gaatttttg acaaataata aaaaaactaa 120
atcgcaaaat gtaggagaat attctgtaga tgaacaagtc actaactttg agtcagatga 180
taacaaaatt caaattgaag aagatgttta tgagaaatct gacgaagaaa caaactttag 240
ccttaggccc tatattaaac tttggcccta ggcctcatat gagcttgagt cgcccctaat 300
tctaatacaa gtattagtgg ctactttcac ggcttgtgac ttatggatta caaacaactt 360
tacagttacg tcaaggctcc acgtagttct caatttatgg agcatatatt agatgattaa 420
cgcagggaaa gattctgctc tcctctgata catggctatt attcctcgtt tagttcaaaa 480
aggaaaaaga gggtagtctt gttatattat tggggaatga attatggttt caaacttttc 540
aaacttaaag gattttgtac atggtaaaac ctaaattgac acgtaacttg gtactttcaa 600
agacacgatc ttttacgcga tattttaaat aaagaaaaga tcaagtcaaa acatgggcca 660
aaaagaaaaa ccccatgatt ttttctgata aaaagctgct aacttttagt ttgttttatc 720
caataaaaca tctttaacgg tctgcctgct ttagtttaat cctcttttta agatgtaatt 780
aagcataaaa tagaaaaggg aaaaaaaagg tccattggat tttggaagaa attttaagaa 840
agtacaagaa ctagtaaagt cattttgtat agagtatgtt aaaaaggtga gtgacaattc 900
gaaaaagaaa gcattgataa gtcaatcact aaataaaaaa gcacacctaa taatcattca 960
ttcaaaaaaa caaatttcta tgaaagataa tcattatcat aagtcactgc agaaatccca 1020
tatacagtag agtaccagga ttttacgata aggtgttagc aaactatcta ttcatttttt 1080
gacaagcatt ttatgtttgg tcatttgttg ggaaaaatta gggagaaatt taaaaatagt 1140
tagatttaca actggtcatt aaaaatagcc caatttcaaa agtaatcgaa atttagccac 1200
ttttcatgta aagataaatc tgagcgaaaa tattgttcaa aacccggaaa atacgcccgt 1260
atattatact ggagttccag cataagtatg cttgaactcc agcatattat acgggagttc 1320
taggataact atgttggaac tccagcataa tatgttggag ttccagcata agtacactag 1380
aactccagca tattatacgg gagttccaac aagtataact gtcccgtata atatattgga 1440
gtttggagca ccggtgctcc agtctcccgt atattataca ggagtcagca aagtataccg 1500
gtccagcata atatgctgga gttcgtacac agatgcaccg aactcacgta tattatgcgg 1560
aaccggtctc tgttgcagca aaatagtggc tatttttcat tgacttcgta aacggtggct 1620
atttttgaat gaccagtccg aaaactggct ataccgtgct attttgacga aaaattatcc 1680
ccccacccac ccacccaccc aaacgcacct tacacacatt agtgcacatc ttttaactag 1740
tttttggtta tttttttatt tgatgcccga tattcgtata tggatttcga ttaattagaa 1800
ttcacaccga aacattcttt cttaggattt tgtacatact taatatgcga atacaaaacc 1860
tatgcggaaa ggtaagggaa cctattcatc cctctacagt acttgtgata atgttatact 1920
tttttgaatt taatttggga gacatgtcaa tctttatttt gaaaaaaaaa tagaataaaa 1980

-continued

```
ccatagggaa atgaacaatt tatctttcac tcctatctca ttttatttgt cttgaatttt   2040
tcaaaatttt gaattatatt ttgaaacttc ttcaatttat tttcttggaa tcttcagaat   2100
tcaatttaaa attccaaaat tccaaggatt tagctcccgt ttggccacag attttggctt   2160
catttttta aaaaaaattt tgaaaacatt ctttgtttat gcaatatgat catgttttag   2220
gggaaaaaaa ttaaaaaaaa taaaaaaaaa tcaaattccc aaaaactggt taggcaattt   2280
ttggatgata tttttcttc cactcacaaa actttaacat gtccaaacac aacttcaact   2340
tcaaaaatta ttttcaacac aattttaaaa actctttttt caagtttcaa tcaaatctat   2400
atccaaatgt tagcttagta tcaaataagt gattgaaatc aaattaaaat cgagtggtaa   2460
ataaaataga ggagagctcg gtaaattaca agagtgcggt aaatcttttc tcctttactc   2520
tcactgtagc ctattctatc tgttgtaact aataagtaac tgagctacgg aaaaagtgcc   2580
tagactttta acttcacaag tataataaat agaagtcaat tctttcataa tattgtttcc   2640
atcctatcaa acagactttg tctcactgac cttccttctg agtgtgtctt ttatatgtca   2700
tttttagtga atccatatga tttagagact ctaatattcc acatgcgggt cttaatttgg   2760
tgtatatgta tatggtaata atttttgtta ggtagctgta gtattctatt attgttatgt   2820
attgactcat catgtaaata aagccggtta gataaggcta gaaaaaatatg agtataccta   2880
gaaattatta gcatattgtt tggaacatgt caaaaatttc aatgacctag ctagagctgt   2940
caattagtca aataacttta ttaatattta cttatgaaaa cactttgaaa ttcttggagt   3000
ttaagggaaa gactactgac taaaaaacaa agcaaaagtc tatgcattac tatactatac   3060
acagcacagc attttccaat agtatttgag atgaatctcc aatcagctac tgttgttctt   3120
ttcttttctt tatttagttt aagttttatg tgttgatggt atacaaatta tttgcacaat   3180
caaatggctt atctggataa tataggtaaa cctcttgtaa tcactaattg gtaatctggt   3240
aaaaataaca ctatttctat tccaatttat gtgatcaatt tcactagaca aaaatttaag   3300
aaagaaataa atttttaga acttgtagtc ataaacaagt tgtaacattt gtatggctat   3360
aattttttta acttgtgatg ttaaacatgt cagattgttt gtgtagctat aaaagttttt   3420
cattaggcgt aaaattaaaa atttagatta aattattatt aaatttagaa agaggtcatt   3480
ttttttagcg aagtaaaaaa gaaatcggtt cacataaacc gaaacataga gtaagtaatc   3540
tgttatgaca aattaaaaat tacttgtagt gtaaaaaaat ctttacaaca ttcgtgtata   3600
tacttaaatc tttttattt tttggcaaga gatagttgtt cagcaaaagt aagttagaaa   3660
taggtctgtc cttctgactt tgtaactctg aaatgaaaat ttcaaaatcc cttctatttt   3720
tactgttacc cccccccccc cctcacaaac cccaactcac tcttatttaa taaaaagctc   3780
tacttagaaa agacaccctt gtccatctgt ctatataggt agaatgagag taaaggagaa   3840
aacatatcct cctctccatt tctgtagaca aagattctca aagagaaaca aattaaacac   3900
tagagagtga gagagtgcta taagaaaaag aatatgggga gagctccatg ttgtgataaa   3960
gcaaatgtga agagagggcc atggtctcct gaagaagatg ctaaactcaa agatttcatt   4020
cacaaatatg gaactggtgg aaattggatt gctcttcctc aaaaagctgg taacaacaac   4080
ttctactcca ctagtcctct atgtgtatgt attttattat tattattatt attattatta   4140
ttattattat tattattatt attcatgaat cgaagggaca aaggtctaaa tctcagtggg   4200
tcgtggtagc aaggccattc cgccatttat aatatcttct tgcaaattcc accagtttca   4260
tatgtgtatg ttttttttctt attagtcata aatcaaagcg acgaagggtt aaatttcagt   4320
tgattgtgat agcaaggtca cactctaccg cttataatat ctcgtggcgt atttaacatt   4380
```

gtttgtatgt atatgtttga gtataaaggg aggaaagctt atatttatat ttgagtggat 4440
tgagtttttt tccttgttgc tgcattattt atgatttgat gagatttatg ttgggaactg 4500
caggactaaa gagatgtggg aagagttgta gattgagatg gctaaattat ttaaggccta 4560
acattaaaca tggtgatttt tctgaggaag aagatagagt tatttgcacc ttgtattcca 4620
ccattggaag caggtaatat atatatacct ttttttggtc gtaatttttt tttcattttt 4680
tatcatcttt ctgatgaatt tgagactgaa acaaaaactg ttcccactaa aaatggaaaa 4740
gtaaaacctc aataagtaag aaaagggaaa aaacaatgag ggctcagaaa gaaatgcaaa 4800
tagtcagttg gatttttaat taaagattct gccatttatg gacatatttt tctgcatgca 4860
tgccaggttt agatctaaga tcaagtcttt atttactcac ttacagatgt ttaattatta 4920
agacaaagtt ccaatttttc ttctttcttc tctttctttt tgtggaaatt ttttctctag 4980
taaaccaatt aatttttgtt ataacatgtg caatataata tgttaacagg tggtcaataa 5040
tagcagctca attaccggga agaactgaca atgatatcaa gaattactgg aatactaagc 5100
tcaagaaaaa acctatggga ttaatgcaat caactaacca aagaaaatca ccatattttc 5160
cagctactaa ttctcttcaa acccaacccc agataaattc aagtcttttt agagacttat 5220
attacacccc aaataatagg cctaatatta caggcctaaa tcatcagtcc atttcttctg 5280
cccaccagac aaattttctc tacactaata ataacatgaa ctttcctaat ttgggtgcta 5340
caaataatca atatccttat aatatccaaa gtcataattt acttatgttt ggagaagcaa 5400
gttgttcttc atcagatgga agttgcagcc aaatgagttt tggtaaagaa atcaagagag 5460
aagaaattat gagtaatagt ttacaacaag gtcaaatttc aagtgttaat gcttttgaag 5520
aaaaccacca gaattttact cttgattatg gcaatagtag tagtaattgg gtggatcaaa 5580
aaccaaatgt gtattttggt actactacta ctcaagtact tcagtatgat aatgttgaag 5640
aagttaagca gcagctaaca agttgtacca atggcaacaa tggtagtact attggatgta 5700
acaacaacaa cagtatgttc gtgttcaatg atgagaatta taacaagtca aatgagatag 5760
agatgttcta ttactaaaga agaaatgact gttgaaaaga aaacaaatgc aagtaccatt 5820
aggaagattt gaaagggcgt ttgggtatgg gggttgccaa gaagattcag acttttttttg 5880
gggttttgtg tagttgtggt agaattatta ttgaatgaaa aaaaaaaact tcctgtactt 5940
taattcgtca gtacatacta catactacta caaagtagtt aaaagcctat tctatttgtg 6000
cttttttttt cactcgatgt tcaataatta tattggtttt tgattaaatt tgaatttgag 6060
caaggaagat caacattgga gggataaatt gtttcctaac gaaggcgatt acatacttag 6120
aacttgaact caatatctct aattaaaaat gaagtaatac ttataataac tccaccacaa 6180
ttcttattgt tgtgcatttc tttataaaat atgtaaataa tgggtcatat atattgttta 6240
ccttttctat tcatatacat agattttaaa ttaattatac acatatatat aatacattaa 6300
ttattcatat attatatttt tgctagctat ttttagttta agcgatttgg taggcgacta 6360
cttgggttaa ttcttttttt ttaatatata tatcaaaata atgaagctgt ataatacact 6420
taaaaatcat atttgaaagg tattaaatac gacttaggag agttcttaaa ccattttgga 6480
accttgtcta cgtactttta tgcaatagct gtttttgttt gtctctgcta aaacctatgc 6540
tccccaaccg tgcaccaatc aacttagaag ttagaactca gaaataaatg taactatact 6600
ccacagaaag ttaaaaagtt ttactgttac cattcactca aggatcagaa actgaaagac 6660
aaatgaatca gtgcttcact gttcttcact aaaagaaata ctgtttacat tagtttcaaa 6720
agagtttaat cataaaaaca aatgtaccat aaaaagggga gattatcaac ctgaaaatga 6780
aacagaacat acgttatata tcaatctata tacggtcgag atcggactcg tctattacac 6840
gacagatcgg gattgaaacg taacagtttt gaagatcaac cccgggttcc gtcggaccga 6900
ggtacaaggt cagaatgccc gttctcgaga acatcgagtc catgacccca gaatcaaccc 6960
tgaccccaaa tgagctcgag gaaacatccg gataacggaa ggcgaaatat ccgtaaccgg 7020
tcgggtatca cggcatgaat ttcggcacgt aacaatgaga aaccggctaa ttagcaaatc 7080
atggaatttt ttacctttta tagaattgta actaaagtgg gattccccta ctatgtaaag 7140
ggggtctgac tatttgtacg ggacattcat taaacgcatc ccaaagtaat ataatattat 7200
tttctttttg taagctattg ttctcctgta tctgatacta tttgaattgc atcaagttca 7260
agtgagactc attttttcaa ggctataatt gttcaagtcg cacggtttga atttattcga 7320
tcattgttcg ctttaattac aattcaattc atcgctttat gtcaaattaa tccacatatc 7380
cttaaaacca cttacaaatt taattgttat caaattttaa gggtaaacag tttggcgctc 7440
accgtggagc taaggataat agtggttgtt tgatatagat tttcataaca cacactattt 7500
tacaattgtt cttcgaagtg tctctcattt caggtttaag ctcaaaatgt caaactcaca 7560
attggcaccc ctacctgcac acaatgagtc tggtcaccat ggtgaaaata acaacatagc 7620
acctggtaac gaggtaccgc ccgctgatcc catcagaatt tcaatcgcgg acccgttgga 7680
cgctaactcg catgtggcta tcgacatgtt acagtctcaa caggcgacga tagctcagtt 7740
acaaaaccaa agccgcacac cgagcagagt tgaactcgat ccgtcccgga aaatcacctg 7800
cagggaagaa ccgtccgcgg agaggtcaaa tggagatgag tcggggacta accccgagat 7860
cataaaaatg cttgaggaac cgatgatacg gattgaatca ggggaaaaga aaatcgaggc 7920
aaatgacaag aaggtaaaaa cttacaattt cacggtcaac caaatcccgg gagcaccgcc 7980
ggtactgaaa agcttggatt ccaagaagtt cgtgcaaaaa catttccctc cgagtgtggc 8040
cccgaaatcg atcccaaaaa catttatatg cccgagattc ttaagtataa tgggacaacc 8100
gacccaaacg agtatgtcac ttcttacaca tgccctatca aagggaacaa cttagaggtt 8160
gatgagatcg agtctgtttt gttgaagaaa ttcggagaga ccctgtcaaa tggagctatg 8220
atatggtatc acttacctcc taattctatt gactcatttg caatgcttgc aaactctttc 8280
gtgaaagcac acgccagggc tatcaaggtc gagacccaga agtcggacct cttcaaagta 8340
agacagaagg ataatgagat gctcaaagag tccgtgtcct agtttcaaat gaaacagaag 8400
gacctaccac cggtcgctga tgattgggcc gttcaagctt tcacccaagg actcaatgtt 8460
cgaagctcgg tggcttcaca gcagttgaag caaaatctga taaagtaccc aactgttatt 8520
tgggccaatg tgcataaccg ctatcaatca aaaatcaaag tcgaagatga tcaacttgag 8580
gctctttccg ggtcggttta ccctgtcaga ctcgtcgaca gaatcaagag agatatcgac 8640
cgtgaaccaa ggtcaaacgt agatcattac tagccatatg atggagattg gaaaagcaat 8700
aggtctgggt gaagttctac acagaatgaa aagagaaatg atccaggtca gagcactcga 8760
ggactcgcaa gcaagaacga cttcgacagg cctatcaggc ctaaagaagc accaaggtta 8820
tcgaaatata actttaatat tgatgcggct gccatcgtat cagctatcag acgcatcaaa 8880
gataccaaat ggcctcgacc tttacaatcc gatccagccc aaagggatcc taaccaaatg 8940
tgcaaatatc atggcacttc tggccacaga ataaaggatt gtcgacggtt aagagaggaa 9000
gtagcccggt tgttcaataa cgggcacctt caagaatttc tgagcgaccg agccaagaat 9060
cattttagaa atagggattc taacaaatag accgaaccag aagaacctca acacgtcatt 9120

```
aacatgatca tcggtggagt cgatgcccct caagtgctga tgttgaagcg caccaaagtg   9180
tccattacaa gggaaaaacg gactcgagat tacatattag aaggaacctt gtctttcaac   9240
gacgaggatg cagaagggat cgtgcagcct cacaatgatg cattggtaat atctgtactc   9300
ataaataaat ctcgagttaa gcgtgtgtta attgatccag gtagctcaac caacatcatc   9360
cgattgaggg tcctagaatg gcttggccta caagatcaaa tcatgcctgc agtccgagtt   9420
ctaaatggat tcaacatagc atgcaaaacc actaagggag aaataacatt gccggtgaat   9480
accaccagaa ccatccagga aaccaagttt tatgtgatcg aaggagacat gaggtacaac   9540
gctctgttcg ggaggctaag gatctacagc atgagggcag caccctcgac tcttcaccaa   9600
gtgttaaagt tcccaacgtc gggagggatc aaaacaatct acggggagca accggccgca   9660
aaagaaatat ttgcagtcga agaagagatc ccggtataga cactagcaac atcaaaggaa   9720
ccgagttcgg ataagaaata ataggctaaa tagcaattat cgacaccagc              9770
```

<210> SEQ ID NO 59
<211> LENGTH: 9150
<212> TYPE: DNA
<213> ORGANISM: Nicotiana tabacum

<400> SEQUENCE: 59

```
tttaagactg tttttttattt gatttatact ctttaattgt attttcgcac gaaaataacc     60
gatcaaagtt agtcgatttt attaaaaaat aaaattaccg accaaagttg gtcggttttt    120
taaaatgacc ggccgaatta accgaccaat tttggtcggt tttttaatat taatttttat    180
ttattttaat tgaaaaactg accaaaattg gtcggtttct tgaaaaataa atttcacggg    240
actcgaaaat agtttttcgc atttttgctc caaagaaaac cgaccaaagt tggtcgattt    300
cgtaaaaaaa aattaaaaat aaaatatttt aaaaaaaccga ccaactttttg tcggtttttt   360
ggtcggtgtt ttgaccgacc aaagttggtc ggtcgacctt ggtcggtttt tgccgaattt    420
ctagtagtga tataccctta gagttacaca attggcacat atatgccctt ctcaaaacga    480
aattcaccca aaaattatgg tttaaacttt aaaataataa aaacatctca aactttaaca    540
atactcaaaa gaccaaaata tttaaattat ttctaaaaag ataatttaat gattaaaagc    600
ctagagttca agttgtagtg ttataaattt gagttgttag tctttttcat cttttttcag    660
ctggacattt tctatttttt ttattaacta tgtaaattag gggtgtacat ggaacgggtt    720
ggatcgattt ttatcaaaac taaaccaaac cgattatatc ggtttgaatt gttcggtttt    780
attggttttt tcagattttt tgttacataa atattatttc aatcttgctt tgttaaattt    840
tttagaacta aatatatgtt cagtaaaact taaaaaattg acaaacatat gatctatctt    900
gattacctta tgggagaatt ttcttagtaa ttggaattca tgagttttgt caagtgaaat    960
tggtgacgaa aatagagaag acatcagtaa ttgaggaaat cggataaggg agaaagaaaa   1020
agaaaaaaag aaaaaaagaa gaaagaaaag agaaaggtaa agaaaaaagc actaataaaa   1080
aggaaatagt atttgtaata tactttaata caattaacgt aagagctaat tagtttgagt   1140
ggattccgtt ttgaaaaggg catacatgtg ccaattatat aactctaagg gcatatatgg   1200
accaactatc tgacggtaag ggcatatttg agttaatata ttaacgaatg acaaatgtgc   1260
tcaatttcgt ataatacaag gacatattac attttcccta ttatgaaatg gttcaaactt   1320
aaggattttg tacatggtaa aacctaaatt gacatgtaac ttggtacttt ccattgggca   1380
aagacacgat cttttacgtg atattttaaa tcaagtaaag atcaagtcgg gccaaaaaga   1440
```

```
aaaaaaccca tgatttttta agataaaaag ctgctaactt ttagtttgtt tcatccaata   1500
aaacatcttt aacgatctgt ctgctttagt ttaatcctct ttttaagatg taactaagca   1560
tgaaatagaa aaggggaaaa aaaaggacca ttggattttg gaagaagttt taagaaagta   1620
caagaactag taaagtcatt ttgtatagag tatgttaaaa aggtgagtga caattcgaaa   1680
aagagagagc attgataagt caatcaataa aataaaagca cacctgataa tcattcattc   1740
agaaaacaaa tttctatgaa tgataatcat tatcataagt cactgcagaa atcccatata   1800
cagtagagta ccaggatttt acgataaggt gttagcagac tatctattca tttttgaca   1860
accattttac gtttggtcat tttttgggaa acgaactctc ccaacattct tccaaattac   1920
cccacgcacc ttactgtgca catcttttaa ccaacttctg gttatttttt cttttgatgt   1980
ccgatattcg tatatgaatt cccattaatt ctaagttgca ccgaaatggt ttttatcaag   2040
attttgtata tatttaatat tcgaattcaa aactaatggt cgaaggtgga agatcgtatc   2100
catcccatca taatatttgg ttggtaatat cacacctttt tgaatttggg agacttgtca   2160
atttttattt tgaaaaaaga aaaaaaaaag aaatagaaac taaaaccata gggaaatgaa   2220
caattttatt ttcactccta cctcatttta tttgtcttga atttttcaat tttgttttga   2280
aacttcttca gtttattttc ttggaatctt cagaatttaa tttgaaattc caaaattcca   2340
aggatttagt gtcaaatcag tgcttgaaat taaatttaaa acgagtggta aataaaatag   2400
aggagaactc ggtaaattac aggagtgcgg taaatctttt ctccttttct ctctttggag   2460
cctactctat tctattgtaa ctaagtaact taactacgaa aaacgtgcct agacttttaa   2520
cttcacaagt ataataaata gaagtcaaat tctttcataa tattgtttcc atcctatcaa   2580
acagactttg cctcactgac tctccttctg agtgtgtctt ttttatgtca tttttagtga   2640
atccaattga tttagagact caaatattcc acatgcgtgt cttaatttgg tgtatatatg   2700
gtaataattt ttgttaggta gctgtagtat tctattattg ttatgtatta actcatgtaa   2760
ataaaagccg gttagataag actagaaaaa atagagtcta cttagaaatt attagcctat   2820
tgtttggaac atgtcaaaaa ttcagtgact cagctagagc tgtcaattag tcaaataact   2880
ttattaatat taacttatga aaacacttgg ggattcttgt agtttaaggg aaagactact   2940
gactgaaaaa caaagcaaaa gtctatgcat tactatatta tacacaatac agcattttcc   3000
aatagtattt tagataaatc tccaatcagc tactgttgtt cttttctttt ctttttagt   3060
ttaagttgta tgtgttgacg gtatacaaat tatttgcaca attagatggc ttatctagat   3120
aatacgtgta aatctattga taatcattaa ttagtaatct ggtaaaaata atattgcttt   3180
tgttctaata taatgtgata tatttgactg ggtacgaaat ttaaaaaaaa ataagacata   3240
tagaacttgt tgtcttaaac aattcataac atttgtgtgg ctataattct tttgaaactt   3300
atggtgttaa acatgtctaa ttgtttgtgt atgtataaaa gattctcatt aagcgtagga   3360
aaatttgaat taaattattt ttttaattta aaaagagatc actcctttta gagctgactt   3420
aaaaagaaat tgattcacat aaactcgcac ggagggaata agtaatatac tatcaaaaat   3480
taaaaatcac ttgtagtgta aaaaaatctt tacaccaatc gtgtatattc tcaatttttt   3540
tttttttttt ggcgagaggt agttgttcag caaaagtaag ttagaaatag gtctgtactt   3600
ttgactttgt aactctgaaa tgaaaaattc aaaatctctt cttttttact gttttaaaaa   3660
ctccaactca ctcttattaa tataaagctc tagttagcaa agacaccctt gtccacttgt   3720
ctatatagca agaaagagag taaaggagaa aacatattct cctctccatt tctgtagaca   3780
agattctcaa aaagaaacaa attaaacact agagagtgag agagaactat aagaaaaaga   3840
```

-continued

```
atatggggag agctccatgt tgtgataaag caaatgtgaa gagagggcca tggtctcctg   3900
aagaagatgc taaactcaaa gatttcattc acaaatatgg aactggtgga aattggattg   3960
ctcttcccca aaaagcaggt aacaacaact tctactccct tattcccaga atcgaagcga   4020
caaagggtta aatctcagtg gattgtggta gcaagatcat attctatcgc ttacaatatc   4080
tcgtcgcgta tttaacactt tcgtatgtat atgtttgaat atagggggag ggaagcttac   4140
attaatattt atactttgag tggattaagt ttttttttgg ttgcttcatt atttatgatt   4200
ttgatgagat atatgtttgg aactgcagga ctaaagagat gtgggaagag ttgtagattg   4260
agatggctaa attatctaag gcctaatatc aaacatggtg atttttcgga ggaagaagat   4320
agagttattt gcagcttgta ttccaccatt ggaagcaggt acaatatacc tttttttagt   4380
cttaaattgt tttccatttt ttatcatctt tctgatgaat ttgagactga aacaaaaact   4440
gttcccacta aaaatggaaa agaagaacct taataaataa gaaaagggaa aaaacaatga   4500
gggctcagaa agaaatgcaa atagtctgtt ggatttttaa ttaaagattc tgccatttat   4560
ggacattttt ttctgcatgc atgccaggtt tagatctaag atcaagtctt tatttactca   4620
cttacagctg tttaagtatt actactacaa aattccaacg tttcttcttt tctctctttt   4680
ttttttttt tttggaaaac ttttcctttt gtaaaccaat taaattttgt tataacatat   4740
gcaatatatt atgttaacag gtggtcaata atagcagctc aattaccagg aaggactgac   4800
aatgatatca agaattactg gaatactaaa ctcaagaaaa agcttatggg attaatgcaa   4860
tcaacaaacc aaagaaaatc accatatttt ccagctacta attctcttca agcccaaccc   4920
cagataaatt caagtctttt tagagactta tattacaacc caaataatag gcctattatt   4980
acaggcctaa atcagtccat ttcttctgcc caccagccaa attttctcta cactaatagt   5040
aacatgaatt ttcctaattt gggtgctaca aatagtcaat atccttataa tattcaaagt   5100
cataatttac ttatgtttgg agaagcaagt tgttcttcat cagatggaag ttgtagccaa   5160
atgagttttg gcaaagaaat caagagagag gaaattatga gtaattgttt acaacaaggt   5220
caaatttcaa gtgttaatgc ttttgaagaa aatcagaatt tcactcttga ttatggtaac   5280
agtagtagta attgggtgga tcaaaaacca aatgtgtatt ttggaaatac tactactact   5340
actcaagtac ttcagtatga tgttgaagaa gttaagcagc agctaacaag ttgtaccaat   5400
ggcaacaatg gcagtactat tggatgtaac aacaacaaca gtatgttcgt gttcaatgat   5460
gagaattata acaagtcaaa tgagataggg atgttctatt actgaagaag aaatgactag   5520
ctgttgaaaa gagaaaacaa atgtaagtac accattagga agatttgaaa gggcgtttgg   5580
gtatgggggt tggcaagaag attcaaactt tttctggggt tttgtgtaat tgtggtggaa   5640
ttattattat tgaaacttct ttacttcaat ttaaatcgtc ggtacatatt acgtagttgt   5700
agtaaaagcc ttttcctttt tgtgcttttt ttttttttc gtgttcgtat taagacttca   5760
ttaaatccaa atttgcatag ggacggtcaa cattagagga ataaattgct tcctaacaaa   5820
gacgatttta tactcaagag ttcgagcccg aaaaacgacc tctggttaag ggtaaaaata   5880
gtaattacaa taactccacc acaatcctta ttggtgtgca tttcttcatt aaatactccc   5940
tccaatccac tttaattgat ttgtttttgg ctatttttat atatattaag gaattatctt   6000
ttagcattaa tcaataatga aattgaccat attaaccttt tagttcattg gaaatataac   6060
aaatactcct aggcttttta attcaagagc aacttttaaa tccgaatttg ggctaagaat   6120
acaagcttgt tctttttat ctgtttttca ctcggtgtac gaggactcaa ttaaatccga   6180
```

atttgagcta agaatacaga cattagaggt aatatgcttt ctaacaaatg tgactcaatg 6240
ttcagactca gaactcgata tctctggtaa ggatgacata gtacttacaa taactccatc 6300
ataatcttta taggtatgta tttctttata aaatatgtaa atagtgttat gatttttttgt 6360
atcaaaaatg atgaagtata atactcttaa aaatcatact ccatccgttt caatttatgt 6420
gaacgtattt tctttttagt ctgtgccaaa aagaatgacc tatttcctta tttggaaata 6480
atttaccttt atgcaatgat ttatagtcac acaaaatata tgtgtctcat ttttaaccac 6540
aagttcaaaa gtcttctatc tttttttaaa ctctgtgccc agtcaaatga gttcacataa 6600
attaaaacgg agggaataat aaaaatgtat taaagactac ttaggagagt tcttaaaaaa 6660
ccattttgga accttgtcta cgtactttta tgcaataact gcttaagttt gtctctgcta 6720
aaacctatgc tccccaaccg tgcaccaatc agcttagaaa tttgaactca ggaataaatg 6780
taactacact ccacagaaac ttaaaaagtt ttactgttac cattcactca aggatcagaa 6840
ctgaaaaaca aaagaatcag tgcttcacta aaagaaatac tgtttacatt attttcaaaa 6900
gagtttaatc attaaaatag atgtaccatc agattagcta aaagataaat aatcgttaaa 6960
aaaaggagat tatcaacttg aaaatgaaac aaattatatg ttataatatg tcaaaatata 7020
ctgacagtat aaaaactcgt taaatgtgtt aaatcctatg aaaaaactgc ccaaataaat 7080
atttgagctt aggtgtcaaa tgttgtactc aacaacaata acaacaacgc attaggatcc 7140
tactagtggg gtgtccaatg ttgtactatt gaacattatt caactaactt ttgttaggtg 7200
ttcctgtagt ttagtgaaat taaagtccac tgttccccta tatattaatc ccaaattaat 7260
taatcaagtg cagataaaaa tttctcattt tctattaatt tattaagtgt aacaaactaa 7320
agaaattcaa gaatcttgaa tgatgagaaa gagtcatgca tgtagaaaaa tagataataa 7380
tacatggaaa tatatatgta tttggggatt tgcatggtag ctcaaagatt attggaaagt 7440
gacaggaaga taaatcaaaa tctcagtgtt atttcaaaaa taaaaggcac agattattta 7500
aataattgac agccagtttt ataatactat gtgggagggg acagagatca atccatgtac 7560
gtgcatggct aatattaaag taagggagaa aaaaatatta agttaattga tgattaaaaa 7620
tagtaaaatt tcagacgtat atcacggcaa tgaagagttt gatctttaat atctgtataa 7680
tggtcccata atatgatgga taggcgttgt ttatgatatg attgattgat cattgatcat 7740
tgactattgt ttcttgaata attaatcagt atgggaaagg ggtcccatta aagttgacca 7800
tttgcttagc aatattatct taggtaagct ccatattagt ttaatccact tgcgaatata 7860
ttccgtcctc gcaaatcaat atttacaatt ctttttttca gttttctatc cggtatctga 7920
tacttgcatt ggtgttcgac aaaatctgta ttcgcgtcaa aaaatttcat attatggggc 7980
aaaatgctcc ataataaaag cgactcaata ttagggctcg aaccaatggc ggaaacaaga 8040
tttttactaa gggaattcaa aaaataaaaa cgataaacac atgaagaacc tcagggaatt 8100
caacatctaa tataaatata tgaaataaaa atttgattct attgtaattt gatatacagt 8160
gtaatttaca ccgtagggga tttggctaaa cctccttccg cgtacctagc tccgtccctg 8220
actcgaatcc gaggtatttg gttaaaaatg aaagagtact tctcataacc tcgtcggttt 8280
ttgtttctaa tcaatcttta tattgttaaa acataaaacg tttacttcct ttcttcttct 8340
tttaagtttt gaaaatgata actacttttg tttgactaat attttgtagt ttttgatgct 8400
aatcaatttt gtaaaaatta ctgtacttca actagcgttt actaccccac ctcactttaa 8460
aaaattccct aaagagataa ctttttgatt aattcataaa ctaaattgaa gaacttttca 8520
aatgagagta agttgaaaat gcatattata ttgtagtata taattgcaat tttgcataac 8580

```
ttaccgtaaa atgttcttcc ttttaatgat ttgttaatat gggaaatttg aacttttctt   8640
tctttgaaat tgtattcttg tcccatggtt tctatgcaat ctcaatcatc aaattgcaat   8700
tatttttttt tgttttttgt tggcaaattc aggagagctt aggtcagtga tatatgaaaa   8760
actatttttt actcttattt attttaccct ttacttatta aagaataaag tccaagacga   8820
atagacgatg tacaacgcaa atgtaaaaat acagaaaaaa tgtttacgac ttcttctcta   8880
tttattttct acttaattta cttattaaac aagtacttac ttgttaaact agctaatctg   8940
accaacaatg tgaaaatgtt tgacattata catcttgact ttttatttct ctattatttt   9000
ctcgatggtt acttcaaatc atagatttgc taatctgacc aatatcgttt aacttcaagt   9060
agaacgaaat gaacatttca aggttttaga aaacagttga aattggaccc taaaataaat   9120
aaaatgaagt tattaatagg tttacacccc                                    9150
```

<210> SEQ ID NO 60
<211> LENGTH: 9227
<212> TYPE: DNA
<213> ORGANISM: Nicotiana tabacum

<400> SEQUENCE: 60

```
gagggtagtc ttgttatatt attggggaat gaattatggt ttcaaacttt tcaaacttaa     60
aggattttgt acatggtaaa acctaaattg acacgtaact tggtactttc aaagacacga    120
tcttttacgc gatattttaa ataaagaaaa gatcaagtca aaacatgggc caaaaagaaa    180
aaccccatga ttttttctga taaaaagctg ctaactttta gtttgtttta tccaataaaa    240
catctttaac ggtctgcctg ctttagttta atcctctttt taagatgtaa ttaagcataa    300
aatagaaaag ggaaaaaaaa ggtccattgg attttggaag aaattttaag aaagtacaag    360
aactagtaaa gtcattttgt atagagtatg ttaaaaaggt gagtgacaat tcgaaaaaga    420
aagcattgat aagtcaatca ctaaataaaa aagcacacct aataatcatt cattcaaaaa    480
aacaaatttc tatgaaagat aatcattatc ataagtcact gcagaaatcc catatacagt    540
agagtaccag gattttacga taaggtgtta gcaaactatc tattcatttt ttgacaagca    600
ttttatgttt ggtcatttgt tgggaaaaat tagggagaaa tttaaaaata gttagattta    660
caactggtca ttaaaaatag cccaatttca aaagtaatcg aaatttagcc acttttcatg    720
taaagataaa tctgagcgaa aatattgttc aaaacccgga aaatacgccc gtatattata    780
ctggagttcc agcataagta tgcttgaact ccagcatatt atacgggagt tctaggataa    840
ctatgttgga actccagcat aatatgttgg agttccagca taagtacact agaactccag    900
catattatac gggagttcca acaagtataa ctgtcccgta taatatattg gagtttggag    960
caccggtgct ccagtctccc gtatattata caggagtcag caaagtatac cggtccagca   1020
taatatgctg gagttcgtac acagatgcac cgaactcacg tatattatgc ggaaccggtc   1080
tctgttgcag caaaatagtg gctatttttc attgacttcg taaacggtgg ctatttttga   1140
atgaccagtc cgaaaactgg ctataccgtg ctattttgac gaaaaattat ccccccaccc   1200
acccacccac ccaaacgcac cttacacaca ttagtgcaca tcttttaact agtttttggt   1260
tatttttta tttgatgccc gatattcgta tatggatttc gattaattag aattcacacc    1320
gaaacattct ttcttaggat tttgtacata cttaatatgc gaatacaaaa cctatgcgga   1380
aaggtaaggg aacctattca tccctctaca gtacttgtga taatgttata cttttttgaa   1440
tttaatttgg gagacatgtc aatctttatt ttgaaaaaaa aaatagaata aaaccatagg   1500
```

```
gaaatgaaca atttatcttt cactcctatc tcattttatt tgtcttgaat ttttcaaaat   1560
tttgaattat attttgaaac ttcttcaatt tattttcttg gaatcttcag aattcaattt   1620
aaaattccaa aattccaagg atttagctcc cgtttggcca cagattttgg cttcattttt   1680
ttaaaaaaaa ttttgaaaac attctttgtt tatgcaatat gatcatgttt taggggaaaa   1740
aaattaaaaa aaataaaaaa aaatcaaatt cccaaaaact ggttaggcaa tttttggatg   1800
atattttttc ttccactcac aaaactttaa catgtccaaa cacaacttca acttcaaaaa   1860
ttattttcaa cacaatttta aaaactcttt tttcaagttt caatcaaatc tatatccaaa   1920
tgttagctta gtatcaaata agtgattgaa atcaaattaa aatcgagtgg taaataaaat   1980
agaggagagc tcggtaaatt acaagagtgc ggtaaatctt ttctccttta ctctcactgt   2040
agcctattct atctgttgta actaataagt aactgagcta cggaaaaagt gcctagactt   2100
ttaacttcac aagtataata aatagaagtc aattctttca taatattgtt tccatcctat   2160
caaacagact ttgtctcact gaccttcctt ctgagtgtgt cttttatatg tcatttttag   2220
tgaatccata tgatttagag actctaatat tccacatgcg ggtcttaatt tggtgtatat   2280
gtatatggta ataatttttg ttaggtagct gtagtattct attattgtta tgtattgact   2340
catcatgtaa ataaagccgg ttagataagg ctagaaaaat atgagtatac ctagaaatta   2400
ttagcatatt gtttggaaca tgtcaaaaat ttcaatgacc tagctagagc tgtcaattag   2460
tcaaataact ttattaatat ttacttatga aaacactttg aaattcttgg agtttaaggg   2520
aaagactact gactaaaaaa caaagcaaaa gtctatgcat tactatacta tacacagcac   2580
agcattttcc aatagtattt gagatgaatc tccaatcagc tactgttgtt cttttctttt   2640
ctttatttag tttaagtttt atgtgttgat ggtatacaaa ttatttgcac aatcaaatgg   2700
cttatctgga taatataggt aaacctcttg taatcactaa ttggtaatct ggtaaaaata   2760
acactatttc tattccaatt tatgtgatca atttcactag acaaaaaattt aagaaagaaa   2820
taaatttttt agaacttgta gtcataaaca agttgtaaca tttgtatggc tataattttt   2880
ttaacttgtg atgttaaaca tgtcagattg tttgtgtagc tataaaagtt tttcattagg   2940
cgtaaaatta aaaatttaga ttaaattatt attaaattta gaaagaggtc attttttta   3000
gcgaagtaaa aaagaaatcg gttcacataa accgaaacat agagtaagta atctgttatg   3060
acaaattaaa aattacttgt agtgtaaaaa aatctttaca acattcgtgt atatacttaa   3120
atcttttta tttttggca agagatagtt gttcagcaaa agtaagttag aaataggtct   3180
gtccttctga ctttgtaact ctgaaatgaa aatttcaaaa tcccttctat ttttactgtt   3240
accccccccc cccctcacaa accccaactc actcttattt aataaaaagc tctacttaga   3300
aaagacaccc ttgtccatct gtctatatag gtagaatgag agtaaaggag aaaacatatc   3360
ctcctctcca tttctgtaga caaagattct caaagagaaa caaattaaac actagagagt   3420
gagagagtgc tataagaaaa agaatatggg gagagctcca tgttgtgata aagcaaatgt   3480
gaagagaggg ccatggtctc ctgaagaaga tgctaaactc aaagatttca ttcacaaata   3540
tggaactggt ggaaattgga ttgctcttcc tcaaaaagct ggtaacaaca acttctactc   3600
cactagtcct ctatgtgtat gtaattttat tattattatt attattatta ttattattat   3660
tattattatt attcatgaat cgaagggaca aaggtctaaa tctcagtggg tcgtggtagc   3720
aaggccattc cgccatttat aatatcttct tgcaaattcc accagtttca tatgtgtatg   3780
tttttttctt attagtcata aatcaaagcg acgaagggtt aaatttcagt tgattgtgat   3840
agcaaggtca cactctaccg cttataatat ctcgtggcgt atttaacatt gtttgtatgt   3900
```

atatgtttga gtataaaggg aggaaagctt atatttatat ttgagtggat tgagtttttt 3960
tccttgttgc tgcattattt atgatttgat gagatttatg ttgggaactg caggactaaa 4020
gagatgtggg aagagttgta gattgagatg gctaaattat ttaaggccta acattaaaca 4080
tggtgatttt tctgaggaag aagatagagt tatttgcacc ttgtattcca ccattggaag 4140
caggtaatat atatatacct ttttttggtc gtaatttttt tttcattttt tatcatcttt 4200
ctgatgaatt tgagactgaa acaaaaactg ttcccactaa aaatggaaaa gaaaaacctc 4260
aataagtaag aaaagggaaa aaacaatgag ggctcagaaa gaaatgcaaa tagtcagttg 4320
gatttttaat taaagattct gccatttatg gacatatttt tctgcatgca tgccaggttt 4380
agatctaaga tcaagtcttt atttactcac ttacagatgt ttaattatta agacaaagtt 4440
ccaatttttc ttctttcttc tctttctttt tgtggaaatt ttttctctag taaaccaatt 4500
aatttttgtt ataacatgtg caatataata tgttaacagg tggtcaataa tagcagctca 4560
attaccggga agaactgaca atgatatcaa gaattactgg aatactaagc tcaagaaaaa 4620
acctatggga ttaatgcaat caactaacca aagaaaatca ccatattttc cagctactaa 4680
ttctcttcaa acccaacccc agataaattc aagtcttttt agagacttat attacacccc 4740
aaataatagg cctaatatta caggcctaaa tcatcagtcc atttcttctg cccaccagac 4800
aaattttctc tacactaata ataacatgaa ctttcctaat ttgggtgcta caaataatca 4860
atatccttat aatatccaaa gtcataattt acttatgttt ggagaagcaa gttgttcttc 4920
atcagatgga agttgcagcc aaatgagttt tggtaaagaa atcaagagag aagaaattat 4980
gagtaatagt ttacaacaag gtcaaatttc aagtgttaat gcttttgaag aaaaccacca 5040
gaattttact cttgattatg gcaatagtag tagtaattgg gtggatcaaa aaccaaatgt 5100
gtattttggt actactacta ctcaagtact tcagtatgat aatgttgaag aagttaagca 5160
gcagctaaca agttgtacca atggcaacaa tggtagtact attggatgta acaacaacaa 5220
cagtatgttc gtgttcaatg atgagaatta taacaagtca aatgagatag agatgttcta 5280
ttactaaaga agaaatgact gttgaaaaga aaacaaatgc aagtaccatt aggaagattt 5340
gaaagggcgt ttgggtatgg gggttgccaa gaagattcag actttttttg gggttttgtg 5400
tagttgtggt agaattatta ttgaatgaaa aaaaaaaact tcctgtactt taattcgtca 5460
gtacatacta catactacta caaagtagtt aaaagcctat tctatttgtg cttttttttt 5520
cactcgatgt ccaataatta tattggtttt tgattaaatt tgaatttgag caaggaagat 5580
caacattgga gggataaatt gtttcctaac gaaggcgatt acatacttag aacttgaact 5640
caatatctct aattaaaaat gaagtaatac ttataataac tccaccacaa ttcttattgt 5700
tgtgcatttc tttataaaat atgtaaataa tgggtcatat atattgttta ccttttctat 5760
tcatatacat agattttaaa ttaattatac acatatatat aatacattaa ttattcatat 5820
attatatttt tgctagctat ttttagttta agcgatttgg taggcgacta cttgggttaa 5880
ttcttttttt ttaatatata tatcaaaata atgaagctgt ataatacact taaaaatcat 5940
atttgaaagg tattaaatac gacttaggag agttcttaaa ccattttgga accttgtcta 6000
cgtactttta tgcaatagct gtttttgttt gtctctgcta aaacctatgc tccccaaccg 6060
tgcaccaatc aacttagaag ttagaactca gaaataaatg taactatact ccacagaaag 6120
ttaaaaagtt ttactgttac cattcactca aggatcagaa actgaaagac aaatgaatca 6180
gtgcttcact gttcttcact aaaagaaata ctgtttacat tagtttcaaa agagtttaat 6240

-continued

```
cataaaaaca aatgtaccat aaaaagggga gattatcaac ctgaaaatga aacagaacat   6300
acgttatata tcaatctata tacggtcgag atcggactcg tctattacac gacagatcgg   6360
gattgaaacg taacagtttt gaagatcaac cccgggttcc gtcggaccga ggtacaaggt   6420
cagaatgccc gttctcgaga acatcgagtc catgacccca gaatcaaccc tgaccccaaa   6480
tgagctcgag gaaacatccg gataacggaa ggcgaaatat ccgtaaccgg tcgggtatca   6540
cggcatgaat ttcggcacgt aacaatgaga aaccggctaa ttagcaaatc atggaatttt   6600
ttacctttta tagaattgta actaaagtgg gattccccta ctatgtaaag gggtctgac    6660
tatttgtacg ggacattcat taaacgcatc ccaaagtaat ataatattat tttctttttg   6720
taagctattg ttctcctgta tctgatacta tttgaattgc atcaagttca agtgagactc   6780
atttttttcaa ggctataatt gttcaagtcg cacggtttga atttattcga tcattgttcg   6840
ctttaattac aattcaattc atcgctttat gtcaaattaa tccacatatc cttaaaacca   6900
cttacaaatt taattgttat caaattttaa gggtaaacag tttggcgctc accgtggagc   6960
taaggataat agtggttgtt tgatatagat tttcataaca cacactattt tacaattgtt   7020
cttcgaagtg tctctcattt caggtttaag ctcaaaatgt caaactcaca attggcaccc   7080
ctacctgcac acaatgagtc tggtcaccat ggtgaaaata acaacatagc acctggtaac   7140
gaggtaccgc ccgctgatcc catcagaatt tcaatcgcgg acccgttgga cgctaactcg   7200
catgtggcta tcgacatgtt acagtctcaa caggcgacga tagctcagtt acaaaaccaa   7260
agccgcacac cgagcagagt tgaactcgat ccgtcccgga aaatcacctg cagggaagaa   7320
ccgtccgcgg agaggtcaaa tggagatgag tcggggacta accccgagat cataaaaatg   7380
cttgaggaac cgatgatacg gattgaatca ggggaaaaga aaatcgaggc aaatgacaag   7440
aaggtaaaaa cttacaattt cacggtcaac caaatcccgg gagcaccgcc ggtactgaaa   7500
agcttggatt ccaagaagtt cgtgcaaaaa catttccctc cgagtgtggc cccgaaatcg   7560
atcccaaaaa catttatatg cccgagattc ttaagtataa tgggacaacc gacccaaacg   7620
agtatgtcac ttcttacaca tgccctatca aagggaacaa cttagaggtt gatgagatcg   7680
agtctgtttt gttgaagaaa ttcggagaga ccctgtcaaa tggagctatg atatggtatc   7740
acttacctcc taattctatt gactcatttg caatgcttgc aaactctttc gtgaaagcac   7800
acgccagggc tatcaaggtc gagacccaga agtcggacct cttcaaagta agacagaagg   7860
ataatgagat gctcaaagag tccgtgtcct agtttcaaat gaaacagaag gacctaccac   7920
cggtcgctga tgattgggcc gttcaagctt tcacccaagg actcaatgtt cgaagctcgg   7980
tggcttcaca gcagttgaag caaaatctga taaagtaccc aactgttatt tgggccaatg   8040
tgcataaccg ctatcaatca aaaatcaaag tcgaagatga tcaacttgag gctctttccg   8100
ggtcggttta ccctgtcaga ctcgtcgaca gaatcaagag agatatcgac cgtgaaccaa   8160
ggtcaaacgt agatcattac tagccatatg atggagattg gaaaagcaat aggtctgggt   8220
gaagttctac acagaatgaa aagagaaatg atccaggtca gagcactcga ggactcgcaa   8280
gcaagaacga cttcgacagg cctatcaggc ctaaagaagc accaaggtta tcgaaatata   8340
actttaatat tgatgcggct gccatcgtat cagctatcag acgcatcaaa gataccaaat   8400
ggcctcgacc tttacaatcc gatccagccc aaagggatcc taaccaaatg tgcaaatatc   8460
atggcacttc tggccacaga ataaaggatt gtcgacggtt aagagaggaa gtagcccggt   8520
tgttcaataa cgggcacctt caagaatttc tgagcgaccg agccaagaat cattttagaa   8580
atagggattc taacaaatag accgaaccag aagaacctca acacgtcatt aacatgatca   8640
```

```
tcggtggagt cgatgcccct caagtgctga tgttgaagcg caccaaagtg tccattacaa   8700

gggaaaaacg gactcgagat tacatattag aaggaacctt gtctttcaac gacgaggatg   8760

cagaagggat cgtgcagcct cacaatgatg cattggtaat atctgtactc ataaataaat   8820

ctcgagttaa gcgtgtgtta attgatccag gtagctcaac caacatcatc cgattgaggg   8880

tcctagaatg gcttggccta caagatcaaa tcatgcctgc agtccgagtt ctaaatggat   8940

tcaacatagc atgcaaaacc actaagggag aaataacatt gccggtgaat accaccagaa   9000

ccatccagga aaccaagttt tatgtgatcg aaggagacat gaggtacaac gctctgttcg   9060

ggaggctaag gatctacagc atgagggcag caccctcgac tcttcaccaa gtgttaaagt   9120

tcccaacgtc gggagggatc aaaacaatct acggggagca accggccgca aaagaaatat   9180

ttgcagtcga agaagagatc ccggtataga cactagcaac atcaaag                 9227
```

<210> SEQ ID NO 61
<211> LENGTH: 9159
<212> TYPE: DNA
<213> ORGANISM: Nicotiana tabacum

<400> SEQUENCE: 61

```
agactgtttt ttatttgatt tatactcttt aattgtattt tcgcacgaaa ataaccgatc     60

aaagttagtc gattttatta aaaaataaaa ttaccgacca aagttggtcg gtttttttaaa   120

atgaccggcc gaattaaccg accaattttg gtcggttttt taatattaat ttttatttat    180

tttaattgaa aaactgacca aaattggtcg gtttcttgaa aaataaattt cacgggactc    240

gaaaatagtt tttcgcattt ttgctccaaa gaaaaccgac caaagttggt cgatttcgta    300

aaaaaaaatt aaaaataaaa tattttaaaa aaccgaccaa cttttgtcgg tttttttggtc   360

ggtgttttga ccgaccaaag ttggtcggtc gaccttggtc ggtttttgcc gaatttctag    420

tagtgatata cccttagagt tacacaattg gcacatatat gcccttctca aaacgaaatt    480

cacccaaaaa ttatggttta aactttaaaa taataaaaac atctcaaact ttaacaatac    540

tcaaaagacc aaaatattta aattatttct aaaaagataa tttaatgatt aaaagcctag    600

agttcaagtt gtagtgttat aaatttgagt tgttagtctt tttcatcttt tttcagctgg    660

acattttcta ttttttttat taactatgta aattaggggt gtacatggaa cgggttggat    720

cgatttttat caaaactaaa ccaaaccgat tatatcggtt tgaattgttc ggttttattg    780

gttttttcag atttttttgtt acataaatat tatttcaatc ttgctttgtt aaattttttta   840

gaactaaata tatgttcagt aaaacttaaa aaattgacaa acatatgatc tatcttgatt    900

accttatggg agaattttct tagtaattgg aattcatgag ttttgtcaag tgaaattggt    960

gacgaaaata gagaagacat cagtaattga ggaaatcgga taagggagaa agaaaaagaa   1020

aaaaagaaaa aaagaagaaa gaaaagagaa aggtaaagaa aaaagcacta ataaaaagga   1080

aatagtattt gtaatatact ttaatacaat taacgtaaga gctaattagt ttgagtggat   1140

tccgttttga aaagggcata catgtgccaa ttatataact ctaagggcat atatggacca   1200

actatctgac ggtaagggca tatttgagtt aatatattaa cgaatgacaa atgtgctcaa   1260

tttcgtataa tacaaggaca tattacattt tccctattat gaaatggttc aaacttaagg   1320

attttgtaca tggtaaaacc taaattgaca tgtaacttgg tactttccat tgggcaaaga   1380

cacgatcttt tacgtgatat tttaaatcaa gtaaagatca agtcgggcca aaaagaaaaa   1440

aacccatgat tttttaagat aaaaagctgc taacttttag tttgtttcat ccaataaaac   1500
```

-continued

```
atctttaacg atctgtctgc tttagtttaa tcctcttttt aagatgtaac taagcatgaa   1560
atagaaaagg ggaaaaaaaa ggaccattgg attttggaag aagttttaag aaagtacaag   1620
aactagtaaa gtcattttgt atagagtatg ttaaaaaggt gagtgacaat tcgaaaaaga   1680
gagagcattg ataagtcaat caataaaata aaagcacacc tgataatcat tcattcagaa   1740
aacaaatttc tatgaatgat aatcattatc ataagtcact gcagaaatcc catatacagt   1800
agagtaccag gattttacga taaggtgtta gcagactatc tattcatttt ttgacaacca   1860
ttttacgttt ggtcattttt tgggaaacga actctcccaa cattcttcca aattacccca   1920
cgcaccttac tgtgcacatc ttttaaccaa cttctggtta tttttctttt tgatgtccga   1980
tattcgtata tgaattccca ttaattctaa gttgcaccga aatggttttt atcaagattt   2040
tgtatatatt taatattcga attcaaaact aatggtcgaa ggtggaagat cgtatccatc   2100
ccatcataat atttggttgg taatatcaca cctttttgaa tttgggagac ttgtcaattt   2160
ttattttgaa aaaagaaaaa aaaaagaaat agaaactaaa accataggga aatgaacaat   2220
tttattttca ctcctacctc attttatttg tcttgaattt ttcaattttg ttttgaaact   2280
tcttcagttt attttcttgg aatcttcaga atttaatttg aaattccaaa attccaagga   2340
tttagtgtca aatcagtgct tgaaattaaa tttaaaacga gtggtaaata aaatagagga   2400
gaactcggta aattacagga gtgcggtaaa tcttttctcc ttttctctct ttggagccta   2460
ctctattcta ttgtaactaa gtaacttaac tacgaaaaac gtgcctagac ttttaacttc   2520
acaagtataa taaatagaag tcaaattctt tcataatatt gtttccatcc tatcaaacag   2580
actttgcctc actgactctc cttctgagtg tgtctttttt atgtcatttt tagtgaatcc   2640
aattgattta gagactcaaa tattccacat gcgtgtctta atttggtgta tatatggtaa   2700
taatttttgt taggtagctg tagtattcta ttattgttat gtattaactc atgtaaataa   2760
aagccggtta gataagacta gaaaaaatag agtctactta gaaattatta gcctattgtt   2820
tggaacatgt caaaaattca gtgactcagc tagagctgtc aattagtcaa ataactttat   2880
taatattaac ttatgaaaac acttggggat tcttgtagtt taagggaaag actactgact   2940
gaaaaacaaa gcaaaagtct atgcattact atattataca caatacagca ttttccaata   3000
gtattttaga taaatctcca atcagctact gttgttcttt tcttttcttt tttagtttaa   3060
gttgtatgtg ttgacggtat acaaattatt tgcacaatta gatggcttat ctagataata   3120
cgtgtaaatc tattgataat cattaattag taatctggta aaaataatat tgcttttgtt   3180
ctaatataat gtgatatatt tgactgggta cgaaatttaa aaaaaaataa gacatataga   3240
acttgttgtc ttaaacaatt cataacattt gtgtggctat aattcttttg aaacttatgg   3300
tgttaaacat gtctaattgt ttgtgtatgt ataaaagatt ctcattaagc gtaggaaaat   3360
ttgaattaaa ttattttttt aatttaaaaa gagatcactc cttttagagc tgacttaaaa   3420
agaaattgat tcacataaac tcgcacggag ggaataagta atatactatc aaaaattaaa   3480
aatcacttgt agtgtaaaaa aatctttaca ccaatcgtgt atattctcaa tttttttttt   3540
ttttttggcg agaggtagtt gttcagcaaa agtaagttag aaataggtct gtacttttga   3600
ctttgtaact ctgaaatgaa aaattcaaaa tctcttcttt tttactgttt taaaaactcc   3660
aactcactct tattaatata aagctctagt tagcaaagac acccttgtcc acttgtctat   3720
atagcaagaa agagagtaaa ggagaaaaca tattctcctc tccatttctg tagacaagat   3780
tctcaaaaag aaacaaatta aacactagag agtgagagag aactataaga aaaagaatat   3840
ggggagagct ccatgttgtg ataaagcaaa tgtgaagaga gggccatggt ctcctgaaga   3900
```

```
agatgctaaa ctcaaagatt tcattcacaa atatggaact ggtggaaatt ggattgctct   3960
tccccaaaaa gcaggtaaca acaacttcta ctcccttatt cccagaatcg aagcgacaaa   4020
gggttaaatc tcagtggatt gtggtagcaa gatcatattc tatcgcttac aatatctcgt   4080
cgcgtattta acactttcgt atgtatatgt ttgaatatag ggggagggaa gcttacatta   4140
atatttatac tttgagtgga ttaagttttt ttttggttgc ttcattattt atgattttga   4200
tgagatatat gtttggaact gcaggactaa agagatgtgg gaagagttgt agattgagat   4260
ggctaaatta tctaaggcct aatatcaaac atggtgattt ttcggaggaa gaagatagag   4320
ttatttgcag cttgtattcc accattggaa gcaggtacaa tataccttt tttagtctta    4380
aattgttttc catttttat catctttctg atgaatttga gactgaaaca aaaactgttc    4440
ccactaaaaa tggaaaagaa gaaccttaat aaataagaaa agggaaaaaa caatgagggc   4500
tcagaaagaa atgcaaatag tctgttggat ttttaattaa agattctgcc atttatggac   4560
atttttttct gcatgcatgc caggtttaga tctaagatca agtctttatt tactcactta   4620
cagctgttta agtattacta ctacaaaatt ccaacgtttc ttcttttctc tcttttttt    4680
tttttttgga aaactttcc ttttgtaaac caattaaatt ttgttataac atatgcaata    4740
tattatgtta acaggtggtc aataatagca gctcaattac caggaaggac tgacaatgat   4800
atcaagaatt actggaatac taaactcaag aaaaagctta tgggattaat gcaatcaaca   4860
aaccaaagaa aatcaccata ttttccagct actaattctc ttcaaaccca accccagata   4920
aattcaagtc tttttagaga cttatattac aacccaaata ataggcctat tattacaggc   4980
ctaaatcagt ccatttcttc tgcccaccag ccaaattttc tctacactaa tagtaacatg   5040
aattttccta atttgggtgc tacaaatagt caatatcctt ataatattca aagtcataat   5100
ttacttatgt ttggagaagc aagttgttct tcatcagatg gaagttgtag ccaaatgagt   5160
tttggcaaag aaatcaagag agaggaaatt atgagtaatt gtttacaaca aggtcaaatt   5220
tcaagtgtta atgcttttga agaaaatcag aatttcactc ttgattatgg taacagtagt   5280
agtaattggg tggatcaaaa accaaatgtg tattttggaa atactactac tactactcaa   5340
gtacttcagt atgatgttga agaagttaag cagcagctaa caagttgtac caatggcaac   5400
aatggcagta ctattggatg taacaacaac aacagtatgt tcgtgttcaa tgatgagaat   5460
tataacaagt caaatgagat agggatgttc tattactgaa gaagaaatga ctagctgttg   5520
aaaagagaaa acaaatgtaa gtacaccatt aggaagattt gaaagggcgt ttgggtatgg   5580
gggttggcaa gaagattcaa acttttctg gggttttgtg taattgtggt ggaattatta    5640
ttattgaaac ttctttactt caatttaaat cgtcggtaca tattacgtag ttgtagtaaa   5700
agccttttcc tttttgtgct tttttttt ttcgtgttcg tattaagact tcattaaatc     5760
caaatttgca tagggacggt caacattaga ggaataaatt gcttcctaac aaagacgatt   5820
ttatactcaa gagttcgagc ccgaaaaacg acctctggtt aagggtaaaa atagtaatta   5880
caataactcc accacaatcc ttattggtgt gcatttcttc attaaatact ccctccaatc   5940
cactttaatt gatttgtttt tggctatttt tatatatatt aaggaattat cttttagcat   6000
taatcaataa tgaaattgac catattaacc ttttagttca ttggaaatat aacaaatact   6060
cctaggcttt ttaattcaag agcaactttt aaatccgaat ttgggctaag aatacaagct   6120
tgttcttttt tatctgtttt tcactcggtg tacgaggact caattaaatc cgaatttgag   6180
ctaagaatac agacattaga ggtaatatgc tttctaacaa atgtgactca atgttcagac   6240
```

tcagaactcg atatctctgg taaggatgac atagtactta caataactcc atcataatct 6300
ttataggtat gtatttcttt ataaaatatg taaatagtgt tatgattttt tgtatcaaaa 6360
atgatgaagt ataatactct taaaaatcat actccatccg tttcaattta tgtgaacgta 6420
ttttcttttt agtctgtgcc aaaaagaatg acctatttcc ttatttggaa ataatttacc 6480
tttatgcaat gatttatagt cacacaaaat atatgtgtct catttttaac cacaagttca 6540
aaagtcttct atcttttttt aaactctgtg cccagtcaaa tgagttcaca taaattaaaa 6600
cggagggaat aataaaaatg tattaaagac tacttaggag agttcttaaa aaaccatttt 6660
ggaaccttgt ctacgtactt ttatgcaata actgcttaag tttgtctctg ctaaaaccta 6720
tgctccccaa ccgtgcacca atcagcttag aaatttgaac tcaggaataa atgtaactac 6780
actccacaga aacttaaaaa gttttactgt taccattcac tcaaggatca gaactgaaaa 6840
acaaaagaat cagtgcttca ctaaaagaaa tactgtttac attattttca aaagagttta 6900
atcattaaaa tagatgtacc atcagattag ctaaaagata aataatcgtt aaaaaaagga 6960
gattatcaac ttgaaaatga aacaaattat atgttataat atgtcaaaat atactgacag 7020
tataaaaact cgttaaatgt gttaaatcct atgaaaaaac tgcccaaata aatatttgag 7080
cttaggtgtc aaatgttgta ctcaacaaca ataacaacaa cgcattagga tcctactagt 7140
ggggtgtcca atgttgtact attgaacatt attcaactaa cttttgttag gtgttcctgt 7200
agtttagtga aattaaagtc cactgttccc ctatatatta atcccaaatt aattaatcaa 7260
gtgcagataa aaatttctca ttttctatta atttattaag tgtaacaaac taaagaaatt 7320
caagaatctt gaatgatgag aaagagtcat gcatgtagaa aaatagataa taatacatgg 7380
aaatatatat gtatttgggg atttgcatgg tagctcaaag attattggaa agtgacagga 7440
agataaatca aaatctcagt gttatttcaa aaataaaagg cacagattat ttaaataatt 7500
gacagccagt tttataatac tatgtgggag gggacagaga tcaatccatg tacgtgcatg 7560
gctaatatta aagtaaggga gaaaaaaata ttaagttaat tgatgattaa aaatagtaaa 7620
atttcagacg tatatcacgg caatgaagag tttgatcttt aatatctgta taatggtccc 7680
ataatatgat ggataggcgt tgtttatgat atgattgatt gatcattgat cattgactat 7740
tgtttcttga ataattaatc agtatgggaa aggggtccca ttaaagttga ccatttgctt 7800
agcaatatta tcttaggtaa gctccatatt agtttaatcc acttgcgaat atattccgtc 7860
ctcgcaaatc aatatttaca attctttttt tcagttttct atccggtatc tgatacttgc 7920
attggtgttc gacaaaatct gtattcgcgt caaaaaattt catattatgg ggcaaaatgc 7980
tccataataa aagcgactca atattagggc tcgaaccaat ggcggaaaca agatttttac 8040
taagggaatt caaaaaataa aaacgataaa cacatgaaga acctcaggga attcaacatc 8100
taatataaat atatgaaata aaaatttgat tctattgtaa tttgatatac agtgtaattt 8160
acaccgtagg ggatttggct aaacctcctt ccgcgtacct agctccgtcc ctgactcgaa 8220
tccgaggtat ttggttaaaa atgaaagagt acttctcata acctcgtcgg tttttgtttc 8280
taatcaatct ttatattgtt aaaacataaa acgtttactt cctttcttct tcttttaagt 8340
tttgaaaatg ataactactt ttgtttgact aatattttgt agtttttgat gctaatcaat 8400
tttgtaaaaa ttactgtact tcaactagcg tttactaccc cacctcactt taaaaaattc 8460
cctaaagaga taactttttg attaattcat aaactaaatt gaagaacttt tcaaatgaga 8520
gtaagttgaa aatgcatatt atattgtagt atataattgc aattttgcat aacttaccgt 8580
aaaatgttct tccttttaat gatttgttaa tatgggaaat ttgaactttt ctttctttga 8640

```
aattgtattc ttgtcccatg gtttctatgc aatctcaatc atcaaattgc aattattttt   8700

ttttgttttt tgttggcaaa ttcaggagag cttaggtcag tgatatatga aaaactattt   8760

tttactctta tttattttac cctttactta ttaaagaata aagtccaaga cgaatagacg   8820

atgtacaacg caaatgtaaa aatacagaaa aaatgtttac gacttcttct ctatttattt   8880

tctacttaat ttacttatta aacaagtact tacttgttaa actagctaat ctgaccaaca   8940

atgtgaaaat gtttgacatt atacatcttg actttttatt tctctattat tttctcgatg   9000

gttacttcaa atcatagatt tgctaatctg accaatatcg tttaacttca agtagaacga   9060

aatgaacatt tcaaggtttt agaaaacagt tgaaattgga ccctaaaata aataaaatga   9120

agttattaat aggtttacac cccaatctta tctaatgct                          9159


<210> SEQ ID NO 62
<211> LENGTH: 6522
<212> TYPE: DNA
<213> ORGANISM: Nicotiana tabacum

<400> SEQUENCE: 62

agaacacatg agttctggta ttcttggact ccgctcaatc ttccattcaa caacagtcct     60

gaggttaaac atgtacctgg gtagagatgt aaaggactta tcccagttac cataaacaac    120

ttcaaacgca cgtttgctcc cgagaaatgc cttttctttt ggtagtggta cacccatata    180

cctggtggac aaatgttata tactctttga tcttgtacct tatggacgct tcaatgtgtg    240

gaatcaagat aagagaaatc aagtcaatat tcaagttaaa atgatgccca ctaaatatgc    300

ccatttcaca attgtgggtg ccaatatatt tacccacaac tcatatattt gttttctgct    360

tcctcgcacg cagcatccag ttacaacctg taaatcatct acggaaaata accttgtata    420

catccggaga tgactcatga accatgatct aacgacactc ttttatgttg tacattcgca    480

ccccctgctt aggcacgctt tatcagcaaa aacatgcctt ttgacagcac tgttactcta    540

tattgatccc atattgatgt ccgaatttta tcaagatccc ttgtgagggc atccacatcc    600

gacatactgg gcaaatgatc aaggtgggga atctcccttg aatgaaacgg cacgtgggac    660

tcgtacgctc ttggtctaat gggaggtgga gcatgctccc ttgtcaaatc tggttcaaca    720

ttctcttcct ccccatcatc atcctcatca gggaagggtg tgtcatctcc agactcatca    780

gcattgttgt catatcacta ttttcttcct gactctacgc atctgccaga tcctgattaa    840

atatgtcgtc ttcgggcaat tgagtaagga cataaccttc aagttactcg ttttcattgc    900

acaatcaata aaataatgag tttcataaat tgatccaaat tttacatata gatttatcac    960

ttcacttaca aatcataatg tgttgatatc ccatgatgga cattgttgtg ttgatgatga   1020

ctcccaaatg gaccaccatg atccaacata ctaaaactag gcatatttca actgggcgtt   1080

ggttcataac ttgtaaaatt catatctggc cagtaccccc tgtgaaatat atgggtatta   1140

atataaattc aatatataaa aataaacatc gtaacacaaa aggaaattga aatttaccac   1200

tcggcttgtg gattatgtaa actaggagag aaattatttc ctcgctcctc attagcccgt   1260

tgagataagt ttagatcagg ccaaactctt tcactcggaa tctgttcggc taaaactgct   1320

acaaaataac cacccgatga ttgagggata tccctacttt gcggaacctc attattgtga   1380

acatcttcag ctttgacgta catttccaat atttttatca taagaaattt attcttccgg   1440

agtcctcaaa aaatctctca gagtttcatg gtcttcgatg ttaaactcag cataacaagc   1500

aacccattgt agagtgacag aatacggata tttttcggtt actttaatat tcaccgaacg   1560
```

tttgctcata ctcatttttt ttacataaca acgatatcaa tgtatcatac tcaattgtaa 1620
gtgacaactt aacatgatac tgtggaaaac aactatagct tattcgtcac cataacctca 1680
cccccaatat aatgaaaccc taattcttcg cttttcaaat attatgacaa aatacaaaat 1740
aacttaatga ataattattt cagacgactt gaaggatcct gaatggattt ttacaaaatc 1800
ctgaaactct ttaaataagg aaaaaaaatc agtcccgggg gcacaattat ttgaggtata 1860
gctccttgaa tatggacgct atacccagtt gaattattgg tgtgctagtt aaatcaagaa 1920
gaattatttg tgggcccaat aaacaccgca ctataccttta acggcaaacg taccgttaag 1980
gtatagcgcg gtaaaatacg acactatata tattatggtg cctaattttt tttctacaca 2040
ttataattct ttgatcgagt ccaaaagccg gactcttatt cctaatgggt atggtgtgtc 2100
ggctatgaat ggacaaaaga gaggatttgg ttaaattccc aaggaatgtc taatatgtca 2160
actacgaaga gaataacaga attactactg ctaattaaag tacttttagg ttgaaaaagc 2220
aaaaagaagt ttgaaatatt agagcacagc actaatattc atgcaaattt tgcacttcaa 2280
aaagaagagc taataaagaa aaagaaggca ctttgttctg actatatcca agaagatatt 2340
ctacagtgat tctcctttta accaaacaaa atgaatccta ggaacagaaa caaaacataa 2400
gccccaaagg ttaattggtt ccggaggtga cataatcaac gacgttcata tatttacccc 2460
tatttcagtc gcatctctga ggaggaaatg gtgttcttct atgttagttt ttaccgattt 2520
ctcgtagaaa gtgtcatgta tagctcaaaa acatttctaa cgagtcttaa aaaccaatct 2580
cccggtatcc tttcctcttc ctttttcttt tcgtttcgca ttcagtgtaa gtatcaattt 2640
tggtctgttt aatttggatt cgtgctaata ttcattttcg gttaaagtca gaggcgaatc 2700
caaactttta agcttatgag ttcctataat aatcccaagt taatctacaa gataactgga 2760
caaatgaact gggctaaata ttcgtatatt tttaatgaat tttttagtat aaatacaggg 2820
tctatgcaaa aattactggg ttcacgagaa cccgtaccgt ttgctctaca tcggctcctg 2880
gttaaagtgc tcctttaatt tgcactccat ttgatatgaa aactttcgtt ttcgactttt 2940
cacaattatt tgacaacact ctgctaacga gttataaagt gaagttctct gtatgaagag 3000
gatagattaa gcttttcata tgtcaaatga atatcttaaa tttctggtaa aatttaaatt 3060
ccatcgataa gaaaaatata aaatgcaatg ggaacagtaa ttttttgtat ttaatttggc 3120
ccctagctag acagtagcac tttcatatgt agcaacttag aattcagtgc tttctcatgt 3180
cccttccagt agtagtgtga aaggacactt aaactattca tttaacctaa tctcagttta 3240
ataatggagt actcagtttc aattctctct tttttttttt ccccccccttt ctccatttta 3300 ggtacatggg actattatct aattactgat cgagacattt ttgtatatct gtatatgtcg 3360
aaactgacaa aaagatgact tcgcatgtta agttaaaata ttgcatctaa caaggtggaa 3420
atattatttt ttggtaagag attaagttta tgtattaaca atataaaaaa tatttatatc 3480
aggacagtta aaaagatata tgtattaatt ggtagagttt aactagtatc catcacccat 3540
agaaatattt tacacaatca agttatcttt gtttgttgta acgaaacaac ttatttaatt 3600
tattttcaaa attataaatt tcacttttaa agagaattac atgtaaatga tttctgaatt 3660
acctgatggt gtaaaatatt aagtcatatt atatatctat aaagaaaaaa aaaatgagga 3720
gatgaggcaa aacatcctac aatccttgcg tatacagaaa tacttttacg tactgtcagt 3780
aatattaggt aattttcaat ggcagacctc ttttgttgcc ctattgaccc tacaattgga 3840
ggggtattta ccccccaaga aactcgtaat cttgccctaa agattggctg actcaaatca 3900
gatgaccata tttctatatt gtccgacgta cctaacgcaa tcttcttcct ctatataaac 3960

```
catgcatgga caatctcatc ttctcaaact tcataaagat atctttaaaa aaaagagaaa   4020
atagaggtaa ttagttgtat caatggatca acaacattcc acttgttttt cttcttcaag   4080
taaaattaat gacaaagaaa agaagaaaaa aagatcagtt gtgaaactat caactgatcc   4140
acaaagtgta gcagctcgtg aaagaaggca tagaatcagt gatcgtttca agattttgca   4200
gagtttaatc cctggtggtt caaaaatgga tacagttact atgttagaag aagcaattca   4260
ctatgtcaaa tttcttaaga ctcaaatatg gctgcatcaa accgtgatta atattgtaga   4320
tgattatgat aatccaaatt atcatgatca gttgctaatg gctcatgact ctaattttgc   4380
taattattat cctcatgaaa tggtggaata ttgcccagct cctgttgaga atgcacaaat   4440
aaattataac ttggaccagc tgcagcttcc aggttatgca ttttcagatg gggatcaatt   4500
ccaaggagaa gaaactaata ttactggtga ttcttttatg tactattagt tagttaatta   4560
tgttgcctaa gtttaattag aatacgtagt gtgtggtagt atggtatgtt gttttctctc   4620
tttctatcta gcagcctaaa gatgggtttg tgttaattaa ttagatgtag taaattgtat   4680
gtgttggtta gttgattaag tatgttgcaa gttattttca ctgatcaatt aatcaatgac   4740
tttgtgaaga agcatctgga agttcaattt gactaatgta taactttttt ttaaaaaaca   4800
atgaatggat aaaaagagtg aaaagaaaga aagagagaaa attatacaaa caaaattacg   4860
ggaggtttag aaacaattta agtactacct gatactataa agaatattta cacaattaaa   4920
tcacttaaaa gaaatttggt atgtgattta gcagtttagc tattatgtag tgaactgttt   4980
ggctaaactt ttaataattg ttcattttta gaattgcttt tatcaaaata acttttcgta   5040
gaggtacttc cggagagaat taaatgcatc tttatttatc atataaggat aatatttgaa   5100
ttaaatagaa gaattaaccc aaatcgtcgt ccgcctaatc tctaaaacta aaaatagcca   5160
acgaatatat atatatatat atatgtgtgt gtgtgtgtaa ctttgtataa tcaatatata   5220
atatatgtat accgtccaaa aaaagtaaat aatgaatctg gccggttatt tatgtaataa   5280
tccggtaaat agaccgtggg cctaaagctg ctgatagagg cctgaaaaca tgggcctatg   5340
tctgctgaaa gcccgttaaa tacgccaacc taaaatagtg cttccttatc cttaaaaagc   5400
aatttgaggt cgtctaaatc aggatggtga ttttatggtt tctctgcatg tcaagaacat   5460
ataggtaaga cacattttta ggagatcact gagataaact gaaacataat ctttctcgtg   5520
tgtttgaaag tagaagaaaa gattactgta gacggtcaaa atcgtgtgtc cccgattttg   5580
taggctcgag gggtcgcatc gagaacaagt tcaatataga ctgagctcga gttcgaaggc   5640
agaatgcgag actcgaagat ctatgtgctc gaggaacatc agagccgaat atggctaatc   5700
tcgagataat accgttatgg ttttgtaaca gaaagggcga gattcccacg gtggccctaa   5760
gatcgtggcg taaattccgg aatagatttg tacgagttag tacggatttg tactaggagg   5820
ttagacagtt gtcccaataa gattctttac tgtaaataga aatgtacatt atttagggtt   5880
cctctactat ataaagggga caccaatcat ttgtaacatt catttaatca ttggcaaaag   5940
aatatactct cttactttct tgttcattac tcatcagaat tgtctcttaa ctttattgtc   6000
tttattttac tattcttgtt gacctacctc gaggtcacca tagctcgagg tcaagacttg   6060
cttaagcact ggtttgattc agcttacttc tttaattttc acgtttgatt tcttggttat   6120
taattagtat tgaactaaat cacgtatctt taaaatcaca aacaagttta attgttactc   6180
gtattttcga ggtaaacagt ttggcgccca ccatggggct aaagataata gtggttattt   6240
cagtactgat tctgataaca cacgttattt ttacacttat tcttttcaag aatttttgtt   6300
```

-continued

```
ctcaagttaa attatgtcaa actcacaaaa cgcacccgta cacggcgatg atggtctagg   6360

atttcatggg gaaaacaaca atgtagtttg tcacacctcc ctttttccta taccctgtaa   6420

agggtataag ggagtttttc caattaaagg acaatcgaaa cgggattcct tattaatttc   6480

agagtcgcca cctgggaact ttatggcgtc ccaagtcacc ga                      6522
```

<210> SEQ ID NO 63
<211> LENGTH: 8524
<212> TYPE: DNA
<213> ORGANISM: Nicotiana tabacum

<400> SEQUENCE: 63

```
agtgattatt agcccaatca cttaaaaact cccgaaggtg cccttcattg aataaccggg     60

ctacttcttc tctcaacttc ctgcaatctt ccattctgtg gccatgggtt ccataatact    120

tgcatacttg attgggattt ctctgggctg gatcggttgg tagaggtcaa gaccatttag    180

tagcttagat atgtccgata gccgatacga tagcggatgc atcaacattg aagctatact    240

tcgagaatcg tggtgcttcc ttaggtccgt tatgcctgtc gaaaccattc ttgcttatca    300

gccctcgaga gccttggcct cgatcacttc tccttttacc tcgtatgggc cccaggtctg    360

ttacccctac gatctctatt atacggctgg tatcgatccc tgttcaacct cgattctcga    420

tcgatgtcac tcttggtaac ggatccagaa ggagccccca gctggtcgtc ttcgactcta    480

atcttcgatt gatatcgatt atgtatatcg gcccaggtaa cagccgggta ctcaatcaag    540

ttctgcttca actgttgtga agccactgaa cttcgttcat ttagtccttg ggtgaaagct    600

tgaacggccc aatcgtccgt gaccggtggt agattcattc gttccatttg gaaacgagat    660

acaaactctc taagcatctc gttatctacc tgctttacct tgaaaaggtc cgactttcta    720

gtctcgacct ttatggctac ggcgtgtgct tttacaaaag aatctgcaag catggcaaaa    780

gaatcgatag agttaggtgg taaattatga taccatatca ttgctccctt tgacagggtt    840

tccccgaatt tctttagtaa tacggatttg atctcgtcgt cctctagatc attcccttta    900

atggcatacg tgtaagaggt gacatgctcg ttggggtcga tcgttccatt atacttagga    960

atctcggtca tgcagaactt cttggagatc ggtttgggag ctgcgctgag ggggaagggc   1020

tttggtacga actttttgga atctaaaccc ttcaatattg gtggtgcccc ggggatcaga   1080

tcaaccctgg agttataagt gtccactttc ttgtcgtttg cttcgatcct cctttcccct   1140

gactctatcc attttgtcat ttcctcgagc atctttataa tttcggggtt agtccccgat   1200

tcttgtacat ttaaccttac cacaactggc cccgttctgt gggtgactta ttggggtgga   1260

tcgggctcaa ccctgctcgg cgcctgggta tggctttgta actgagctat cgccacctgt   1320

tgagcttgta gcatttcaaa tatcatacgc aagttgatcc cgtcttctcc aatattttgg   1380

atatttctaa ctgcagatcg agttccacca tgtatgctat tttcgggacc ggaatgttgg   1440

ttcgcttcga tggccacatg cgaattaacg tcaatcggat ccacggcttg agtcccaacg   1500

gggtcagcag gtggcctttc atccctgggc gtcacgttgt tattctcacc ttgatggcca   1560

aattcattat cgatatgcac ggggagtaat tgagagttcg tcatctttag cctgaaatca   1620

aagatacttc caagagcaag tgcaaaatat ggtgttttat agagatttgt atcaaataac   1680

cactattatc cttagcccca cagtgggcgc caaactgtta acccaaaaaa tggataacaa   1740

ttgaatttat aagcggttct aaggatacgt agtataactt ggtacaaatt gagaaaatat   1800

ataaatgaat atcgaaatta actgtaaaaa aaatgaatgc aaaccgaatg aattaattag   1860

cctaggccct caagtttgat caccctcaaa ctgaatggag agtagactga tacaagaaca   1920
```

```
aaatgattga atatcgaaac cagaaaaagg cagtatattg ctttatattc tatgaatctg   1980
aatctcctcc cttacaaata atcagacccc ctttatatag tagggaagtc ctattcttaa   2040
tataatttct aaataccgta aggaatccca tgatagatta attaattggc ctcttcttga   2100
tatgcgccgg gatttccgtt cagattttcg cccaattgcg gatattccgg ttttctattt   2160
tttggctcga taagctctcc tcaattttgg ctgacctcga tcttgatcgg tctctaactt   2220
gctcgatctc gatctcgatc ttggccgatc tcgatcgtga ccggtctcga tcttgctcga   2280
tctcaatctt ggccgatatc gatcttgatc ggtctctgga tcacgagctc ggtaacctaa   2340
ctttgcatta tggctcgatt ctacacgagg ccataccttg gtctatcata ttccaatctc   2400
gattaatcat acgaagggca aactcggttt tgaccgtata cagaaatgat gttctataat   2460
cgattacaat ttcaataaaa gaaaataatc ttatagtaat aaagtttata tataaatctc   2520
ctgtcttatt tttttaccga ttcttataga aagtgtcata tatagctcaa aaacatttca   2580
aatgagtctt aaaaaccaat ctcccggtat ccttgcctct tcctttttct tttggtttct   2640
cattcagtat aagtatcaat tttggtctat ctaatttgga ttcgtgctaa aaattcattg   2700
tcggttaaag tgctccttta atttgcactc catttgatat ggacactttc gttttcgact   2760
tttcacaatt atttgacaac actctgctaa tgagttataa agtgaagttc tctgtatgaa   2820
gaggatagat taagcttttc atatgtcaag tgaatattaa tttctggtaa aatttaaata   2880
ccatcgataa gaaaaatata aaatgcaatg tgaacagtaa ttttttggat ttggccccta   2940
gttaggcagt agcactttca tatgtagcag cttagaattc agtgttttct catgtccctt   3000
ccagtagtag tatgaaagga cacttaaact attcatttaa cctaatctca gtttaataat   3060
ggagtactca gtttcaattc tcttttttt tttccctttc tccattttag gtacatggga   3120
atattatcta attactgatc gacacatttt tgtatatctg tatatgtcga aattgacaaa   3180
aagataactt tgcatgttaa gttaattaaa atattgcatc taactaggtg gaaataatat   3240
ttttggcaat agtactttaa gtttatgtat taagaataca aaaactattt atatcaggag   3300
agtaaaaaag atatatgcat taattggtag agcttaacta gtatccatcg cctatagaga   3360
tcttttacac aatcaaatta tcattgtttg ttctaacaaa caacttattt aatttatttt   3420
caaaattata aatttcagtt ttaaagagaa ttacttgtaa ataatttctg aattacctga   3480
tggtgtaaaa tattaagcca tattatatat acaaagaaaa aaatcaggag atgaggcaaa   3540
acatccaaca atccttgcgt atacagaaat acttttacgt actgtcagta atattaggta   3600
attttcaatg gcagacctct tttgttgccc tattgaccct acaattggag ggtatttac    3660
ccccaagaaa ctcgatcgta atcttgccct aaagattggc tgactcaaat cagatgacca   3720
catttctata ttgtcccacg tacctaacgc aatcttcttc ctctatataa accatgcatg   3780
gacaatctcc tcttctcaaa cttcataaag atattatatt aaaaaaaata aagaagaaga   3840
gaagatagag gtaattagct atagcaatgg atcaacaaca ttccacttgt ttttcttctt   3900
caagcaaaat taatgacaaa gaaaagaaga aaaaaggatc agttgtgaaa ctatcaactg   3960
atccacaaag tgtagcagct cgtgaaagaa ggcatagaat cagtgatcgt ttcaagattt   4020
tgcagagttt agtccctggt ggttctaaaa tggacacagt tacaatgtta gaagaagcaa   4080
ttcactatgt caaatttctc aagatgcaaa tatggctgca tcaaaccatg attaatattg   4140
tagatgatta tgataatcca aattatcatc atcagttgct aatggctcat gactctaatt   4200
ttgctaatta ttatcctcat gagaataact caactcctgt tgagaatgca caaataaatt   4260
```

```
ataacttgga ccagctgcag cttccaggtt atgcattttc agatggagat caattccaag   4320
gagaagaaac taatatttct ggtgatgctt ttatgtacta ttaattagta attagttaat   4380
tatgttgcct aagtttaatt agaatacgta gtgtgtggta gtatggtatg ttgttttctc   4440
tctttctatc tagcagccta atgatgggtt tgtgttaatt aattagatgt agtaaattgt   4500
aagtgttggt tagttgatta agtatgttgc aagtttgtga agaagcatct ggaagttcaa   4560
tttgcctaat gtataacatt ttttaaataa aaactgaacg gacaaaaaga gtgaaagagg   4620
aaagaaagag agaaaattaa agaaaccaaa ttacgggagg tttagaaaca atttaagtct   4680
atactacctc ttattacctc ttattaatta taatataaag aatatttaca taattaaatc   4740
atttttatgg tatttaacgg tttagctatt atgtagtgaa acgtctatct tttctggtgg   4800
caacgtatca agtctgcttg gccaaacttt taaaaacggc tcaaattttg gaattacttt   4860
tgtcaaaata acttttcgtg gaggttcttc cggagagaat taaatgcata tttatttgtc   4920
atactgggat aatattcgaa ttaaatatcc agtgggccta aagctgctga tagaggcctg   4980
aaaacatggg cctaagtctg ctgaaagctc gttaaatacg ctaacctgaa atagtgcttc   5040
cttaaaaata agggattttg gcatggtgtg acaacttacc tacataattg gtagaaacaa   5100
atcctagtta taaatattgg caccagatag ccaataaata tatatcacaa aaagaatgtg   5160
tatatcacaa tatttttctt ctttgtgtat atcgaaatat atattaattt tttttctttg   5220
tatatctaaa atataaaatg ataaatatag ttgtttaaaa tttattgtta tctctatatc   5280
aatctatatc acaacaaaaa taaatgcatt gcttgtatat cacagtatat gacacatcaa   5340
atatgtgtat accaaaatgg acatcacaaa tttatgtttc ttctttgtgt atatcaaact   5400
gtatatcaaa aaattatttt cctttttat atattaaaat ttatataaaa tttatttatt   5460
cctacaatta tatttattgt ttatatttta gaactttctc taaacctatt atatcgggga   5520
aaaaaattat ttgacaagaa caaaattgaa ataagtttat tcaaaataaa tttctccctc   5580
ttaaaattaa actggacgat ttgattccga tttaatatat tgccaaatct aacaatgtat   5640
attacgatat acaacatgat atacacacag gtatatatgg tgatagacgt agatgtacac   5700
cacctcaaac acacatattt ttatcttaca ataagaaaaa aagaaaaaaa aaggaagaag   5760
aagaaaattg gaatatgccg cttgaaaaaa gaaagagaag aacggcgaaa ttcattagta   5820
cgagaattta catataagat atgtaaatat cgaatgaaaa atatgatccg gcaatcgcaa   5880
tattggattc tcataataat tagtgcgaga aacttttgtg acatgcggca tacttcggcc   5940
atatcattgg aattgaaaca acacaaaaaa aaaaatcaaa aatccttacc ctaacttcgt   6000
ttgaggcgca gaccaagttc tacaaggaaa ctttataatt ctattttttt tcttttactt   6060
caagacctta aaattctatc aaaagtaatt ctcacacgca atattaaagg gtccaagtaa   6120
aaattattga aatacgggga aagaaaagat aaaaacattg aagaagaaat acgggggatt   6180
ttaggatttg gctatataat ggcaattctt ttaggctgcc tttgccgaat ttaatacaag   6240
gctaaaaaag tgtcaattct ctttatgggt tgtcatacca tgccattttc tctataaaga   6300
atttaggggt attattattt ttagcccccg tcagaaacta tttatattaa ttaggtagcc   6360
aaaaaagtat ataaattttt tataattttt atatataaca tacataatgt gtgtgtgtgt   6420
gtgtatatat atatatatat atatatatat atattcggct attattttga gagcggttat   6480
ataatgtcat tttcccaaaa tttgagatca tctaaattag gattgtgatt ttatggaatt   6540
ttatggtttc tctgcatgtc aagaacatat aggtaagaca catttttagg agatttcgga   6600
gataaactga acaataattt tttcttgtgt gtttgaaagt aaaagaaaag attacaataa   6660
```

-continued gaagaaaaaa gattcatctt ttatttttat tatatgaacc gtaatatctt ataactaagg 6720
gaaaagggca aaatatactc ctcaactttc ggatattatc taaatttaat attcgttata 6780
ctatcatgtc aaatttatcc ctatcgttat attatccagc caaatttacc cctatcatca 6840
ccaaattttt aaaaattaac ccttgatctg ttaggttatc caaaatctcc caattttttt 6900
tttaatttaa attgcttgtt attcttcttg ctccactatt ttcagaaatt actattgaat 6960
gctatatgta ctagactata caaattattt atggatattt tttgattacc attgcaccca 7020
cttctcttct tgtgataatg ggtttggaat tggtttaaaa ttttatttat ttttcaacta 7080
tatacacact gtagaattca gttggtctat ttattgtgta ttatatgcag ctgctcatca 7140
tgtatataca tgcatatttg aatatatttt gttattgtct agttagtata gagttcgatc 7200
gactagctta agagtgcaca atccataggc atttgattaa agcaaagttg aattcgataa 7260
tgtaaattct ccaaagaact tcaacttcta tcactaatat ttgtaaagtc tccatacttt 7320
tggtgcagca aattcattaa agatagggtg ttgtaaatac ttttaaaatt tagataagct 7380
acttaatttc gattcttcaa tttactatat tttgtttact aaccgttgta ttattttaat 7440
atttcttttt cttatttttt ttaattaagg acgcaggtaa atgccaacta tttcgaaaat 7500
agtgaatcaa gaagaagaat gagtgactta attaaaataa tttggaagat tctgggtcac 7560
ctgacggatt gaggggtaac ttttaaaagt ttgttgatga taggggtaaa tttggctgga 7620
taatataacg ataaggataa atttgactga atagtataac aaaggttaaa tgtaaagaat 7680
attcgaaagt agagggataa atttggacat tttccctata actaaaaggt aatgactaat 7740
ggggaatgac ttagacttct caagtagctt ttggttattt tttacgttat aatatacttt 7800
tctaatgaca aaaaacctag gcatctagct ttcagcatgc atgcctacat attagactaa 7860
aatataaaat ttcaatacaa ctaagcttct ttatgtgtgg gatcttagac aaaaatctaa 7920
tcaaattaaa ttggccgaat agtctcgtag actcttgtat ttgtttcagt ttgtcatttc 7980
ggtccttgta atccacaaag tttcatccaa acacttatag ttatcaaaat atactacttt 8040
aaattcctct gacagttgac tgaacatatg tggcaacttg atggctgagg aggacaaaat 8100
atgtgtgttt cacgtgtata acaagcgtga gtatgaatat taaaacaaaa aataattaaa 8160
taagaaagaa tgttttaaaa taaaagaaaa agacgagaca aatagtaaga aaagaaaatt 8220
agacaaaacc caaaaatgaa aaactccagt tactcaatcc ctgtcgttct cctcctcatc 8280
gtccgccccc ctctctcaaa agtaaataaa ggataaagct tagatctaaa aacaccgata 8340
ttctgttgta aaaaaaaagt ttgttctttc ataaaactaa ataccgcaat tcaatcacaa 8400
ctgtttctcc caaaaccata tccaaatata catgcatgtt ttccattaat taaaccaaaa 8460
tgcaaaagta aaactgttcc aatctgtacg cttttagcat ctggaacttc gttttggcaa 8520
tcta 8524

<210> SEQ ID NO 64
<211> LENGTH: 181
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 64

Met Ala Met Val Val Gln Gln His Arg Glu Ser Ser Ser Gly Ser Ile
1               5                   10                  15

```
Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Tyr Arg Asn Cys Cys
            180
```

<210> SEQ ID NO 65
<211> LENGTH: 837
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 65

```
Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Thr Gly
                165                 170                 175
```

```
Thr Ala Val Asp Trp Val Pro Met Pro Gly Met Lys Pro Gly Pro Asp
            180                 185                 190

Ser Val Gly Ile Phe Ala Ile Ser His Ser Cys Ser Gly Val Ala Ala
        195                 200                 205

Arg Ala Cys Gly Leu Val Ser Leu Glu Pro Thr Lys Ile Ala Glu Ile
    210                 215                 220

Leu Lys Asp Arg Ser Ser Trp Phe Arg Asp Cys Arg Asn Val Glu Val
225                 230                 235                 240

Phe Thr Met Phe Ser Ala Gly Asn Gly Thr Ile Glu Leu Leu Tyr Thr
                245                 250                 255

Gln Ile Tyr Ala Pro Thr Thr Leu Ala Pro Ala Arg Asp Phe Trp Thr
            260                 265                 270

Leu Arg Tyr Thr Thr Thr Leu Glu Asn Gly Ser Phe Val Val Cys Glu
        275                 280                 285

Arg Ser Leu Ser Gly Thr Gly Ala Gly Pro Asn Ala Ala Ser Ala Ser
    290                 295                 300

Gln Phe Val Arg Ala Gln Met Leu Pro Ser Gly Tyr Leu Ile Arg Pro
305                 310                 315                 320

Cys Asp Gly Gly Gly Ser Ile Ile His Ile Val Asp His Leu Asn Leu
                325                 330                 335

Glu Ala Trp Ser Ala Pro Glu Ile Leu Arg Pro Leu Tyr Glu Ser Ser
            340                 345                 350

Lys Val Val Ala Gln Lys Met Thr Ile Ala Ala Leu Arg Tyr Ala Arg
        355                 360                 365

Gln Ile Ala Gln Glu Thr Ser Gly Glu Val Val Tyr Gly Leu Gly Arg
    370                 375                 380

Gln Pro Ala Val Leu Arg Thr Phe Ser Gln Arg Leu Ser Arg Gly Phe
385                 390                 395                 400

Asn Asp Ala Ile Asn Gly Phe Ser Asp Asp Gly Trp Ser Leu Leu Ser
                405                 410                 415

Ser Asp Gly Gly Glu Asp Val Ile Val Ala Val Asn Ser Arg Lys Asn
            420                 425                 430

Ile Ala Thr Thr Ser Val Pro Leu Ser Pro Leu Gly Gly Ile Leu Cys
        435                 440                 445

Ala Lys Ala Ser Met Leu Leu Gln Asn Val Pro Pro Ala Val Leu Val
    450                 455                 460

Arg Phe Leu Arg Glu His Arg Ser Glu Trp Ala Asp Phe Asn Val Asp
465                 470                 475                 480

Ala Tyr Val Ala Ser Ser Met Lys Ser Cys Ser Tyr Ala Tyr Pro Gly
                485                 490                 495

Val Arg Pro Thr Arg Phe Thr Gly Ser Gln Ile Ile Met Pro Leu Gly
            500                 505                 510

His Thr Ile Glu His Glu Glu Met Leu Glu Val Ile Arg Leu Glu Gly
        515                 520                 525

His Ser Ile Gly Gln Glu Asp Ala Phe Met Pro Arg Asp Ile His Leu
    530                 535                 540

Leu Gln Met Cys Ser Gly Thr Asp Glu Asn Ala Val Gly Ala Cys Ser
545                 550                 555                 560

Glu Leu Val Phe Ala Ala Ile Asp Glu Met Phe Pro Asp Asp Ala Pro
                565                 570                 575

Leu Leu Pro Ser Gly Phe Arg Ile Ile Pro Leu Glu Ser Lys Ser Ser
            580                 585                 590

Asp Pro Gln Asp Thr Ser Asn Ala His Arg Thr Leu Asp Leu Ala Ser
```

595 600 605

Ser Leu Glu Val Gly Pro Ala Thr Asn Pro Ala Thr Gly Asp Val Val
610 615 620

Ser Gly Tyr Ser Ala Arg Ser Val Leu Thr Ile Ala Phe Gln Phe Pro
625 630 635 640

Phe Glu Asp Asn Leu Gln Asp Asn Val Ala Thr Met Ala Arg Gln Tyr
645 650 655

Val Arg Ser Val Val Ser Ser Val Gln Arg Val Ala Met Ala Ile Ser
660 665 670

Pro Ala Gly Val Asn Ser Thr Phe Gly Ser Lys Leu Ser Pro Gly Ser
675 680 685

Pro Glu Ala Val Thr Leu Ser His Trp Ile Cys Gln Ser Tyr Ser Tyr
690 695 700

His Met Gly Thr Glu Leu Leu Gln Ala Asp Ser Arg Gly Asp Glu Ser
705 710 715 720

Val Leu Lys Asn Leu Trp Gln His Gln Asp Ala Ile Leu Cys Cys Ser
725 730 735

Leu Lys Ser Leu Pro Val Phe Ile Phe Ala Asn Lys Ala Gly Leu Asp
740 745 750

Met Leu Glu Thr Thr Leu Val Ala Leu Gln Asp Ile Thr Leu Asp Arg
755 760 765

Ile Phe Asp Glu Ser Gly Arg Lys Val Leu Phe Ala Glu Phe Pro Lys
770 775 780

Ile Met Asp Gln Gly Phe Ala Tyr Leu Pro Gly Gly Ile Cys Met Ser
785 790 795 800

Ala Met Gly Arg His Ile Ser Tyr Glu Gln Ala Ile Ala Trp Lys Val
805 810 815

Phe Ala Ser Glu Glu Thr Ser Val His Cys Leu Ala Phe Ser Phe Ile
820 825 830

Asn Trp Ser Phe Val
835

<210> SEQ ID NO 66
<211> LENGTH: 181
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 66

Met Ala Met Val Val Gln Gln His Arg Glu Ser Ser Ser Gly Ser Ile
1 5 10 15

Thr Lys His Leu Asp Ser Ser Gly Lys Tyr Val Arg Tyr Thr Ala Glu
20 25 30

Gln Val Glu Ala Leu Glu Arg Val Tyr Ala Glu Cys Pro Lys Pro Ser
35 40 45

Ser Leu Arg Arg Gln Gln Leu Ile Arg Glu Cys Pro Ile Leu Ser Asn
50 55 60

Ile Glu Pro Lys Gln Ile Lys Val Trp Phe Gln Asn Arg Arg Cys Arg
65 70 75 80

Glu Lys Gln Arg Lys Glu Ser Ser Arg Leu Gln Thr Val Asn Arg Lys
85 90 95

Leu Ser Ala Met Asn Lys Leu Leu Met Glu Glu Asn Asp Arg Leu Gln
100 105 110

```
Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Tyr Arg Asn Cys Cys
            180


<210> SEQ ID NO 67
<211> LENGTH: 204
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 67

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Tyr Arg Asn Cys Cys Leu Gly Pro Asp Ala Trp Asp Glu Ala Trp Ser
            180                 185                 190

Gly Phe Ser Trp Asp Phe Cys His Leu Thr Gln Leu
        195                 200


<210> SEQ ID NO 68
<211> LENGTH: 216
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 68
```

```
Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Ala Met Trp Ser Cys
    210                 215
```

<210> SEQ ID NO 69
<211> LENGTH: 219
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 69

```
Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
```

```
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Ala Arg His Val Val Leu Leu Val
    210                 215


<210> SEQ ID NO 70
<211> LENGTH: 837
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 70

Met Ala Met Val Val Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
        195                 200                 205

Ala Ala Arg Cys Gly Leu Val Ser Leu Glu Pro Thr Lys Ile Ala Glu
    210                 215                 220

Ile Leu Lys Asp Arg Pro Ser Trp Phe Arg Asp Cys Arg Asn Val Glu
225                 230                 235                 240

Val Phe Thr Met Phe Ser Ala Gly Asn Gly Thr Ile Glu Leu Leu Tyr
                245                 250                 255

Thr Gln Ile Tyr Ala Pro Thr Thr Leu Ala Pro Ala Arg Asp Phe Trp
            260                 265                 270
```

-continued

```
Thr Leu Arg Tyr Thr Thr Thr Leu Glu Asn Gly Ser Phe Val Val Cys
        275                 280                 285

Glu Arg Ser Leu Ser Gly Thr Gly Ala Gly Pro Asn Ala Ala Ser Ala
    290                 295                 300

Ser Gln Phe Val Arg Ala Gln Met Leu Pro Ser Gly Tyr Leu Ile Arg
305                 310                 315                 320

Pro Cys Asp Gly Gly Gly Ser Ile Ile His Ile Val Asp His Leu Asn
                325                 330                 335

Leu Glu Ala Trp Ser Ala Pro Glu Ile Leu Arg Pro Leu Tyr Glu Ser
            340                 345                 350

Ser Lys Val Val Ala Gln Lys Met Thr Ile Ala Ala Leu Arg Tyr Ala
        355                 360                 365

Arg Gln Ile Ala Gln Glu Thr Ser Gly Glu Val Val Tyr Gly Leu Gly
    370                 375                 380

Arg Gln Pro Ala Val Leu Arg Thr Phe Ser Gln Arg Leu Ser Arg Gly
385                 390                 395                 400

Phe Asn Asp Ala Ile Asn Gly Phe Ser Asp Asp Gly Trp Ser Leu Leu
                405                 410                 415

Ser Ser Asp Gly Gly Glu Asp Val Ile Val Ala Val Asn Ser Arg Lys
            420                 425                 430

Asn Ile Ala Thr Thr Ser Val Pro Leu Ser Pro Leu Gly Gly Ile Leu
        435                 440                 445

Cys Ala Lys Ala Ser Met Leu Leu Gln Asn Val Pro Pro Val Val Leu
    450                 455                 460

Val Arg Phe Leu Arg Glu His Arg Ser Glu Trp Ala Asp Phe Asn Val
465                 470                 475                 480

Asp Ala Tyr Val Ala Ser Ser Met Lys Ser Cys Ser Tyr Ala Tyr Pro
                485                 490                 495

Gly Met Arg Pro Thr Arg Phe Thr Gly Ser Gln Ile Ile Met Pro Leu
            500                 505                 510

Gly His Thr Ile Glu His Glu Glu Met Leu Glu Val Ile Arg Leu Glu
        515                 520                 525

Gly His Ser Ile Gly Gln Glu Asp Thr Phe Met Pro Arg Asp Val His
    530                 535                 540

Leu Leu Gln Met Cys Ser Gly Thr Asp Glu Asn Ala Val Gly Ala Cys
545                 550                 555                 560

Ser Glu Leu Val Phe Ala Ala Ile Asp Glu Met Phe Pro Asp Asp Ala
                565                 570                 575

Pro Leu Leu Pro Ser Gly Phe Arg Ile Ile Pro Leu Glu Ser Lys Ser
            580                 585                 590

Ser Asp Pro Gln Asp Thr Ser Asn Ala His Arg Thr Leu Asp Leu Ala
        595                 600                 605

Ser Ser Leu Glu Val Gly Pro Ala Thr Asn Pro Ala Thr Gly Asp Val
    610                 615                 620

Val Ser Gly Tyr Ser Ala Arg Ser Val Leu Thr Ile Ala Phe Gln Phe
625                 630                 635                 640

Pro Phe Glu Asp Asn Leu Gln Asp Asn Val Ala Thr Met Ala Arg Gln
                645                 650                 655

Tyr Val Arg Ser Val Val Ser Ser Val Gln Arg Val Ala Met Ala Ile
            660                 665                 670

Ser Pro Ala Gly Val Asn Ser Thr Phe Gly Ser Lys Leu Ser Pro Gly
        675                 680                 685
```

```
Ser Pro Glu Ala Val Thr Leu Ser His Trp Ile Cys Gln Ser Tyr Ser
    690                 695                 700

Tyr His Met Gly Thr Glu Leu Leu Gln Thr Asp Ser Arg Gly Asp Glu
705                 710                 715                 720

Ser Val Leu Lys Asn Leu Trp Gln His Gln Asp Ala Ile Leu Cys Cys
                725                 730                 735

Ser Leu Lys Ser Leu Pro Val Phe Ile Phe Ala Asn Lys Ala Gly Leu
            740                 745                 750

Asp Met Leu Glu Thr Thr Leu Val Ala Leu Gln Asp Ile Thr Leu Asp
        755                 760                 765

Lys Ile Phe Asp Glu Ser Gly Arg Lys Val Leu Phe Ala Glu Phe Pro
    770                 775                 780

Lys Ile Met Glu Gln Gly Phe Ala Tyr Leu Pro Gly Gly Ile Cys Met
785                 790                 795                 800

Ser Ala Met Gly Arg His Ile Ser Tyr Glu Gln Ala Ile Ala Trp Lys
                805                 810                 815

Val Phe Ala Ser Glu Glu Thr Val His Cys Leu Ala Phe Ser Phe Ile
            820                 825                 830

Asn Trp Ser Phe Val
        835


<210> SEQ ID NO 71
<211> LENGTH: 265
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 71

Met Ala Met Val Ala Gln Gln His Arg Glu Ser Ser Ser Gly Ser Ile
1               5                   10                  15

Thr Lys His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ser Ser Arg Leu Gln Thr Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Phe Met Arg Gln Gln
        115                 120                 125

Leu His Thr Ala Ser Ala Ala Thr Thr Asp Val Ser Cys Glu Ser Val
    130                 135                 140

Val Thr Thr Pro Gln His Ser Leu Arg Asp Ala Asn Asn Pro Ala Gly
145                 150                 155                 160

Leu Leu Ser Ile Ala Glu Glu Thr Leu Ala Glu Phe Leu Ser Lys Ala
                165                 170                 175

Thr Gly Thr Ala Val Asp Trp Val Pro Met Pro Gly Met Lys Pro Gly
            180                 185                 190

Pro Asp Ser Val Gly Ile Phe Ala Ile Ser His Ser Cys Ser Gly Val
```

```
        195                 200                 205

Ala Ala Arg Gln Arg Leu Leu Arg Ser Ser Lys Ile Asp Leu Leu Gly
    210                 215                 220

Ser Glu Ile Ala Gly Thr Leu Lys Phe Ser Gln Cys Phe Leu Gln Glu
225                 230                 235                 240

Met Glu Gln Leu Asn Phe Cys Thr Arg Arg Tyr Met Leu Leu Pro Pro
                245                 250                 255

Trp Leu Leu His Val Ile Phe Gly Leu
            260                 265


<210> SEQ ID NO 72
<211> LENGTH: 258
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 72

Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met Gln Ala Leu Ala Asp Arg Tyr Pro Pro Pro Thr Leu Arg
                165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
        195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Pro Gln Ala Leu Glu Arg Pro Arg Lys Val Lys Asp Phe
                245                 250                 255

Phe Ala


<210> SEQ ID NO 73
<211> LENGTH: 262
```

<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 73

```
Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
    210                 215                 220

Pro Ser Ile Ile Ser Ser Ile Val Leu Leu Pro Asp Glu Thr Leu Ala
225                 230                 235                 240

Ile Asn Cys Val Phe Tyr Leu Thr Gln Ala Leu Lys Arg Pro Arg Asn
                245                 250                 255

Val Lys Asp Phe Phe Ala
            260
```

<210> SEQ ID NO 74
<211> LENGTH: 259
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 74

```
Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
```

```
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met Gln Ala Leu Ala Asp Arg Tyr Pro Pro Pro Thr Leu Arg
                165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
        195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Leu Thr Gln Ala Leu Glu Arg Pro Arg Lys Val Lys Asp
                245                 250                 255

Phe Phe Ala


<210> SEQ ID NO 75
<211> LENGTH: 259
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 75

Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125
```

```
Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met Gln Ala Leu Ala Asp Arg Tyr Pro Pro Pro Thr Leu Arg
                165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
        195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Leu Ser Gln Ala Leu Glu Arg Pro Arg Lys Val Lys Asp
                245                 250                 255

Phe Phe Ala


<210> SEQ ID NO 76
<211> LENGTH: 249
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 76

Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
    210                 215                 220
```

```
Pro Ser Ile Ile Ser Ser Ile Val Leu Leu Pro Asp Glu Thr Leu Ala
225                 230                 235                 240

Ile Asn Cys Val Phe Tyr Thr Gly Ser
                245


<210> SEQ ID NO 77
<211> LENGTH: 457
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 77

Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160

Pro Leu Met Gln Ala Leu Ala Asp Arg Tyr Pro Pro Pro Thr Leu Arg
                165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
        195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Leu His Arg Leu Leu Lys Asp Arg Glu Lys Leu Arg Ile
                245                 250                 255

Phe Leu His Arg Ile Lys Ser Met Asn Pro Lys Val Val Thr Leu Ala
            260                 265                 270

Glu Arg Glu Ala Asn His Asn His Pro Leu Phe Leu Gln Arg Phe Val
        275                 280                 285

Glu Ala Leu Asp Tyr Tyr Ala Ala Val Phe Asp Ser Leu Glu Ala Thr
    290                 295                 300

Leu Pro Pro Ser Ser Arg Glu Arg Met Thr Val Glu Gln Val Trp Phe
305                 310                 315                 320
```

```
Gly Arg Glu Ile Ile Asp Ile Val Ala Ala Glu Gly Asp Lys Arg Arg
            325                 330                 335

Glu Arg His Glu Arg Phe Arg Ser Trp Glu Val Met Leu Arg Ser Cys
            340                 345                 350

Gly Phe Ser Asn Val Ala Leu Ser Pro Phe Ala Leu Ser Gln Ala Lys
        355                 360                 365

Leu Leu Leu Arg Leu His Tyr Pro Ser Glu Gly Tyr Gln Leu Ser Val
    370                 375                 380

Ser Ser Thr Ser Asn Ser Phe Ser Trp Val Gly Lys Ile Asn Pro Phe
385                 390                 395                 400

Phe Pro Tyr Leu Leu Gly Val Lys Phe Lys Thr Leu Lys Asn Lys Ile
                405                 410                 415

Phe Ile Tyr Leu His Gly Glu Gly Gln Arg Gly Leu Gln Ser Gln Val
            420                 425                 430

Leu Phe Phe Phe Phe Tyr Ile Tyr Ile Leu Phe Gly Phe Lys Val Ile
        435                 440                 445

Gly Leu Met Asn Val Leu Ile Leu Thr
    450                 455


<210> SEQ ID NO 78
<211> LENGTH: 412
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 78

Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
```

```
    210                 215                 220

Pro Ser Ile Ile Ser Ser Ile Val Leu Leu Pro Asp Glu Thr Leu Ala
225                 230                 235                 240

Ile Asn Cys Val Phe Tyr Leu His Arg Leu Leu Lys Asp Arg Glu Met
                245                 250                 255

Leu Arg Ile Phe Leu His Arg Ile Lys Ser Met Asn Pro Lys Val Val
            260                 265                 270

Thr Leu Ala Glu Arg Glu Ala Asn His Asn His Pro Leu Phe Leu Gln
        275                 280                 285

Arg Phe Val Glu Ala Leu Asp Tyr Tyr Ala Ala Val Phe Asp Ser Leu
    290                 295                 300

Glu Ala Thr Leu Pro Pro Ser Ser Arg Glu Arg Met Thr Val Glu Gln
305                 310                 315                 320

Val Trp Phe Gly Arg Glu Ile Ile Asp Ile Val Ala Ala Glu Gly Asp
                325                 330                 335

Lys Arg Arg Glu Arg His Glu Arg Phe Arg Ser Trp Glu Val Met Leu
            340                 345                 350

Arg Ser Cys Gly Phe Ser Asn Val Ala Leu Ser Pro Phe Ala Leu Ser
        355                 360                 365

Gln Ala Lys Leu Leu Leu Arg Leu His Tyr Pro Ser Glu Gly Tyr Gln
    370                 375                 380

Leu Ser Val Ser Ser Thr Ser Asn Ser Phe Ser Trp Val Gly Lys Ile
385                 390                 395                 400

Asn Pro Phe Phe Pro Tyr Leu Leu Gly Val Lys Leu
                405                 410


<210> SEQ ID NO 79
<211> LENGTH: 457
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 79

Met Leu Gly Ser Phe Gly Ser Ser Ser Gln Ser His Asp Glu Glu Thr
1               5                   10                  15

Asp Asp Gln Arg Arg Arg Phe Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Leu Arg Leu Asn Arg Tyr Ile Ser Ser Ala Thr Asn Phe Leu Thr
                85                  90                  95

Pro Ser Asn Val Val Glu Ser Ser Asn Asp Ser Ala Leu Leu Gln Ser
            100                 105                 110

Ser Tyr Leu Ser Leu Asn Gln Val Thr Pro Phe Ile Arg Phe Ser Gln
        115                 120                 125

Leu Thr Ala Asn Gln Ala Ile Leu Glu Ala Ile Asn Asp Asn Gln Gln
    130                 135                 140

Ala Ile His Ile Val Asp Phe Asp Ile Asn His Gly Val Gln Trp Pro
145                 150                 155                 160
```

```
Pro Leu Met Gln Ala Leu Ala Asp Arg Tyr Pro Pro Pro Thr Leu Arg
                165                 170                 175

Ile Thr Gly Thr Gly Asn Asp Leu Asp Thr Leu Arg Arg Thr Gly Asp
            180                 185                 190

Arg Leu Ala Lys Phe Ala His Ser Leu Gly Leu Arg Phe Gln Phe His
        195                 200                 205

Pro Leu Leu Ile Thr Asn Asn Asn Asp Asn Asp His Asp Pro Ser Ile
    210                 215                 220

Ile Ser Ser Ile Val Leu Leu Pro Asp Glu Thr Leu Ala Ile Asn Cys
225                 230                 235                 240

Val Phe Tyr Leu His Arg Leu Leu Lys Asp Arg Glu Lys Leu Arg Ile
                245                 250                 255

Phe Leu His Arg Ile Lys Ser Met Asn Pro Lys Val Val Thr Leu Ala
            260                 265                 270

Glu Arg Glu Ala Asn His Asn His Pro Leu Phe Leu Gln Arg Phe Val
        275                 280                 285

Glu Ala Leu Asp Tyr Tyr Ala Ala Val Phe Asp Ser Leu Glu Ala Thr
    290                 295                 300

Leu Pro Pro Ser Ser Arg Glu Arg Met Thr Val Glu Gln Val Trp Phe
305                 310                 315                 320

Gly Arg Glu Ile Ile Asp Ile Val Ala Ala Glu Gly Asp Lys Arg Arg
                325                 330                 335

Glu Arg His Glu Arg Phe Arg Ser Trp Glu Val Met Leu Arg Ser Cys
            340                 345                 350

Gly Phe Ser Asn Val Ala Leu Ser Pro Phe Ala Leu Ser Gln Ala Lys
        355                 360                 365

Leu Leu Leu Arg Leu His Tyr Pro Ser Glu Gly Tyr Gln Leu Ser Val
    370                 375                 380

Ser Ser Thr Ser Asn Ser Phe Ser Trp Val Gly Lys Ile Asn Pro Phe
385                 390                 395                 400

Phe Pro Tyr Leu Leu Gly Val Lys Phe Lys Thr Leu Lys Asn Lys Ile
                405                 410                 415

Phe Ile Tyr Leu His Gly Glu Gly Gln Arg Gly Leu Gln Ser Gln Val
            420                 425                 430

Leu Phe Phe Phe Phe Tyr Ile Tyr Ile Leu Phe Gly Phe Lys Val Ile
        435                 440                 445

Gly Leu Met Asn Val Leu Ile Leu Thr
    450                 455
```

<210> SEQ ID NO 80
<211> LENGTH: 412
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 80

```
Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45
```

```
Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
    210                 215                 220

Pro Ser Ile Ile Ser Ser Ile Val Leu Leu Pro Asp Glu Thr Leu Ala
225                 230                 235                 240

Ile Asn Cys Val Phe Tyr Leu His Arg Leu Leu Lys Asp Arg Glu Met
                245                 250                 255

Leu Arg Ile Phe Leu His Arg Ile Lys Ser Met Asn Pro Lys Val Val
            260                 265                 270

Thr Leu Ala Glu Arg Glu Ala Asn His Asn His Pro Leu Phe Leu Gln
        275                 280                 285

Arg Phe Val Glu Ala Leu Asp Tyr Tyr Ala Ala Val Phe Asp Ser Leu
    290                 295                 300

Glu Ala Thr Leu Pro Pro Ser Ser Arg Glu Arg Met Thr Val Glu Gln
305                 310                 315                 320

Val Trp Phe Gly Arg Glu Ile Ile Asp Ile Val Ala Ala Glu Gly Asp
                325                 330                 335

Lys Arg Arg Glu Arg His Glu Arg Phe Arg Ser Trp Glu Val Met Leu
            340                 345                 350

Arg Ser Cys Gly Phe Ser Asn Val Ala Leu Ser Pro Phe Ala Leu Ser
        355                 360                 365

Gln Ala Lys Leu Leu Leu Arg Leu His Tyr Pro Ser Glu Gly Tyr Gln
    370                 375                 380

Leu Ser Val Ser Ser Thr Ser Asn Ser Phe Ser Trp Val Gly Lys Ile
385                 390                 395                 400

Asn Pro Phe Phe Pro Tyr Leu Leu Gly Val Lys Leu
                405                 410
```

<210> SEQ ID NO 81
<211> LENGTH: 412
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 81

Met Leu Gly Ser Phe Gly Ser Ser Ser Gln Ser His Asp Glu Glu Thr
1 5 10 15

Asp Asp Gln Arg Arg Arg Phe Ser Ser Thr Ser Pro Ala Ile Gln Ile
20 25 30

Arg Gln Leu Leu Ile Ser Cys Ala Glu Leu Ile Ser Arg Ser Asp Phe
35 40 45

Ser Ala Ala Asn Arg Leu Leu Thr Ile Leu Ser Thr Asn Ser Ser Pro
50 55 60

Phe Gly Asp Ser Thr Glu Arg Leu Val His Gln Phe Thr Arg Ala Leu
65 70 75 80

Ser Leu Arg Leu Asn Arg Tyr Ile Ser Ser Ala Thr Asn Phe Leu Thr
85 90 95

Pro Ser Asn Val Val Glu Ser Ser Asn Asp Ser Ala Leu Leu Gln Ser
100 105 110

Ser Tyr Leu Ser Leu Asn Gln Val Thr Pro Phe Ile Arg Phe Ser Gln
115 120 125

Leu Thr Ala Asn Gln Ala Ile Leu Glu Ala Ile Asn Asp Asn Gln Gln
130 135 140

Ala Ile His Ile Val Asp Phe Asp Ile Asn His Gly Val Gln Trp Pro
145 150 155 160

Pro Leu Met Gln Ala Leu Ala Asp Arg Tyr Pro Pro Pro Thr Leu Arg
165 170 175

Ile Thr Gly Thr Gly Asn Asp Leu Asp Thr Leu Arg Arg Thr Gly Asp
180 185 190

Arg Leu Ala Lys Phe Ala His Ser Leu Gly Leu Arg Phe Gln Phe His
195 200 205

Pro Leu Leu Ile Thr Asn Asn Asn Asp Asn Asp His Asp Pro Ser Ile
210 215 220

Ile Ser Ser Ile Val Leu Leu Pro Asp Glu Thr Leu Ala Ile Asn Cys
225 230 235 240

Val Phe Tyr Leu His Arg Leu Leu Lys Asp Arg Glu Lys Leu Arg Ile
245 250 255

Phe Leu His Arg Ile Lys Ser Met Asn Pro Lys Val Val Thr Leu Ala
260 265 270

Glu Arg Glu Ala Asn His Asn His Pro Leu Phe Leu Gln Arg Phe Val
275 280 285

Glu Ala Leu Asp Tyr Tyr Ala Ala Val Phe Asp Ser Leu Glu Ala Thr
290 295 300

Leu Pro Pro Ser Ser Arg Glu Arg Met Thr Val Glu Gln Val Trp Phe
305 310 315 320

Gly Arg Glu Ile Ile Asp Ile Val Ala Ala Glu Gly Asp Lys Arg Arg
325 330 335

Glu Arg His Glu Arg Phe Arg Ser Trp Glu Val Met Leu Arg Ser Cys
340 345 350

Gly Phe Ser Asn Val Ala Leu Ser Pro Phe Ala Leu Ser Gln Ala Lys
355 360 365

Leu Leu Leu Arg Leu His Tyr Pro Ser Glu Gly Tyr Gln Leu Ser Val
370 375 380

Ser Ser Thr Ser Asn Ser Phe Leu Leu Gly Leu Ala Lys Ser Thr Pro
385 390 395 400

Phe Phe His Ile Phe Leu Ala Leu Asn Leu Lys Pro
405 410

<210> SEQ ID NO 82
<211> LENGTH: 411
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 82

```
Met Leu Gly Ser Phe Gly Ser Ser Ser Gln Ser His Asp Glu Glu Ala
1               5                   10                  15

Asp Asp Gln Arg Arg Arg Cys Ser Ser Thr Ser Pro Ala Ile Gln Ile
            20                  25                  30

Arg Gln Leu Leu Ile Ser Cys Ala Glu Leu Ile Ser Arg Ser Asp Phe
        35                  40                  45

Ser Ala Ala Asn Arg Leu Leu Thr Ile Leu Ser Thr Asn Ser Ser Pro
    50                  55                  60

Phe Gly Asp Ser Thr Glu Arg Leu Val His Gln Phe Thr Arg Ala Leu
65                  70                  75                  80

Ser Ile Arg Leu Asn Arg Tyr Ile Ser Ser Ala Thr Asn Phe Leu Thr
                85                  90                  95

Pro Asn Ala Ser Ser Asn Val Val Glu Ser Ser Asn Asp Ser Ala Leu
            100                 105                 110

Leu Gln Ser Ser Tyr Leu Ser Leu Asn Gln Val Thr Pro Phe Ile Arg
        115                 120                 125

Phe Ser Gln Leu Thr Ala Asn Gln Ala Ile Leu Glu Ala Ile Asn Asp
    130                 135                 140

Asn Gln Gln Ala Ile His Ile Val Asp Phe Asp Ile Asn His Gly Val
145                 150                 155                 160

Gln Trp Pro Pro Leu Met Gln Ala Leu Ala Asp Arg Tyr Pro Pro Pro
                165                 170                 175

Thr Leu Arg Ile Thr Gly Thr Gly Asn Asp Leu Asp Thr Leu Arg Arg
            180                 185                 190

Thr Gly Asp Arg Leu Ala Lys Phe Ala His Ser Leu Gly Leu Arg Phe
        195                 200                 205

Gln Phe His Pro Leu Leu Ile Thr Asn Asn Asn Asp Asn Asp His Asp
    210                 215                 220

Pro Ser Ile Ile Ser Ser Ile Val Leu Leu Pro Asp Glu Thr Leu Ala
225                 230                 235                 240

Ile Asn Cys Val Phe Tyr Leu His Arg Leu Leu Lys Asp Arg Glu Met
                245                 250                 255

Leu Arg Ile Phe Leu His Arg Ile Lys Ser Met Asn Pro Lys Val Val
            260                 265                 270

Thr Leu Ala Glu Arg Glu Ala Asn His Asn His Pro Leu Phe Leu Gln
        275                 280                 285

Arg Phe Val Glu Ala Leu Asp Tyr Tyr Ala Ala Val Phe Asp Ser Leu
    290                 295                 300

Glu Ala Thr Leu Pro Pro Ser Ser Arg Glu Arg Met Thr Val Glu Gln
305                 310                 315                 320

Val Trp Phe Gly Arg Glu Ile Ile Asp Ile Val Ala Ala Glu Gly Asp
                325                 330                 335

Lys Arg Arg Glu Arg His Glu Arg Phe Arg Ser Trp Glu Val Met Leu
            340                 345                 350
```

```
Arg Ser Cys Gly Phe Ser Asn Val Ala Leu Ser Pro Phe Ala Leu Ser
        355                 360                 365

Gln Ala Lys Leu Leu Leu Arg Leu His Tyr Pro Ser Glu Gly Tyr Gln
    370                 375                 380

Leu Ser Val Ser Ser Thr Ser Asn Ser Phe Phe Leu Gly Leu Ala Lys
385                 390                 395                 400

Ser Thr Pro Phe Phe His Ile Phe Leu Ala Leu
                405                 410


<210> SEQ ID NO 83
<211> LENGTH: 109
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 83

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Leu Glu Tyr
            100                 105


<210> SEQ ID NO 84
<211> LENGTH: 119
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 84

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110

Ser Arg Lys Ser Leu Trp Asp
```

115

<210> SEQ ID NO 85
<211> LENGTH: 109
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 85

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Leu Glu Tyr
            100                 105
```

<210> SEQ ID NO 86
<211> LENGTH: 119
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 86

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110

Ser Arg Lys Ser Leu Trp Asp
        115
```

<210> SEQ ID NO 87
<211> LENGTH: 337
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 87

Met Gly Arg Ala Pro Cys Cys Asp Lys Ala Asn Val Lys Arg Gly Pro
1 5 10 15

Trp Ser Pro Glu Glu Asp Ala Lys Leu Lys Asp Phe Ile His Lys Tyr
20 25 30

Gly Thr Gly Gly Asn Trp Ile Ala Leu Pro Gln Lys Ala Gly Leu Lys
35 40 45

Arg Cys Gly Lys Ser Cys Arg Leu Arg Trp Leu Asn Tyr Leu Arg Pro
50 55 60

Asn Ile Lys His Gly Asp Phe Ser Glu Glu Glu Asp Arg Val Ile Cys
65 70 75 80

Thr Leu Tyr Ser Thr Ile Gly Ser Arg Trp Ser Ile Ile Ala Ala Gln
85 90 95

Leu Pro Gly Arg Thr Asp Asn Asp Ile Lys Asn Tyr Trp Asn Thr Lys
100 105 110

Leu Lys Lys Lys Pro Met Gly Leu Met Gln Ser Thr Asn Gln Arg Lys
115 120 125

Ser Pro Tyr Phe Pro Ala Thr Asn Ser Leu Gln Thr Gln Pro Gln Ile
130 135 140

Asn Ser Ser Leu Phe Arg Asp Leu Tyr Tyr Thr Pro Asn Asn Arg Pro
145 150 155 160

Asn Ile Thr Gly Leu Asn His Gln Ser Ile Ser Ser Ala His Gln Thr
165 170 175

Asn Phe Leu Tyr Thr Asn Asn Asn Met Asn Phe Pro Asn Leu Gly Ala
180 185 190

Thr Asn Asn Gln Tyr Pro Tyr Asn Ile Gln Ser His Asn Leu Leu Met
195 200 205

Phe Gly Glu Ala Ser Cys Ser Ser Ser Asp Gly Ser Cys Ser Gln Met
210 215 220

Ser Phe Gly Lys Glu Ile Lys Arg Glu Glu Ile Met Ser Asn Ser Leu
225 230 235 240

Gln Gln Gly Gln Ile Ser Ser Val Asn Ala Phe Glu Glu Asn His Gln
245 250 255

Asn Phe Thr Leu Asp Tyr Gly Asn Ser Ser Ser Asn Trp Val Asp Gln
260 265 270

Lys Pro Asn Val Tyr Phe Gly Thr Thr Thr Thr Gln Val Leu Gln Tyr
275 280 285

Asp Asn Val Glu Glu Val Lys Gln Gln Leu Thr Ser Cys Thr Asn Gly
290 295 300

Asn Asn Gly Ser Thr Ile Gly Cys Asn Asn Asn Asn Ser Met Phe Val
305 310 315 320

Phe Asn Asp Glu Asn Tyr Asn Lys Ser Asn Glu Ile Glu Met Phe Tyr
325 330 335

Tyr

<210> SEQ ID NO 88
<211> LENGTH: 119
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 88

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110

Ser Arg Lys Ser Leu Trp Asp
        115
```

<210> SEQ ID NO 89
<211> LENGTH: 337
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 89

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Pro Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Thr Pro Asn Asn Arg Pro
145                 150                 155                 160

Asn Ile Thr Gly Leu Asn His Gln Ser Ile Ser Ser Ala His Gln Thr
                165                 170                 175

Asn Phe Leu Tyr Thr Asn Asn Asn Met Asn Phe Pro Asn Leu Gly Ala
            180                 185                 190

Thr Asn Asn Gln Tyr Pro Tyr Asn Ile Gln Ser His Asn Leu Leu Met
        195                 200                 205

Phe Gly Glu Ala Ser Cys Ser Ser Ser Asp Gly Ser Cys Ser Gln Met
    210                 215                 220
```

Ser Phe Gly Lys Glu Ile Lys Arg Glu Glu Ile Met Ser Asn Ser Leu
225 230 235 240

Gln Gln Gly Gln Ile Ser Ser Val Asn Ala Phe Glu Glu Asn His Gln
245 250 255

Asn Phe Thr Leu Asp Tyr Gly Asn Ser Ser Ser Asn Trp Val Asp Gln
260 265 270

Lys Pro Asn Val Tyr Phe Gly Thr Thr Thr Thr Gln Val Leu Gln Tyr
275 280 285

Asp Asn Val Glu Glu Val Lys Gln Gln Leu Thr Ser Cys Thr Asn Gly
290 295 300

Asn Asn Gly Ser Thr Ile Gly Cys Asn Asn Asn Asn Ser Met Phe Val
305 310 315 320

Phe Asn Asp Glu Asn Tyr Asn Lys Ser Asn Glu Ile Glu Met Phe Tyr
325 330 335

Tyr

<210> SEQ ID NO 90
<211> LENGTH: 119
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 90

Met Gly Arg Ala Pro Cys Cys Asp Lys Ala Asn Val Lys Arg Gly Pro
1 5 10 15

Trp Ser Pro Glu Glu Asp Ala Lys Leu Lys Asp Phe Ile His Lys Tyr
20 25 30

Gly Thr Gly Gly Asn Trp Ile Ala Leu Pro Gln Lys Ala Gly Leu Lys
35 40 45

Arg Cys Gly Lys Ser Cys Arg Leu Arg Trp Leu Asn Tyr Leu Arg Pro
50 55 60

Asn Ile Lys His Gly Asp Phe Ser Glu Glu Glu Asp Arg Val Ile Cys
65 70 75 80

Ser Leu Tyr Ser Thr Ile Gly Ser Arg Trp Ser Ile Ile Ala Ala Gln
85 90 95

Leu Pro Gly Arg Thr Asp Asn Asp Ile Lys Asn Thr Gly Ile Leu Asn
100 105 110

Ser Arg Lys Ser Leu Trp Asp
115

<210> SEQ ID NO 91
<211> LENGTH: 109
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 91

Met Gly Arg Ala Pro Cys Cys Asp Lys Ala Asn Val Lys Arg Gly Pro
1 5 10 15

Trp Ser Pro Glu Glu Asp Ala Lys Leu Lys Asp Phe Ile His Lys Tyr
20 25 30

Gly Thr Gly Gly Asn Trp Ile Ala Leu Pro Gln Lys Ala Gly Leu Lys

```
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Leu Glu Tyr
            100                 105


<210> SEQ ID NO 92
<211> LENGTH: 119
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 92

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110

Ser Arg Lys Ser Leu Trp Asp
        115


<210> SEQ ID NO 93
<211> LENGTH: 109
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 93

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95
```

Leu Pro Gly Arg Thr Asp Asn Asp Ile Lys Leu Glu Tyr
100 105

<210> SEQ ID NO 94
<211> LENGTH: 119
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 94

Met Gly Arg Ala Pro Cys Cys Asp Lys Ala Asn Val Lys Arg Gly Pro
1 5 10 15

Trp Ser Pro Glu Glu Asp Ala Lys Leu Lys Asp Phe Ile His Lys Tyr
20 25 30

Gly Thr Gly Gly Asn Trp Ile Ala Leu Pro Gln Lys Ala Gly Leu Lys
35 40 45

Arg Cys Gly Lys Ser Cys Arg Leu Arg Trp Leu Asn Tyr Leu Arg Pro
50 55 60

Asn Ile Lys His Gly Asp Phe Ser Glu Glu Glu Asp Arg Val Ile Cys
65 70 75 80

Ser Leu Tyr Ser Thr Ile Gly Ser Arg Trp Ser Ile Ile Ala Ala Gln
85 90 95

Leu Pro Gly Arg Thr Asp Asn Asp Ile Lys Asn Thr Gly Ile Leu Asn
100 105 110

Ser Arg Lys Ser Leu Trp Asp
115

<210> SEQ ID NO 95
<211> LENGTH: 336
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 95

Met Gly Arg Ala Pro Cys Cys Asp Lys Ala Asn Val Lys Arg Gly Pro
1 5 10 15

Trp Ser Pro Glu Glu Asp Ala Lys Leu Lys Asp Phe Ile His Lys Tyr
20 25 30

Gly Thr Gly Gly Asn Trp Ile Ala Leu Pro Gln Lys Ala Gly Leu Lys
35 40 45

Arg Cys Gly Lys Ser Cys Arg Leu Arg Trp Leu Asn Tyr Leu Arg Pro
50 55 60

Asn Ile Lys His Gly Asp Phe Ser Glu Glu Glu Asp Arg Val Ile Cys
65 70 75 80

Thr Leu Tyr Ser Thr Ile Gly Ser Arg Trp Ser Ile Ile Ala Ala Gln
85 90 95

Leu Pro Gly Arg Thr Asp Asn Asp Ile Lys Tyr Trp Asn Thr Lys Leu
100 105 110

Lys Lys Lys Pro Met Gly Leu Met Gln Ser Thr Asn Gln Arg Lys Ser
115 120 125

Pro Tyr Phe Pro Ala Thr Asn Ser Leu Gln Thr Gln Pro Gln Ile Asn
130 135 140

```
Ser Ser Leu Phe Arg Asp Leu Tyr Tyr Thr Pro Asn Asn Arg Pro Asn
145                 150                 155                 160

Ile Thr Gly Leu Asn His Gln Ser Ile Ser Ser Ala His Gln Thr Asn
                165                 170                 175

Phe Leu Tyr Thr Asn Asn Asn Met Asn Phe Pro Asn Leu Gly Ala Thr
            180                 185                 190

Asn Asn Gln Tyr Pro Tyr Asn Ile Gln Ser His Asn Leu Leu Met Phe
        195                 200                 205

Gly Glu Ala Ser Cys Ser Ser Ser Asp Gly Ser Cys Ser Gln Met Ser
    210                 215                 220

Phe Gly Lys Glu Ile Lys Arg Glu Glu Ile Met Ser Asn Ser Leu Gln
225                 230                 235                 240

Gln Gly Gln Ile Ser Ser Val Asn Ala Phe Glu Glu Asn His Gln Asn
                245                 250                 255

Phe Thr Leu Asp Tyr Gly Asn Ser Ser Ser Asn Trp Val Asp Gln Lys
            260                 265                 270

Pro Asn Val Tyr Phe Gly Thr Thr Thr Thr Gln Val Leu Gln Tyr Asp
        275                 280                 285

Asn Val Glu Glu Val Lys Gln Gln Leu Thr Ser Cys Thr Asn Gly Asn
    290                 295                 300

Asn Gly Ser Thr Ile Gly Cys Asn Asn Asn Asn Ser Met Phe Val Phe
305                 310                 315                 320

Asn Asp Glu Asn Tyr Asn Lys Ser Asn Glu Ile Glu Met Phe Tyr Tyr
                325                 330                 335
```

<210> SEQ ID NO 96
<211> LENGTH: 119
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 96

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110

Ser Arg Lys Ser Leu Trp Asp
        115
```

<210> SEQ ID NO 97
<211> LENGTH: 337
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived
from Nicotiana tabacum

<400> SEQUENCE: 97

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Pro Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Thr Pro Asn Asn Arg Pro
145                 150                 155                 160

Asn Ile Thr Gly Leu Asn His Gln Ser Ile Ser Ser Ala His Gln Thr
                165                 170                 175

Asn Phe Leu Tyr Thr Asn Asn Asn Met Asn Phe Pro Asn Leu Gly Ala
            180                 185                 190

Thr Asn Asn Gln Tyr Pro Tyr Asn Ile Gln Ser His Asn Leu Leu Met
        195                 200                 205

Phe Gly Glu Ala Ser Cys Ser Ser Ser Asp Gly Ser Cys Ser Gln Met
    210                 215                 220

Ser Phe Gly Lys Glu Ile Lys Arg Glu Glu Ile Met Ser Asn Ser Leu
225                 230                 235                 240

Gln Gln Gly Gln Ile Ser Ser Val Asn Ala Phe Glu Glu Asn His Gln
                245                 250                 255

Asn Phe Thr Leu Asp Tyr Gly Asn Ser Ser Ser Asn Trp Val Asp Gln
            260                 265                 270

Lys Pro Asn Val Tyr Phe Gly Thr Thr Thr Thr Gln Val Leu Gln Tyr
        275                 280                 285

Asp Asn Val Glu Glu Val Lys Gln Gln Leu Thr Ser Cys Thr Asn Gly
    290                 295                 300

Asn Asn Gly Ser Thr Ile Gly Cys Asn Asn Asn Asn Ser Met Phe Val
305                 310                 315                 320

Phe Asn Asp Glu Asn Tyr Asn Lys Ser Asn Glu Ile Glu Met Phe Tyr
                325                 330                 335

Tyr
```

<210> SEQ ID NO 98
<211> LENGTH: 119
<212> TYPE: PRT
<213> ORGANISM: Artificial sequence
<220> FEATURE:
<223> OTHER INFORMATION: Synthetic: mutated polypeptide biosynthesized
by tobacco plants whose genomes are mutated by CRISPR, derived
from Nicotiana tabacum

<400> SEQUENCE: 98

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110

Ser Arg Lys Ser Leu Trp Asp
        115
```

<210> SEQ ID NO 99
<211> LENGTH: 336
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 99

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Tyr Trp Asn Thr Lys Leu
            100                 105                 110

Lys Lys Lys Pro Met Gly Leu Met Gln Ser Thr Asn Gln Arg Lys Ser
        115                 120                 125

Pro Tyr Phe Pro Ala Thr Asn Ser Leu Gln Thr Gln Pro Gln Ile Asn
    130                 135                 140

Ser Ser Leu Phe Arg Asp Leu Tyr Tyr Thr Pro Asn Asn Arg Pro Asn
145                 150                 155                 160

Ile Thr Gly Leu Asn His Gln Ser Ile Ser Ser Ala His Gln Thr Asn
                165                 170                 175

Phe Leu Tyr Thr Asn Asn Asn Met Asn Phe Pro Asn Leu Gly Ala Thr
            180                 185                 190

Asn Asn Gln Tyr Pro Tyr Asn Ile Gln Ser His Asn Leu Leu Met Phe
        195                 200                 205

Gly Glu Ala Ser Cys Ser Ser Ser Asp Gly Ser Cys Ser Gln Met Ser
```

```
    210                 215                 220

Phe Gly Lys Glu Ile Lys Arg Glu Glu Ile Met Ser Asn Ser Leu Gln
225                 230                 235                 240

Gln Gly Gln Ile Ser Ser Val Asn Ala Phe Glu Glu Asn His Gln Asn
                245                 250                 255

Phe Thr Leu Asp Tyr Gly Asn Ser Ser Ser Asn Trp Val Asp Gln Lys
            260                 265                 270

Pro Asn Val Tyr Phe Gly Thr Thr Thr Thr Gln Val Leu Gln Tyr Asp
        275                 280                 285

Asn Val Glu Glu Val Lys Gln Gln Leu Thr Ser Cys Thr Asn Gly Asn
    290                 295                 300

Asn Gly Ser Thr Ile Gly Cys Asn Asn Asn Asn Ser Met Phe Val Phe
305                 310                 315                 320

Asn Asp Glu Asn Tyr Asn Lys Ser Asn Glu Ile Glu Met Phe Tyr Tyr
                325                 330                 335
```

<210> SEQ ID NO 100
<211> LENGTH: 119
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 100

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110

Ser Arg Lys Ser Leu Trp Asp
        115
```

<210> SEQ ID NO 101
<211> LENGTH: 336
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 101

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45
```

```
Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Tyr Trp Asn Thr Lys Leu
            100                 105                 110

Lys Lys Lys Pro Met Gly Leu Met Gln Ser Thr Asn Gln Arg Lys Ser
        115                 120                 125

Pro Tyr Phe Pro Ala Thr Asn Ser Leu Gln Thr Gln Pro Gln Ile Asn
    130                 135                 140

Ser Ser Leu Phe Arg Asp Leu Tyr Tyr Thr Pro Asn Asn Arg Pro Asn
145                 150                 155                 160

Ile Thr Gly Leu Asn His Gln Ser Ile Ser Ser Ala His Gln Thr Asn
                165                 170                 175

Phe Leu Tyr Thr Asn Asn Asn Met Asn Phe Pro Asn Leu Gly Ala Thr
            180                 185                 190

Asn Asn Gln Tyr Pro Tyr Asn Ile Gln Ser His Asn Leu Leu Met Phe
        195                 200                 205

Gly Glu Ala Ser Cys Ser Ser Ser Asp Gly Ser Cys Ser Gln Met Ser
    210                 215                 220

Phe Gly Lys Glu Ile Lys Arg Glu Glu Ile Met Ser Asn Ser Leu Gln
225                 230                 235                 240

Gln Gly Gln Ile Ser Ser Val Asn Ala Phe Glu Glu Asn His Gln Asn
                245                 250                 255

Phe Thr Leu Asp Tyr Gly Asn Ser Ser Ser Asn Trp Val Asp Gln Lys
            260                 265                 270

Pro Asn Val Tyr Phe Gly Thr Thr Thr Thr Gln Val Leu Gln Tyr Asp
        275                 280                 285

Asn Val Glu Glu Val Lys Gln Gln Leu Thr Ser Cys Thr Asn Gly Asn
    290                 295                 300

Asn Gly Ser Thr Ile Gly Cys Asn Asn Asn Asn Ser Met Phe Val Phe
305                 310                 315                 320

Asn Asp Glu Asn Tyr Asn Lys Ser Asn Glu Ile Glu Met Phe Tyr Tyr
                325                 330                 335


<210> SEQ ID NO 102
<211> LENGTH: 119
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 102

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60
```

```
Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110

Ser Arg Lys Ser Leu Trp Asp
        115


<210> SEQ ID NO 103
<211> LENGTH: 110
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 103

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Lys Leu Glu Tyr
            100                 105                 110


<210> SEQ ID NO 104
<211> LENGTH: 112
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 104

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Glu Ile Leu Asn Ser Arg Lys Ser Leu Trp Asp
            100                 105                 110
```

<210> SEQ ID NO 105
<211> LENGTH: 110
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 105

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Lys Leu Glu Tyr
            100                 105                 110
```

<210> SEQ ID NO 106
<211> LENGTH: 119
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 106

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Thr Gly Ile Leu Asn
            100                 105                 110

Ser Arg Lys Ser Leu Trp Asp
        115
```

<210> SEQ ID NO 107
<211> LENGTH: 110
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 107

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Lys Leu Glu Tyr
            100                 105                 110


<210> SEQ ID NO 108
<211> LENGTH: 112
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 108

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Glu Ile Leu Asn Ser Arg Lys Ser Leu Trp Asp
            100                 105                 110


<210> SEQ ID NO 109
<211> LENGTH: 56
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 109

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu
    50                  55
```

<210> SEQ ID NO 110
<211> LENGTH: 64
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 110

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Lys Met Ala Lys Leu Ser Lys Ala
    50                  55                  60
```

<210> SEQ ID NO 111
<211> LENGTH: 61
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 111

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Met Ala Lys Leu Phe Lys Ala
    50                  55                  60
```

<210> SEQ ID NO 112
<211> LENGTH: 334
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 112

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Trp Leu Asn Tyr Leu Arg Pro Asn Ile
    50                  55                  60

Lys His Gly Asp Phe Ser Glu Glu Glu Asp Arg Val Ile Cys Ser Leu
65                  70                  75                  80

Tyr Ser Thr Ile Gly Ser Arg Trp Ser Ile Ile Ala Ala Gln Leu Pro
                85                  90                  95

Gly Arg Thr Asp Asn Asp Ile Lys Asn Tyr Trp Asn Thr Lys Leu Lys
```

```
            100                 105                 110

Lys Lys Leu Met Gly Leu Met Gln Ser Thr Asn Gln Arg Lys Ser Pro
        115                 120                 125

Tyr Phe Pro Ala Thr Asn Ser Leu Gln Thr Gln Pro Gln Ile Asn Ser
    130                 135                 140

Ser Leu Phe Arg Asp Leu Tyr Tyr Asn Pro Asn Asn Arg Pro Ile Ile
145                 150                 155                 160

Thr Gly Leu Asn Gln Ser Ile Ser Ser Ala His Gln Pro Asn Phe Leu
                165                 170                 175

Tyr Thr Asn Ser Asn Met Asn Phe Pro Asn Leu Gly Ala Thr Asn Ser
            180                 185                 190

Gln Tyr Pro Tyr Asn Ile Gln Ser His Asn Leu Leu Met Phe Gly Glu
        195                 200                 205

Ala Ser Cys Ser Ser Ser Asp Gly Ser Cys Ser Gln Met Ser Phe Gly
    210                 215                 220

Lys Glu Ile Lys Arg Glu Glu Ile Met Ser Asn Cys Leu Gln Gln Gly
225                 230                 235                 240

Gln Ile Ser Ser Val Asn Ala Phe Glu Glu Asn Gln Asn Phe Thr Leu
                245                 250                 255

Asp Tyr Gly Asn Ser Ser Ser Asn Trp Val Asp Gln Lys Pro Asn Val
            260                 265                 270

Tyr Phe Gly Asn Thr Thr Thr Thr Thr Gln Val Leu Gln Tyr Asp Val
        275                 280                 285

Glu Glu Val Lys Gln Gln Leu Thr Ser Cys Thr Asn Gly Asn Asn Gly
    290                 295                 300

Ser Thr Ile Gly Cys Asn Asn Asn Asn Ser Met Phe Val Phe Asn Asp
305                 310                 315                 320

Glu Asn Tyr Asn Lys Ser Asn Glu Ile Gly Met Phe Tyr Tyr
                325                 330
```

<210> SEQ ID NO 113
<211> LENGTH: 56
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 113

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu
    50                  55
```

<210> SEQ ID NO 114
<211> LENGTH: 58
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 114

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Asp Gly
    50                  55


<210> SEQ ID NO 115
<211> LENGTH: 58
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 115

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ala Lys Leu Phe Lys Ala
    50                  55


<210> SEQ ID NO 116
<211> LENGTH: 55
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 116

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Ile
    50                  55


<210> SEQ ID NO 117
<211> LENGTH: 58
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 117

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30
```

```
Gly Thr Gly Gly Asn Trp Ile Ala Leu Pro Gln Lys Ala Gly Leu Lys
        35                  40                  45

Arg Cys Gly Lys Ala Lys Leu Phe Lys Ala
    50                  55


<210> SEQ ID NO 118
<211> LENGTH: 55
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 118

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Ile
    50                  55


<210> SEQ ID NO 119
<211> LENGTH: 306
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 119

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Pro Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Thr Pro Asn Asn Arg Pro
145                 150                 155                 160

Asn Ile Thr Gly Leu Asn His Gln Ser Ile Ser Ser Ala His Gln Thr
                165                 170                 175

Asn Phe Leu Tyr Thr Asn Asn Asn Met Asn Phe Pro Asn Leu Gly Ala
            180                 185                 190

Thr Asn Asn Gln Tyr Pro Tyr Asn Ile Gln Ser His Asn Leu Leu Met
```

```
        195                 200                 205

Phe Gly Glu Ala Ser Cys Ser Ser Ser Asp Gly Ser Cys Ser Gln Met
    210                 215                 220

Ser Phe Gly Lys Glu Ile Lys Arg Glu Glu Ile Met Ser Asn Ser Leu
225                 230                 235                 240

Gln Gln Gly Gln Ile Ser Ser Val Asn Ala Phe Glu Glu Asn His Gln
                245                 250                 255

Asn Phe Thr Leu Asp Tyr Gly Asn Ser Ser Ser Asn Trp Val Asp Gln
            260                 265                 270

Lys Pro Asn Val Tyr Phe Gly Thr Thr Thr Thr Gln Val Leu Gln Tyr
        275                 280                 285

Asp Asn Val Glu Glu Val Lys Gln Gln Leu Thr Ser Cys Thr Tyr Tyr
    290                 295                 300

Trp Met
305


<210> SEQ ID NO 120
<211> LENGTH: 307
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 120

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Thr Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Pro Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Thr Pro Asn Asn Arg Pro
145                 150                 155                 160

Asn Ile Thr Gly Leu Asn His Gln Ser Ile Ser Ser Ala His Gln Thr
                165                 170                 175

Asn Phe Leu Tyr Thr Asn Asn Asn Met Asn Phe Pro Asn Leu Gly Ala
            180                 185                 190

Thr Asn Asn Gln Tyr Pro Tyr Asn Ile Gln Ser His Asn Leu Leu Met
        195                 200                 205

Phe Gly Glu Ala Ser Cys Ser Ser Ser Asp Gly Ser Cys Ser Gln Met
    210                 215                 220

Ser Phe Gly Lys Glu Ile Lys Arg Glu Glu Ile Met Ser Asn Ser Leu
225                 230                 235                 240
```

```
Gln Gln Gly Gln Ile Ser Ser Val Asn Ala Phe Glu Glu Asn His Gln
                245                 250                 255

Asn Phe Thr Leu Asp Tyr Gly Asn Ser Ser Ser Asn Trp Val Asp Gln
            260                 265                 270

Lys Pro Asn Val Tyr Phe Gly Thr Thr Thr Thr Gln Val Leu Gln Tyr
        275                 280                 285

Asp Asn Val Glu Glu Val Lys Gln Gln Leu Thr Ser Cys Thr Gln Trp
    290                 295                 300

Gln Gln Trp
305


<210> SEQ ID NO 121
<211> LENGTH: 330
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 121

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Glu Asp Arg Val Ile Cys
65                  70                  75                  80

Ser Leu Tyr Ser Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Leu Met Gln Ser Thr Asn Gln Arg Lys
        115                 120                 125

Ser Pro Tyr Phe Pro Ala Thr Asn Ser Leu Gln Thr Gln Pro Gln Ile
    130                 135                 140

Asn Ser Ser Leu Phe Arg Asp Leu Tyr Tyr Asn Pro Asn Asn Arg Pro
145                 150                 155                 160

Ile Ile Thr Gly Leu Asn Gln Ser Ile Ser Ser Ala His Gln Pro Asn
                165                 170                 175

Phe Leu Tyr Thr Asn Ser Asn Met Asn Phe Pro Asn Leu Gly Ala Thr
            180                 185                 190

Asn Ser Gln Tyr Pro Tyr Asn Ile Gln Ser His Asn Leu Leu Met Phe
        195                 200                 205

Gly Glu Ala Ser Cys Ser Ser Ser Asp Gly Ser Cys Ser Gln Met Ser
    210                 215                 220

Phe Gly Lys Glu Ile Lys Arg Glu Glu Ile Met Ser Asn Cys Leu Gln
225                 230                 235                 240

Gln Gly Gln Ile Ser Ser Val Asn Ala Phe Glu Glu Asn Gln Asn Phe
                245                 250                 255

Thr Leu Asp Tyr Gly Asn Ser Ser Ser Asn Trp Val Asp Gln Lys Pro
            260                 265                 270
```

```
Asn Val Tyr Phe Gly Asn Thr Thr Thr Thr Thr Gln Val Leu Gln Tyr
        275                 280                 285

Asp Val Glu Glu Val Lys Gln Gln Leu Thr Ser Cys Thr Met Ala Thr
    290                 295                 300

Met Ala Val Leu Leu Asp Val Thr Thr Thr Thr Val Cys Ser Cys Ser
305                 310                 315                 320

Met Met Arg Ile Ile Thr Ser Gln Met Arg
                325                 330


<210> SEQ ID NO 122
<211> LENGTH: 54
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 122

Met Asp Gln Gln His Ser Thr Cys Phe Ser Ser Ser Ser Lys Ile Asn
1               5                   10                  15

Asp Lys Glu Lys Lys Lys Lys Arg Ser Val Val Lys Leu Ser Thr Asp
            20                  25                  30

Pro Gln Ser Val Ala Ala Arg Glu Glu Gly Ile Glu Ser Val Ile Val
        35                  40                  45

Ser Arg Phe Cys Arg Val
    50


<210> SEQ ID NO 123
<211> LENGTH: 43
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 123

Met Asp Gln Gln His Ser Thr Cys Phe Ser Ser Ser Ser Lys Ile Asn
1               5                   10                  15

Asp Lys Glu Lys Lys Lys Lys Gly Ser Val Val Lys Leu Ser Thr Asp
            20                  25                  30

Pro Gln Ser Val Ala Ala Arg Glu Lys Lys Ala
        35                  40


<210> SEQ ID NO 124
<211> LENGTH: 54
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 124

Met Asp Gln Gln His Ser Thr Cys Phe Ser Ser Ser Ser Lys Ile Asn
1               5                   10                  15

Asp Lys Glu Lys Lys Lys Lys Arg Ser Val Val Lys Leu Ser Thr Asp
            20                  25                  30

Pro Gln Ser Val Ala Ala Arg Glu Glu Gly Ile Glu Ser Val Ile Val
        35                  40                  45

Ser Arg Phe Cys Arg Val
```

50

<210> SEQ ID NO 125
<211> LENGTH: 43
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 125

```
Met Asp Gln Gln His Ser Thr Cys Phe Ser Ser Ser Ser Lys Ile Asn
1               5                   10                  15

Asp Lys Glu Lys Lys Lys Lys Gly Ser Val Val Lys Leu Ser Thr Asp
            20                  25                  30

Pro Gln Ser Val Ala Ala Arg Glu Lys Lys Ala
        35                  40
```

<210> SEQ ID NO 126
<211> LENGTH: 43
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 126

```
Met Asp Gln Gln His Ser Thr Cys Phe Ser Ser Ser Ser Lys Ile Asn
1               5                   10                  15

Asp Lys Glu Lys Lys Lys Lys Arg Ser Val Val Lys Leu Ser Thr Asp
            20                  25                  30

Pro Gln Ser Val Ala Ala Arg Glu Glu Lys Ala
        35                  40
```

<210> SEQ ID NO 127
<211> LENGTH: 39
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 127

```
Met Asp Gln Gln His Ser Thr Cys Phe Ser Ser Ser Ser Lys Ile Asn
1               5                   10                  15

Asp Lys Glu Lys Lys Lys Lys Gly Ser Val Val Lys Leu Ser Thr Asp
            20                  25                  30

Pro Gln Ser Val Glu Asn Gln
        35
```

<210> SEQ ID NO 128
<211> LENGTH: 43
<212> TYPE: PRT
<213> ORGANISM: Artificial sequence
<220> FEATURE:
<223> OTHER INFORMATION: Synthetic: mutated polypeptide biosynthesized by tobacco plants whose genomes are mutated by CRISPR, derived from Nicotiana tabacum

<400> SEQUENCE: 128

```
Met Asp Gln Gln His Ser Thr Cys Phe Ser Ser Ser Ser Lys Ile Asn
1               5                   10                  15
```

```
Asp Lys Glu Lys Lys Lys Lys Arg Ser Val Val Lys Leu Ser Thr Asp
            20                  25                  30

Pro Gln Ser Val Ala Ala Arg Phe Leu Cys Gly
        35                  40


<210> SEQ ID NO 129
<211> LENGTH: 54
<212> TYPE: PRT
<213> ORGANISM: Artificial sequence
<220> FEATURE:
<223> OTHER INFORMATION: Synthetic: mutated polypeptide biosynthesized
      by tobacco plants whose genomes are mutated by CRISPR, derived
      from Nicotiana tabacum

<400> SEQUENCE: 129

Met Asp Gln Gln His Ser Thr Cys Phe Ser Ser Ser Ser Lys Ile Asn
1               5                   10                  15

Asp Lys Glu Lys Lys Lys Lys Gly Ser Val Val Lys Leu Ser Thr Asp
            20                  25                  30

Pro Gln Ser Val Ala Ala Arg Glu Glu Gly Ile Glu Ser Val Ile Val
        35                  40                  45

Ser Arg Phe Cys Arg Val
    50


<210> SEQ ID NO 130
<211> LENGTH: 26
<212> TYPE: DNA
<213> ORGANISM: Artificial Sequence
<220> FEATURE:
<223> OTHER INFORMATION: Synthetic primer

<400> SEQUENCE: 130

aggttcttct tccttaatat tgagtc                                            26


<210> SEQ ID NO 131
<211> LENGTH: 26
<212> TYPE: DNA
<213> ORGANISM: Artificial Sequence
<220> FEATURE:
<223> OTHER INFORMATION: Synthetic primer

<400> SEQUENCE: 131

atctaaggcc taaagagtga gcaaat                                            26


<210> SEQ ID NO 132
<211> LENGTH: 24
<212> TYPE: DNA
<213> ORGANISM: Artificial Sequence
<220> FEATURE:
<223> OTHER INFORMATION: Synthetic primer

<400> SEQUENCE: 132

acacctaatg catcatctaa tgtt                                              24


<210> SEQ ID NO 133
<211> LENGTH: 26
<212> TYPE: DNA
<213> ORGANISM: Artificial Sequence
<220> FEATURE:
<223> OTHER INFORMATION: Synthetic primer

<400> SEQUENCE: 133

caaataaaga ttaagttcag gatctg                                            26
```

<210> SEQ ID NO 134
<211> LENGTH: 21
<212> TYPE: DNA
<213> ORGANISM: Artificial Sequence
<220> FEATURE:
<223> OTHER INFORMATION: Synthetic primer

<400> SEQUENCE: 134
atttcccctc ctccatcatt g 21

<210> SEQ ID NO 135
<211> LENGTH: 21
<212> TYPE: DNA
<213> ORGANISM: Artificial Sequence
<220> FEATURE:
<223> OTHER INFORMATION: Synthetic primer

<400> SEQUENCE: 135
tccctgtact ttgggacatg a 21

<210> SEQ ID NO 136
<211> LENGTH: 23
<212> TYPE: DNA
<213> ORGANISM: Artificial Sequence
<220> FEATURE:
<223> OTHER INFORMATION: Synthetic primer

<400> SEQUENCE: 136
cttgacacca tctaatgttg ttg 23

<210> SEQ ID NO 137
<211> LENGTH: 23
<212> TYPE: DNA
<213> ORGANISM: Artificial Sequence
<220> FEATURE:
<223> OTHER INFORMATION: Synthetic primer

<400> SEQUENCE: 137
aagctgtttg cagggaatat atc 23

<210> SEQ ID NO 138
<211> LENGTH: 21
<212> TYPE: DNA
<213> ORGANISM: Artificial Sequence
<220> FEATURE:
<223> OTHER INFORMATION: Synthetic primer

<400> SEQUENCE: 138
tctctggcta aatgttcgaa g 21

<210> SEQ ID NO 139
<211> LENGTH: 26
<212> TYPE: DNA
<213> ORGANISM: Artificial Sequence
<220> FEATURE:
<223> OTHER INFORMATION: Synthetic primer

<400> SEQUENCE: 139
gtaagttgtg agtctgtggt aactac 26

<210> SEQ ID NO 140
<211> LENGTH: 22
<212> TYPE: DNA
<213> ORGANISM: Artificial Sequence
<220> FEATURE:
<223> OTHER INFORMATION: Synthetic primer

<400> SEQUENCE: 140
ggaaacaaac atctgcactc aa 22

<210> SEQ ID NO 141
<211> LENGTH: 26
<212> TYPE: DNA
<213> ORGANISM: Artificial Sequence
<220> FEATURE:
<223> OTHER INFORMATION: Synthetic primer

<400> SEQUENCE: 141
gtccatctgt ctatataggt agaatg 26

<210> SEQ ID NO 142
<211> LENGTH: 21
<212> TYPE: DNA
<213> ORGANISM: Artificial Sequence
<220> FEATURE:
<223> OTHER INFORMATION: Synthetic primer

<400> SEQUENCE: 142
tgaatcttct tggcaacccc c 21

<210> SEQ ID NO 143
<211> LENGTH: 26
<212> TYPE: DNA
<213> ORGANISM: Artificial Sequence
<220> FEATURE:
<223> OTHER INFORMATION: Synthetic primer

<400> SEQUENCE: 143
ttgtttggga ttttggggtt tgaggg 26

<210> SEQ ID NO 144
<211> LENGTH: 31
<212> TYPE: DNA
<213> ORGANISM: Artificial Sequence
<220> FEATURE:
<223> OTHER INFORMATION: Synthetic primer

<400> SEQUENCE: 144
aattgtatgg ccaagtggca ttattatctg a 31

<210> SEQ ID NO 145
<211> LENGTH: 25
<212> TYPE: DNA
<213> ORGANISM: Artificial Sequence
<220> FEATURE:
<223> OTHER INFORMATION: Synthetic primer

<400> SEQUENCE: 145
cacttccgtt cctctttcac cgctg 25

<210> SEQ ID NO 146
<211> LENGTH: 21
<212> TYPE: DNA
<213> ORGANISM: Artificial Sequence
<220> FEATURE:
<223> OTHER INFORMATION: Synthetic primer

<400> SEQUENCE: 146
tccgttcaac tgtgttcctg g 21

<210> SEQ ID NO 147

<211> LENGTH: 20
<212> TYPE: DNA
<213> ORGANISM: Artificial Sequence
<220> FEATURE:
<223> OTHER INFORMATION: Synthetic primer

<400> SEQUENCE: 147
tccgttcaac tgtgttcctg 20

<210> SEQ ID NO 148
<211> LENGTH: 24
<212> TYPE: DNA
<213> ORGANISM: Artificial Sequence
<220> FEATURE:
<223> OTHER INFORMATION: Synthetic primer

<400> SEQUENCE: 148
aacattagat gatgcattag gtgt 24

<210> SEQ ID NO 149
<211> LENGTH: 26
<212> TYPE: DNA
<213> ORGANISM: Artificial Sequence
<220> FEATURE:
<223> OTHER INFORMATION: Synthetic primer

<400> SEQUENCE: 149
ttggcctcta attaaataga ctgata 26

<210> SEQ ID NO 150
<211> LENGTH: 25
<212> TYPE: DNA
<213> ORGANISM: Artificial Sequence
<220> FEATURE:
<223> OTHER INFORMATION: Synthetic primer

<400> SEQUENCE: 150
tctcaaagct ggctgtttta tgtat 25

<210> SEQ ID NO 151
<211> LENGTH: 26
<212> TYPE: DNA
<213> ORGANISM: Artificial Sequence
<220> FEATURE:
<223> OTHER INFORMATION: Synthetic primer

<400> SEQUENCE: 151
taccattctc cagggtggtt gtgtat 26

<210> SEQ ID NO 152
<211> LENGTH: 22
<212> TYPE: DNA
<213> ORGANISM: Artificial Sequence
<220> FEATURE:
<223> OTHER INFORMATION: Synthetic primer

<400> SEQUENCE: 152
gaaaattcag tattgccatg tc 22

<210> SEQ ID NO 153
<211> LENGTH: 20
<212> TYPE: DNA
<213> ORGANISM: Artificial Sequence
<220> FEATURE:
<223> OTHER INFORMATION: Synthetic primer

<400> SEQUENCE: 153
gcaaaaacta gttcagaaca 20

<210> SEQ ID NO 154
<211> LENGTH: 25
<212> TYPE: DNA
<213> ORGANISM: Artificial Sequence
<220> FEATURE:
<223> OTHER INFORMATION: Synthetic primer

<400> SEQUENCE: 154
caccgcctat gtagcttcgt caatg 25

<210> SEQ ID NO 155
<211> LENGTH: 25
<212> TYPE: DNA
<213> ORGANISM: Artificial Sequence
<220> FEATURE:
<223> OTHER INFORMATION: Synthetic primer

<400> SEQUENCE: 155
aaaaaaattc agtattgcca cgtgc 25

<210> SEQ ID NO 156
<211> LENGTH: 20
<212> TYPE: DNA
<213> ORGANISM: Artificial Sequence
<220> FEATURE:
<223> OTHER INFORMATION: Synthetic primer

<400> SEQUENCE: 156
tcgcttgatt agcagtcagc 20

<210> SEQ ID NO 157
<211> LENGTH: 25
<212> TYPE: DNA
<213> ORGANISM: Artificial Sequence
<220> FEATURE:
<223> OTHER INFORMATION: Synthetic primer

<400> SEQUENCE: 157
caccgaagaa actgatgatc aacgg 25

<210> SEQ ID NO 158
<211> LENGTH: 28
<212> TYPE: DNA
<213> ORGANISM: Artificial Sequence
<220> FEATURE:
<223> OTHER INFORMATION: Synthetic primer

<400> SEQUENCE: 158
gaagacctct ttgtccttca ccatgcag 28

<210> SEQ ID NO 159
<211> LENGTH: 24
<212> TYPE: DNA
<213> ORGANISM: Artificial Sequence
<220> FEATURE:
<223> OTHER INFORMATION: Synthetic primer

<400> SEQUENCE: 159
caccatgttt gatattaggc ctta 24

<210> SEQ ID NO 160
<211> LENGTH: 24
<212> TYPE: DNA

<213> ORGANISM: Artificial Sequence
<220> FEATURE:
<223> OTHER INFORMATION: Synthetic primer

<400> SEQUENCE: 160
tgatgagatt tatgttggga actg 24

<210> SEQ ID NO 161
<211> LENGTH: 25
<212> TYPE: DNA
<213> ORGANISM: Artificial Sequence
<220> FEATURE:
<223> OTHER INFORMATION: Synthetic primer

<400> SEQUENCE: 161
tctcatcatt gaacacgaac atact 25

<210> SEQ ID NO 162
<211> LENGTH: 25
<212> TYPE: DNA
<213> ORGANISM: Artificial Sequence
<220> FEATURE:
<223> OTHER INFORMATION: Synthetic primer

<400> SEQUENCE: 162
ccacttgtct atatagcaag aaaga 25

<210> SEQ ID NO 163
<211> LENGTH: 24
<212> TYPE: DNA
<213> ORGANISM: Artificial Sequence
<220> FEATURE:
<223> OTHER INFORMATION: Synthetic primer

<400> SEQUENCE: 163
ctaaggccta atatcaaaca tggt 24

<210> SEQ ID NO 164
<211> LENGTH: 26
<212> TYPE: DNA
<213> ORGANISM: Artificial Sequence
<220> FEATURE:
<223> OTHER INFORMATION: Synthetic primer

<400> SEQUENCE: 164
gaaccaccag ggactaaact ctgcaa 26

<210> SEQ ID NO 165
<211> LENGTH: 26
<212> TYPE: DNA
<213> ORGANISM: Artificial Sequence
<220> FEATURE:
<223> OTHER INFORMATION: Synthetic primer

<400> SEQUENCE: 165
ttgcagagtt tagtccctgg tggttc 26

<210> SEQ ID NO 166
<211> LENGTH: 23
<212> TYPE: DNA
<213> ORGANISM: Artificial Sequence
<220> FEATURE:
<223> OTHER INFORMATION: Synthetic primer

<400> SEQUENCE: 166
gaaacgatca ctgattctat gcc 23

<210> SEQ ID NO 167
<211> LENGTH: 25
<212> TYPE: DNA
<213> ORGANISM: Artificial Sequence
<220> FEATURE:
<223> OTHER INFORMATION: Synthetic primer

<400> SEQUENCE: 167
tacaatgtta gaagaagcaa ttcac 25

<210> SEQ ID NO 168
<211> LENGTH: 25
<212> TYPE: DNA
<213> ORGANISM: Artificial Sequence
<220> FEATURE:
<223> OTHER INFORMATION: Synthetic primer

<400> SEQUENCE: 168
tacttccctt tctcactttg gtttc 25

<210> SEQ ID NO 169
<211> LENGTH: 25
<212> TYPE: DNA
<213> ORGANISM: Artificial Sequence
<220> FEATURE:
<223> OTHER INFORMATION: Synthetic primer

<400> SEQUENCE: 169
aatattccca tcaatagatc acaac 25

<210> SEQ ID NO 170
<211> LENGTH: 27
<212> TYPE: DNA
<213> ORGANISM: Artificial Sequence
<220> FEATURE:
<223> OTHER INFORMATION: Synthetic primer

<400> SEQUENCE: 170
ctactacatc acttaatatc attcatt 27

<210> SEQ ID NO 171
<211> LENGTH: 27
<212> TYPE: DNA
<213> ORGANISM: Artificial Sequence
<220> FEATURE:
<223> OTHER INFORMATION: Synthetic primer

<400> SEQUENCE: 171
caatagattg caactttaca ttagtcg 27

<210> SEQ ID NO 172
<211> LENGTH: 27
<212> TYPE: DNA
<213> ORGANISM: Artificial Sequence
<220> FEATURE:
<223> OTHER INFORMATION: Synthetic primer

<400> SEQUENCE: 172
tactatcact taataccatc attcatc 27

<210> SEQ ID NO 173
<211> LENGTH: 25
<212> TYPE: DNA
<213> ORGANISM: Artificial Sequence
<220> FEATURE:

<223> OTHER INFORMATION: Synthetic primer

<400> SEQUENCE: 173
cccatcaata gatcacaact ttagt 25

<210> SEQ ID NO 174
<211> LENGTH: 28
<212> TYPE: DNA
<213> ORGANISM: Artificial Sequence
<220> FEATURE:
<223> OTHER INFORMATION: Synthetic primer

<400> SEQUENCE: 174
aaatagaggt aattagttgt atcaatgg 28

<210> SEQ ID NO 175
<211> LENGTH: 26
<212> TYPE: DNA
<213> ORGANISM: Artificial Sequence
<220> FEATURE:
<223> OTHER INFORMATION: Synthetic primer

<400> SEQUENCE: 175
acaacatacc atactaccac acacta 26

<210> SEQ ID NO 176
<211> LENGTH: 20
<212> TYPE: DNA
<213> ORGANISM: Artificial Sequence
<220> FEATURE:
<223> OTHER INFORMATION: Synthetic primer

<400> SEQUENCE: 176
tgcatggaca atctcctctt 20

<210> SEQ ID NO 177
<211> LENGTH: 22
<212> TYPE: DNA
<213> ORGANISM: Artificial Sequence
<220> FEATURE:
<223> OTHER INFORMATION: Synthetic primer

<400> SEQUENCE: 177
gcatggacaa tctcatcttc tc 22

<210> SEQ ID NO 178
<211> LENGTH: 24
<212> TYPE: DNA
<213> ORGANISM: Artificial Sequence
<220> FEATURE:
<223> OTHER INFORMATION: Synthetic primer

<400> SEQUENCE: 178
caacaggagt tgagttattc tcat 24

<210> SEQ ID NO 179
<211> LENGTH: 26
<212> TYPE: DNA
<213> ORGANISM: Artificial Sequence
<220> FEATURE:
<223> OTHER INFORMATION: Synthetic primer

<400> SEQUENCE: 179
caccttcttc aagcaaaatt aatgac 26

<210> SEQ ID NO 180
<211> LENGTH: 22
<212> TYPE: DNA
<213> ORGANISM: Artificial Sequence
<220> FEATURE:
<223> OTHER INFORMATION: Synthetic primer

<400> SEQUENCE: 180
attagagtca tgagccatta gc 22

<210> SEQ ID NO 181
<211> LENGTH: 20
<212> TYPE: DNA
<213> ORGANISM: Artificial Sequence
<220> FEATURE:
<223> OTHER INFORMATION: Synthetic primer

<400> SEQUENCE: 181
ctgggcaata ttccaccatt 20

<210> SEQ ID NO 182
<211> LENGTH: 20
<212> TYPE: DNA
<213> ORGANISM: Artificial Sequence
<220> FEATURE:
<223> OTHER INFORMATION: Synthetic primer

<400> SEQUENCE: 182
aatggtggaa tattgcccag 20

<210> SEQ ID NO 183
<211> LENGTH: 24
<212> TYPE: DNA
<213> ORGANISM: Artificial Sequence
<220> FEATURE:
<223> OTHER INFORMATION: Synthetic primer

<400> SEQUENCE: 183
atgagaataa ctcaactcct gttg 24

<210> SEQ ID NO 184
<211> LENGTH: 24
<212> TYPE: DNA
<213> ORGANISM: Artificial Sequence
<220> FEATURE:
<223> OTHER INFORMATION: Synthetic primer

<400> SEQUENCE: 184
gtgtaccagc tagttattat tgcg 24

<210> SEQ ID NO 185
<211> LENGTH: 22
<212> TYPE: DNA
<213> ORGANISM: Artificial Sequence
<220> FEATURE:
<223> OTHER INFORMATION: Synthetic primer

<400> SEQUENCE: 185
cctgatccgt tctgatagat cg 22

<210> SEQ ID NO 186
<211> LENGTH: 28
<212> TYPE: DNA
<213> ORGANISM: Artificial Sequence
<220> FEATURE:
<223> OTHER INFORMATION: Synthetic primer

<400> SEQUENCE: 186
atttgttaaa aagttgtaat aaaattgg 28

<210> SEQ ID NO 187
<211> LENGTH: 23
<212> TYPE: DNA
<213> ORGANISM: Artificial Sequence
<220> FEATURE:
<223> OTHER INFORMATION: Synthetic primer

<400> SEQUENCE: 187
tttctttgaa ttgctaacga gga 23

<210> SEQ ID NO 188
<211> LENGTH: 23
<212> TYPE: DNA
<213> ORGANISM: Artificial Sequence
<220> FEATURE:
<223> OTHER INFORMATION: Synthetic primer

<400> SEQUENCE: 188
tcctcgttag caattcaaag aaa 23

<210> SEQ ID NO 189
<211> LENGTH: 26
<212> TYPE: DNA
<213> ORGANISM: Artificial Sequence
<220> FEATURE:
<223> OTHER INFORMATION: Synthetic primer

<400> SEQUENCE: 189
agaatataaa gagcagcctg aattac 26

<210> SEQ ID NO 190
<211> LENGTH: 20
<212> TYPE: DNA
<213> ORGANISM: Artificial Sequence
<220> FEATURE:
<223> OTHER INFORMATION: Synthetic primer

<400> SEQUENCE: 190
tgcattaaca tgaatgcgac 20

<210> SEQ ID NO 191
<211> LENGTH: 27
<212> TYPE: DNA
<213> ORGANISM: Artificial Sequence
<220> FEATURE:
<223> OTHER INFORMATION: Synthetic primer

<400> SEQUENCE: 191
tctaaatagc gagtaataag gatgaga 27

<210> SEQ ID NO 192
<211> LENGTH: 28
<212> TYPE: DNA
<213> ORGANISM: Artificial Sequence
<220> FEATURE:
<223> OTHER INFORMATION: Synthetic primer

<400> SEQUENCE: 192
gtttgttaaa aaattgtaat aaacttgg 28

<210> SEQ ID NO 193
<211> LENGTH: 23

<212> TYPE: DNA
<213> ORGANISM: Artificial Sequence
<220> FEATURE:
<223> OTHER INFORMATION: Synthetic primer

<400> SEQUENCE: 193
tttctttgaa gtgcaaaagg aat 23

<210> SEQ ID NO 194
<211> LENGTH: 23
<212> TYPE: DNA
<213> ORGANISM: Artificial Sequence
<220> FEATURE:
<223> OTHER INFORMATION: Synthetic primer

<400> SEQUENCE: 194
attccttttg cacttcaaag aaa 23

<210> SEQ ID NO 195
<211> LENGTH: 25
<212> TYPE: DNA
<213> ORGANISM: Artificial Sequence
<220> FEATURE:
<223> OTHER INFORMATION: Synthetic primer

<400> SEQUENCE: 195
attatggaaa aacaactctt ctatt 25

<210> SEQ ID NO 196
<211> LENGTH: 25
<212> TYPE: DNA
<213> ORGANISM: Artificial Sequence
<220> FEATURE:
<223> OTHER INFORMATION: Synthetic primer

<400> SEQUENCE: 196
aagaacattg gctttagtcc tctaa 25

<210> SEQ ID NO 197
<211> LENGTH: 26
<212> TYPE: DNA
<213> ORGANISM: Artificial Sequence
<220> FEATURE:
<223> OTHER INFORMATION: Synthetic primer

<400> SEQUENCE: 197
accatcactc atctaactta tcccat 26

<210> SEQ ID NO 198
<211> LENGTH: 23
<212> TYPE: DNA
<213> ORGANISM: Artificial Sequence
<220> FEATURE:
<223> OTHER INFORMATION: Synthetic primer

<400> SEQUENCE: 198
agacaggaac acagttgaac gga 23

<210> SEQ ID NO 199
<211> LENGTH: 25
<212> TYPE: DNA
<213> ORGANISM: Artificial Sequence
<220> FEATURE:
<223> OTHER INFORMATION: Synthetic primer

<400> SEQUENCE: 199
cttgacaaac actctgattc tacac 25

<210> SEQ ID NO 200
<211> LENGTH: 27
<212> TYPE: DNA
<213> ORGANISM: Artificial Sequence
<220> FEATURE:
<223> OTHER INFORMATION: Synthetic primer

<400> SEQUENCE: 200
ttgagatagc ttgtatatta tgcatgc 27

<210> SEQ ID NO 201
<211> LENGTH: 25
<212> TYPE: DNA
<213> ORGANISM: Artificial Sequence
<220> FEATURE:
<223> OTHER INFORMATION: Synthetic primer

<400> SEQUENCE: 201
ttgtacccat tgaaggatga ctact 25

<210> SEQ ID NO 202
<211> LENGTH: 26
<212> TYPE: DNA
<213> ORGANISM: Artificial Sequence
<220> FEATURE:
<223> OTHER INFORMATION: Synthetic primer

<400> SEQUENCE: 202
tccatcactg atctaactaa tccaag 26

<210> SEQ ID NO 203
<211> LENGTH: 24
<212> TYPE: DNA
<213> ORGANISM: Artificial Sequence
<220> FEATURE:
<223> OTHER INFORMATION: Synthetic primer

<400> SEQUENCE: 203
cacgggcgtt acctccacta gtat 24

<210> SEQ ID NO 204
<211> LENGTH: 23
<212> TYPE: DNA
<213> ORGANISM: Artificial Sequence
<220> FEATURE:
<223> OTHER INFORMATION: Synthetic primer

<400> SEQUENCE: 204
aaggtcatta gaatatgcgg agc 23

<210> SEQ ID NO 205
<211> LENGTH: 23
<212> TYPE: DNA
<213> ORGANISM: Artificial Sequence
<220> FEATURE:
<223> OTHER INFORMATION: Synthetic primer

<400> SEQUENCE: 205
tcttcactag tttcgggctc aag 23

<210> SEQ ID NO 206
<211> LENGTH: 22
<212> TYPE: DNA
<213> ORGANISM: Artificial Sequence
<220> FEATURE:
<223> OTHER INFORMATION: Synthetic primer

<400> SEQUENCE: 206
gtggaggctt tggattatta tg 22

<210> SEQ ID NO 207
<211> LENGTH: 26
<212> TYPE: DNA
<213> ORGANISM: Artificial Sequence
<220> FEATURE:
<223> OTHER INFORMATION: Synthetic primer

<400> SEQUENCE: 207
cgtcagaact tcggattaat tacttc 26

<210> SEQ ID NO 208
<211> LENGTH: 20
<212> TYPE: DNA
<213> ORGANISM: Artificial Sequence
<220> FEATURE:
<223> OTHER INFORMATION: Synthetic primer

<400> SEQUENCE: 208
aaatgaggcc tgagcacaag 20

<210> SEQ ID NO 209
<211> LENGTH: 23
<212> TYPE: DNA
<213> ORGANISM: Artificial Sequence
<220> FEATURE:
<223> OTHER INFORMATION: Synthetic primer

<400> SEQUENCE: 209
caacaacatt agatggtgtc aag 23

<210> SEQ ID NO 210
<211> LENGTH: 23
<212> TYPE: DNA
<213> ORGANISM: Artificial Sequence
<220> FEATURE:
<223> OTHER INFORMATION: Synthetic primer

<400> SEQUENCE: 210
ttatgggatt tgatgatgca gag 23

<210> SEQ ID NO 211
<211> LENGTH: 26
<212> TYPE: DNA
<213> ORGANISM: Artificial Sequence
<220> FEATURE:
<223> OTHER INFORMATION: Synthetic primer

<400> SEQUENCE: 211
acctagattc ctttacataa ccactc 26

<210> SEQ ID NO 212
<211> LENGTH: 30
<212> TYPE: DNA
<213> ORGANISM: Artificial Sequence
<220> FEATURE:
<223> OTHER INFORMATION: Synthetic primer

<400> SEQUENCE: 212
atatagaagg atgagacata gtaacatacc 30

<210> SEQ ID NO 213
<211> LENGTH: 25
<212> TYPE: DNA
<213> ORGANISM: Artificial Sequence
<220> FEATURE:
<223> OTHER INFORMATION: Synthetic primer

<400> SEQUENCE: 213
gtctacaaga aaatatgcat ccgga 25

<210> SEQ ID NO 214
<211> LENGTH: 21
<212> TYPE: DNA
<213> ORGANISM: Artificial Sequence
<220> FEATURE:
<223> OTHER INFORMATION: Synthetic primer

<400> SEQUENCE: 214
ctttgtccct tcgattcatg a 21

<210> SEQ ID NO 215
<211> LENGTH: 20
<212> TYPE: DNA
<213> ORGANISM: Artificial Sequence
<220> FEATURE:
<223> OTHER INFORMATION: Synthetic primer

<400> SEQUENCE: 215
aggcctaaat catcagtcca 20

<210> SEQ ID NO 216
<211> LENGTH: 25
<212> TYPE: DNA
<213> ORGANISM: Artificial Sequence
<220> FEATURE:
<223> OTHER INFORMATION: Synthetic primer

<400> SEQUENCE: 216
gctggtgtcg ataattgcta tttag 25

<210> SEQ ID NO 217
<211> LENGTH: 25
<212> TYPE: DNA
<213> ORGANISM: Artificial Sequence
<220> FEATURE:
<223> OTHER INFORMATION: Synthetic primer

<400> SEQUENCE: 217
ccttagtggt tttgcatgct atgtt 25

<210> SEQ ID NO 218
<211> LENGTH: 25
<212> TYPE: DNA
<213> ORGANISM: Artificial Sequence
<220> FEATURE:
<223> OTHER INFORMATION: Synthetic primer

<400> SEQUENCE: 218
ggcaggatac tattctacca ctagg 25

<210> SEQ ID NO 219
<211> LENGTH: 21
<212> TYPE: DNA
<213> ORGANISM: Artificial Sequence
<220> FEATURE:
<223> OTHER INFORMATION: Synthetic primer

<400> SEQUENCE: 219
cgcttcgatt ctgggaataa g 21

<210> SEQ ID NO 220
<211> LENGTH: 20
<212> TYPE: DNA
<213> ORGANISM: Artificial Sequence
<220> FEATURE:
<223> OTHER INFORMATION: Synthetic primer

<400> SEQUENCE: 220
tacaggccta aatcagtcca 20

<210> SEQ ID NO 221
<211> LENGTH: 22
<212> TYPE: DNA
<213> ORGANISM: Artificial Sequence
<220> FEATURE:
<223> OTHER INFORMATION: Synthetic primer

<400> SEQUENCE: 221
atgtgaagac aatgaattcc gc 22

<210> SEQ ID NO 222
<211> LENGTH: 24
<212> TYPE: DNA
<213> ORGANISM: Artificial Sequence
<220> FEATURE:
<223> OTHER INFORMATION: Synthetic primer

<400> SEQUENCE: 222
gtgtcgtcta tggatattat cggc 24

<210> SEQ ID NO 223
<211> LENGTH: 23
<212> TYPE: DNA
<213> ORGANISM: Artificial Sequence
<220> FEATURE:
<223> OTHER INFORMATION: Synthetic primer

<400> SEQUENCE: 223
gttcgcagaa tgacaaacag agt 23

<210> SEQ ID NO 224
<211> LENGTH: 27
<212> TYPE: DNA
<213> ORGANISM: Artificial Sequence
<220> FEATURE:
<223> OTHER INFORMATION: Synthetic primer

<400> SEQUENCE: 224
catgagtaca gatattacca gtgcatc 27

<210> SEQ ID NO 225
<211> LENGTH: 23
<212> TYPE: DNA
<213> ORGANISM: Artificial Sequence
<220> FEATURE:
<223> OTHER INFORMATION: Synthetic primer

<400> SEQUENCE: 225
gtgaataatg tgttgcaggt ctc 23

<210> SEQ ID NO 226

<211> LENGTH: 25
<212> TYPE: DNA
<213> ORGANISM: Artificial Sequence
<220> FEATURE:
<223> OTHER INFORMATION: Synthetic primer

<400> SEQUENCE: 226
tctcaacagg agttgagtta ttctc 25

<210> SEQ ID NO 227
<211> LENGTH: 22
<212> TYPE: DNA
<213> ORGANISM: Artificial Sequence
<220> FEATURE:
<223> OTHER INFORMATION: Synthetic primer

<400> SEQUENCE: 227
agtttgaaca ttggatatgg tg 22

<210> SEQ ID NO 228
<211> LENGTH: 24
<212> TYPE: DNA
<213> ORGANISM: Artificial Sequence
<220> FEATURE:
<223> OTHER INFORMATION: Synthetic primer

<400> SEQUENCE: 228
tcatactcac gcttgttata cacg 24

<210> SEQ ID NO 229
<211> LENGTH: 23
<212> TYPE: DNA
<213> ORGANISM: Artificial Sequence
<220> FEATURE:
<223> OTHER INFORMATION: Synthetic primer

<400> SEQUENCE: 229
gctctcctct gatacatggc tat 23

<210> SEQ ID NO 230
<211> LENGTH: 20
<212> TYPE: DNA
<213> ORGANISM: Artificial Sequence
<220> FEATURE:
<223> OTHER INFORMATION: Synthetic primer

<400> SEQUENCE: 230
tgtttcagtc tcaaattcat 20

<210> SEQ ID NO 231
<211> LENGTH: 24
<212> TYPE: DNA
<213> ORGANISM: Artificial Sequence
<220> FEATURE:
<223> OTHER INFORMATION: Synthetic primer

<400> SEQUENCE: 231
accacctggt tttaggtttc atcc 24

<210> SEQ ID NO 232
<211> LENGTH: 22
<212> TYPE: DNA
<213> ORGANISM: Artificial Sequence
<220> FEATURE:
<223> OTHER INFORMATION: Synthetic primer

<400> SEQUENCE: 232
tattctgcat atcacccatt cc 22

<210> SEQ ID NO 233
<211> LENGTH: 23
<212> TYPE: DNA
<213> ORGANISM: Artificial Sequence
<220> FEATURE:
<223> OTHER INFORMATION: Synthetic primer

<400> SEQUENCE: 233
cacctcaaga aaaagcttat ggg 23

<210> SEQ ID NO 234
<211> LENGTH: 20
<212> TYPE: DNA
<213> ORGANISM: Artificial Sequence
<220> FEATURE:
<223> OTHER INFORMATION: Synthetic primer

<400> SEQUENCE: 234
gcagcagcta acaagttgta 20

<210> SEQ ID NO 235
<211> LENGTH: 20
<212> TYPE: DNA
<213> ORGANISM: Artificial Sequence
<220> FEATURE:
<223> OTHER INFORMATION: Synthetic primer

<400> SEQUENCE: 235
cactgtagcc agagaccaca 20

<210> SEQ ID NO 236
<211> LENGTH: 22
<212> TYPE: DNA
<213> ORGANISM: Artificial Sequence
<220> FEATURE:
<223> OTHER INFORMATION: Synthetic primer

<400> SEQUENCE: 236
ccggtactgg aaatgacctt ga 22

<210> SEQ ID NO 237
<211> LENGTH: 29
<212> TYPE: DNA
<213> ORGANISM: Artificial Sequence
<220> FEATURE:
<223> OTHER INFORMATION: Synthetic probe

<400> SEQUENCE: 237
cccttcgtag aaccggagat cgtttagct 29

<210> SEQ ID NO 238
<211> LENGTH: 29
<212> TYPE: DNA
<213> ORGANISM: Artificial Sequence
<220> FEATURE:
<223> OTHER INFORMATION: Synthetic primer

<400> SEQUENCE: 238
gagaaaacaa atgtaagtac accattagg 29

<210> SEQ ID NO 239
<211> LENGTH: 25
<212> TYPE: DNA

<213> ORGANISM: Artificial Sequence
<220> FEATURE:
<223> OTHER INFORMATION: Synthetic primer

<400> SEQUENCE: 239
gaaaaagttt gaatcttctt gccaa 25

<210> SEQ ID NO 240
<211> LENGTH: 26
<212> TYPE: DNA
<213> ORGANISM: Artificial Sequence
<220> FEATURE:
<223> OTHER INFORMATION: Synthetic probe

<400> SEQUENCE: 240
gatttgaaag ggcgtttggg tatggg 26

<210> SEQ ID NO 241
<211> LENGTH: 19
<212> TYPE: DNA
<213> ORGANISM: Artificial Sequence
<220> FEATURE:
<223> OTHER INFORMATION: Synthetic primer

<400> SEQUENCE: 241
tctccaggct cccctgaag 19

<210> SEQ ID NO 242
<211> LENGTH: 24
<212> TYPE: DNA
<213> ORGANISM: Artificial Sequence
<220> FEATURE:
<223> OTHER INFORMATION: Synthetic primer

<400> SEQUENCE: 242
tgtccccatg tgataactgt agct 24

<210> SEQ ID NO 243
<211> LENGTH: 24
<212> TYPE: DNA
<213> ORGANISM: Artificial Sequence
<220> FEATURE:
<223> OTHER INFORMATION: Synthetic probe

<400> SEQUENCE: 243
aacgttgtcg cactggatct gcca 24

<210> SEQ ID NO 244
<211> LENGTH: 23
<212> TYPE: DNA
<213> ORGANISM: Artificial Sequence
<220> FEATURE:
<223> OTHER INFORMATION: Synthetic primer

<400> SEQUENCE: 244
atggctaccc tacaagcttg aaa 23

<210> SEQ ID NO 245
<211> LENGTH: 23
<212> TYPE: DNA
<213> ORGANISM: Artificial Sequence
<220> FEATURE:
<223> OTHER INFORMATION: Synthetic primer

<400> SEQUENCE: 245
ttgccaatgt gtagttgttg tgg 23

<210> SEQ ID NO 246
<211> LENGTH: 30
<212> TYPE: DNA
<213> ORGANISM: Artificial Sequence
<220> FEATURE:
<223> OTHER INFORMATION: Synthetic probe

<400> SEQUENCE: 246
tcttaacaca gcaacatcag cagaagcagc 30

<210> SEQ ID NO 247
<211> LENGTH: 25
<212> TYPE: DNA
<213> ORGANISM: Artificial Sequence
<220> FEATURE:
<223> OTHER INFORMATION: Synthetic primer

<400> SEQUENCE: 247
actcctgttg agaatgcaca aataa 25

<210> SEQ ID NO 248
<211> LENGTH: 27
<212> TYPE: DNA
<213> ORGANISM: Artificial Sequence
<220> FEATURE:
<223> OTHER INFORMATION: Synthetic primer

<400> SEQUENCE: 248
ccagaaatat tagtttcttc tccttgg 27

<210> SEQ ID NO 249
<211> LENGTH: 30
<212> TYPE: DNA
<213> ORGANISM: Artificial Sequence
<220> FEATURE:
<223> OTHER INFORMATION: Synthetic probe

<400> SEQUENCE: 249
ccatctgaaa atgcataacc tggaagctgc 30

<210> SEQ ID NO 250
<211> LENGTH: 26
<212> TYPE: DNA
<213> ORGANISM: Artificial Sequence
<220> FEATURE:
<223> OTHER INFORMATION: Synthetic primer

<400> SEQUENCE: 250
ttggtttggg attttgaggt ttgagg 26

<210> SEQ ID NO 251
<211> LENGTH: 26
<212> TYPE: DNA
<213> ORGANISM: Artificial Sequence
<220> FEATURE:
<223> OTHER INFORMATION: Synthetic primer

<400> SEQUENCE: 251
tttggaattg agggtgaaca ttgtgc 26

<210> SEQ ID NO 252
<211> LENGTH: 25
<212> TYPE: DNA
<213> ORGANISM: Artificial Sequence
<220> FEATURE:

<223> OTHER INFORMATION: Synthetic primer

<400> SEQUENCE: 252
acgttaccat tcgtctacag taagc 25

<210> SEQ ID NO 253
<211> LENGTH: 25
<212> TYPE: DNA
<213> ORGANISM: Artificial Sequence
<220> FEATURE:
<223> OTHER INFORMATION: Synthetic primer

<400> SEQUENCE: 253
ccaataaaca agaaacagat gatgg 25

<210> SEQ ID NO 254
<211> LENGTH: 25
<212> TYPE: DNA
<213> ORGANISM: Artificial Sequence
<220> FEATURE:
<223> OTHER INFORMATION: Synthetic primer

<400> SEQUENCE: 254
gaatggacac catagacgga aagga 25

<210> SEQ ID NO 255
<211> LENGTH: 25
<212> TYPE: DNA
<213> ORGANISM: Artificial Sequence
<220> FEATURE:
<223> OTHER INFORMATION: Synthetic primer

<400> SEQUENCE: 255
tttccgtcta tggtgtccat tctcc 25

<210> SEQ ID NO 256
<211> LENGTH: 25
<212> TYPE: DNA
<213> ORGANISM: Artificial Sequence
<220> FEATURE:
<223> OTHER INFORMATION: Synthetic primer

<400> SEQUENCE: 256
gagacatggc aatactgaat tttca 25

<210> SEQ ID NO 257
<211> LENGTH: 25
<212> TYPE: DNA
<213> ORGANISM: Artificial Sequence
<220> FEATURE:
<223> OTHER INFORMATION: Synthetic primer

<400> SEQUENCE: 257
agcctacgtg aagattgatg agaag 25

<210> SEQ ID NO 258
<211> LENGTH: 26
<212> TYPE: DNA
<213> ORGANISM: Artificial Sequence
<220> FEATURE:
<223> OTHER INFORMATION: Synthetic primer

<400> SEQUENCE: 258
tcgattgggt tgtatgagtt aaccgt 26

<210> SEQ ID NO 259
<211> LENGTH: 26
<212> TYPE: DNA
<213> ORGANISM: Artificial Sequence
<220> FEATURE:
<223> OTHER INFORMATION: Synthetic primer

<400> SEQUENCE: 259
gttaccataa gctgtggaat atcagg 26

<210> SEQ ID NO 260
<211> LENGTH: 26
<212> TYPE: DNA
<213> ORGANISM: Artificial Sequence
<220> FEATURE:
<223> OTHER INFORMATION: Synthetic primer

<400> SEQUENCE: 260
aaccaatgga caagaaacgg atggca 26

<210> SEQ ID NO 261
<211> LENGTH: 26
<212> TYPE: DNA
<213> ORGANISM: Artificial Sequence
<220> FEATURE:
<223> OTHER INFORMATION: Synthetic primer

<400> SEQUENCE: 261
tttagctatc cagtcaaaga ggcacg 26

<210> SEQ ID NO 262
<211> LENGTH: 25
<212> TYPE: DNA
<213> ORGANISM: Artificial Sequence
<220> FEATURE:
<223> OTHER INFORMATION: Synthetic primer

<400> SEQUENCE: 262
agcctacgtg aagattgatg agaaa 25

<210> SEQ ID NO 263
<211> LENGTH: 20
<212> TYPE: DNA
<213> ORGANISM: Artificial Sequence
<220> FEATURE:
<223> OTHER INFORMATION: Synthetic primer

<400> SEQUENCE: 263
ttcgtagaac cggagatcgt 20

<210> SEQ ID NO 264
<211> LENGTH: 21
<212> TYPE: DNA
<213> ORGANISM: Artificial Sequence
<220> FEATURE:
<223> OTHER INFORMATION: Synthetic primer

<400> SEQUENCE: 264
gcaaagttgc ttccaatgaa t 21

<210> SEQ ID NO 265
<211> LENGTH: 20
<212> TYPE: DNA
<213> ORGANISM: Artificial Sequence
<220> FEATURE:
<223> OTHER INFORMATION: Synthetic primer

<400> SEQUENCE: 265
cccagacccc cttttcctct 20

<210> SEQ ID NO 266
<211> LENGTH: 23
<212> TYPE: DNA
<213> ORGANISM: Artificial Sequence
<220> FEATURE:
<223> OTHER INFORMATION: Synthetic primer

<400> SEQUENCE: 266
aatttccctt ataatttaac gcc 23

<210> SEQ ID NO 267
<211> LENGTH: 21
<212> TYPE: DNA
<213> ORGANISM: Artificial Sequence
<220> FEATURE:
<223> OTHER INFORMATION: Synthetic primer

<400> SEQUENCE: 267
ccctagagag acccctttt c 21

<210> SEQ ID NO 268
<211> LENGTH: 21
<212> TYPE: DNA
<213> ORGANISM: Artificial Sequence
<220> FEATURE:
<223> OTHER INFORMATION: Synthetic primer

<400> SEQUENCE: 268
gggttttaaa tttaacgcca a 21

<210> SEQ ID NO 269
<211> LENGTH: 19
<212> TYPE: DNA
<213> ORGANISM: Artificial Sequence
<220> FEATURE:
<223> OTHER INFORMATION: Synthetic primer

<400> SEQUENCE: 269
gtgaatgccc tattctgtc 19

<210> SEQ ID NO 270
<211> LENGTH: 23
<212> TYPE: DNA
<213> ORGANISM: Artificial Sequence
<220> FEATURE:
<223> OTHER INFORMATION: Synthetic primer

<400> SEQUENCE: 270
atcactgatc taactaatcc aag 23

<210> SEQ ID NO 271
<211> LENGTH: 12
<212> TYPE: DNA
<213> ORGANISM: Artificial Sequence
<220> FEATURE:
<223> OTHER INFORMATION: Synthetic probe

<400> SEQUENCE: 271
ctttgatcta ct 12

<210> SEQ ID NO 272
<211> LENGTH: 10

<212> TYPE: DNA
<213> ORGANISM: Artificial Sequence
<220> FEATURE:
<223> OTHER INFORMATION: Synthetic probe

<400> SEQUENCE: 272
tgatctgctt 10

<210> SEQ ID NO 273
<211> LENGTH: 19
<212> TYPE: DNA
<213> ORGANISM: Artificial Sequence
<220> FEATURE:
<223> OTHER INFORMATION: Synthetic primer

<400> SEQUENCE: 273
attgatggag gagaatgat 19

<210> SEQ ID NO 274
<211> LENGTH: 21
<212> TYPE: DNA
<213> ORGANISM: Artificial Sequence
<220> FEATURE:
<223> OTHER INFORMATION: Synthetic primer

<400> SEQUENCE: 274
gacaagatac gttaagtgaa a 21

<210> SEQ ID NO 275
<211> LENGTH: 10
<212> TYPE: DNA
<213> ORGANISM: Artificial Sequence
<220> FEATURE:
<223> OTHER INFORMATION: Synthetic probe

<400> SEQUENCE: 275
acaagctacg 10

<210> SEQ ID NO 276
<211> LENGTH: 17
<212> TYPE: DNA
<213> ORGANISM: Artificial Sequence
<220> FEATURE:
<223> OTHER INFORMATION: Synthetic primer

<400> SEQUENCE: 276
ccatttcagg tgtcgag 17

<210> SEQ ID NO 277
<211> LENGTH: 20
<212> TYPE: DNA
<213> ORGANISM: Artificial Sequence
<220> FEATURE:
<223> OTHER INFORMATION: Synthetic primer

<400> SEQUENCE: 277
acgttaccat tcgtctacag 20

<210> SEQ ID NO 278
<211> LENGTH: 10
<212> TYPE: DNA
<213> ORGANISM: Artificial Sequence
<220> FEATURE:
<223> OTHER INFORMATION: Synthetic probe

<400> SEQUENCE: 278
ttacaagcga 10

<210> SEQ ID NO 279
<211> LENGTH: 10
<212> TYPE: DNA
<213> ORGANISM: Artificial Sequence
<220> FEATURE:
<223> OTHER INFORMATION: Synthetic primer

<400> SEQUENCE: 279
gcaaaaacag 10

<210> SEQ ID NO 280
<211> LENGTH: 20
<212> TYPE: DNA
<213> ORGANISM: Artificial Sequence
<220> FEATURE:
<223> OTHER INFORMATION: Synthetic primer

<400> SEQUENCE: 280
tccctaaacc aagtgactcc 20

<210> SEQ ID NO 281
<211> LENGTH: 20
<212> TYPE: DNA
<213> ORGANISM: Artificial Sequence
<220> FEATURE:
<223> OTHER INFORMATION: Synthetic primer

<400> SEQUENCE: 281
ggtatcaagg tcatttccag 20

<210> SEQ ID NO 282
<211> LENGTH: 11
<212> TYPE: DNA
<213> ORGANISM: Artificial Sequence
<220> FEATURE:
<223> OTHER INFORMATION: Synthetic probe

<400> SEQUENCE: 282
tgtaagcact a 11

<210> SEQ ID NO 283
<211> LENGTH: 20
<212> TYPE: DNA
<213> ORGANISM: Artificial Sequence
<220> FEATURE:
<223> OTHER INFORMATION: Synthetic primer

<400> SEQUENCE: 283
agaggatgac agtggagcaa 20

<210> SEQ ID NO 284
<211> LENGTH: 21
<212> TYPE: DNA
<213> ORGANISM: Artificial Sequence
<220> FEATURE:
<223> OTHER INFORMATION: Synthetic primer

<400> SEQUENCE: 284
taacgccaag aagatatgga a 21

<210> SEQ ID NO 285
<211> LENGTH: 12
<212> TYPE: DNA
<213> ORGANISM: Artificial Sequence
<220> FEATURE:
<223> OTHER INFORMATION: Synthetic probe

<400> SEQUENCE: 285
ggtaaaatca ac 12

<210> SEQ ID NO 286
<211> LENGTH: 10
<212> TYPE: DNA
<213> ORGANISM: Artificial Sequence
<220> FEATURE:
<223> OTHER INFORMATION: Synthetic probe

<400> SEQUENCE: 286
ggcaaaatca 10

<210> SEQ ID NO 287
<211> LENGTH: 22
<212> TYPE: DNA
<213> ORGANISM: Artificial Sequence
<220> FEATURE:
<223> OTHER INFORMATION: Synthetic primer

<400> SEQUENCE: 287
gttgaaagtt caaatgattc ag 22

<210> SEQ ID NO 288
<211> LENGTH: 18
<212> TYPE: DNA
<213> ORGANISM: Artificial Sequence
<220> FEATURE:
<223> OTHER INFORMATION: Synthetic primer

<400> SEQUENCE: 288
gaggagggta acgatcag 18

<210> SEQ ID NO 289
<211> LENGTH: 11
<212> TYPE: DNA
<213> ORGANISM: Artificial Sequence
<220> FEATURE:
<223> OTHER INFORMATION: Synthetic probe

<400> SEQUENCE: 289
gcttgttagt t 11

<210> SEQ ID NO 290
<211> LENGTH: 11
<212> TYPE: DNA
<213> ORGANISM: Artificial Sequence
<220> FEATURE:
<223> OTHER INFORMATION: Synthetic probe

<400> SEQUENCE: 290
cttgttggtt a 11

<210> SEQ ID NO 291
<211> LENGTH: 447
<212> TYPE: DNA
<213> ORGANISM: Artificial Sequence
<220> FEATURE:
<223> OTHER INFORMATION: Synthetic

<400> SEQUENCE: 291
aattggtacc tttactttaa attttttctt atgcagcctg tgatggataa ctgaatcaaa 60
caaatggcgt ctgggtttaa gaagatctgt tttggctatg ttggacgaaa caagtgaact 120
tttaggatca acttcagttt atatatggag cttatatcga gcaataagat aagtgggctt 180
tttatgtaat ttaatgggct atcgtccata gattcactaa tacccatgcc cagtacccat 240
gtatgcgttt catataagct cctaatttct cccacatcgc tcaaatctaa acaaatcttg 300
ttgtatatat aacactgagg gagcaacatt ggtcacaatg atatcaagaa ttacgtttta 360
gagctagaaa tagcaagtta aaataaggct agtccgttat caacttgaaa aagtggcacc 420
gagtcggtgc ttttttgga tccaatt 447

<210> SEQ ID NO 292
<211> LENGTH: 4452
<212> TYPE: DNA
<213> ORGANISM: Artificial Sequence
<220> FEATURE:
<223> OTHER INFORMATION: Synthetic Cas 9

<400> SEQUENCE: 292
catatggatt acaaggatga tgatgataag gattacaagg atgatgatga taagatggct 60
ccaaagaaga agagaaaggt tggaatccac ggagttccag ctgctgataa gaagtactct 120
atcggacttg acatcggaac caactctgtt ggatgggctg ttatcaccga tgagtacaag 180
gttccatcta agaagttcaa ggttcttgga aacaccgata gacactctat caagaagaac 240
cttatcggtg ctcttctttt cgattctgga gagaccgctg aggctaccag attgaagaga 300
accgctagaa gaagatacac cagaagaaag aacagaatct gctaccttca ggaaatcttc 360
tctaacgaga tggctaaggt tgatgattct ttcttccaca gacttgagga gtctttcctt 420
gttgaggagg ataagaagca cgagagacac ccaatcttcg gaaacatcgt tgatgaggtt 480
gcttaccacg agaagtaccc aaccatctac caccttagaa agaagttggt tgattctacc 540
gataaggctg atcttagact tatctacctt gctcttgctc acatgatcaa gttcagagga 600
cacttcctta tcgagggaga ccttaaccca gataactctg atgttgataa gttgttcatc 660
cagcttgttc agacctacaa ccagcttttc gaggagaacc caatcaacgc ttctggagtt 720
gatgctaagg ctatcctttc tgctagactt tctaagtctc gtagacttga gaaccttatc 780
gctcagcttc caggagagaa gaagaacgga cttttcggaa accttatcgc tctttctctt 840
ggacttaccc caaacttcaa gtctaacttc gatcttgctg aggatgctaa gttgcagctt 900
tctaaggata cctacgatga tgatcttgat aaccttcttg ctcagatcgg agatcagtac 960
gctgatcttt tccttgctgc taagaacctt tctgatgcta tccttctttc tgacatcctt 1020
agagttaaca ccgagatcac caaggctcca ctttctgctt ctatgatcaa gagatacgat 1080
gagcaccacc aggatcttac ccttttgaag gctcttgtta gacagcagct tccagagaag 1140
tacaaggaaa tcttcttcga tcagtctaag aacggatacg ctggatacat cgatggagga 1200
gcttctcagg aggagttcta caagttcatc aagccaatcc ttgagaagat ggatggaacc 1260
gaggagcttc ttgttaagtt gaacagagag gatcttctta gaaagcagag aaccttcgat 1320
aacggatcta tcccacacca gatccacctt ggagagcttc acgctatcct tcgtagacag 1380
gaggatttct acccattctt gaaggataac agagagaaga tcgagaagat ccttaccttc 1440
agaatcccat actacgttgg accacttgct agaggaaact ctcgtttcgc ttggatgacc 1500
agaaagtctg aggagaccat caccccttgg aacttcgagg aggtaagttt ctgcttctac 1560
ctttgatata tatataataa ttatcattaa ttagtagtaa tataatattt caaatatttt 1620
tttcaaaata aaagaatgta gtatatagca attgcttttc tgtagtttat aagtgtgtat 1680

```
atttttaattt ataacttttc taatatatga ccaaaatttg ttgatgtgca ggttgttgat   1740
aagggagctt ctgctcagtc tttcatcgag agaatgacca acttcgataa gaaccttcca   1800
aacgagaagg ttcttccaaa gcactctctt ctttacgagt acttcaccgt ttacaacgag   1860
cttaccaagg ttaagtacgt taccgaggga atgagaaagc cagctttcct ttctggagag   1920
cagaagaagg ctatcgttga tcttcttttc aagaccaaca gaaaggttac cgttaagcag   1980
ttgaaggagg attacttcaa gaagatcgag tgcttcgatt ctgttgaaat ctctggagtt   2040
gaggatagat tcaacgcttc tcttggaacc taccacgatc ttttgaagat catcaaggat   2100
aaggatttcc ttgataacga ggagaacgag gacatccttg aggacatcgt tcttaccctt   2160
acccttttcg aggatagaga gatgatcgag gagagactca agacctacgc tcaccttttc   2220
gatgataagg ttatgaagca gttgaagaga agaagataca ccggatgggg tagactttct   2280
cgtaagttga tcaacggaat cagagataag cagtctggaa agaccatcct tgatttcttg   2340
aagtctgatg gattcgctaa cagaaacttc atgcagctta tccacgatga ttctcttacc   2400
ttcaaggagg acatccagaa ggctcaggtt tctggacagg gagattctct tcacgagcac   2460
atcgctaacc ttgctggatc tccagctatc aagaagggaa tccttcagac cgttaaggtt   2520
gttgatgagc ttgttaaggt tatgggtaga cacaagccag agaacatcgt tatcgagatg   2580
gctagagaga accagaccac ccagaaggga cagaagaact ctcgtgagag aatgaagaga   2640
atcgaggagg gaatcaagga gcttggatct caaatcttga aggagcaccc agttgagaac   2700
acccagcttc agaacgagaa gttgtacctt tactaccttc agaacggaag agatatgtac   2760
gttgatcagg agcttgacat caacagactt tctgattacg atgttgatca catcgttcca   2820
cagtctttct tgaaggatga ttctatcgat aacaaggttc ttacccgttc tgataagaac   2880
agaggaaagt ctgataacgt tccatctgag gaggttgtta agaagatgaa gaactactgg   2940
agacagcttc ttaacgctaa gttgatcacc cagagaaagt tcgataacct taccaaggct   3000
gagagaggag gactttctga gcttgataag gctggattca tcaagagaca gcttgttgag   3060
accagacaga tcaccaagca cgttgctcag atccttgatt ctcgtatgaa caccaagtac   3120
gatgagaacg ataagttgat cagagaggtt aaggttatca ccttgaagtc taagttggtt   3180
tctgatttca gaaaggattt ccagttctac aaggttagag agatcaacaa ctaccaccac   3240
gctcacgatg cttaccttaa cgctgttgtt ggaaccgctc ttatcaagaa gtacccaaag   3300
ttggagtctg agttcgttta cggagattac aaggtttacg atgttagaaa gatgatcgct   3360
aagtctgagc aggagatcgg aaaggctacc gctaagtact tcttctactc taacatcatg   3420
aacttcttca agaccgagat caccccttgct aacggagaga tcagaaagag accacttatc   3480
gagaccaacg gagagaccgg agagatcgtt tgggataagg gaagagattt cgctaccgtt   3540
agaaaggttc tttctatgcc acaggttaac atcgttaaga aaaccgaggt tcagaccgga   3600
ggattctcta aggagtctat ccttccaaag agaaactctg ataagttgat cgctagaaag   3660
aaggattggg acccaaagaa gtacggagga ttcgattctc caaccgttgc ttactctgtt   3720
cttgttgttg ctaaggttga gaagggaaag tctaagaagt tgaagtctgt taaggagctt   3780
cttggaatca ccatcatgga gcgttcttct ttcgagaaga acccaatcga tttccttgag   3840
gctaagggat acaaggaggt taagaaggat cttatcatca agttgccaaa gtactctctt   3900
ttcgagcttg agaacggaag aaagagaatg cttgcttctg ctggagagct tcagaaggga   3960
aacgagcttg ctcttccatc taagtacgtt aacttccttt accttgcttc tcactacgag   4020
```

-continued

```
aagttgaagg gatctccaga ggataacgag cagaagcagc ttttcgttga gcagcacaag   4080

cactaccttg atgagatcat cgagcaaatc tctgagttct ctaagagagt tatccttgct   4140

gatgctaacc ttgataaggt tctttctgct tacaacaagc acagagataa gccaatcaga   4200

gagcaggctg agaacatcat ccaccttttc acccttacca accttggtgc tccagctgct   4260

ttcaagtact tcgataccac catcgataga aaaagataca cctctaccaa ggaggttctt   4320

gatgctaccc ttatccacca gtctatcacc ggactttacg agaccagaat cgatctttct   4380

cagcttggag gagataagag accagctgct accaagaagg ctggacaggc taagaagaag   4440

aagtgagtcg ac                                                       4452
```

<210> SEQ ID NO 293
<211> LENGTH: 27
<212> TYPE: DNA
<213> ORGANISM: Artificial Sequence
<220> FEATURE:
<223> OTHER INFORMATION: Synthetic primer

<400> SEQUENCE: 293

```
aagtattact actacaaaat tccaacg                                         27
```

<210> SEQ ID NO 294
<211> LENGTH: 23
<212> TYPE: DNA
<213> ORGANISM: Artificial Sequence
<220> FEATURE:
<223> OTHER INFORMATION: Synthetic primer

<400> SEQUENCE: 294

```
ccatctgatg aagaacaact tgc                                             23
```

<210> SEQ ID NO 295
<211> LENGTH: 26
<212> TYPE: DNA
<213> ORGANISM: Artificial Sequence
<220> FEATURE:
<223> OTHER INFORMATION: Synthetic primer

<400> SEQUENCE: 295

```
ttaaacacta gagagtgaga gagtgc                                          26
```

<210> SEQ ID NO 296
<211> LENGTH: 29
<212> TYPE: DNA
<213> ORGANISM: Artificial Sequence
<220> FEATURE:
<223> OTHER INFORMATION: Synthetic primer

<400> SEQUENCE: 296

```
cagatgttta attattaaga caaagttcc                                       29
```

<210> SEQ ID NO 297
<211> LENGTH: 571
<212> TYPE: DNA
<213> ORGANISM: Artificial Sequence
<220> FEATURE:
<223> OTHER INFORMATION: Synthetic

<400> SEQUENCE: 297

```
aattggtacc aagcttcgtt gaacaacgga aactcgactt gccttccgca caatacatca     60

tttcttctta gcttttttc ttcttcttcg ttcatacagt tttttttgt ttatcagctt    120

acattttctt gaaccgtagc tttcgttttc ttctttttaa ctttccattc ggagtttttg    180
```

```
tatcttgttt catagtttgt cccaggatta gaatgattag gcatcgaacc ttcaagaatt    240
tgattgaata aaacatcttc attcttaaga tatgaagata atcttcaaaa ggcccctggg    300
aatctgaaag aagagaagca ggcccattta tatgggaaag aacaatagta tttcttatat    360
aggcccattt aagttgaaaa caatcttcaa aagtcccaca tcgcttagat aagaaaacga    420
agctgagttt atatacagct agagtcgaag tagtgattga gttcctttcc aaggctacgt    480
tttagagcta gaaatagcaa gttaaaataa ggctagtccg ttatcaactt gaaaaagtgg    540
caccgagtcg gtgctttttt tggatccaat t                                  571
```

<210> SEQ ID NO 298
<211> LENGTH: 571
<212> TYPE: DNA
<213> ORGANISM: Artificial Sequence
<220> FEATURE:
<223> OTHER INFORMATION: Synthetic

<400> SEQUENCE: 298

```
aattggtacc aagcttcgtt gaacaacgga aactcgactt gccttccgca caatacatca     60
tttcttctta gctttttttc ttcttcttcg ttcatacagt tttttttgt ttatcagctt    120
acattttctt gaaccgtagc tttcgttttc ttctttttaa ctttccattc ggagtttttg    180
tatcttgttt catagtttgt cccaggatta gaatgattag gcatcgaacc ttcaagaatt    240
tgattgaata aaacatcttc attcttaaga tatgaagata atcttcaaaa ggcccctggg    300
aatctgaaag aagagaagca ggcccattta tatgggaaag aacaatagta tttcttatat    360
aggcccattt aagttgaaaa caatcttcaa aagtcccaca tcgcttagat aagaaaacga    420
agctgagttt atatacagct agagtcgaag tagtgattgg agtggcagcc cgagcatggt    480
tttagagcta gaaatagcaa gttaaaataa ggctagtccg ttatcaactt gaaaaagtgg    540
caccgagtcg gtgctttttt tggatccaat t                                  571
```

<210> SEQ ID NO 299
<211> LENGTH: 571
<212> TYPE: DNA
<213> ORGANISM: Artificial Sequence
<220> FEATURE:
<223> OTHER INFORMATION: Synthetic

<400> SEQUENCE: 299

```
aattggtacc aagcttcgtt gaacaacgga aactcgactt gccttccgca caatacatca     60
tttcttctta gctttttttc ttcttcttcg ttcatacagt tttttttgt ttatcagctt    120
acattttctt gaaccgtagc tttcgttttc ttctttttaa ctttccattc ggagtttttg    180
tatcttgttt catagtttgt cccaggatta gaatgattag gcatcgaacc ttcaagaatt    240
tgattgaata aaacatcttc attcttaaga tatgaagata atcttcaaaa ggcccctggg    300
aatctgaaag aagagaagca ggcccattta tatgggaaag aacaatagta tttcttatat    360
aggcccattt aagttgaaaa caatcttcaa aagtcccaca tcgcttagat aagaaaacga    420
agctgagttt atatacagct agagtcgaag tagtgattgt gtagcagctc gtgaaagagt    480
tttagagcta gaaatagcaa gttaaaataa ggctagtccg ttatcaactt gaaaaagtgg    540
caccgagtcg gtgctttttt tggatccaat t                                  571
```

<210> SEQ ID NO 300
<211> LENGTH: 427
<212> TYPE: DNA

<213> ORGANISM: Artificial Sequence
<220> FEATURE:
<223> OTHER INFORMATION: Synthetic

<400> SEQUENCE: 300
aattggtacc agaaatctca aaattccggc agaacaattt tgaatctcga tccgtagaaa 60
cgagacggtc attgttttag ttccaccacg attatatttg aaatttacgt gagtgtgagt 120
gagacttgca taagaaaata aaatctttag ttgggaaaaa attcaataat ataaatgggc 180
ttgagaagga agcgagggat aggccttttt ctaaaatagg cccatttaag ctattaacaa 240
tcttcaaaag taccacagcg cttaggtaaa gaaagcagct gagtttatat atggttagag 300
acgaagtagt gattggaaga gttgtagatt gagagtttta gagctagaaa tagcaagtta 360
aaataaggct agtccgttat caacttgaaa aagtggcacc gagtcggtgc ttttttttgga 420 tccaatt 427

<210> SEQ ID NO 301
<211> LENGTH: 447
<212> TYPE: DNA
<213> ORGANISM: Artificial Sequence
<220> FEATURE:
<223> OTHER INFORMATION: Synthetic

<400> SEQUENCE: 301
aattggtacc tttactttaa attttttctt atgcagcctg tgatggataa ctgaatcaaa 60
caaatggcgt ctgggtttaa gaagatctgt tttggctatg ttggacgaaa caagtgaact 120
tttaggatca acttcagttt atatatggag cttatatcga gcaataagat aagtgggctt 180
tttatgtaat ttaatgggct atcgtccata gattcactaa tacccatgcc cagtacccat 240
gtatgcgttt catataagct cctaatttct cccacatcgc tcaaatctaa acaaatcttg 300
ttgtatatat aacactgagg gagcaacatt ggtcactgtg tattttatct tcacgtttta 360
gagctagaaa tagcaagtta aaataaggct agtccgttat caacttgaaa aagtggcacc 420
gagtcggtgc tttttttgga tccaatt 447

<210> SEQ ID NO 302
<211> LENGTH: 447
<212> TYPE: DNA
<213> ORGANISM: Artificial Sequence
<220> FEATURE:
<223> OTHER INFORMATION: Synthetic

<400> SEQUENCE: 302
aattggtacc tttactttaa attttttctt atgcagcctg tgatggataa ctgaatcaaa 60
caaatggcgt ctgggtttaa gaagatctgt tttggctatg ttggacgaaa caagtgaact 120
tttaggatca acttcagttt atatatggag cttatatcga gcaataagat aagtgggctt 180
tttatgtaat ttaatgggct atcgtccata gattcactaa tacccatgcc cagtacccat 240
gtatgcgttt catataagct cctaatttct cccacatcgc tcaaatctaa acaaatcttg 300
ttgtatatat aacactgagg gagcaacatt ggtcacgagt aattctttct tcttgtttta 360
gagctagaaa tagcaagtta aaataaggct agtccgttat caacttgaaa aagtggcacc 420
gagtcggtgc tttttttgga tccaatt 447

<210> SEQ ID NO 303
<211> LENGTH: 446
<212> TYPE: DNA
<213> ORGANISM: Artificial Sequence
<220> FEATURE:
<223> OTHER INFORMATION: Synthetic

<400> SEQUENCE: 303
aattggtacc tttactttaa attttttctt atgcagcctg tgatggataa ctgaatcaaa 60
caaatggcgt ctgggtttaa gaagatctgt tttggctatg ttggacgaaa caagtgaact 120
tttaggatca acttcagttt atatatggag cttatatcga gcaataagat aagtgggctt 180
tttatgtaat ttaatgggct atcgtccata gattcactaa tacccatgcc cagtacccat 240
gtatgcgttt catataagct cctaatttct cccacatcgc tcaaatctaa acaaatcttg 300
ttgtatatat aacactgagg gagcaacatt ggtcagctaa caagttgtac caagttttag 360
agctagaaat agcaagttaa aataaggcta gtccgttatc aacttgaaaa agtggcaccg 420
agtcggtgct ttttttggat ccaatt 446

<210> SEQ ID NO 304
<211> LENGTH: 24
<212> TYPE: DNA
<213> ORGANISM: Artificial Sequence
<220> FEATURE:
<223> OTHER INFORMATION: Synthetic primer

<400> SEQUENCE: 304
atatgtttga atataggggg aggg 24

<210> SEQ ID NO 305
<211> LENGTH: 24
<212> TYPE: DNA
<213> ORGANISM: Artificial Sequence
<220> FEATURE:
<223> OTHER INFORMATION: Synthetic primer

<400> SEQUENCE: 305
tggtttacaa aaggaaaagt tttc 24

<210> SEQ ID NO 306
<211> LENGTH: 24
<212> TYPE: DNA
<213> ORGANISM: Artificial Sequence
<220> FEATURE:
<223> OTHER INFORMATION: Synthetic primer

<400> SEQUENCE: 306
atatgtttga gtataaaggg agga 24

<210> SEQ ID NO 307
<211> LENGTH: 25
<212> TYPE: DNA
<213> ORGANISM: Artificial Sequence
<220> FEATURE:
<223> OTHER INFORMATION: Synthetic primer

<400> SEQUENCE: 307
ttggtttact agagaaaaaa tttcc 25

<210> SEQ ID NO 308
<211> LENGTH: 22
<212> TYPE: DNA
<213> ORGANISM: Artificial Sequence
<220> FEATURE:
<223> OTHER INFORMATION: Synthetic primer

<400> SEQUENCE: 308
taccggtact ggaaatgacc tc 22

<210> SEQ ID NO 309
<211> LENGTH: 20
<212> TYPE: DNA
<213> ORGANISM: Artificial Sequence
<220> FEATURE:
<223> OTHER INFORMATION: Synthetic primer

<400> SEQUENCE: 309
tccttaacat ttcgcggtct 20

<210> SEQ ID NO 310
<211> LENGTH: 21
<212> TYPE: DNA
<213> ORGANISM: Artificial Sequence
<220> FEATURE:
<223> OTHER INFORMATION: Synthetic primer

<400> SEQUENCE: 310
ccggtactgg aaatgacctt g 21

<210> SEQ ID NO 311
<211> LENGTH: 25
<212> TYPE: DNA
<213> ORGANISM: Artificial Sequence
<220> FEATURE:
<223> OTHER INFORMATION: Synthetic primer

<400> SEQUENCE: 311
gtttggttcg gaagagaaat tatag 25

<210> SEQ ID NO 312
<211> LENGTH: 20
<212> TYPE: DNA
<213> ORGANISM: Artificial Sequence
<220> FEATURE:
<223> OTHER INFORMATION: Synthetic primer

<400> SEQUENCE: 312
ctttgtcctt caccatgcag 20

<210> SEQ ID NO 313
<211> LENGTH: 24
<212> TYPE: DNA
<213> ORGANISM: Artificial Sequence
<220> FEATURE:
<223> OTHER INFORMATION: Synthetic primer

<400> SEQUENCE: 313
ttggttcggg agagaaataa ttga 24

<210> SEQ ID NO 314
<211> LENGTH: 20
<212> TYPE: DNA
<213> ORGANISM: Artificial Sequence
<220> FEATURE:
<223> OTHER INFORMATION: Synthetic primer

<400> SEQUENCE: 314
cgccaagaag atatggaaaa 20

<210> SEQ ID NO 315
<211> LENGTH: 19
<212> TYPE: DNA
<213> ORGANISM: Artificial Sequence -continued

```
<220> FEATURE:
<223> OTHER INFORMATION: Synthetic primer

<400> SEQUENCE: 315

atttcttctg cccaccagc                                                19


<210> SEQ ID NO 316
<211> LENGTH: 21
<212> TYPE: DNA
<213> ORGANISM: Artificial Sequence
<220> FEATURE:
<223> OTHER INFORMATION: Synthetic primer

<400> SEQUENCE: 316

tctcatcatt gaacacgaac a                                             21


<210> SEQ ID NO 317
<211> LENGTH: 24
<212> TYPE: DNA
<213> ORGANISM: Artificial Sequence
<220> FEATURE:
<223> OTHER INFORMATION: Synthetic primer

<400> SEQUENCE: 317

cctaatttgg gtgctacaaa taat                                          24
```

TOBACCO PLANT AND METHOD FOR MANUFACTURING SAME

CROSS REFERENCE TO RELATED APPLICATIONS

This application is a Divisional of U.S. application Ser. No. 16/144,479, filed on Sep. 27, 2018, which is a Continuation of PCT International Application No. PCT/JP2017/013115, filed on Mar. 29, 2017, which claims priority under 35 U.S.C. 119(a) to Patent Application No. 2016-069742, filed in Japan on Mar. 30, 2016, all of which are hereby expressly incorporated by reference into the present application.

REFERENCE TO SEQUENCE LISTING SUBMITTED VIA EFS-WEB

This application includes an electronically submitted sequence listing in .txt format. The .txt file contains a sequence listing entitled "2019-04-01_1248-1824PUS1_ST25.txt" created on Mar. 28, 2019 and is 462,075 bytes in size. The sequence listing contained in this .txt file is part of the specification and is hereby incorporated by reference herein in its entirety.

TECHNICAL FIELD

The present invention relates to (i) a tobacco plant which is suitable for cultivation for harvesting leaf tobaccos and (ii) a method of producing the tobacco plant.

BACKGROUND ART

In the process of the growth of seed plants, embryos in seeds develop so as to form cotyledons and apical meristems (shoot apical meristems). Cell division of the apical meristem (shoot apical meristem) causes leaf primordia to be sequentially formed, and causes axillary meristems to be formed on an adaxial side of the leaf primordia. The axillary meristems then serve as apical meristems (shoot apical meristems) and result in axillary buds. During vegetative growth of a plant, usually, the development of axillary buds is temporarily in a dormant state (suppressed). In a case where apical meristems (shoot apical meristems) of a primary shoot is transitioned from a vegetative growth state to a reproductive growth state, or in a case where the apical meristems (shoot apical meristems) die, the development of the axillary buds is no longer in a dormant state and is promoted. With respect to the development of axillary buds, there are a plurality of research reports on solanaceous plants (e.g., tomatoes and tobaccos) and on other plants (e.g., rice and *Arabidopsis thaliana*).

A tobacco plant, which is cultivated for harvesting leaves, is subjected to topping (cutting off a stem of an apical portion with a flower) during cultivation, for the purpose of enhancing the quality and quantity of leaves to be harvested (e.g., for the purpose of accumulating composition of the leaves and maturing and expanding leaves). Topping causes axillary buds of the tobacco plant to start vigorously developing from, bases of leaves (leaf axil). The development of axillary buds naturally consumes nutrients, and therefore causes a relative decrease in nutrient which are supplied to leaves to be harvested. Therefore, the development and outgrowth of axillary buds leads to a decrease in quality and yield of leaves to be harvested. For a reason similar to that for topping, axillary buds are subjected to a treatment, such as removal or developmental suppression, during a period between topping and harvesting of leaves. Note that in the case of at least tobacco plants, it is known that even after an axillary bud is removed, axillary buds repeatedly develop from a base of the same leaf. Therefore, in cultivation of tobacco plants for harvesting leaf tobaccos, control of axillary buds is an important issue that should be dissolved.

Examples of a method of removing an axillary bud encompass a method in which an axillary bud is picked by hand or by machine. Picking an axillary bud by hand involves (i) a large amount of work (and accordingly an increase in labor costs) and (ii) a problem of low efficiency. Picking an axillary bud by machine is less accurate than picking by hand, and therefore brings a problem of damaging a plant. Examples of a method of suppressing the development of an axillary bud encompass (i) suppression by use of agrochemicals and (ii) suppression by genetic modification. The use of agrochemicals involves problems such as repeated application for maintaining an effect, an impact on the growth of a plant, an impact on leaves to be harvested due to agrochemicals residue, and an increase in inspection cost for agrochemicals residue.

Note that Patent Literatures 1 and 2 and Non-Patent Literatures 1 through 19 disclose matters in regard to development of axillary buds. Patent Literatures 1 and 2 disclose techniques for suppressing the development of axillary buds.

With reference to Non-Patent Literatures 1 through 19, genes involved in the formation of axillary meristem will be described below.

A plurality of genes from plants other than tobacco plants have been reported as genes involved in the formation of axillary meristem. Representative examples of such a gene encompass LATERAL SUPPLESSOR (LS), Blind (Bl), REVOLUTA (REV), and CUP-SHAPED COTYLEDON (CUC).

It has been reported that LS is isolated from *Arabidopsis thaliana* (Non-Patent Literature 1), tomato (Non-Patent Literature 2), and rice (Non-Patent Literature 3), and is a gene necessary for the formation of an axillary meristem. In a mutant of LS gene of *Arabidopsis thaliana*, while axillary buds of cauline leaves were normal, axillary buds of rosette leaves other than two topmost rosette leaves were hardly observed (Non-Patent Literature 1). In a mutant of LS gene of a tomato, while axillary buds during a vegetative stage were not present, axillary buds were formed at two topmost parts during a reproductive stage (Non-Patent Literature 2). In a mutant of LS gene of rice (moc1), no tillers, which are equivalent to axillary buds of rice, were observed at all during both a tillering stage and a heading stage (Non-Patent Literature 3). Regarding tobaccos, while the cDNA sequence predicted as an LS orthologue gene is published (Accession number: EU0935581.1), the function of the gene in tobaccos is not confirmed.

Bl gene is isolated from *Arabidopsis thaliana* (Non-Patent Literatures 4 and 5) and tomato (Non-Patent Literature 6). In tomatoes, even in a case where topping had been performed, axillary buds were hardly formed regardless of leaf position, due to a mutant of one gene (Non-Patent Literatures 6 and 7). Regarding *Arabidopsis thaliana*, at least three genes which are redundant and Bl orthologue (REGULATOR OF AXILLARY MERISTEM (RAX) 1, 2, and 3) have been reported. While RAX1 single mutant showed suppression of axillary buds, in RAX1, 2, 3 triple mutants, axillary buds of rosette leaves were hardly formed and those of cauline leaves were largely reduced (Non-Patent Literatures 4 and 5). In the RAX1 single mutants, even after topping, the outgrowth of axillary buds from bottom rosette leaves where no formation of axillary buds was observed before topping was not observed. Based on homology comparison between (i) the putative amino acid sequences predicted from the RAX gene sequence of *Arabidopsis thaliana* and (ii) the putative amino acid sequence predicted from genome sequences of grape and tomato, it was predicted that tomato orthologous genes of RAX1 of *Arabidopsis thaliana* include C gene other than Blind. However, the C gene was not relevant to the formation of axillary buds, but was relevant to morphogenesis of leaves (Non-Patent Literature 8). Although there has not been any report on a cDNA sequence predicted as Bl orthologue gene in tobaccos, putative amino acid sequence predicted from an EST sequence identical by 93% to the amino acid sequence of tomato Bl has been published (Accession number: FS402940.1). However, the function of the gene in tobacco remains unknown.

REV gene was isolated from *Arabidopsis thaliana* (Non-Patent Literatures 10 and 11). In a mutant of REV, the formation of axillary buds was decreased at both rosette leaves and cauline leaves, and promotion of the formation of an axillary meristem by decapitation was not observed (Non-Patent Literatures 9, 10, and 12). Although there has not been any report on a cDNA sequence predicted as REV orthologue gene in tobaccos, putative amino acid sequence predicted from an EST sequence identical by 79% on an amino acid level to *Arabidopsis thaliana* REV has been published (Accession number: FG135778.1). In addition, a full-length cDNA sequence predicted as REV orthologous gene in a tobacco (variety: SR-1) has been published (Accession number: JQ686937). However, there has not been any report on the function of a gene, in a tobacco, which is highly homologous to the REV.

Three genes (CUC1, CUC2, and CUC3) as CUC are isolated from *Arabidopsis thaliana* (Non-Patent Literatures 16 through 18). The function of both CUC1 and CUC2 is control of shoot apical meristems and redundant (Non-Patent Literature 15). Although cuc3 single mutation repressed formation of axillary buds, cuc2 and 3 double mutation showed enhanced repression (Non-Patent Literatures 13 and 14). Although there has not been any report on a cDNA sequence predicted as CUC orthologue in tobaccos, putative amino acid sequence predicted from an EST sequence (FG644078.1) identical by 81% to the amino acid sequence of NAM domain sequence, which is a conserved domain of CUC1 gene of *Arabidopsis thaliana*, has been published. It has also been reported that RNAi transgenic tobacco using the sequence predicted as CUC3 of *Apocynum venetum* showed reduced expression of a certain gene (the sequence is not published) and morphological abnormality of leaves shown in CUC mutants of *Arabidopsis thaliana* (Non-Patent Literature 19). However, the function of a gene, in a tobacco, which gene is highly homologous to CUC, is not clear, and, at least, the function with respect to an axillary bud has not been reported.

CITATION LIST

Patent Literature

[Patent Literature 1]
US Patent Application Publication No. 2009/0249518 (Publication Date: Oct. 1, 2009)

[Patent Literature 2]
Pamphlet of International Publication No. WO 2010/081917 (Publication Date: Jul. 22, 2010)

Non-Patent Literature

[Non-patent Literature 1]
Greb T, Clarenz O, Schafer E, Muller D, Herrero R, Schmitz G, Theres K (2003) Molecular analysis of the LATERAL SUPPRESSOR gene in *Arabidopsis* reveals a conserved control mechanism for axillary meristem formation. Genes Dev. 17: 1175-1187

[Non-patent Literature 2]
Schumacher K, Schmitt T, Rossberg M, Schmitz G, Theres K (1999) The Lateral suppressor (Ls) gene of tomato encodes a new member of the VHIID protein family. Proc Natl Acad Sci USA 96: 290-295

[Non-patent Literature 3]
Xueyong L, Qian Q, Zhiming F, Yonghong W, Guosheng X, Dali Z, Xiaoqun W, Xinfang L, Sheng T, Fujimoto H, Ming Y, Da L, Bin H & Jiayang L (2003) Control of tillering in rice. Nature 402(10): 618-621

[Non-patent Literature 4]
Keller, T., Abbott, J., Moritz, T., and Doerner, P (2006) *Arabidopsis* REGULATOR OF AXILLARY MERISTEMS1 controls a leaf axil stem cell niche and modulates vegetative development. The Plant Cell 18: 598-611

[Non-patent Literature 5]
Muller D, Schmitz G, Theres K (2006) Blind homologous R2R3 Myb genes control the pattern of lateral meristem initiation in *Arabidopsis*. The Plant Cell 18: 586-597

[Non-patent Literature 6]
Schmitz G, Tillman E, Carriero F, Fiore C, Cellini F, TheresK (2002) The tomato Blind gene encodes a MYB transcription factor that controls the formation of lateral meristems. Proc Natl Acad Sci USA 99: 1064-1069

[Non-patent Literature 7]
Mapelli S C, Lombardi L (1982) A comparative auxin and cytokinin study in normal and to-2 mutant tomato plants. Plant Cell Physiol. 23: 751-757

[Non-patent Literature 8]
Busch B L, Schmitz G, Rossmann S, Piron F, Ding J, BendahmaneA, Theres K (2011) Shoot branching and leaf dissection in totamto are regulated by homologous gene modules. The Plant Cell 23: 3595-3609

[Non-patent Literature 9]
Talbert P B, Adler H T, Parks D W, Comai L (1995) The REVOLUTA gene is necessary for apical meristem development and for limiting cell divisions in the leaves and stems of *Arabidopsis thaliana*. Development 121: 2723-2735.

[Non-patent Literature 10]
Otsuga D, DeGuzman B, Prigge M J, Drews G N, Clark S E (2001) REVOLUTA regulates meristem initiation at lateral positions. The Plant Journal 25: 223-236

[Non-patent Literature 11]
Zhong R, Ye Z H (1999) IFL1, a gene regulating interfascicular fiber differentiation in Arabiodpsis, encodes a homeodomain-leucine zipper protein. The Plant Cell 11: 2139-2152

[Non-patent Literature 12]
Zhong R, Taylor J J, Ye Z H (1997) Disruption of interfascicular fiber differentiation in an *Arabidopsis* mutant. The Plant Cell 9: 2159-2170

[Non-patent Literature 13]
Hibara K, Karim M R, Takada S, Taoka K, Furutani M, Aida M, Tasaka M (2006) *Arabidopsis* CUP-SHAPED COTY- LEDON3 regulates postembryonic shoot meristem and organ boundary formation. The Plant Cell 18: 2946-2957
[Non-patent Literature 14]
Raman, S., Greb, T., Peaucelle, A., Blein, T., Laufs, P. and Theres, K (2008) Interplay of miR164, CUP-SHAPED COTYLEDON genes and LATERALSUPPRESSOR controls axillary meristem formation in *Arabidopsis thaliana*. The Plant Journal 55: 65-76
[Non-patent Literature 15]
Takada, S., Hibara, K., Ishida, T., and Tasaka, M (2001) The CUP-SHAPED COTYLEDON1 gene of *Arabidopsis* regulates shoot apical meristem formation. Development 128: 1127-1135
[Non-patent Literature 16]
Aida M, Ishida T, Fukaki H, Fujisawa H, and Tasaka M (1997) Genes involved in Organ Separation in *Arabidopsis*: An Analysis of the cup-shaped cotyledon Mutant. The Plant Cell 9: 841-857
[Non-patent Literature 17]
Takada S, Hibara K, Ishida T, and Tasaka M (2001) The CUP-SHAPED COTYLEDON1 gene of *Arabidopsis* regulates shoot apical meristem formation. Development 128: 1127-1135
[Non-patent Literature 18]
Vroemen C W, Mordhorst A P, Albrecht C, Kwaaitaal M A, de Vries S C (2003) The CUP-SHAPED COTYLEDON3 gene is required for boundary and shoot meristem formation in *Arabidopsis*. The Plant Cell 15(7): 1563-77
[Non-patent Literature 19]
Sun J, Jia H, Wang X, Yuan X and Zhao B (2012) Inhibition of tobacco axillary bud differentiation by silencing CUP-SHAPED COTYLEDON3 Afr. J. Biotech 11(16): 3929-3927

SUMMARY OF INVENTION

Technical Problem

However, what can be known from the above literature is merely that axillary buds can be reduced in plants other than tobacco plants. Therefore, it is still unclear how to obtain a tobacco plant in which the problems resulting from the development of axillary buds are resolved or reduced and which is to be cultivated for harvesting leaf tobaccos.

It is an object of the present invention to provide a tobacco plant which is suitable for cultivation for harvesting leaf tobaccos.

Solution to Problem

In view of the problems above, the inventors of the present invention identified the gene which is expected to be involved in the development of axillary buds in tobacco plants, and then searched for an advantageous effect which can be obtained by decreasing the abundance, in a tobacco plant, of protein expressed from the gene. This led to the completion of the present invention.

Specifically, in order to attain the object, a tobacco plant in accordance with an aspect of the present invention is a tobacco plant in which a mutation is introduced into a genome, which mutation causes functional suppression of a gene containing, as a coding region, a polynucleotide encoding any of the following polypeptides (1) through (5):

polypeptides (1) through (5)

(1) at least one of a polypeptide having a sequence identity of 90% or higher with an amino acid sequence represented by SEQ ID NO. 1 and a polypeptide having a sequence identity of 90% or higher with an amino acid sequence represented by SEQ ID NO. 3;

(2) at least one of a polypeptide having a sequence identity of 90% or higher with an amino acid sequence represented by SEQ ID NO. 5 and a polypeptide having a sequence identity of 90% or higher with an amino acid sequence represented by SEQ ID NO. 7;

(3) at least one of a polypeptide having a sequence identity of 90% or higher with an amino acid sequence represented by SEQ ID NO. 9 and a polypeptide having a sequence identity of 90% or higher with an amino acid sequence represented by SEQ ID NO. 11;

(4) at least one of a polypeptide having a sequence identity of 90% or higher with an amino acid sequence represented by SEQ ID NO. 13 and a polypeptide having a sequence identity of 90% or higher with an amino acid sequence represented by SEQ ID NO. 15; and (5) at least one of a polypeptide having a sequence identity of 90% or higher with an amino acid sequence represented by SEQ ID NO. 17 and a polypeptide having a sequence identity of 90% or higher with an amino acid sequence represented by SEQ ID NO. 19, the functional suppression suppressing development of axillary buds.

In order to attain the object, a tobacco plant production method in accordance with an aspect of the present invention is a method of producing a tobacco plant, including the step of: (a) introducing a mutation that causes functional suppression of a gene containing, as a coding region, a polynucleotide encoding any of the following polypeptides (1) through (5):

polypeptides (1) through (5)

(1) at least one of a polypeptide having a sequence identity of 90% or higher with an amino acid sequence represented by SEQ ID NO. 1 and a polypeptide having a sequence identity of 90% or higher with an amino acid sequence represented by SEQ ID NO. 3;

(2) at least one of a polypeptide having a sequence identity of 90% or higher with an amino acid sequence represented by SEQ ID NO. 5 and a polypeptide having a sequence identity of 90% or higher with an amino acid sequence represented by SEQ ID NO. 7;

(3) at least one of a polypeptide having a sequence identity of 90% or higher with an amino acid sequence represented by SEQ ID NO. 9 and a polypeptide having a sequence identity of 90% or higher with an amino acid sequence represented by SEQ ID NO. 11;

(4) at least one of a polypeptide having a sequence identity of 90% or higher with an amino acid sequence represented by SEQ ID NO. 13 and a polypeptide having a sequence identity of 90% or higher with an amino acid sequence represented by SEQ ID NO. 15; and (5) at least one of a polypeptide having a sequence identity of 90% or higher with an amino acid sequence represented by SEQ ID NO. 17 and a polypeptide having a sequence identity of 90% or higher with an amino acid sequence represented by SEQ ID NO. 19, the functional suppression suppressing development of axillary buds.

Advantageous Effects of Invention

The present invention can selectively suppress the development of axillary buds, and can therefore advantageously provide a tobacco plant which is suitable for cultivation for harvesting leaf tobaccos.

DESCRIPTION OF EMBODIMENTS

[1. Tobacco Plant]

Figure 1:
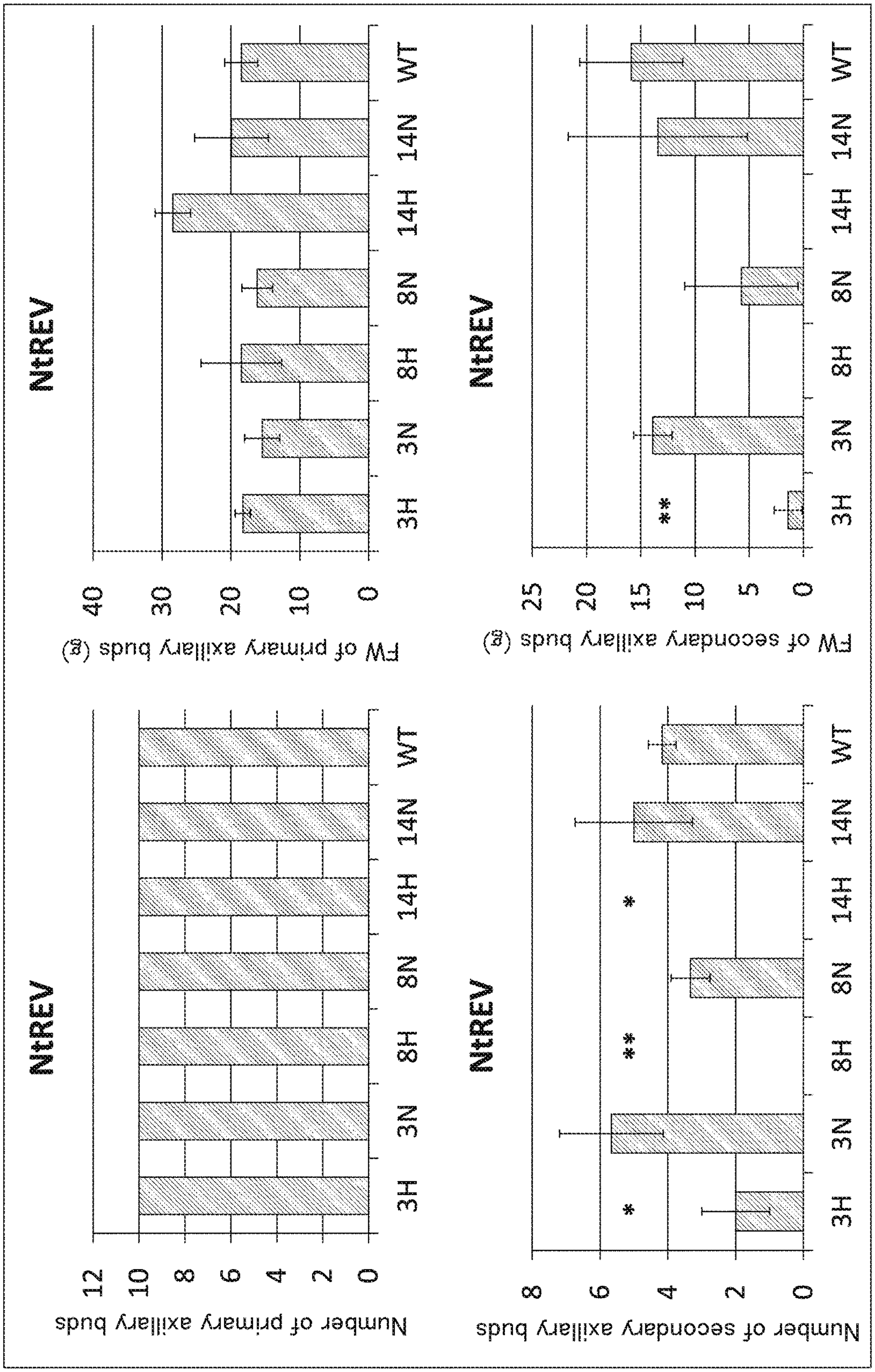
FIG. 1 is a view showing the results of the effects on the development of axillary buds by suppressed expression of NtREV gene in accordance with Examples of the present invention.

In one aspect, the present invention provides a tobacco plant in which a mutation is introduced into genome, which mutation causes suppression of the function of a gene containing, as a coding region, a polynucleotide encoding a specific polypeptide. It should be noted that the above functional suppression is to suppress the development of axillary buds.

Concrete examples of the specific polypeptide encompass (i) at least one of (a) a polypeptide having a sequence identity of 90% or higher with an amino acid sequence represented by SEQ ID NO. 1 and (b) a polypeptide having a sequence identity of 90% or higher with an amino acid sequence represented by SEQ ID NO. 3; (ii) at least one of (a) a polypeptide having a sequence identity of 90% or higher with an amino acid sequence represented by SEQ ID NO. 5 and (b) a polypeptide having a sequence identity of 90% or higher with an amino acid sequence represented by SEQ ID NO. 7; (iii) at least one of (a) a polypeptide having a sequence identity of 90% or higher with an amino acid sequence represented by SEQ ID NO. 9 and (b) a polypeptide having a sequence identity of 90% or higher with an amino acid sequence represented by SEQ ID NO. 11; (iv) at least one of (a) a polypeptide having a sequence identity of 90% or higher with an amino acid sequence represented by SEQ ID NO. 13 and (b) a polypeptide having a sequence identity of 90% or higher with an amino acid sequence represented by SEQ ID NO. 15; and (v) at least one of (a) a polypeptide having a sequence identity of 90% or higher with an amino acid sequence represented by SEQ ID NO. 17 and (b) a polypeptide having a sequence identity of 90% or higher with an amino acid sequence represented by SEQ ID NO. 19.

As demonstrated in Examples described later, although the tobacco plant does not show any substantial difference from a wild-type one in terms of the number or weight of primary axillary buds, the tobacco plant either (i) shows a considerable decrease (for example, ½ or lower than a wild-type plant) in the number or weight of axillary buds (i.e., secondary axillary buds and tertiary axillary buds) to be generated after the removal of the primary axillary buds or (ii) does not show any axillary buds after the removal of the primary axillary buds. Therefore, axillary buds are completely removed from the tobacco plant in accordance with an aspect of the present invention by substantially a single removal process. This allows the amount of labor, which is involved in control of axillary buds in cultivation of a tobacco plant for harvesting leaf tobaccos, to be less than a fraction of the amount of labor involved in such a conventional control of axillary buds.

As described above, the literature disclosing the conventional technologies merely discloses that the development of axillary buds is entirely suppressed in plants other than tobacco plants. For the reasons described below, however, suppression of entire development of axillary buds does not necessarily bring only advantages. The capability of development of axillary buds is an important function for maintaining the health of individuals of seed plants. For example, in a case where shoot apical meristem is damaged, an individual tries to survive by causing an axillary bud to start growing instead of the tissue. Therefore, it is expected that in a case where this function is entirely lost, the health of individuals is inevitably at risk. In fact, Non-Patent Literature 9 (legend of FIG. 1) mentions partly slowing down the growth of a plant. In addition, an individual, which has completely lost axillary buds and is damaged by, for example, wind or flood, is at high risk of death. Therefore, in view of production of leaf tobaccos, the development of axillary buds is highly meaningful in some cases. In a case where a primary shoot is damaged during growth, a yield of leaf tobaccos can be secured by causing an axillary bud at a lower node to extend and develop instead of the primary shoot.

As used herein, "tobacco plant" and "tobacco" encompass (i) an entire individual (such as a mature plant, a seedling, and a seed), (ii) tissue (such as a leaf, a stem, a flower, a root, a reproductive organ, an embryo, and a part of any of these), and (iii) a dried product of any of these.

As used herein, "axillary bud" refers to both (i) a bud which is generated from an axillary meristem formed at a leaf axil of a leaf primordia and (ii) a shoot obtained as a result of the development of the bud. After topping, axillary buds develop in an order of primary axillary buds, secondary axillary buds, and then tertiary axillary buds, at a base of the same leaf. First, after topping, the primary axillary buds develop. After the primary axillary buds are removed, the secondary axillary buds develop. The "development" of an axillary bud means that the axillary bud, which remained as differentiated tissues from the axillary meristem, starts vigorous development due to, for example, removal of a shoot apex (topping), so that the axillary bud grows and extends.

The "number or weight" of axillary buds means the number or a total mass (fresh weight) of axillary buds which have developed in one individual and have been collected. The "number or weight" applies to any of primary axillary buds, secondary axillary buds, and tertiary axillary buds.

As used herein, "sequence identity (of an amino acid sequence)" means a percentage ratio at which a concerned (amino acid) sequence matches a reference (amino acid) sequence. Note that a part of the sequence, which part does not match, is a part at which an amino acid residue is substituted, added, deleted, or inserted.

Note that the term "polypeptide having a sequence identity of 90% or higher with an amino acid sequence represented by [ . . . ]", which specifies the polypeptide with use of an amino acid sequence listed in a sequence listing, means a wild-type polypeptide. The wild-type polypeptide means a polypeptide which is typically present in a *Nicotiana* plant described later.

Therefore, a specific polypeptide, which is decreased in abundance in the tobacco plant in accordance with an aspect of the present invention, need only be a polypeptide having a sequence identity of 90% or higher with each of the amino acid sequences listed in the sequence listing. A higher sequence identity is more preferable (e.g., 91%, 92%, 93%, 94%, 95%, 96%, 97%, 98%, or 99% or higher).

The "decrease in abundance" of a polypeptide means the presence of the polypeptide in an amount of 70% or lower, 60% or lower, 50% or lower, 40% or lower, 30% or lower, 20% or lower, 10% or lower, 5% or lower, or 1% or lower, relative to the abundance of a wild-type polypeptide as a reference. The abundance of the polypeptide relative to that of the wild-type polypeptide as a reference can be selected as appropriate from the above values which result in a decrease in the number or weight of secondary axillary buds.

It is preferable that the above-described decrease in abundance of a polypeptide in the tobacco plant in accordance with an aspect of the present invention is, with stability, genetically inherited by cultured cell, callus, protoplast, seed, and offspring, any of which is obtained from the tobacco plant. Therefore, the tobacco plant in accordance with an aspect of the present invention can be an individual developed from cultured cell, cell, callus, protoplast, seed, and offspring, any of which is produced through artificial operation. In addition, these materials, from which the individual develops, are also encompassed in the scope of the present invention.

The scope of the tobacco plant in accordance with an aspect of the present invention can further encompass bred progeny obtained by crossing. Breeding with use of mutants has been done in many plant species. Representative examples of such plant species encompass rice, wheat, barley, and soybean. For example, a mutant isolated from a mutant population treated by a mutagen has multiple mutations other than at a region of a target gene. In general, therefore, backcrossing is to be performed to remove excess mutations. In the course of breeding, the mutant can be crossed with a cultivar having excellent character so that a character of the mutant is introduced into the cultivar. This results in obtaining a cultivar having high additional values. Since the character of a mutant is derived from a mutation, it is necessary to select an individual having a mutation so as to proceed backcrossing. In order to proceed efficient backcrossing, it is necessary to carry out a method in which it is easy to determine (i) whether or not there is a mutation and (ii) whether or not the mutation is homozygous or heterozygous. This method can be carried out through a method of detecting a mutation (described later). In addition, in a case where marker assisted selection (MAS) is performed with use of a background marker indicative of a polymorphism between the mutant and the cultivar, it is possible to efficiently obtain, with the fewer times of crossing, a line having a high proportion of genome from the cultivar. A polymorphic marker can be SNP or Simple Sequence Repeat (SSR), each of which is publicly known in tobacco. If necessary, a genome sequence of tobacco is analyze so as to identify (i) a difference in nucleotide sequence and (ii) a difference in the number of repeat sequences. This allows a new polymorphic marker to be obtained and utilized.

As used herein, "functional suppression of a gene" means a state in which the gene on a genome is not fulfilling its original function. Therefore, "functional suppression of a gene" is a term encompassing (i) "gene disruption", (ii) "gene mutation", and (iii) "suppression of gene expression" by another gene (including an exogenous gene).

Gene and genome will be described below by taking *Nicotiana tabacum* (*N. tabacum*) as a reference. *Nicotiana tabacum* (*N. tabacum*), which serves as a reference in the description below, is an amphidiploid and has both an S genome and a T genome derived from *Nicotiana sylvestris* and *Nicotiana tomentosiformis*, respectively, each of which is an ancestor species thereof. In *N. tabacum*, in many cases, genes indicated by an identical name are present in each genome. Therefore, such genes include two alleles in an S genome and two allelic genes in a T genome. In other words, on the genome of *N. tabacum*, four genes indicated by an identical name are present in many cases.

Note that in a coding region of a tobacco plant, a nucleotide sequence of part (not the whole) of genes encoding proteins, which possesses the substantially same function between species, may have (i) 1% to several % difference between cultivars and (ii) approximately 10% or lower difference between a cultivar and wild species.

"Gene disruption" means that (i) a gene, which is originally present on a genome, is not present on the genome or (ii) a transcribed product is not produced from a gene on a genome. "Gene mutation" means (i) a mutation of a gene such that a protein having an original function is not produced, (ii) a mutation of the gene such that while a protein is produced, the amount of the protein produced is decreased, or (iii) a mutation of the gene such that although a protein is produced, the stability of the protein is decreased. "Suppression of gene expression" means a state in which although no change has occurred to the gene, the function of the gene (from transcription into mRNA to subsequent translation into protein) is modified through another factor so that (i) the amount of protein produced is decreased or (ii) no protein is produced. "Suppression of gene expression" may occur as a result of, for example, degradation of mRNA which is transcribed from the gene.

As used herein, "mutation" has the meaning as ordinarily understood in the technical field of the present application, and means, for example, a change in a nucleotide on a wild-type genome or a change in an amino acid residue in a wild-type protein (examples of the change encompass substitution, deletion, insertion, addition, duplication, and inversion). Examples of the change in the nucleotide on the genome further encompass translocation of a plurality of nucleotides.

A polypeptide, which has a sequence identity of 90% or higher with an amino acid sequence represented by SEQ ID NO. 1, 3, 5, 7, 9, 11, 13, 15, 17, or 19, is a polypeptide which is present in a wild-type plant (or a variant thereof). Therefore, the abundance of the polypeptide in the tobacco plant in accordance with an aspect of the present invention is decreased in comparison with that of a wild-type plant. This causes the tobacco plant to be inferior to the wild-type plant in terms of the function. Examples of the function encompass a function of a wild-type plant, such as (i) a function to form axillary meristem, (ii) a function to differentiate an axillary bud from axillary meristem, or (iii) a function to maintain or promote the capability of the development of an axillary bud.

A polypeptide having an amino acid sequence represented by SEQ ID NO. 1 is encoded by, for example, a polynucleotide having a nucleotide sequence represented by SEQ ID NO. 2. A polypeptide having an amino acid sequence represented by SEQ ID NO. 3 is encoded by, for example, a polynucleotide having a nucleotide sequence represented by SEQ ID NO. 4. These polynucleotides are each cDNA of NtREV gene demonstrated in Examples described later. SEQ ID NO. 2 represents a cDNA sequence of NtREV gene of an S genome. SEQ ID NO. 4 represents a cDNA sequence of NtREV gene of a T genome. SEQ ID NOs. 21 and 22 represent nucleotide sequences of an S genome and a T genome, respectively, of NtREV gene. SEQ ID NOs. 54 and 55 represent nucleotide sequences of an S genome and a T genome, respectively, of NtREV gene (including 5' upstream and 3' downstream).

A polypeptide having an amino acid sequence represented by SEQ ID NO. 5 is encoded by, for example, a polynucleotide having a nucleotide sequence represented by SEQ ID NO. 6. A polypeptide having an amino acid sequence represented by SEQ ID NO. 7 is encoded by, for example, a polynucleotide having a nucleotide sequence represented by SEQ ID NO. 8. These polynucleotides are each cDNA of NtLS gene demonstrated in Examples described later. SEQ ID NO. 6 represents a cDNA sequence of NtLS gene of an S genome. SEQ ID NO. 8 represents a cDNA sequence of NtLS gene of a T genome. SEQ ID NOs. 23 and 24 represent nucleotide sequences of an S genome and a T genome, respectively, of NtLS gene. SEQ ID NOs. 56 and 57 represent nucleotide sequences of an S genome and a T genome, respectively, of NtLS gene (including 5' upstream and 3' downstream).

A polypeptide having an amino acid sequence represented by SEQ ID NO. 9 is encoded by, for example, a polynucleotide having a nucleotide sequence represented by SEQ ID NO. 10. A polypeptide having an amino acid sequence represented by SEQ ID NO. 11 is encoded by, for example, a polynucleotide having a nucleotide sequence represented by SEQ ID NO. 12. These polynucleotides are each cDNA of NtBl1 gene demonstrated in Examples described later. SEQ ID NO. 10 represents a cDNA sequence of NtBl1 gene of an S genome. SEQ ID NO. 12 represents a cDNA sequence of NtBl1 gene of a T genome. SEQ ID NOs. 25 and 26 represent nucleotide sequences of an S genome and a T genome, respectively, of NtBl1 gene. SEQ ID NOs. 58 through 61 represent nucleotide sequences of an S genome and a T genome, respectively, of NtBl1 gene (including 5' upstream and 3' downstream).

A polypeptide having an amino acid sequence represented by SEQ ID NO. 13 is encoded by, for example, a polynucleotide having a nucleotide sequence represented by SEQ ID NO. 14. A polypeptide having an amino acid sequence represented by SEQ ID NO. 15 is encoded by, for example, a polynucleotide having a nucleotide sequence represented by SEQ ID NO. 16. These polynucleotides are each cDNA of #15360 demonstrated in Examples described later. SEQ ID NO. 14 represents a cDNA sequence of #15360 of an S genome. SEQ ID NO. 16 represents a cDNA sequence of #15360 of a T genome. SEQ ID NOs. 27 and 28 represent nucleotide sequences of an S genome and a T genome, respectively, of #15360. SEQ ID NOs. 62 and 63 represent nucleotide sequences of an S genome and a T genome, respectively, of #15360 (including 5' upstream and 3' downstream).

A polypeptide having an amino acid sequence represented by SEQ ID NO. 17 is encoded by, for example, a polynucleotide having a nucleotide sequence represented by SEQ ID NO. 18. A polypeptide having an amino acid sequence represented by SEQ ID NO. 19 is encoded by, for example, a polynucleotide having a nucleotide sequence represented by SEQ ID NO. 20. These polynucleotides are each cDNA of #07437 demonstrated in Examples described later. SEQ ID NO. 18 represents a cDNA sequence of #07437 of an S genome. SEQ ID NO. 20 represents a cDNA sequence of #07437 of a T genome. SEQ ID NOs. 29 and 30 represent nucleotide sequences of an S genome and a T genome, respectively, of #07437.

It is believed that the #07437 gene is, due to sequence homology, a gene which is to be classified as CUC. As for CUC genes in *Arabidopsis thaliana*, three CUC genes, CUC1 through CUC3, have been reported. It is also known that a plurality of accumulated mutations show a larger effect on a phenotype of a mutant than a single mutation. The inventors of the present invention isolated five genes as family genes from tobacco, other than #07437. These family genes are expected to produce a larger effect by being used together with #07437.

In the tobacco plant in accordance with an aspect of the present invention, an abundance of the above-described specific polypeptide is preferably decreased. Specifically, the abundance is decreased through mutation, disruption, or suppressed expression of a gene encoding the wild-type polypeptide.

The gene mutation or the gene disruption occurs as a result of, for example, spontaneous mutation, mutagen treatment, genome editing, or gene knockout. The spontaneous mutation of the gene generally occurs due to (i) replication errors and (ii) damage to the gene. The cause of the damage is, for example, exposure to publicly-known, naturally-occurring mutagens or publicly-known mutagens which have been artificially produced and then remaining in a natural environment (for example, radiation, ultraviolet rays, or mutation-inducing substances (such as EMS)). The gene can be subjected to a mutagen treatment by artificially causing the mutagen to take effect on a tobacco plant (as necessary, in combination with suppression of a gene repair function). Recombination of the gene can be performed by homologous recombination of all or part of a target gene with a recombinant sequence according to a publicly-known genetic recombination method. Genome editing of the gene can be performed by a publicly-known technique (for example, zinc-finger nucleases: ZFN, transcription activator-like effector nucleases: TALEN, and CRISPR/Cas9 system). The gene knockout can be performed by (i) transfer of the gene with use of a publicly-known transposase or (ii) introduction of T-DNA.

As described above, a tobacco plant in many cases has 2 sets of genes in each of a T genome and an S genome. Therefore, in order for the functions of the genes to completely disappear, it is necessary to impair the functions of all of the (four) genes in the T genome and the S genome. However, in a case where a dosage effect is exhibited, the functions of the genes can be suppressed even if the functions of all genes in the T genome and the S genome are not impaired.

In a case where the functions are impaired by substitution, the substitution can be present in at least one of the following: a promoter sequence (such as a sequence upstream (5' end) and a sequence downstream (3' end) with the coding region as a reference), a 5' untranslated region and a 3' untranslated region, a conserved sequence (5'GT-AG3') present at both ends of an intron, and a coding region. It is expected that in a case where substitution occurs to nucleotide sequences (a promoter sequence, a 5' untranslated region, and a 3' untranslated region) which are important for regulating transcription activity of genes, the amount of transcribed product of the genes, which depends on transcriptional activity and stability of the genes, decreases, so that the amount of proteins decreases. In a case where substitution occurs to a conserved sequence of an intron, splicing does not occur normally, so that the intron can be translated additionally. It is expected that proteins having amino acid sequences different from original sequences are therefore generated by the translation due to frame shifting. It is expected that in a case where the substitution occurs to a coding region, for example, substitution into a stop codon which does not encode an amino acid (nonsense mutation) causes translation into a protein having a C-terminus side shortened so as to have an incomplete length, so that a function is impaired. While a position at which a nonsense mutation occurs is not limited provided that a full-length protein is not generated, it is preferable that the length is shortened by equal to or longer than several amino acids.

Alternatively, it is expected that substitution of an amino acid sequence causes the function of a protein to decrease. It is also expected that substitution of an amino acid sequence results in (i) a change of a tertiary structure and (ii) a change of an amino acid which is important for a function. Non-conservative substitution easily causes a decrease in function, and is therefore preferable as substitution of an amino acid. Examples of the non-conservative substitution encompass (i) substitution of an amino acid by another amino acid having a different electric charge or a different hydrophobicity (e.g., substitution of a basic amino acid by an acidic amino acid or substitution of a polar amino acid by a non-polar amino acid) and (ii) substitution of an amino acid by another amino acid having a different bulk (three-dimensional size) of a side chain.

In a case of a mutation other than substitution such as deletion and insertion, it is expected that the mutation, which occurred within a promoter sequence, a 5' untranslated region, and a 3' untranslated region, causes a decrease in transcriptional activity and stability as in the case of the substitution, so that (i) the amount of transcribed product is reduced and (ii) the amount of protein is reduced. In a conserved sequence of an intron, it is also expected that as in the case of substitution, proteins having amino acid sequences different from original sequences are generated by the translation. It is expected that the mutation, which occurred in a coding region, causes proteins, which have amino acid sequences different from original sequences, to be generated by the translation, the difference in amino acid sequences occurring due to (i) deletion or insertion of an amino acid residue (caused by deletion or insertion of consecutive nucleotides which are multiples of 3) or (ii) frame shifting. In a case where a large deletion of the entire gene itself or an insertion of a large fragment, it is also expected that the expression of the gene may be completely lost.

An individual, which was generated as a result of the gene mutation or gene disruption, is herein called a mutant (hereinafter simply referred to as “mutant”) of a tobacco plant. The mutant can have the mutation in any of an S genome or a T genome, and preferably has the mutation in both the S genome and the T genome. Note that (i) a single mutation or a plurality of mutations can occur in a single gene and (ii) the kind of mutation to impair a function is not limited. The total of four genes, which include two genes in an S genome and two genes in a T genome, can have identical mutations or different mutations.

Examples of suppression of the gene expression encompass (i) suppression of transcription from the gene to an mRNA, (ii) suppression (e.g., degradation of the mRNA) of translation from the gene into a protein through an mRNA and (iii) suppression of the function of the protein which is generated by the translation. The suppression of the transcription can be achieved by, for example, (i) inhibition of a transcription factor which promotes the transcription from the gene or (ii) inhibition of access of a transcription initiation factor to the gene. The suppression of the translation can be achieved by use of an antisense RNA molecule, an RNAi molecule, or a co-suppression molecule. The suppression of the function of the protein can be achieved by a molecule which inhibits the function of a functional protein by binding to the functional protein. Examples of such a molecule encompass decoy nucleic acid, ribozyme, antibody, and inhibitory peptide.

The various mutations described above can be easily introduced into a tobacco plant by a person skilled in the art who has referred to, for example, (i) any of the following publicly-known genome sequences of genes and (ii) genome sequences of genes represented by SEQ ID NOs. 54 through 63. Specifically, based on these pieces of sequence information, it is possible to appropriately determine a region which is present in a genome of any of various tobacco plants encompassed in the scope of the present invention and at which a mutation should be introduced.

NtREV: (S genome) Sol Genomics Network (SOL) accession #Ntab-K326_AWOJ-5517907, and (T genome) Sol accession #Ntab-K326_AWOJ-SS9429

NtLS: (S genome) SOL accession #Ntab-K326_AWOJ-551238, and (T genome) SOL accession #Ntab-K326_AWOJ-555309

NtBl1: (S genome) SOL accession #Ntab-K326_AWOJ-SS18396, and (T genome) SOL accession #Ntab-K326_AWOJ-SS12956

#15360: (S genome) SOL accession #Ntab-K326_AWOJ-55587, and (T genome) SOL accession #Ntab-K326_AWOJ-SS20471

#07437: (S genome) SOL accession #Ntab-K326_AWOJ-55943, and (T genome) GeneBank accession #AYMY01348769.1, AWOK01667329.1, and ASAG01052465.1.

The above-described suppression (of the transcription, translation, and protein function) can be achieved by, for example, (i) directly introducing molecules for achieving the suppression into a plant or (ii) expression of the molecules which are expressed from genes in a vector introduced into a plant by transformation. In the transformation of the plant, the target gene for expressing the molecules only needs to be integrated with any region of a genome of the plant, and does not necessarily need to be integrated with both an S genome and a T genome.

The tobacco plant is not limited to any particular one provided that the tobacco plant is a *Nicotiana* plant which is not limited to any particular one provided that the *Nicotiana* plant is a plant belonging to *Nicotiana*. Examples of the tobacco plant encompass *Nicotiana acaulis, Nicotiana acuminata, Nicotiana acuminata* var. *multzjlora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa, Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana ingulba, Nicotiana kawakamii, Nicotiana knightiana, Nicotiana langsdorfi, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *Hesperis, Nicotiana otophora, Nicotiana paniculata, Nicotiana pauczjlora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *Ingulba, Nicotiana rotundifolia, Nicotiana rustica, Nicotiana setchellii, Nicotiana simulans, Nicotiana solanifolia, Nicotiana spegauinii, Nicotiana stocktonii, Nicotiana suaveolens, Nicotiana sylvestris, Nicotiana tabacum, Nicotiana thyrsiflora, Nicotiana tomentosa, Nicotiana tomentosifomis, Nicotiana trigonophylla, Nicotiana umbratica, Nicotiana undulata, Nicotiana velutina, Nicotiana wigandioides*, and a hybrid of *Nicotiana* plants. Among these *Nicotiana* plants, *Nicotiana benthamiana, Nicotiana rustica*, and *Nicotiana tabacum* are more preferable. *Nicotiana rustica* and *Nicotiana tabacum*, which are used as materials to produce leaf tobacco, are particularly preferable.

In addition to the above action, the tobacco plant in accordance with an aspect of the present invention has a characteristic that the position of a primary axillary bud shifts from a base of a leaf. This brings about practicality in an actual cultivation site that axillary buds can be removed without damaging leaves. In connection to this practicality, the tobacco plant in accordance with an aspect of the present invention is preferably configured so that a genome is introduced with a mutation that causes suppression of a function of a gene containing, as a coding region, a polynucleotide encoding any one of: a polypeptide having a sequence identity of 90% or higher with an amino acid sequence represented by SEQ ID NO. 5 and a polypeptide having a sequence identity of 90% or higher with an amino acid sequence represented by SEQ ID NO. 7; and a polypeptide having a sequence identity of 90% or higher with an amino acid sequence represented by SEQ ID NO. 9 and a polypeptide having a sequence identity of 90% or higher with an amino acid sequence represented by SEQ ID NO. 11. The suppression of the function is preferably suppression of the development of an axillary bud. In addition, as demonstrated in Examples described later, the tobacco plant in accordance with an aspect of the present invention is particularly preferably a mutant in which the mutation is introduced into NtBl1 and NtLS.

[2. Method of Producing Tobacco Plant]

In one aspect, the present invention provides a method of producing the tobacco plant. The method includes a step of introducing a mutation that causes suppression of a function of a gene containing, as a coding region, a polynucleotide encoding any of the specific polypeptides described above.

This introducing step results in the suppression of the development of axillary buds through the functional suppression of the gene, which is caused by the mutation. The suppression of the development of axillary buds through the functional suppression of the gene is performed as outlined above. Therefore, as concrete examples of carrying out the introducing step, the following description will discuss suppression of gene expression and introduction of a mutation into a gene, which are performed through transformation of a tobacco plant with use of a vector.

The vector to be used for the transformation of a tobacco plant for the purpose of the suppression of the gene expression or the introduction of the mutation into the gene is not limited to any particular one, provided that a polynucleotide inserted into the vector can be expressed in a plant cell. Examples of a suitable vector encompass pBI, pPZP, and pSMA vectors each of which allows introduction of a target polynucleotide into a plant cell via *Agrobacterium*. In particular, plasmids of binary vectors (e.g., pBIG, pBIN19, pBI101, pBI121, pBI221, and pPZP202) are preferable.

In a case where the suppression of the gene expression is achieved by RNAi, a trigger sequence, which is used by the RNAi to suppress the expression of the target gene, is inserted into the vector. Examples of the trigger sequence encompass (i) a polynucleotide (sense RNA portion) which is (a) a part of a polynucleotide (which can have a substitution of 0.1% to 1%) encoding a polypeptide having an amino acid sequence represented by SEQ ID NO. 1, 3, 5, 7, 9, 11, 13, 15, 17, or 19 or a part of a polynucleotide (which can have a substitution of 0.1% to 1%) having SEQ ID NO. 2, 4, 6, 8, 10, 12, 14, 16, 18, or 20 and (b) represented by a nucleotide sequence of at least 21 to 30 consecutive bases (e.g., 21 or more s, 22 or more s, 23 or more s, 24 or more bases, 25 or more bases, 26 or more bases, 27 or more bases, 28 or more bases, 29 or more bases, and 30 or more bases) and (ii) a polynucleotide (antisense RNA portion) represented by a nucleotide sequence which is complementary to the polynucleotide (i). More specifically, the nucleotide sequence of the "at least 21 to 30 consecutive bases" described above means a nucleotide sequence of 21 or more consecutive bases, 23 or more consecutive bases, 25 or more consecutive bases, 30 or more consecutive bases, 35 or more consecutive bases, 40 or more consecutive bases, 45 or more consecutive bases, 50 or more consecutive bases, 60 or more consecutive bases, 70 or more consecutive bases, 80 or more consecutive bases, 90 or more consecutive bases, or 100 or more consecutive bases.

As described above, the suppression of the gene expression in the tobacco plant in accordance with an aspect of the present invention is preferably genetically inherited. Therefore, the trigger sequence is preferably integrated with a genome of the tobacco plant.

The introduction of a mutation into the gene of the tobacco plant can be achieved by a publicly-known genome editing technique. Examples of the genome editing technique encompass CRISPR/Cas9 system, TALEN, and ZFN. According to the CRISPR/Cas9 system, the genome editing is possible if guide RNAs and a Cas9 protein is present in a target cell. According to TALEN and ZFN, the genome editing is possible if a fusion protein (in which DNA-binding domains and nuclease are fused) is present in a target cell. Therefore, the guide RNAs, the Cas9 proteins, and the fusion proteins can be directly introduced into a target cell. Examples of a method of directly introducing any of these into a target cell encompass a PEG method, an electroporation method, and a particle bombardment method.

According to the CRISPR/Cas9 system, (i) a sequence, which is complementary to a nucleotide sequence located immediately upstream of XGG on a genome, forms a base pair with part of a guide RNA and (ii) a double stranded genomic DNA is cut by Cas9 in the nucleotide sequence. Examples of the nucleotide sequence encompass a part of (i) a polynucleotide (which can have a substitution of 0.1% to 1%) encoding a polypeptide having an amino acid sequence represented by SEQ ID NO. 1, 3, 5, 7, 9, 11, 13, 15, 17, or 19 or (ii) a polynucleotide (which can have a substitution of 0.1% to 1%) having SEQ ID NO. 2, 4, 6, 8, 10, 12, 14, 16, 18, or 20, which part is 10 or more consecutive bases (e.g., 15 or more consecutive bases, preferably 17 or more consecutive bases, more preferably 18 or more consecutive bases, still more preferably 19 or more consecutive bases, and most preferably 20 or more consecutive bases) located immediately upstream of XGG.

According to the TALEN, a pair of DNA-binding domains in artificial nucleases forming a dimer each bind to a corresponding one of nucleotide sequences, which is present at each terminus of a FokI cleavage domain so as to be away from the terminus by a spacer of 5 to 20 bases. The nucleotide sequence is present at one and the other strands of double stranded genomic DNA. Therefore, one of the pair of DNA-binding domains binds to the one strand, and the other of the pair of DNA-binding domains binds to the other strand. The DNA binding domain is composed of a repeating unit (module) which include 33 to 34 amino acid residues. The number of module corresponds to the number of nucleotides to which the DNA bind domain bind. Provided that 33 to 34 amino acid residues serve as a repeating unit (module), the DNA-binding domain contains modules, the number of which corresponds to the number of nucleotides to bind to. The nucleotide sequence to which the DNA-binding domain binds is 6 or more consecutive bases, preferably 10 or more consecutive bases, and more preferably 18 or more consecutive bases, which are present at each terminus of a FokI cleavage domain so as to be away from the terminus by a spacer of 5 to 20 bases and which are (i) a part of a polynucleotide (which can have a substitution of 0.1% to 1%) encoding a polypeptide having an amino acid sequence represented by SEQ ID NO. 1, 3, 5, 7, 9, 11, 13, 15, 17, or 19, or a polynucleotide (which can have a substitution of 0.1% to 1%) having SEQ ID NO. 2, 4, 6, 8, 10, 12, 14, 16, 18, or 20 and (ii) a part of a polynucleotide forming complementary strand with the above polynucleotide.

According to ZFN, as in the case of TALEN, a pair of DNA-binding domains in artificial nucleases forming a dimer each bind to a corresponding one of nucleotide sequences, which is present at each terminus of a FokI cleavage domain so as to be away from the terminus by a spacer of 5 to 20 bases. The DNA-binding domain contains a plurality of zinc finger modules. The nucleotide sequence is 9 or more consecutive bases, preferably 12 or more consecutive bases, and more preferably 18 or more consecutive bases, which are present at respective termini of a FokI cleavage domain with a spacer of 5 to 20 bases therebetween and which are (i) a part of a polynucleotide (which can have a substitution of 0.1% to 1%) encoding a polypeptide having an amino acid sequence represented by SEQ ID NO. 1, 3, 5, 7, 9, 11, 13, 15, 17, or 19, or a polynucleotide (which can have a substitution of 0.1% to 1%) having SEQ ID NO. 2, 4, 6, 8, 10, 12, 14, 16, 18, or 20 and (ii) a part of a polynucleotide forming complementary strand with the above polynucleotide.

The descriptions of RNAi, CRISPR/Cas9 system, TALEN, and ZFN can each be read so that, according to the description of each detail, the polypeptide having an amino acid sequence represented by SEQ ID NO. 1, 3, 5, 7, 9, 11, 13, 15, 17, or 19 is replaced with an orthologous polypeptide which (i) has a sequence identity of 90% or higher with the polypeptide and (ii) is present in another kind included in *Nicotiana* plant. Likewise, the description of the previous paragraph can be read so that a polynucleotide having SEQ ID NO. 2, 4, 6, 8, 10, 12, 14, 16, 18, or 20 is replaced with a polynucleotide of orthologous gene, which (i) has a sequence identity of 90% or higher with the polynucleotide and (ii) is present in another kind included in *Nicotiana* plant.

As described above, the gene mutation introduced in the tobacco plant in accordance with an aspect of the present invention is preferably genetically inherited. However, an exogenous polynucleotide introduced in a tobacco plant by genome editing is preferably eliminated from the tobacco plant after it is confirmed that a desired mutation is introduced in the tobacco plant. In a case where the exogenous polynucleotide is retained in the tobacco plant, an undesired mutation may (continue to) be introduced. This may cause a desired character (such as suppression of secondary axillary buds) to be lost, or may threaten the survival of the tobacco plant.

The introduction of a mutation into a gene of a tobacco plant can be achieved through another biotechnological method (e.g., a method in which transposon or *Agrobacterium* is utilized). Concrete examples of the method encompass a method in which a tobacco plant is introduced with (i) retrotransposon tnt1 of tobacco or transposon of another plant or (ii) T-DNA of T1 plasmid of *Agrobacterium.*

Alternatively, the introduction of a mutation into a gene of the tobacco plant can be achieved through another method (mutagen treatment of a tobacco plant). Examples of a source of the mutation encompass small molecule compounds (such as ethyl methane sulfonate (EMS), N-ethyl-N-nitrosourea (ENU), sodium azide) and radiations (such as gamma rays, heavy ion beams, X-rays, neutron beams, and ultraviolet rays).

A mutation can be introduced into any regenerable tobacco plant. Examples of the tobacco plant encompass seeds, roots, leaves, flowers, reproductive organs, and embryos. A preferable example is embryos.

What can be obtained by the methods above can be a mutant population of a plant which has various mutations (or no mutation). Therefore, an individual exhibiting a desired phenotype can be further selected from the mutant population. As an example of the selection of an individual, the following description will discuss a procedure for selecting a desired individual from a mutant population (panel) which is obtained in a case where tobacco is treated with use of a mutagen.

A loss-of-function tobacco mutant, which has mutations in the total of four genes at a T genome and an S genome, can be obtained by, for example, the following method. Tobacco is treated with a mutagen as described above to prepare a population (panel) of tobacco mutants with mutations in the whole tobacco genome, and genomic DNAs are extracted. By utilizing gene-specific primers of each of the S genome and the T genome, target genes (polynucleotide) are amplified from the genomic DNAs of the panel. Subsequently, nucleotide sequences of resulting products are determined, and a line having a homozygous mutation is then selected. First, a line (M2) having a homozygous mutation in an S genome and a line (M2) having a homozygous mutation in a T genome are obtained and then crossed to obtain $F_1$ individuals. Subsequently, a selfed progeny ($F_2$) is cultivated from the $F_1$ individuals. From the selfed progeny ($F_2$) is obtained a line having homozygous mutations in both an S genome and a T genome (such a line is obtained at a probability of 1/16 since two elements are recessive).

The method of producing the tobacco plant in accordance with an aspect of the present invention further includes the step of selecting, from the tobacco plant produced by the above producing step, an individual in which the number or weight of secondary axillary buds developing after removal of primary axillary buds is decreased to ½ or lower in comparison with the wild-type plant. This selecting step is carried out based on, for example, disruption, mutation, or suppressed expression of genes encoding specific polypeptides described above.

The mutation or disruption of a gene is determined by identifying the presence/absence of a mutation of the gene. A method of identifying the mutation of the gene needs to allow the determination of the presence/absence of the mutation. Examples of the method encompass (1) a method in which a DNA sequence is directly decoded with use of a commercially available sequencer, (2) a method in which a difference in sequence is detected by a difference in distance of electrophoresis with use of the Single Strand ConformationPolymorphism (SSCP) method, (3) a method in which Single Nucleotide Polymorphism (SNP) is detected by the Cycleave PCR method, (4) a method in which the presence/absence of a mutation is identified by cleaving a mismatch site(s) with use of T7 EndonucleaseI or the like, (5) a Cleaved Amplified Polymorphic Sequence (CAPS) method in which the presence/absence of a mutation can be determined by the presence/absence of cleavage by a restriction enzyme treatment, (6) a derived CAPS (dCAPS) method in which a set of primers including a mismatch is intentionally used so that the presence/absence of a mutation can be determined by the presence/absence of cleavage by restriction enzymes, (7) a method (e.g., a PCR method in which a TaqMan probe is used, MassARRAY analysis) in which the presence/absence of a mutation is determined by identifying, by use of a probe which specifically hybridizes to a mutant sequence, whether or not a probe is hybridized, and (8) a method in which, in a case where the mutation is deletion or insertion, the mutation is detected by a difference in mobility of electrophoresis. Alternatively, the mutation or disruption of a gene can be determined by detection (e.g., Western blotting) of (i) a protein which results from modification of the gene or (ii) an expression level of a wild-type protein.

Prior to the above-described step of introducing a mutation, procedures (1 and 2) described below are carried out as necessary so as to determine (i) a gene whose expression is to be suppressed and/or (ii) a gene into which a mutation is to be introduced.

1. Isolation of tobacco gene which is predicted to regulate development of axillary bud A gene, which possibly regulates axillary buds, can be obtained from genes of tobacco by (i) selecting a gene from other plants based on a prior art document (e.g., Non-Patent Literature in which a relationship between a gene and an axillary bud is confirmed) and (ii) using, as an index, identity of nucleotide sequence and identity of amino acid sequence of the selected genes. For example, a nucleotide sequence and an amino acid sequence of a publicly-known tobacco gene or a gene of a plant species (e.g., tomato) which is closely related to tobacco can be obtained by conducting a search in sequences registered in a publicly-known database with use of Basic Local Alignment Search Tool (blast). In a case where a publicly-known sequence is of a partial length, a full-length cDNA can be obtained from known sequence information by a common method such as (i) screening from a cDNA library or (ii) Rapid amplification of cDNA ends (Race) method.

A gene, which possibly regulates an axillary bud in a novel manner, can be obtained by, for example, selecting a gene which is expressed according to a target tissue or target a treatment. The target tissue and the target treatment can be selected based on information listed below. It is known that (i) a gene, which is involved in the formation of an axillary meristem, is expressed prior to the formation of the axillary meristem and (ii) a gene, which is involved in maintenance and growth of an axillary meristem, is expressed at the axillary meristem (e.g., LS, Blind gene). It is known that a gene, which is involved in dormancy or development of an axillary bud, is expressed in an increased or decreased amount, depending on the dormancy or non-dormancy of the axillary bud (e.g., BRANCHED1). It is also known that some plant hormones are involved in the regulating of axillary buds. Auxin is involved in apical dominance. Strigolactone is involved in suppression of the development of axillary buds. Cytokinin is involved in outgrowth of axillary buds. Abscisic acid is involved in dormancy.

New selection of a gene which possibly regulates the development of an axillary bud can be performed by a common method in which expression specificity is utilized. The following (1) through (3) are examples of the method. (1) Methods such as (a) a method in which gene expression profiling data is obtained from a nucleotide sequence of cDNA, (b) a method in which a cDNA library of genes that are expressed in a subject tissue is prepared and then a terminal sequence is sequenced, and (c) a Serial Analysis of Gene Expression (SAGE) method in which restriction fragments are connected in series and sequenced. (2) A method in which gene expression profiling data is obtained by differential hybridization. Macro arrays and DNA chips are well known. (3) Genes (Differentially Expressed Genes: DEGs) which differ in expression level between a plurality of samples can be obtained by a differential display method. Examples encompass a method in which the amounts of PCR amplification fragments are compared.

Amplification of Isolated Genes

Amplification of a polynucleotide can be performed by Polymerase Chain Reaction (PCR), but alternatively can be performed by, for example, Ligase Chain Reaction (LCR) or Loop-Mediated Isothermal Amplification (LAMP).

A primer for amplifying a polynucleotide only needs to be a primer which enables specific amplification of a target gene of each genome from tobacco genomes in which genes of an S genome and a T genome are mixed. Provided that the target gene can be specifically amplified, one or more substitutions, deletions, insertions, and additions can be included. In addition, as necessary, the primer can be labeled with, for example, a fluorescent substance or a radiation.

Extraction of genomic DNA to be used as a template of the amplification can be performed by a publicly-known method, and can be performed by using a commercially available extraction kit. Genomic DNA can be a crudely purified one obtained through simple extraction or can be a purified one obtained through a purification step.

2. Identification of Gene which is Expected to be Involved in Development of Axillary Bud Effects of a target gene can be confirmed by (i) preparing recombinants and mutants in which expressions and functions of the target gene are suppressed and (ii) cultivating the recombinants and the mutants in a greenhouse, a phytotron, a mesh house, or a field. By comparing the number and weight of developed axillary buds with the controls, it is possible to confirm effects of the outgrowth and development of axillary buds. While the number and weight of the axillary buds can be performed without performing topping, the number and weight of the axillary buds is preferably performed while (i) the axillary buds are in a non-dormancy state due to topping and (ii) the development of the axillary buds are therefore promoted. Examination of the number and weight of the axillary buds can be performed once or more than once in any season. One-time measurement allows evaluation of primary axillary buds, but is not suitable for evaluations of secondary axillary buds and tertiary axillary buds. Therefore, it is preferable to perform measurement a plurality of times. In order to confirm the effects of secondary axillary buds and tertiary axillary buds, it is preferable to remove primary axillary buds and secondary axillary buds, respectively. While the removal of primary axillary buds and secondary axillary buds can be performed after the development thereof, it is preferable not to leave remaining axillary buds. It is preferable to remove axillary buds when the extension of stems of the axillary buds is confirmed. In a case where the examinations is performed a plurality of times, it is preferable to separately examine the primary axillary buds, the secondary axillary buds, and the tertiary axillary buds. For example, it is possible to carry out a method of (i) separately counting the respective numbers of primary axillary buds, secondary axillary buds, and tertiary axillary buds, once each week, (ii) collecting the primary axillary buds, the secondary axillary buds, and the tertiary axillary buds, and (iii) examining the respective weights of the primary axillary buds, the secondary axillary buds, and the tertiary axillary buds.

The examination can be performed with the focus only on specific axillary buds (e.g., secondary buds), or the examination can be performed such that examination with the focus only on the number of axillary buds and examination with the focus only on the weight are separately performed. In such a case, it is preferable that a suitable number of times of examinations and suitable intervals between the examinations are determined according to each examination.

[3. Method of Selectively Suppressing Secondary Axillary Buds of Tobacco Plant]

In one aspect, the present invention provides a method of selectively suppressing secondary axillary buds of a tobacco plant. Selective suppression of secondary axillary buds occurs as a result of introducing a mutation which causes suppression of the function of a gene containing, as a coding region, a polynucleotide encoding any of the specific polypeptides described above in a tobacco plant. It should be noted that the above functional suppression is to suppress the development of axillary buds. Specifically, the functional suppression occurs in a tobacco plant in accordance with one aspect of the present invention. In the method of producing the tobacco plant in accordance with another aspect of the present invention, the functional suppression occurs in the tobacco plant during a step of producing the tobacco plant. Therefore, for details of the method of causing the functional suppression to occur in a tobacco plant, a reference can be made to the previous descriptions regarding the method of producing the tobacco plant.

With the above embodiments considered together, the present invention can be summarized as follows.

Specifically, a tobacco plant in which a mutation is introduced into a genome, which mutation causes functional suppression of a gene containing, as a coding region, a polynucleotide encoding any of the following polypeptides (1) through (5):

(1) at least one of a polypeptide having a sequence identity of 90% or higher with an amino acid sequence represented by SEQ ID NO. 1 and a polypeptide having a sequence identity of 90% or higher with an amino acid sequence represented by SEQ ID NO. 3;

(2) at least one of a polypeptide having a sequence identity of 90% or higher with an amino acid sequence represented by SEQ ID NO. 5 and a polypeptide having a sequence identity of 90% or higher with an amino acid sequence represented by SEQ ID NO. 7;

(3) at least one of a polypeptide having a sequence identity of 90% or higher with an amino acid sequence represented by SEQ ID NO. 9 and a polypeptide having a sequence identity of 90% or higher with an amino acid sequence represented by SEQ ID NO. 11;

(4) at least one of a polypeptide having a sequence identity of 90% or higher with an amino acid sequence represented by SEQ ID NO. 13 and a polypeptide having a sequence identity of 90% or higher with an amino acid sequence represented by SEQ ID NO. 15; and (5) at least one of a polypeptide having a sequence identity of 90% or higher with an amino acid sequence represented by SEQ ID NO. 17 and a polypeptide having a sequence identity of 90% or higher with an amino acid sequence represented by SEQ ID NO. 19, the functional suppression suppressing development of axillary buds.

According to the tobacco plant, the functional suppression preferably suppresses development of, of all of the axillary buds, secondary axillary buds which develop after removal of primary axillary buds.

According to the tobacco plant, the functional suppression preferably causes the number or weight of the secondary axillary buds to decrease to not more than ½ of that of a wild-type plant.

According to the tobacco plant, the functional suppression is preferably a decrease in abundance of the polypeptide in comparison with a wild-type plant.

According to the tobacco plant, the functional suppression is preferably a decrease in an amount of translation of the polypeptide in comparison with a wild-type plant.

According to the tobacco plant, the functional suppression is preferably a decrease in an amount of transcription from the gene to an mRNA in comparison with a wild-type plant.

According to the tobacco plant, the functional suppression is preferably promotion of degradation of an mRNA transcribed from the gene.

According to the plant, the mutation is preferably introduced into the gene.

According to the tobacco plant, the mutation is preferably introduced by spontaneous mutation, mutagen treatment, genome editing, or gene knockout.

According to the tobacco plant, the mutation is preferably insertion, into an outside of a region in which the gene is present, of a polynucleotide expressing a factor which promotes the degradation of the mRNA.

According to the tobacco plant, the factor is preferably an antisense RNA molecule, an RNAi molecule, or a co-suppression molecule.

The tobacco plant preferably belongs to *Nicotiana tabacum* or *Nicotiana rustica.*

A method of producing a tobacco plant, including the step of:

(a) introducing a mutation that causes functional suppression of a gene containing, as a coding region, a polynucleotide encoding any of the following polypeptides (1) through (5):

(1) at least one of a polypeptide having a sequence identity of 90% or higher with an amino acid sequence represented by SEQ ID NO. 1 and a polypeptide having a sequence identity of 90% or higher with an amino acid sequence represented by SEQ ID NO. 3;

(2) at least one of a polypeptide having a sequence identity of 90% or higher with an amino acid sequence represented by SEQ ID NO. 5 and a polypeptide having a sequence identity of 90% or higher with an amino acid sequence represented by SEQ ID NO. 7;

(3) at least one of a polypeptide having a sequence identity of 90% or higher with an amino acid sequence represented by SEQ ID NO. 9 and a polypeptide having a sequence identity of 90% or higher with an amino acid sequence represented by SEQ ID NO. 11;

(4) at least one of a polypeptide having a sequence identity of 90% or higher with an amino acid sequence represented by SEQ ID NO. 13 and a polypeptide having a sequence identity of 90% or higher with an amino acid sequence represented by SEQ ID NO. 15; and (5) at least one of a polypeptide having a sequence identity of 90% or higher with an amino acid sequence represented by SEQ ID NO. 17 and a polypeptide having a sequence identity of 90% or higher with an amino acid sequence represented by SEQ ID NO. 19, the functional suppression suppressing development of axillary buds.

The method preferably further includes the step of: (b) selecting, from individuals produced by the step (a), an individual in which development of, of all of the axillary buds, secondary axillary buds that develop after removal of primary axillary buds is suppressed.

According to the method, in the step (b), an individual, in which the number or weight of the secondary axillary buds is decreased in comparison with that of a wild-type plant, is preferably selected.

According to the method, the step (a) preferably includes introducing the mutation into the gene.

According to the method, the step (a) is preferably carried out by spontaneous mutation, mutagen treatment, genome editing, or gene knockout.

According to the method, the step (a) preferably includes inserting, into an outside of a region in which the gene is present, a polynucleotide expressing a factor which promotes degradation of an mRNA transcribed from the gene.

According to the method, the factor is preferably an antisense RNA molecule, an RNAi molecule, or a co-suppression molecule.

An offspring or a bred progeny, in which: the offspring is of (i) the tobacco plant or (ii) a tobacco plant produced by the above method; and the bred progeny is obtained by crossing (i) the tobacco plant or (ii) a tobacco plant produced by the above method.

A leaf tobacco harvested from (i) the above tobacco plant, (ii) a tobacco plant produced by the above method, or (iii) the above offspring or the above bred progeny.

The following description will discuss details of the embodiment of the present invention with reference to Examples. The present invention is of course not limited to the Examples below and particulars can have various aspects. Further, the present invention is not limited to the embodiments, but can be altered by a skilled person in the art within the scope of the claims. An embodiment derived from a proper combination of technical means disclosed in respective different embodiments is also encompassed in the technical scope of the present invention. Moreover, all the literatures described in this specification are hereby incorporated by reference.

EXAMPLES

[1. Candidate Gene Involved in Development of Axillary Buds of Tobacco]

Candidates of tobacco orthologue of a plurality of genes (Revolutla (REV) of *Arabidopsis thaliana*, Lateral suppressor (LS) of tomato, and Blind (Bl) of tomato) involved in the development of axillary buds of other plants (such candidates are hereinafter simply referred to as "candidate group A") were determined by Basic Local Alignment Search Tool (blast) analysis. Meanwhile, candidates of genes involved in the development of axillary buds in a tobacco plant (such candidates are hereinafter simply referred to as "candidate group B") were determined by transcriptome analysis. The genes, which were obtained based on the analyses and the results of the analyses, will be described below.

(1-1. Candidate Group A)

(a) Blast Analysis

With an amino acid sequence of REV gene of *Arabidopsis thaliana* serving as a query, tblastn search was conducted on a web page of NCBI (http://blast.ncbi.nlm.nih.gov/Blast.cgi). As a result, REV homologous gene sequences of tomato having a high amino acid sequence identity of 80% were obtained. With an amino acid sequence of REV homologous gene of tomato serving as a query, tblastn search was conducted with respect to the results of analysis of Expressed Sequence Tag (EST) of cDNA library (derived from a mixture of leaves, shoot apex, and roots of Tsukuba No. 1). As a result, putative REV cDNA clone group of tobacco was selected.

cDNA sequence of tobacco having an amino acid sequence identity of 87% with LS gene of tomato was registered in public DB (Accession number: EU935581). Furthermore, a tobacco EST sequence (Accession number: AM848584) having a high identity with EU935581 was registered in public DB.

With an amino acid sequence of Bl gene of tomato serving as a query, tblastn search was conducted with respect to the results of analysis of EST of cDNA library (derived from a mixture of leaves, shoot apex, and roots of Tsukuba No. 1). As a result, putative Bl clone group of tobacco was selected.

(b) Preparation of Individual-Derived Genomic DNA Fragments and cDNA (Total RNA-Derived)

Genomic DNA fragments were extracted from leaves of tobacco (Tsukuba No. 1 or Petit Havana SR-1 (SR-1)) according to a simple extraction method or a CTAB method. The CTAB method is publicly known, and therefore will not be described in detail. The simple extraction method was carried out according to the following procedure. A leaf segment, which was placed in 0.3 ml to 0.5 ml of extraction buffer (0.2 M Tris-HCl pH 8.0, 0.4 M NaCl, 25 mM EDTA, and 0.5% SDS), was ground (2500 rpm, 1 minute) with use of a crushing device (e.g., Multi Beads Shocker (Yasui Kiki Corporation) or Shake Master Neo (Bio Medical Science)). A supernatant is taken from a homogenate after the grinding. Then, genomic DNA fragments are purified from the supernatant through ethanol precipitation.

Total RNA was extracted as follows. A shoot apex, a seedling, and an axillary bud of tobacco were each immersed in RNAlater (Ambion), and then cryopreserved. Then, a sample was melted, and then 0.5 ml of an RTL buffer (QIAGEN), to which 20 μl of 1 M DTT had been added, was added to the melted sample. A resultant mixture was ground (2500 rpm, 1 minute) with use of Multi Beads Shocker (Yasui Kiki Corporation). The homogenate after the grinding was subjected to centrifugal separation (15000 rpm, 10 minutes), so that a supernatant was obtained. From the supernatant, total RNA was purified with use of Magtration (Precision System Science Co., Ltd.) or RNeasy Kit (QIAGEN), in the presence of DNase.

From the total RNA, cDNA was prepared with use of any one of the following kits according to the manual included in the kit.

PrimeScript II 1st strand cDNA Synthesis Kit (Takara-Bio Inc.)

PrimeScript RT reagent kit with gDNA Eraser (Takara-Bio Inc.)

(c) Production of Genes of Candidate Group A

By RT-PCR in which the cDNA obtained in (b) was used as a template, three genes were amplified. In a case where PrimeSTAR Max DNA Polymerase (Takara-Bio Inc.) was used as an enzyme, the reaction conditions were set as follows.

30 seconds at 94° C.

30 cycles to 40 cycles while each cycle includes 10 seconds at 98° C., 5 seconds at 55° C., and 10 seconds at 72° C.

10 seconds at 72° C.*

* An extension reaction at 72° C. was set to 10 seconds per kb of the length of an amplification fragment.

In a case where Tks Gflex DNA Polymerase (Takara-Bio Inc.) was used as an enzyme, the reaction conditions were set as follows.

30 seconds at 94° C.

30 cycles to 40 cycles while each cycle includes 10 seconds at 98° C., 15 seconds at 55° C., and 60 seconds at 68° C.

60 seconds at 68° C.*

* An extension reaction at 68° C. was set to 60 seconds per kb of the length of an amplification fragment.

Combinations of a target gene and a primer for RT-PCR are as follows.

```
(Set 1: NtLS, T genome, seedling of Tsukuba No. 1)
Combination of LS_Tom_F1:
                                        (SEQ ID NO. 130)
AGGTTCTTCTTCCTTAATATTGAGTC,
and

NtLS_qRV1:
                                        (SEQ ID NO. 131)
ATCTAAGGCCTAAAGAGTGAGCAAAT

Combination of LS2_F2:
                                        (SEQ ID NO. 132)
ACACCTAATGCATCATCTAATGTT,
and

LS_Syl_R1:
                                        (SEQ ID NO. 133)
CAAATAAAGATTAAGTTCAGGATCTG

(Set 2; NtLS, S genome, seedling of Tsukuba No. 1)
Combination of LS_F2_seq:
                                        (SEQ ID NO. 134)
ATTTCCCCTCCTCCATCATTG,
and

NtLS_qRV1:
                                        (SEQ ID NO. 131)
ATCTAAGGCCTAAAGAGTGAGCAAAT

Combination of LS1_F2:
                                        (SEQ ID NO. 136)
CTTGACACCATCTAATGTTGTTG,
and

LS_Tom_R1:
                                        (SEQ ID NO. 133)
CAAATAAAGATTAAGTTCAGGATCTG

(Set 3; NtREV, T genome, seedling of Tsukuba No. 1)
Combination of REV_RT_F2:
                                        (SEQ ID NO. 137)
AAGCTGTTTGCAGGGAATATATC,
and

G053330_RV3:
                                        (SEQ ID NO. 138)
TCTCTGGCTAAATGTTCGAAG

Combination of REV_RT_F3:
                                        (SEQ ID NO. 139)
GTAAGTTGTGAGTCTGTGGTAACTAC,
and
```

-continued

REV_RT_R1:
(SEQ ID NO. 140)
GGAAACAAACATCTGCACTCAA (Set 4: NtB1, S genome, seedling of Tsukuba No. 1)
Combination of B11_F1seq2:
(SEQ ID NO. 141)
GTCCATCTGTCTATATAGGTAGAATG,
and

B11-2_RT_R1:
(SEQ ID NO. 142)
TGAATCTTCTTGGCAACCCCC (Set 5: NtREV, S genome, axillary bud of SR-1)
NS_in0_F1:
(SEQ ID NO. 143)
TTGTTTGGGATTTTGGGGTTTGAGGG,
and

REV_S_R1:
(SEQ ID NO. 144)
AATTGTATGGCCAAGTGGCATTATTATCTGA

REV_S_F1:
(SEQ ID NO. 145)
CACTTCCGTTCCTCTTTCACCGCTG,
and

NtREV_S_RV1:
(SEQ ID NO. 146)
TCCGTTCAACTGTGTTCCTGG (Set 6: NtREV, T genome, axillary bud of SR-1)
REV_RT_F2:
(SEQ ID NO. 137)
AAGCTGTTTGCAGGGAATATATC, and NtREV1_RV1:
(SEQ ID NO. 147)
TCCGTTCAACTGTGTTCCTG (Set 7: NtLS, S genome, axillary bud of SR-1)
Combination of LS_Tom_F1:
(SEQ ID NO. 130)
AGGTTCTTCTTCCTTAATATTGAGTC,
and LS_Tom_R1:
(SEQ ID NO. 133)
CAAATAAAGATTAAGTTCAGGATCTG (Set 8: NtLS, T genome, axillary bud of SR-1)
Combination of LS_Tom_F1:
(SEQ ID NO. 130)
AGGTTCTTCTTCCTTAATATTGAGTC, and LS2-F2compR:
(SEQ ID NO. 148)
AACATTAGATGATGCATTAGGTGT Combination of LS2-F2:
(SEQ ID NO. 132)
ACACCTAATGCATCATCTAATGTT,
and LS_Syl_R1:
(SEQ ID NO. 149)
TTGGCCTCTAATTAAATAGACTGATA.

By genomic PCR in which the genomic DNA fragment obtained in (b) was used as a template, three genes were amplified. Since the enzymes used and the reaction conditions for the enzymes are similar to those in the RT-PCR, combinations of a target gene and a primer are as follows.

(Set 1: NtREV, S genome, leaves of Tsukuba No. 1)
Combination of REV_F3:
(SEQ ID NO. 150)
TCTCAAAGCTGGCTGTTTTATGTAT,
and

REV_R14:
(SEQ ID NO. 151)
TACCATTCTCCAGGGTGGTTGTGTAT

Combination of NS_in4_F1:
(SEQ ID NO. 152)
GAAAATTCAGTATTGCCATGTC,
and

G053330_RV2:
(SEQ ID NO. 153)
GCAAAAACTAGTTCAGAACA

Combination of NtREV_TrFW2:
(SEQ ID NO. 154)
CACCGCCTATGTAGCTTCGTCAATG,
and

NtREV_RT-R1:
(SEQ ID NO. 140)
GGAAACAAACATCTGCACTCAA (Set 2: NtREV, T genome, leaves of Tsukuba No. 1)
Combination of REV_F3:
(SEQ ID NO. 150)
TCTCAAAGCTGGCTGTTTTATGTAT,
and

REV_R14:
(SEQ ID NO. 151)
TACCATTCTCCAGGGTGGTTGTGTAT

Combination of Nt_in4_F1:
(SEQ ID NO. 155)
AAAAAAATTCAGTATTGCCACGTGC,
and

G053330_RV2:
(SEQ ID NO. 153)
GCAAAAACTAGTTCAGAACA

Combination of NtREV_TrFW2:
(SEQ ID NO. 154)
CACCGCCTATGTAGCTTCGTCAATG,
and

NtREV_RT-R1:
(SEQ ID NO. 140)
GGAAACAAACATCTGCACTCAA (Set 3: NtLS, S genome, leaves of Tsukuba No. 1)
Combination of LS_F1_seq:
(SEQ ID NO. 130)
AGGTTCTTCTTCCTTAATATTGAGTC,
and

LS_TRV_R3:
(SEQ ID NO. 156)
TCGCTTGATTAGCAGTCAGC

LS_F 1_seq:
(SEQ ID NO. 130)
AGGTTCTTCTTCCTTAATATTGAGTC,
and

NtLS_QPCR_RV1:
(SEQ ID NO. 131)
ATCTAAGGCCTAAAGAGTGAGCAAAT

-continued

Combination of LS_TRV_F3:

(SEQ ID NO. 157)
CACCGAAGAAACTGATGATCAACGG,
and

LS_TRV_R2:

(SEQ ID NO. 158)
GAAGACCTCTTTGTCCTTCACCATGCAG (Set 4: NtLS, T genome, leaves of Tsukuba No. 1)
Combination of LS_F2_seq:

(SEQ ID NO. 134)
ATTTCCCCTCCTCCATCATTG, and NtLS_QPCR_RV1:

(SEQ ID NO. 131)
ATCTAAGGCCTAAAGAGTGAGCAAAT

Combination of LS_TRV_F3:

(SEQ ID NO. 157)
CACCGAAGAAACTGATGATCAACGG,
and

LS_TRV_R2:

(SEQ ID NO. 158)
GAAGACCTCTTTGTCCTTCACCATGCAG (Set 5: NtB11, S genome, leaves of Tsukuba No. 1
and SR-1) Combination of B11_F1seq2:

(SEQ ID NO. 141)
GTCCATCTGTCTATATAGGTAGAATG,
and

B11_R1seq:

(SEQ ID NO. 159)
CACCATGTTTGATATTAGGCCTTA

Combination of B11_F3seq2:

(SEQ ID NO. 160)
TGATGAGATTTATGTTGGGAACTG,
and

B11_R2seq:

(SEQ ID NO. 161)
TCTCATCATTGAACACGAACATACT (Set 6: NtB11, T genome, leaves of Tsukuba No. 1
and SR-1) Combination of B11_F1seq1:

(SEQ ID NO. 162)
CCACTTGTCTATATAGCAAGAAAGA,
and

B11_R1seq:

(SEQ ID NO. 159)
CACCATGTTTGATATTAGGCCTTA

Combination of B11_F2seq:

(SEQ ID NO. 163)
CTAAGGCCTAATATCAAACATGGT,
and

B11_R2seq:

(SEQ ID NO. 161)
TCTCATCATTGAACACGAACATACT.

(d) Determination of Sequence of Genes Obtained

Each of the PCR products, which were obtained by amplifying the three genes, were cloned with use of Zero Blunt TOPO PCR Cloning Kit for Sequencing Kit (Life Technologies Corporation). As necessary, the PCR products were purified before the cloning by a common method in which agarose gel electrophoresis and MiniElute column (QIAGEN) were combined. The respective nucleotide sequences of the cloned genes were determined (SEQ ID NOs. 21 through 30) by a capillary sequencer 3730x1 DNA Analyzer (ABI) with use of BigDye (registered trademark) Terminator v3.1 Cycle Sequencing Kit (ABI).

(1-2. Candidate Group B)

Transcriptome analysis was performed in order to identify genes which are expected to be increasingly expressed in the leaf primordia of a plant.

(a) Preparation of RNA Extraction Sample

A paraffin block, in which the shoot apex portion obtained from a young tobacco plant (variety: SR-1) 4 weeks to 5 weeks after the sowing was embedded, was prepared (for details, see Takahashi H, Kamakura H, Sato Y, Shiono K, Abiko T, Tsutsumi N, Nagamura Y, Nishizawa N K, Nakazono M. (2010) A method for obtaining high quality RNA from paraffin sections of plant tissues by laser microdissection. J Plant Res 123: 807-813). The paraffin block was cut into serial sections having a thickness of 20 μm with use of a microtome (RM2125 RTS; Leica). From the serial sections, sections including a center part and its vicinity of Shoot Apical Meristem (SAM) were selected. From the sections, with use of Applied Biosystems (registered trademark) ArcturusxT (trademark) laser capture microdissection system, a base of leaf primordia whose axillary meristem is unformed (axillary meristem sample), leaf primordium, and a lower part of shoot apical meristem (control sample) were cut out to have a size so that the diameter was 100 μm to 200 μm. The axillary meristem sample and the control sample were each collected in CapSure (registered trademark) LCM Cap (Applied Biosystems, Inc.), transferred to a tube for RNA extraction, and cryopreserved at −80° C. until the RNA extraction.

(b) RNA Purification

With use of PicoPure RNA isolation Kit (Arcturus), total RNA was purified from the RNA extraction samples of (a), according to the manual included in the kit. With use of a Bioanalyzer (Agilent Technologies Inc.), the RNA concentration of the solution of the purified RNA was estimated, and the quality of the solution (degree of decomposition of the RNA) was confirmed.

(c) Sequencing with Use of Next-Generation Sequencer (454 Genome Sequencer Titanium, Roche) and Prediction of Gene Expression Level The RNA obtained in (b) was sent to Takara-Bio Inc., and it was requested that Takara-Bio Inc. prepare cDNA library for use in sequencer analysis. Then, Genaris was entrusted with the nucleotide sequence analysis of the 5' ends of cDNAs of the cDNA library. In determination of the nucleotide sequence, ¾ of a plate of each plant portion, from which the cDNA libraries were derived, was subjected to the sequencing. By de novo assembly analysis in which entire sequence information obtained for each portion was used, an assembly sequence was obtained. To the assembly sequence thus obtained, a read sequence obtained from the cDNA libraries, which are derived from each portion, was mapped (aligned). The number of reads corresponding to each gene was counted for each portion. The number of reads thus counted was normalized between the cDNA libraries from which the each portion was obtained. Based on the normalized number of reads, the entire gene expression level was predicted for each portion.

(d) Determination of Candidate Group B

From the axillary meristem sample (see (a) described above), the following genes were selected as primary candidate genes which are involved in the formation of axillary meristem: Genes which have a sequence of 200 or more bases in data and whose number of reads is 4 or more so as to have an expression level 10 times or more in comparison with that of the control sample. It is expected that a gene, which is to serve as a master switch for controlling the formation of organs such as the formation of axillary meristem, is a transcription factor which controls a plurality of expressions of genes. Therefore, secondary candidate genes, which are likely to encode transcription factors, were further selected (narrowed) from the candidate genes selected by the primary expression characteristics. By examining whether or not the suppression of the expression of these genes suppresses the development of axillary buds of tobacco, the candidate group B (2 genes) were ultimately determined.

(e) Production of Full-Length Sequence and cDNA Sequence of 2 Genes

By assembling the read sequence based on the results of the next-generation sequence analysis, consensus sequences "isogroup15360" and "isogroup07437" were obtained. By Race, RT-PCR, and genomic PCR using these consensus sequences, a full-length sequence and a cDNA sequence of the 2 genes were produced.

The Race was performed with use of the total RNA prepared according to the description in (b) of 1-1. above and with use of SMARTer RACE cDNA Amplification Kit (Clonetech) according to the manual included in the kit. For nested PCR of the Race, 1st PCR products, which had been 300-fold diluted, were used as a template. The reaction conditions in the Race were set as follows.

(1st PCR)

5 cycles while each cycle includes 10 seconds at 98° C. and 10 seconds at 72° C.

5 cycles while each cycle includes 10 seconds at 98° C., 5 seconds at 70° C., and 5 seconds at 72° C.

25 cycles while each cycle includes 10 seconds at 98° C., 5 seconds at 60° C., and 5 seconds at 72° C.

(Nested PCR)

25 cycles while each cycle includes 10 seconds at 98° C., 5 seconds at 55° C., and 5 seconds at 72° C.

As primers for the Race, primers included in the kit and primers specific to the following genes were used.

```
(1st PCR: #15360, S genome and T genome,
shoot apex of SR-1)
Combination of 5' Race 1st primer:
                                   (SEQ ID NO. 164)
R-GAACCACCAGGGACTAAACTCTGCAA,
and

3' Race 1st primer:
                                   (SEQ ID NO. 165)
F-TTGCAGAGTTTAGTCCCTGGTGGTTC

(nested PCR: #15360, S genome and T genome,
shoot apex of SR-1)
Combination of 5' Race Nested primer:
                                   (SEQ ID NO. 166)
R-GAAACGATCACTGATTCTATGCC,
and

3' Race Nested primer:
                                   (SEQ ID NO. 167)
F-TACAATGTTAGAAGAAGCAATTCAC.
```

According to the description in (c) of 1-1., RT-PCR was performed. The primers used and target genes were as follows.

```
(Set 1: #07437, S genome,
shoot apex of SR-1)
Combination of forward:
                                   (SEQ ID NO. 168)
TACTTCCCTTTCTCACTTTGGTTTC,
and
```

-continued

```
reverse:
                                   (SEQ ID NO. 169)
AATATTCCCATCAATAGATCACAAC

(Set 2: #07437, T genome,
seedling of Tsukuba No. 1)
Combination of 07437_T_F1:
                                   (SEQ ID NO. 170)
CTACTACATCACTTAATATCATTCATT,
and

07437_Tom_RT_R1:
                                   (SEQ ID NO. 171)
CAATAGATTGCAACTTTACATTAGTCG

(Set 3: #07437, S genome,
seedling of Tsukuba No. 1)
Combination of 07437_S_F1:
                                   (SEQ ID NO. 172)
TACTATCACTTAATACCATCATTCATC,
and

07437_Syl_RT_R1:
                                   (SEQ ID NO. 173)
CCCATCAATAGATCACAACTTTAGT

(Set 4: #15360, S genome,
seedling of Tsukuba No. 1)
Combination of 15360-2_F2:
                                   (SEQ ID NO. 174)
AAATAGAGGTAATTAGTTGTATCAATGG,
and

15360-NtS_R2:
                                   (SEQ ID NO. 175)
ACAACATACCATACTACCACACACTA

(Set 5: #15360, T genome,
seedling of Tsukuba No. 1)
Combination of 15360-1_F1:
                                   (SEQ ID NO. 176)
TGCATGGACAATCTCCTCTT ),
and

15360-Nts_R2:
                                   (SEQ ID NO. 175)
ACAACATACCATACTACCACACACTA

(Set 6: #15360, S genome,
axillary bud of SR-1)
Combination of 15360-2_F1:
                                   (SEQ ID NO. 177)
GCATGGACAATCTCATCTTCTC,
and

15360-1 R1-2:
                                   (SEQ ID NO. 178)
CAACAGGAGTTGAGTTATTCTCAT

(Set 7: #15360, T genome,
axillary bud of SR-1)
Combination of 15360_TrFW1:
                                   (SEQ ID NO. 179)
CACCTTCTTCAAGCAAAATTAATGAC,
and

15360_TrRV1:
                                   (SEQ ID NO. 180)
ATTAGAGTCATGAGCCATTAGC.
```

According to the description in (c) of 1-1., genomic PCR was performed. The primers used and target genes were as follows.

(Set 1: #15360, S genome, leaves of Tsukuba No. 1)
Combination of 15360-2_F1:
(SEQ ID NO. 177)
GCATGGACAATCTCATCTTCTC,
and 15360-2_R1:
(SEQ ID NO. 181)
CTGGGCAATATTCCACCATT Combination of 15360-2_F2:
(SEQ ID NO. 182)
AATGGTGGAATATTGCCCAG,
and 15360 NtsR2:
(SEQ ID NO. 175)
ACAACATACCATACTACCACACACTA (Set 2: #15360, T genome, leaves of Tsukuba No. 1)
Combination of 15360-1_F1:
(SEQ ID NO. 176)
TGCATGGACAATCTCCTCTT,
and 15360-1_R1-2:
(SEQ ID NO. 178)
CAACAGGAGTTGAGTTATTCTCAT Combination of 15360-1_F2-2:
(SEQ ID NO. 183)
ATGAGAATAACTCAACTCCTGTTG,
and 15360 NtsR2:
(SEQ ID NO. 175)
ACAACATACCATACTACCACACACTA (Set 3: #07437, S genome, leaves of Tsukuba No. 1)
Combination of 07437-S_F1:
(SEQ ID NO. 172)
TACTATCACTTAATACCATCATTCATC,
and

07437-S R1:
(SEQ ID NO. 135)
TCCCTGTACTTTGGGACATGA

Combination of 07437-S_F2:
(SEQ ID NO. 184)
GTGTACCAGCTAGTTATTATTGCG,
and

07437-S_R2:
(SEQ ID NO. 185)
CCTGATCCGTTCTGATAGATCG

Combination of 07427-S_F3:
(SEQ ID NO. 186)
ATTTGTTAAAAAGTTGTAATAAAATTGG,
and

07437-S_R3:
(SEQ ID NO. 187)
TTTCTTTGAATTGCTAACGAGGA

Combination of 07437-S_F4:
(SEQ ID NO. 188)
TCCTCGTTAGCAATTCAAAGAAA,
and

07437-S_R5:
(SEQ ID NO. 189)
AGAATATAAAGAGCAGCCTGAATTAC

-continued

Combination of 07437-S_F1:
(SEQ ID NO. 172)
TACTATCACTTAATACCATCATTCATC,
and

07437-S_R2:
(SEQ ID NO. 185)
CCTGATCCGTTCTGATAGATCG

Combination of 07437-S_F2:
(SEQ ID NO. 184)
GTGTACCAGCTAGTTATTATTGCG,
and

07437-S_R3:
(SEQ ID NO. 187)
TTTCTTTGAATTGCTAACGAGGA (Set 4: #07437, T genome, leaves of Tsukuba No. 1)
Combination of 07437-T_F1:
(SEQ ID NO. 170)
CTACTACATCACTTAATATCATTCATT,
and

07437-T_R1:
(SEQ ID NO. 135)
TCCCTGTACTTTGGGACATGA

Combination of 07437-T_F2:
(SEQ ID NO. 190)
TGCATTAACATGAATGCGAC,
and

07437-T_R2:
(SEQ ID NO. 191)
TCTAAATAGCGAGTAATAAGGATGAGA

Combination of 07437-T_F3:
(SEQ ID NO. 192)
GTTTGTTAAAAAATTGTAATAAACTTGG,
and

07437-T_R3:
(SEQ ID NO. 193)
TTTCTTTGAAGTGCAAAAGGAAT

Combination of 07437-T_F4:
(SEQ ID NO. 194)
ATTCCTTTTGCACTTCAAAGAAA,
and

07437-T_R4:
(SEQ ID NO. 195)
ATTATGGAAAAACAACTCTTCTATT

Combination of 07437-T_F1:
(SEQ ID NO. 170)
CTACTACATCACTTAATATCATTCATT,
and

07437-T_R2:
(SEQ ID NO. 191)
TCTAAATAGCGAGTAATAAGGATGAGA

Combination of 07437-T_F2:
(SEQ ID NO. 190)
TGCATTAACATGAATGCGAC,
and

07437-T_R3:
(SEQ ID NO. 193)
TTTCTTTGAAGTGCAAAAGGAAT.

(1-3. Determination of Full-Length Sequence of Target Gene on Genome)

Genomic DNA fragments were obtained according to the description in (b) of 1-1. By PCR in which the genomic DNA fragments were used as templates, 5' upstream and 3' downstream of the target gene were each amplified. The reaction conditions of the PCR were set as described in (c) of 1-1. The primers used in the PCR are as follows.

TABLE 1

| Primer name | Sequence | Target sample | Analyzed genome |
|---|---|---|---|
| REV_Sg_FW1 | AAGAACATTGGCTTTAGTCCTCTAA (SEQ ID NO. 196) | Tsukuba No. 1 | S genome_5'upstream |
| Ns_ex1_R1 | ACCATCACTCATCTAACTTATCCCAT (SEQ ID NO. 197) | | |
| REV_3Tg_F1 | AGACAGGAACACAGTTGAACGGA (SEQ ID NO. 198) | | S genome_3'downstream |
| REV_Sg_RV1 | CTTGACAAACACTCTGATTCTACAC (SEQ ID NO. 199) | | |
| REV_Sg_RV2 | TTGAGATAGCTTGTATATTATGCATGC (SEQ ID NO. 200) | | |
| REV_Tg_FW1 | TTGTACCCATTGAAGGATGACTACT (SEQ ID NO. 201) | | T genome_5'upstream |
| Nt_ex1_R1 | TCCATCACTGATCTAACTAATCCAAG (SEQ ID NO. 202) | | |
| REV_3Tg_F1 | AGACAGGAACACAGTTGAACGGA (SEQ ID NO. 198) | | T genome_3'downstream |
| REV_Tg_RV2 | CACGGGCGTTACCTCCACTAGTAT (SEQ ID NO. 203) | | |
| LS_Sg_FW1 | AAGGTCATTAGAATATGCGGAGC (SEQ ID NO. 204) | | S genome_5'upstream |
| LS_Sg_FW2 | TCTTCACTAGTTTCGGGCTCAAG (SEQ ID NO. 205) | | |
| L52-R1 | AACATTAGATGATGCATTAGGTGT (SEQ ID NO. 148) | | |
| LS1,2-F4 | GTGGAGGCTTTGGATTATTATG (SEQ ID NO. 206) | | S genome_3'downstream |
| LS_Sg_RV1 | CGTCAGAACTTCGGATTAATTACTTC (SEQ ID NO. 207) | | |
| LS_Tg_FW1 | AAATGAGGCCTGAGCACAAG (SEQ ID NO. 208) | | T genome_5'upstream |
| LS1-R1 | CAACAACATTAGATGGTGTCAAG (SEQ ID NO. 209) | | |
| LS1,2-F4 | GTGGAGGCTTTGGATTATTATG (SEQ ID NO. 206) | | T genome_3'downstream |
| LS_Tg_RV1 | TTATGGGATTTGATGATGCAGAG (SEQ ID NO. 210) | | |
| LS_Tg_RV2 | ACCTAGATTCCTTTACATAACCACTC (SEQ ID NO. 211) | | |
| BI_Sg_FW1 | ATATAGAAGGATGAGACATAGTAACATACC (SEQ ID NO. 212) | | S genome_5'upstream |
| BI_Sg_FW2 | GTCTACAAGAAAATATGCATCCGGA (SEQ ID NO. 213) | | |
| BI1-2_R1 | CTTTGTCCCTTCGATTCATGA (SEQ ID NO. 214) | | |
| BI1-2_F4 | AGGCCTAAATCATCAGTCCA (SEQ ID NO. 215) | | S genome_3'downstream |
| BI_Sg_RV1 | GCTGGTGTCGATAATTGCTATTTAG (SEQ ID NO. 216) | | |
| BI_Sg_RV2 | CCTTAGTGGTTTTGCATGCTATGTT (SEQ ID NO. 217) | | |
| BI_Tg_FW2 | GGCAGGATACTATTCTACCACTAGG (SEQ ID NO. 218) | Tsukuba No. 1 | T genome_5'upstream |
| BI1-1_R1 | CGCTTCGATTCTGGGAATAAG (SEQ ID NO. 219) | | |
| BI1-1_F4 | TACAGGCCTAAATCAGTCCA (SEQ ID NO. 220) | | T genome_3'downstream |
| BI_Tg_RV2 | ATGTGAAGACAATGAATTCCGC (SEQ ID NO. 221) | | |
| 15360_Sg_FW1 | GTGTCGTCTATGGATATTATCGGC (SEQ ID NO. 222) | | S genome_5'upstream |
| 15360-2_Nsyl_R1 | CTGGGCAATATTCCACCATT (SEQ ID NO. 181) | | |
| 15360-2_Nsyl_F2 | AATGGTGGAATATTGCCCAG (SEQ ID NO. 182) | | S genome_3'downstream |
| 15360_Sg_RV1 | GTTCGCAGAATGACAAACAGAGT (SEQ ID NO. 223) | | |
| 15360_Tg_FW1 | CATGAGTACAGATATTACCAGTGCATC (SEQ ID NO. 224) | | T genome_5'upstream |
| 15360_Tg_FW2 | GTGAATAATGTGTTGCAGGTCTC (SEQ ID NO. 225) | | |
| 15360-1_Ntom_R1 | TCTCAACAGGAGTTGAGTTATTCTC (SEQ ID NO. 226) | | |
| 15360-1_Ntom_F2-2 | ATGAGAATAACTCAACTCCTGTTG (SEQ ID NO. 183) | | T genome_3'downstream |
| 15360_Tg_RV1 | AGTTTGAACATTGGATATGGTG (SEQ ID NO. 227) | | |
| 15360_Tg_RV2 | TCATACTCACGCTTGTTATACACG (SEQ ID NO. 228) | | |
| BI_Sg_FW3 | GCTCTCCTCTGATACATGGCTAT (SEQ ID NO. 229) | SR1 | S genome_5'upstream |
| BI1-1,2_R1 | TGTTTCAGTCTCAAATTCAT (SEQ ID NO. 230) | | |
| BI1-2_F4 | AGGCCTAAATCATCAGTCCA (SEQ ID NO. 215) | | S genome_3'downstream |
| BI_Sg_RV1 | GCTGGTGTCGATAATTGCTATTTAG (SEQ ID NO. 216) | | |
| BI_Tg_FW2 | GGCAGGATACTATTCTACCACTAGG (SEQ ID NO. 218) | | T genome_5'upstream |
| BI1-1_R1 | CGCTTCGATTCTGGGAATAAG (SEQ ID NO. 219) | | |
| BI1-1_F4 | TACAGGCCTAAATCAGTCCA (SEQ ID NO. 220) | | T genome_3'downstream |
| BI_Tg_RV2 | ATGTGAAGACAATGAATTCCGC (SEQ ID NO. 221) | | |

With use of Zero Blunt (registered trademark) TOPO (registered trademark) PCR Cloning Kit (Thermo Fisher Scientific), *E. coli* (Mach1 (trademark)-T1R) was transformed with each of the amplified PCR products according to the manual included in the kit. The transformed *E. coli* was inoculated on a plate. Colony PCR was performed with use of the colony formed on the plate. The amplification product obtained by the colony PCR was purified with use of ExoSAP-IT (registered trademark) For PCR Product Clean-UP (Affimetrix) according to the manual thereof. Then, the resulting product was used as a template in a sequence reaction described later. At the same time, the colony was subjected to liquid culture. Then, with use of QIAGEN Plasmid Mini Kit (QIAGEN), a plasmid was extracted from bacterial cells cultured. The plasmid thus extracted was also used as the template in the sequence reaction described later.

The template was reacted with use of BigDye (registered trademark) Terminator v3.1 Cycle Sequencing Kit (Applied Biosystems) according to the manual thereof. The reaction product was purified with use of BigDye (registered trademark) XTerminator (trademark) Purification Kit (Thermo Fisher Scientific). The nucleotide sequence of the purified reaction product was determined by use of a capillary sequencer 3730x1 DNA Analyzer (Applied Biosystems). The sequence primer was designed as appropriate from sequence information and was used.

The nucleotide sequence thus determined was connected with use of ATGC sequence assembly software (GENETYX CORPORATION) so that the nucleotide sequence in an untranslated region of the target gene was determined. The untranslated region and the structural gene part were further connected, so that a full-length genomic DNA sequence of the target gene was determined (SEQ ID NOs. 54 through 63).

(1-4. Results)

Tobacco orthologous genes of REV, LS, and Bl, which were determined as the candidate group A, were named NtREV, NtLS, and NtBl1, respectively. In addition, from the results of the transcriptome analysis, the genes determined as the candidate group B were named #15360 and #07437.

[2. Examination of Effects of Expression Suppression of Each of Candidate Groups A and B on Development of Axillary Buds]

In order to examine the effects of expression suppression of each of the candidate groups A and B on the development of axillary buds, checking was performed of changes in development of axillary buds in recombinants in which each gene expression was suppressed (such a recombinant is hereinafter referred to simply "recombinant").

(2-1. Preparation of Recombinants)

(a) Preparation for Transformation

In order to prepare the recombinants, vectors for transformation were first prepared as described below.

RNAi trigger sequences for suppressing the expression of NtREV, NtBl1, NtLS, #15360, and #07437 (hereinafter also collectively referred to as "target genes") were amplified by PCR in which PrimeSTAR Max DNA Polymerase (Takara-Bio Inc.) was used, while cDNA derived from SR-1 produced based on the results of 1. was used as a template. The conditions and primers of the PCR are as follows.

(Conditions of PCR)

30 seconds at 94° C.

30 cycles to 40 cycles while each cycle includes 10 seconds at 98° C., 5 seconds at 55° C., and 10 seconds at 72° C.

10 seconds at 72° C.

```
(Primer for #15360)
Combination of 15360_TrFW1:
                                        (SEQ ID NO. 179)
CACCTTCTTCAAGCAAAATTAATGAC,
and

15360_TrRV1:
                                        (SEQ ID NO. 180)
ATTAGAGTCATGAGCCATTAGC

(Primer for #07437)
Combination of 07437_TrFW1:
                                        (SEQ ID NO. 231)
ACCACCTGGTTTTAGGTTTCATCC,
and

07437_TrRV1:
                                        (SEQ ID NO. 232)
TATTCTGCATATCACCCATTCC

(Primer for NtLs)
Combination of LS_TRV_F3:
                                        (SEQ ID NO. 157)
CACCGAAGAAACTGATGATCAACGG,
and

LS_TRV_R3:
                                        (SEQ ID NO. 156)
TCGCTTGATTAGCAGTCAGC

(Primer for NtB11)
Combination of N.t_BL(hit1)_TRV_F1:
                                        (SEQ ID NO. 233)
CACCTCAAGAAAAAGCTTATGGG,
and

N.t_BL(hit1)_TRV_R1:
                                        (SEQ ID NO. 234)
GCAGCAGCTAACAAGTTGTA
```

-continued

```
(Primer for NtREV)
Combination of NtREV_TrFW2:
                                        (SEQ ID NO. 154)
CACCGCCTATGTAGCTTCGTCAATG,
and

NtREV_TrRV2:
                                        (SEQ ID NO. 235)
CACTGTAGCCAGAGACCACA.
```

For the expression suppression of NtREV, a sequence of a translated region downstream (3' end) of an HD-Zip domain was selected as an RNAi trigger sequence. For the expression suppression of NtBl1, a sequence of a translated region downstream (3' end) of a Myb domain was selected as an RNAi trigger sequence. For the expression suppression of NtLS, a 5' end side of a translated region was selected as an RNAi trigger sequence. For the expression suppression of #15360, a sequence including a bHLH domain was selected as an RNAi trigger sequence. For the expression suppression of #07437, a sequence of a NAM domain region was selected as an RNAi trigger sequence. In addition, each RNAi trigger sequence amplified by the PCR was added with CCAC at the 5' end, and was designed so that the RNAi trigger sequence has a length of 400 bp to 500 bp.

The PCR products were cloned to pENTR (trademark)/D-TOPO vectors (Life Technologies Corporation). Then, the nucleotide sequence of each RNAi trigger sequence was checked. Then, with use of Gateway LR Clonase II Enzyme Mix (Life Technologies Corporation), each RNAi trigger sequence was introduced into a pSP231 vector. In order to check the introduced sequence, each RNAi trigger sequence introduced into the pSP231 vector was amplified by PCR in which TakaRa Ex Taq and PrimeSTAR Max DNA Polymerase (Takara-Bio Inc.) were used, such that a sense strand and an antisense strand were individually amplified (the vector pSP231 is a vector in which a GFP (Green-fluorescent protein gene) expression cassette was inserted into a SacI site of pHellsgate 12 (see the literature: Wesley et al., 2001, Plant J., 27, 581-590) and is a binary vector that can express, with a cauliflower mosaic virus 35S RNA gene promoter, an RNAi sequence formed with a pdk/cat intron located between inverted repeat sequences of the trigger sequence). The PCR products were purified with use of MiniElute (QIAGEN), and then subjected to sequencing. The nucleotide sequences of the RNAi trigger sequences introduced into the pSP231 vector are as represented by SEQ ID NO. 31 (NtREV), SEQ ID NO. 32 (NtBl1), SEQ ID NO. 33 (NtLS), SEQ ID NO. 34 (#15360), and SEQ ID NO. 35 (#07437). Note that in the nucleotide sequences shown in a sequence listing, CACC at the 5' end is omitted.

With use of the pSP231 vector containing each trigger sequence, *Agrobacterium* (*Agrobacterium tumefaciens*) LBA4404 was transformed by electroporation. After it was confirmed by PCR that each RNAi trigger sequence was amplified in LBA4404, the *Agrobacterium* was used for the transformation of tobacco.

(b) Transformation of Tobacco and Collection of Transformed Seeds

With use of the variety MC1 (transformation of NtBl1) or SR-1 (transformation of each of NtREV, NtLS, #15360, and #07437), tobacco was transformed by a common method as described below. A section of a tobacco leaf was infected with the *Agrobacterium* thus transformed, and was cultured in Linsmaier and Skoog medium containing kanamycin, so that calluses were obtained. From the calluses thus obtained, redifferentiated individuals, which are kanamycin-resistant, were obtained. From these redifferentiated individuals, the following individuals were selected: the individual in which (i) intense fluorescence based on GFP in the entire leaf was confirmed and (ii) high-level expression at a spacer portion (PPDK intron) was confirmed. The individuals thus selected (T0 individuals) were transplanted to 9-cm pots, and were cultivated under fixed conditions in a containment greenhouse at 23° C. to 25° C. The T0 individuals were selfed, so that T1 seeds were collected.

(c) Selection of T1 Recombinants

The T1 seeds were aseptically sowed in Linsmaier and Skoog medium, and fluorescence based on GFP of sprout was observed. From a segregation ratio of genotypes ((homo)/hemizygous (hetero) and null segregant (null)) of transgenes, lines in which the number of loci of the transgenes was predicted to be 1 to 2 were selected.

By qPCR in which total RNA isolated from a leaf or root of T1 line was used, the expression level of target genes was determined. The expression level was evaluated as a ratio of the expression level in homo lines to the expression level in null lines. From the homo lines and null lines, lines in which the ratio above is small (i.e., the degree to which the expressions of the target genes are suppressed is large) were selected. The details of the qPCR are as follows.

The primers and probes of the qPCR were designed with use of dedicated software (PrimerExpress, ABI) or Sigma-Aldrich Japan was requested to perform such designing. As described in (b) of 1-1., cDNA was synthesized from total RNA isolated from the leaf or root. The qPCR was performed with use of (i) cDNA which was 2 to 5-fold diluted, (ii) the primers obtained as described above, and (iii) Taq Man Fast Advanced Master Mix (ABI). As a quantification control, eukaryotic elongation factor-1a gene (accession No. AF120093, efla) was amplified. As a quantification probe, a combination of reporter dye and quencher (FAM-TAMURA (gene to be analyzed) and VIC-TAMURA (control)) was used. The sequences of the primers and probes for the qPCR are shown below. In the sequence targeting each gene below, the first is a forward primer, the second is a reverse primer, and the third is a probe.

```
(NtLS)
NtLS_qFW1:
                                   (SEQ ID NO. 236)
CCGGTACTGGAAATGACCTTGA

NtLS_qRV1:
                                   (SEQ ID NO. 131)
ATCTAAGGCCTAAAGAGTGAGCAAAT

NtLS_P1:
                                   (SEQ ID NO. 237)
CCCTTCGTAGAACCGGAGATCGTTTAGCT

(NtB11)
NtB11_qFW1:
                                   (SEQ ID NO. 238)
GAGAAAACAAATGTAAGTACACCATTAGG

NtB11_qRV1:
                                   (SEQ ID NO. 239)
GAAAAAGTTTGAATCTTCTTGCCAA

NtB11_P1:
                                   (SEQ ID NO. 240)
GATTTGAAAGGGCGTTTGGGTATGGG

(NtREV)
NtREV1_qFW1:
                                   (SEQ ID NO. 241)
TCTCCAGGCTCCCCTGAAG
```

-continued

```
NtREV1_qRV1:
                                   (SEQ ID NO. 242)
TGTCCCCATGTGATAACTGTAGCT

NtREV1_P1:
                                   (SEQ ID NO. 243)
AACGTTGTCGCACTGGATCTGCCA

(#07437)
Nt_07437_1-F:
                                   (SEQ ID NO. 244)
ATGGCTACCCTACAAGCTTGAAA

Nt_07437_1-R:
                                   (SEQ ID NO. 245)
TTGCCAATGTGTAGTTGTTGTGG

Nt_07437_1-P:
                                   (SEQ ID NO. 246)
TCTTAACACAGCAACATCAGCAGAAGCAGC

(#15360)
Nt_15360_48821-F:
                                   (SEQ ID NO. 247)
ACTCCTGTTGAGAATGCACAAATAA

Nt_15360_48821-R:
                                   (SEQ ID NO. 248)
CCAGAAATATTAGTTTCTTCTCCTTGG

Nt_15360_48821-P:
                                   (SEQ ID NO. 249)
CCATCTGAAAATGCATAACCTGGAAGCTGC.
```

As a result of the selection above, the individuals to be subjected to test for evaluation of axillary bud were selected per target gene whose expression is suppressed. The individuals are as follows.

NtREV: 3 individuals of T1 line, selected from 10 individuals of T1 line whose expression level was evaluated, which has one locus and exhibits remarkable expression suppression (line number: 3, 8, and 14)

NtBl1: 3 individuals of T1 line, selected from 15 individuals of T1 line whose expression level was evaluated, which has one locus and exhibits remarkable expression suppression (line number: 6, 9, and 12)

NtLS: 3 individuals of T1 line, selected from 24 individuals of T1 line whose expression level was evaluated, which has one locus and exhibits remarkable expression suppression (line number: 10, 15, and 19)

#15360: 3 individuals of T1 line, selected from 22 individuals of T1 line whose expression level was evaluated, which has one or two loci and exhibits remarkable expression suppression (line number: 11, 14, and 17)

#07437: 3 individuals of T1 line, selected from 20 individuals of T1 line whose expression level was evaluated, which has one locus and exhibits remarkable expression suppression (line number: 1, 10, and 22)

The ratios of expression levels of the target genes in the T1 family of each recombinant (where the expression level in null lines is set to 1) are as follows.

NtREV—line 3: 0.56, line 8: 0.57, line 14: 0.74
NtBl1—line 6: 0.33, line 9: 0.35, line 12: 0.25
NtLS—line 10: 0.50, line 15: 0.58, line 19: 0.43
#15360—line 11: 0.07, line 14: 0.10, line 17: 0.08
#07437—line 1: 0.24, line 10: 0.17, line 22: 0.13

(2-2. Evaluation of Axillary Buds in Greenhouse)

The seeds of T1 line of each recombinant obtained as described above were sowed and cultivated in a containment greenhouse or Koitotron (Koito Manufacturing Co., Ltd.). The conditions of the containment greenhouse were set so that the temperature was maintained at room temperature of 23° C. to 25° C., and the day length was that of a natural day. The conditions of Koitotron were set so that the day length was 12 hours, and the temperature was 25° C. (light period) and 18° C. (dark period). The individuals were cultivated in 15-cm pots which were filled with rich soil having a volume of 500 mL/pot. The composition of the rich soil was as follows. Compost: 40 L, wild soil: 30 L, Akadama soil (small): 10 L, Akadama soil (medium): 10 L, vermiculite: 10 L, fertilizer (S625): 1000 g.

Topping was performed when 12 to 13 true leaves were produced during a period starting at budding and ending before flowering. The target selected to be evaluated was an axillary bud which was produced in a fourth true leaf from the bottom of an aerial part or a higher leaf. Each week since the topping, the number of axillary buds with a stem having a length of approximately 5 mm or longer was recorded. The axillary buds thus recorded were picked by hand from the base thereof, and the fresh weight (FW) of the axillary buds thus picked was measured. Until the development of new axillary buds was no longer found, the number and weight of axillary buds were measured over substantially 5 times.

First, FIG. 1 shows the results of the evaluation of axillary bud development in the recombinants in which NtREV expression was suppressed (cultivated in the containment greenhouse). All of the 3 homo lines (in FIG. 1, "H" is added after the line number) of the recombinants in which NtREV expression was suppressed showed that the number of secondary axillary buds was statistically significantly decreased in comparison with the corresponding null lines (in FIG. 1, "N" is added after the line number). Of the 3 homo lines, 2 lines produced no secondary axillary buds. Meanwhile, there was no statistically significant difference found between the home lines and the null lines in terms of the number and fresh weight of primary axillary buds, except that the 12 homo lines showed that the number of primary axillary buds was statistically significantly increased in comparison with the corresponding null lines. In FIGS. 2 through 5, what is meant by "N" and "H" is identical to that in FIG. 1.

Figure 2:
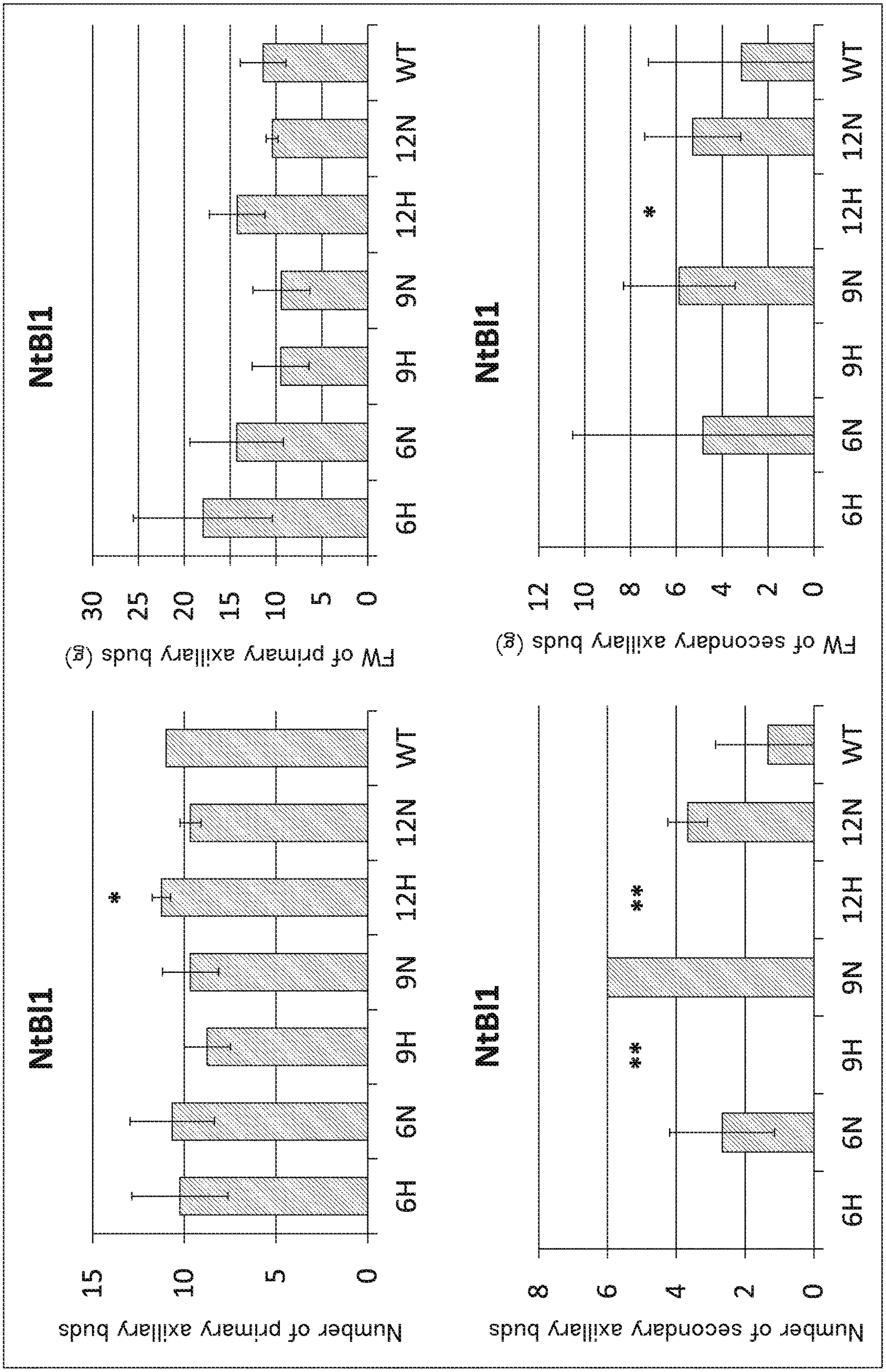
FIG. 2 is a view showing the results of the effects on the development of axillary buds by suppressed expression of NtBl1 gene in accordance with Examples of the present invention.

FIG. 2 shows the results of the evaluation of axillary bud development in the recombinants in which NtBl1 expression was suppressed (cultivated in Koitotron). None of the 3 homo lines of the recombinants in which NtBl1 expression was suppressed produced secondary axillary buds, and the corresponding null lines produced secondary axillary buds. Meanwhile, there was no statistically significant difference found between the home lines and the null lines in terms of the number and fresh weight of primary axillary buds.

Figure 3:
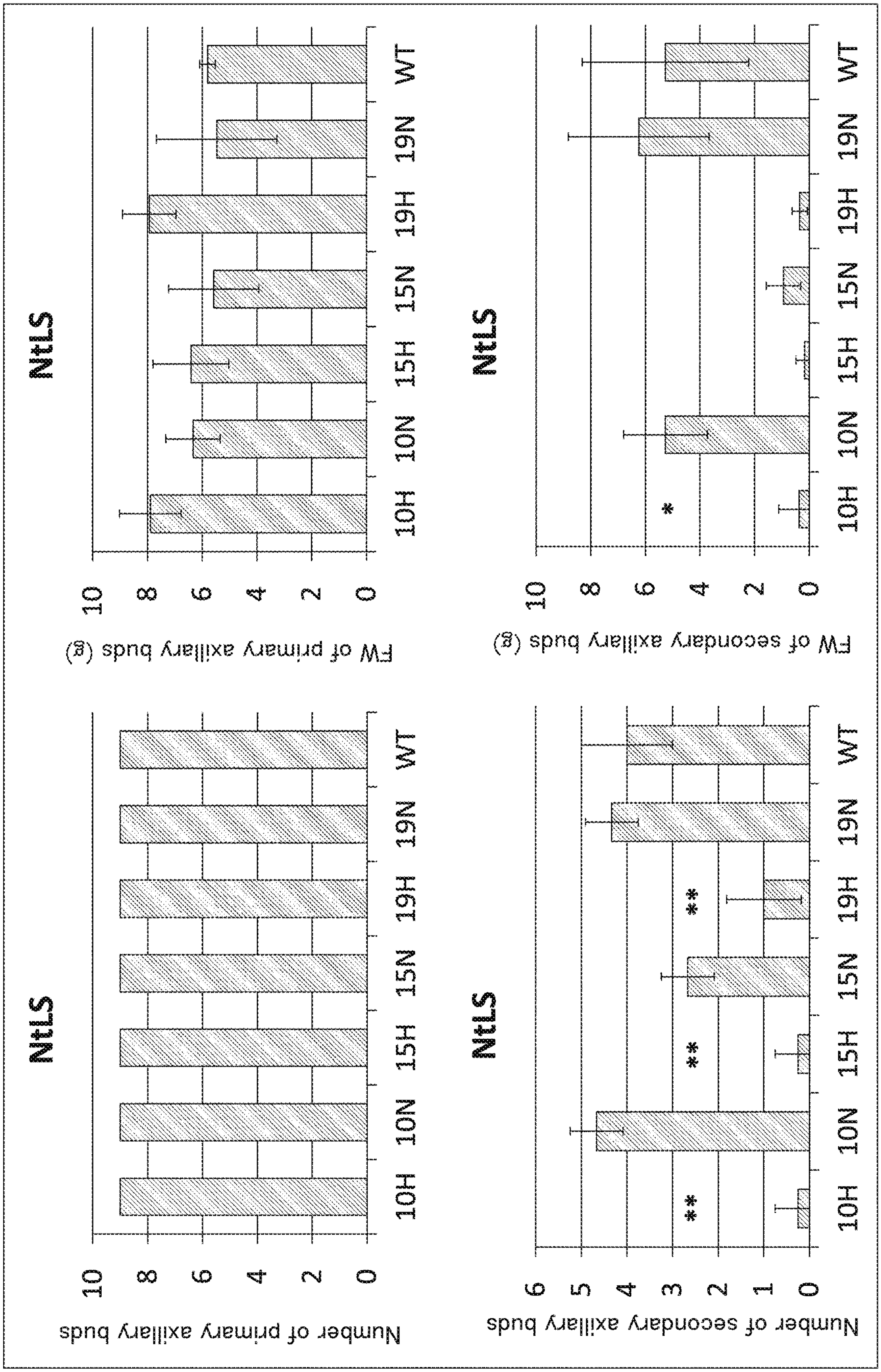
FIG. 3 is a view showing the results of the effects on the development of axillary buds by suppressed expression of NtLS gene in accordance with Examples of the present invention.

FIG. 3 shows the results of the evaluation of axillary bud development in the recombinants in which NtLS expression was suppressed (cultivated in Koitotron). All of the 3 homo lines of the recombinants in which NtLS expression was suppressed showed that the number of secondary axillary buds was statistically significantly decreased in comparison with the corresponding null lines. In addition, 1 homo line showed a statistically significant decrease in fresh weight of secondary axillary buds in comparison with the corresponding null line, and the remaining 2 homo lines showed a decrease in fresh weight although not statistically significant. Meanwhile, there was no statistically significant difference found between the home lines and the null lines in terms of the number and fresh weight of primary axillary buds.

Figure 4:
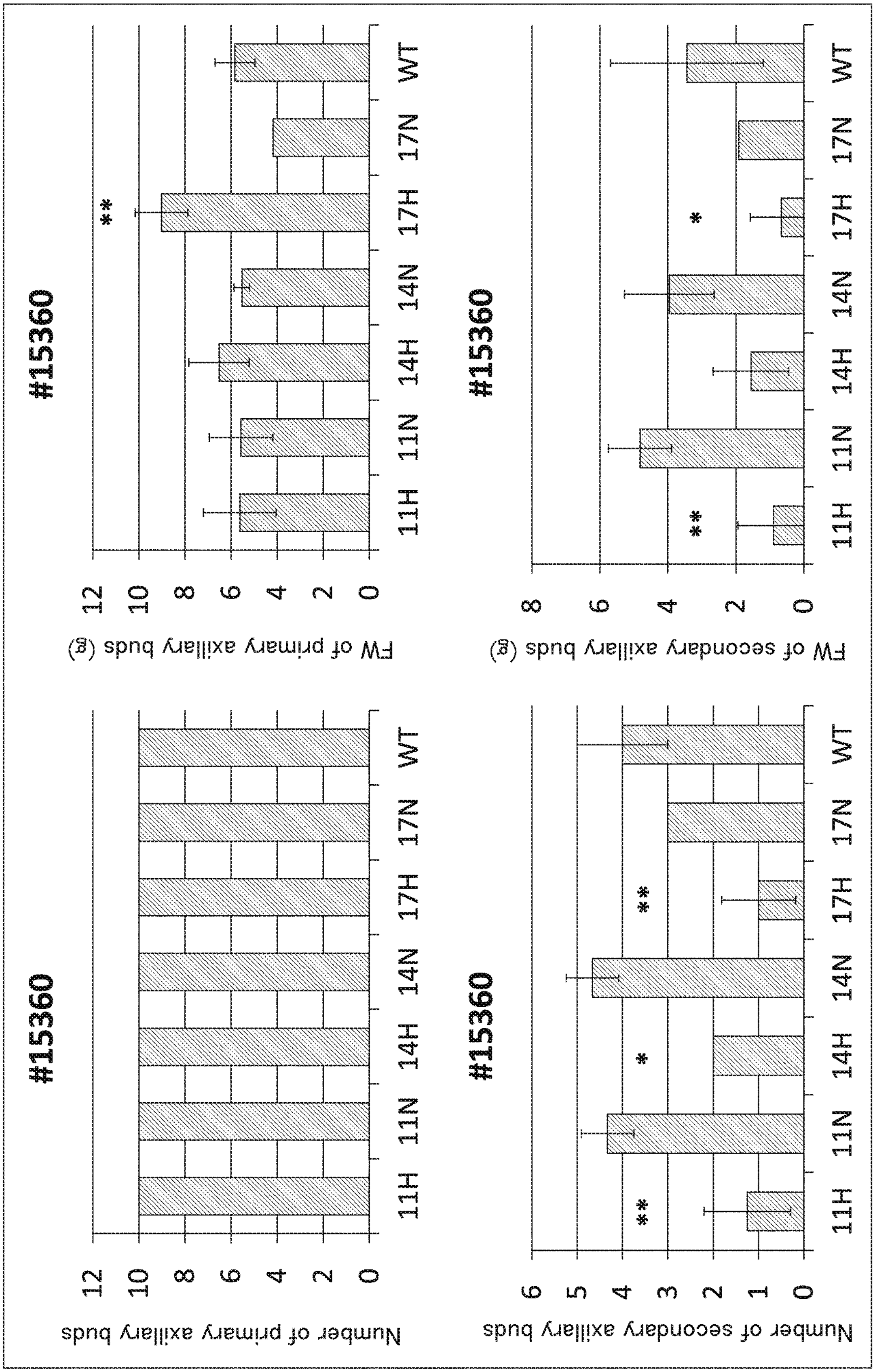
FIG. 4 is a view showing the results of the effects on the development of axillary buds by suppressed expression of #15360 gene in accordance with Examples of the present invention.

FIG. 4 shows the results of the evaluation of axillary bud development in the recombinants in which #15360 expression was suppressed (cultivated in Koitotron). All of the 3 homo lines of the recombinants in which #15360 expression was suppressed showed that the number of secondary axillary buds was statistically significantly decreased in comparison with the corresponding null lines. In addition, 2 homo lines showed a statistically significant decrease in fresh weight of secondary axillary buds in comparison with the corresponding null lines, and the remaining 1 homo line showed a decrease in fresh weight although not statistically significant. Meanwhile, there was no statistically significant difference found between the home lines and the null lines in terms of the number and fresh weight of primary axillary buds, except that the 17 homo lines showed that the fresh weight of primary axillary buds was statistically significantly increased in comparison with the corresponding null lines.

Figure 5:
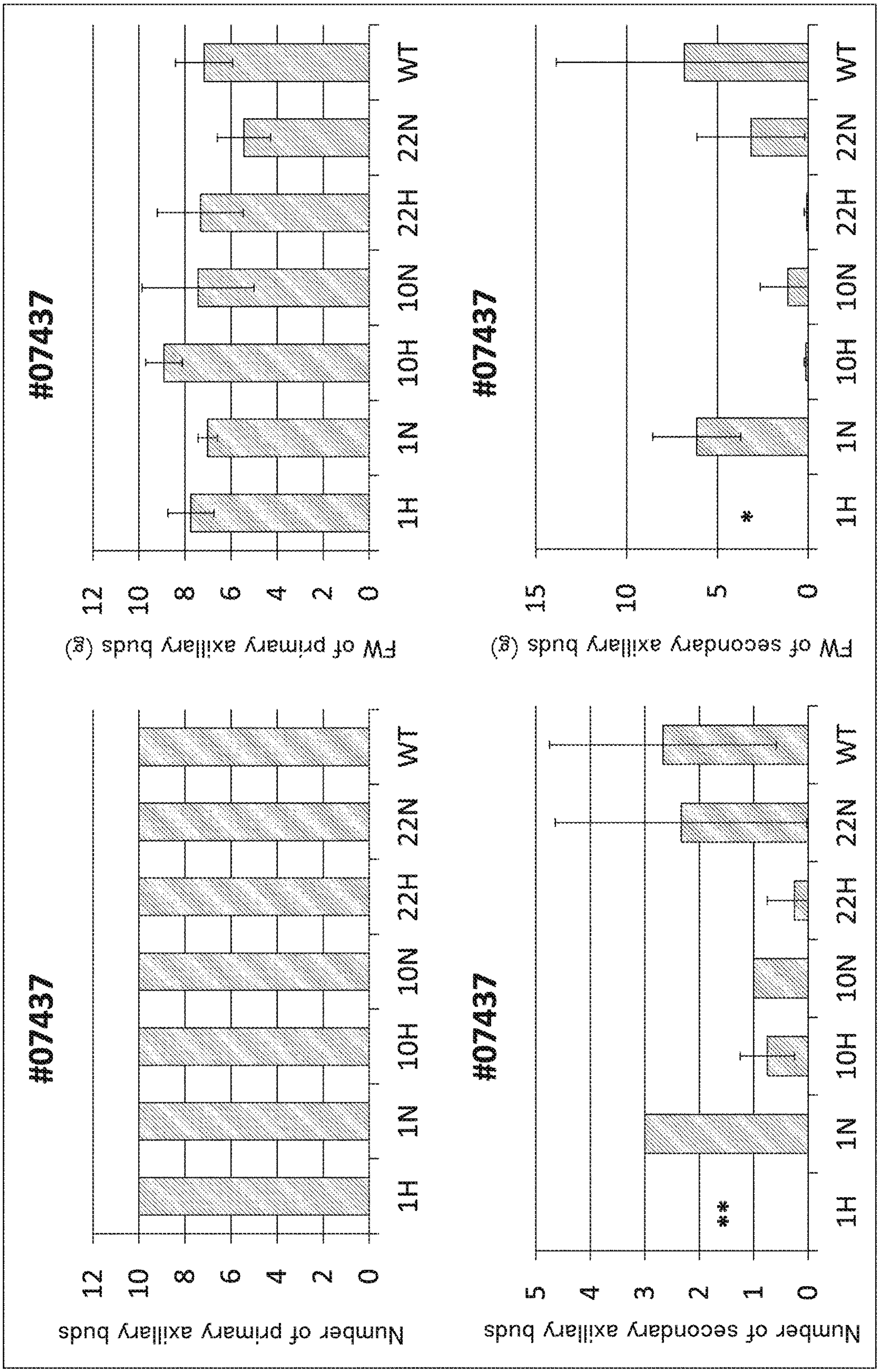
FIG. 5 is a view showing the results of the effects on the development of axillary buds by suppressed expression of #07437 gene in accordance with Examples of the present invention.

FIG. 5 shows the results of the evaluation of axillary bud development in the recombinants in which #07437 expression was suppressed (cultivated in Koitotron). 1 homo line out of the 3 homo lines of the recombinants in which #07437 expression was suppressed showed that the number and fresh weight of secondary axillary buds were statistically significantly decreased in comparison with the corresponding null line. In addition, the remaining 2 homo lines showed a decrease in the number and fresh weight of secondary axillary buds in comparison with the corresponding null lines, although the decrease was not statistically significant. Meanwhile, there was no statistically significant difference found between the home lines and the null lines in terms of the number and fresh weight of primary axillary buds.

From the results above, it was found that the suppressed expression in the 5 target genes can selectively suppress the development of secondary axillary buds without suppressing the development of primary axillary buds.

[3. Confirmation of Effect of Mutation Introduced into Target Gene on Development of Axillary Buds (1)]

(3-1. Mutant Produced by EMS Treatment)

(a) Screening of Mutant

Seeds were subjected to ethylmethane sulfonate (EMS) treatment so that mutant panel (TUM) of tobacco (variety: Tsukuba No. 1) was prepared (Literature: The 2011 Annual Meeting of the Phytopathological Society of Japan, P234, "Construction of mutant panel in *Nicotiana tabacum* L."). This mutant panel consists of (i) a set of seeds (M2 bulk seeds) of selfed mutant progeny obtained from each individual (M1 generation) bred from several thousands of seeds which were subjected to the EMS treatment as a mutagen treatment and (ii) a set of bulk DNA extracted from seedlings of 8 individuals of each line grown from the sown M2 seeds. Mutants having mutations in NtREV or NUS were selected based on the results of performing, with this DNA samples as a template, Single-strand conformation polymorphism (SSCP) analysis of genomes of a mutant library or direct sequencing of PCR amplification fragments. In the SSCP, the target site was amplified by PCR using PCR primers to which fluorescent dye was binding. Then, the amplified fragments were detected with use of a capillary electrophoresis apparatus (ABI 3130x1DNA analyzer). With use of QIAGEN Multiplex PCR Kit (QIAGEN), PCR was performed according to the manual included in the kit. The sequences of the PCR primers are as follows.

```
(NtREV, S genome)
Combination of Nt_in0_F1:
                                   (SEQ ID NO. 250)
TTGGTTTGGGATTTTGAGGTTTGAGG,
and
```

-continued

Nt_ex1_R1:
(SEQ ID NO. 202)
TCCATCACTGATCTAACTAATCCAAG

Combination of Ns_in1_F1:
(SEQ ID NO. 251)
TTTGGAATTGAGGGTGAACATTGTGC,
and

Ns_in2_R1:
(SEQ ID NO. 252)
ACGTTACCATTCGTCTACAGTAAGC

Combination of Ns_in2_F1:
(SEQ ID NO. 253)
CCAATAAACAAGAAACAGATGATGG,
and

Ns_in3_R1:
(SEQ ID NO. 254)
GAATGGACACCATAGACGGAAAGGA

Combination of Ns_in3_F1:
(SEQ ID NO. 255)
TTTCCGTCTATGGTGTCCATTCTCC,
and

Ns_in4_R1:
(SEQ ID NO. 256)
GAGACATGGCAATACTGAATTTTCA

Combination of Ns_in4_F1:
(SEQ ID NO. 152)
GAAAATTCAGTATTGCCATGTC,
and

Ns_in6_R1:
(SEQ ID NO. 257)
AGCCTACGTGAAGATTGATGAGAAG (NtREV, T genome)
Combination of Nt_in0_F1:
(SEQ ID NO. 250)
TTGGTTTGGGATTTTGAGGTTTGAGG,
and Nt_ex1_R1:
(SEQ ID NO. 202)
TCCATCACTGATCTAACTAATCCAAG Combination of Nt_in1_F1:
(SEQ ID NO. 258)
TCGATTGGGTTGTATGAGTTAACCGT,
and Nt_in2_R1:
(SEQ ID NO. 259)
GTTACCATAAGCTGTGGAATATCAGG Combination of Nt_in2_F1:
(SEQ ID NO. 260)
AACCAATGGACAAGAAACGGATGGCA,
and Nt_in4_R1:
(SEQ ID NO. 261)
TTTAGCTATCCAGTCAAAGAGGCACG Combination of Nt_in4_F1:
(SEQ ID NO. 155)
AAAAAAATTCAGTATTGCCACGTGC,
and Nt_in6_R1:
(SEQ ID NO. 262)
AGCCTACGTGAAGATTGATGAGAAA (NtLS, S genome)
Combination of LS_F2_seq:
(SEQ ID NO. 134)
ATTTCCCCTCCTCCATCATTG, -continued and

LS1-R1:
(SEQ ID NO. 209)
CAACAACATTAGATGGTGTCAAG

Combination of LS1-F2:
(SEQ ID NO. 136)
CTTGACACCATCTAATGTTGTTG,
and

NtLS_QPCR_RV1:
(SEQ ID NO. 131)
ATCTAAGGCCTAAAGAGTGAGCAAAT

Combination of LS1,2-F3:
(SEQ ID NO. 263)
TTCGTAGAACCGGAGATCGT,
and

LS1,2_R3:
(SEQ ID NO. 264)
GCAAAGTTGCTTCCAATGAAT

Combination of LS1,2_F4:
(SEQ ID NO. 206)
GTGGAGGCTTTGGATTATTATG,
and

N.t_LS_TRV_R2:
(SEQ ID NO. 158)
GAAGACCTCTTTGTCCTTCACCATGCAG (NtLS, T genome)
Combination of LS_F2_seq:
(SEQ ID NO. 134)
ATTTCCCCTCCTCCATCATTG,
and

LS2-R1:
(SEQ ID NO. 148)
AACATTAGATGATGCATTAGGTGT

Combination of LS2-F2:
(SEQ ID NO. 132)
ACACCTAATGCATCATCTAATGTT,
and

NtLS_QPCR_RV1:
(SEQ ID NO. 131)
ATCTAAGGCCTAAAGAGTGAGCAAAT

Combination of LS1,2-F3:
(SEQ ID NO. 263)
TTCGTAGAACCGGAGATCGT,
and

LS1,2_R3:
(SEQ ID NO. 264)
GCAAAGTTGCTTCCAATGAAT

Combination of LS1,2_F4:
(SEQ ID NO. 206)
GTGGAGGCTTTGGATTATTATG,
and

N.t_LS_TRV_R2:
(SEQ ID NO. 158)
GAAGACCTCTTTGTCCTTCACCATGCAG.

The sequence of the genes into which the mutation was introduced was identified by (i) cloning PCR amplification fragments obtained from the genomes of mutants of M2 generation and (ii) determining the nucleotide sequence of fragments of the clones. The differences between polypeptide, which were expressed by the genes into which mutations was introduced and wild-type protein (WT), are as follows.

The polypeptide (MT, Ns1630 mutant, SEQ ID NO. 36) expressed by NtREV into which a mutation at an S genome was introduced had the following difference from the wild-type protein.

Mt: 111aa, Wt: 838aa

The full length was shortened to 111aa due to the fact that 112th glutamine (Q) was changed to a stop codon.

The polypeptide (Nt1605 mutant, SEQ ID NO. 37) expressed by NtREV into which a mutation at a T genome was introduced had the following difference from the wild-type protein.

Mt: 116aa, Wt: 839aa

The full length was shortened to 116aa due to the fact that 117th glutamine (Q) was changed to a stop codon.

The polypeptide (Nt5850 mutant, SEQ ID NO. 38) expressed by NtREV into which a mutation at a T genome was introduced had the following difference from the wild-type protein.

Mt: 68aa, Wt: 839aa

The full length was shortened to 68aa due to the fact that 69th glutamine (Q) was changed to a stop codon.

The polypeptide (Nt1145 mutant, SEQ ID NO. 39) expressed by NtLS into which a mutation at a T genome was introduced had the following difference from the wild-type protein.

Mt: 398aa, Wt: 410aa

The full length was shortened to 398aa due to the fact that 399th glutamine (Q) was changed to a stop codon.

The polypeptide (Nt1025 mutant, SEQ ID NO. 40) expressed by NtLS into which a mutation at a T genome was introduced had the following difference from the wild-type protein.

Mt: 145aa, Wt: 410aa

The full length was shortened to 145aa due to the fact that 146th glutamine (Q) was changed to a stop codon.

The polypeptide (Ns369 mutant, SEQ ID NO. 41) expressed by NtLS into which a mutation at an S genome was introduced had the following difference from the wild-type protein.

Mt: 163aa, Wt: 407aa

The full length was shortened to 163aa due to the fact that 164th glutamine (Q) was changed to a stop codon.

(b) Selection of Desired Mutant from M2 Mutant Population

From the M2 mutant population predicted to have mutations in the target genes, mutants ($T^+S^+$) homozygously having a mutation in each target gene in both a T genome and an S genome and mutants ($T^-S^-$) having no mutation in each target gene in both a T genome and an S genome were prepared according to the following procedure.

First, the following 4 groups were selected from the M2 mutant population:

M2 mutants ($T^+$) homozygously having mutations in target gene in T genome

M2 mutants ($S^+$) homozygously having mutations in target gene in S genome

M2 mutants ($T^-$) having no mutation in target gene in T genome

M2 mutants ($S^-$) having no mutation in target gene in S genome

Then, F1 line prepared by crossing $T^+$ and $S^+$ was selfed, so that target F2 mutants ($T^+S^+$) were prepared. $T^-S^-$ was likewise prepared.

In the procedure above, Cycleave PCR method was carried out as described in the next paragraph in order to determine the presence/absence of a mutation on a genome. Genomic DNA which was extracted by use of a simple extraction method was used as a template in the Cycleave PCR for checking a mutation of NtREV gene. Fragments amplified by PCR from genomic DNA (each of T genome and S genome) were 300-fold to 500-fold diluted and then used as templates in the Cycleave PCR for checking a mutation of NtLS gene. The PCR was performed with use of Tks Gflex (trademark) DNA polymerase (Takara-Bio Inc.). The reaction conditions and primers of the PCR are as follows.

(Reaction Conditions)

30 seconds at 94° C.

35 cycles while each cycle includes 10 seconds at 98° C., 15 seconds at 55° C., and 90 seconds at 68° C.

90 seconds at 68° C.

```
(Primers)
T genome
NtLS_prePCR_Ntom_F1:
                                     (SEQ ID NO. 265)
CCCAGACCCCCTTTTCCTCT

NtLS_prePCR_Ntom_R1:
                                     (SEQ ID NO. 266)
AATTTCCCTTATAATTTAACGCC

S genome
NtLS_prePCR_Nsy1_F1:
                                     (SEQ ID NO. 267)
CCCTAGAGAGACCCCTTTTTC

NtLS_prePCR_Nsy1_R1:
                                     (SEQ ID NO. 268)
GGGTTTTAAATTTAACGCCAA.
```

The primers and probes for the Cycleave PCR method (Table 1) were designed with use of Cycleave (registered trademark) PCR Assay Designer (SNPs) which is available on a web page of Takara-Bio Inc. Along with the primers and probes, Cycleave PCR Reaction Mix (Takara-Bio Inc.) was used according to the manual provided by Takara-Bio Inc. to carry out the Cycleave PCR method. PCR reaction was made with use of Applied Biosystems (registered trademark) StepOnePlus (trademark) real-time PCR system (Thermo Fisher Scientific Inc.).

TABLE 2

| Gene | Primer/probe name | Sequence | Genome type |
|---|---|---|---|
| REV | Nt_5850_P2-1Primer F | GTGAATGCCCTATTCTGTC (SEQ ID NO. 269) | T genome |
| | Nt_5850_P2-1Primer R | ATCACTGATCTAACTAATCCAAG (SEQ ID NO. 270) | |
| | Nt_5850_P2-1Probe T-FAM | ctttgatct(A)ct 5'-Eclipse/3'-FAM (SEQ ID NO. 271) | |
| | Nt_5850_P2-1Probe C-HEX | tgatct(G)ctt 5'-Eclipse/3'-HEX (SEQ ID NO. 272) | |
| | Nt_1605_P4-2Primer F | ATTGATGGAGGAGAATGAT (SEQ ID NO. 273) | T genome |
| | Nt_1605_P4-2Primer R | GACAAGATACGTTAAGTGAAA (SEQ ID NO. 274) | |
| | Nt_1605_P4-2Probe T-FAM | acaagct(A)cg 5'-Eclipse/3'-FAM (SEQ ID NO. 275) | |
| | Nt_1605_P4-2Probe C-HEX | caagct(G)cg 5'-Eclipse/3'-HEX | |
| | Ns_1630_P3-1Primer F | CCATTTCAGGTGTCGAG (SEQ ID NO. 276) | S genome |

TABLE 2-continued

| Gene | Primer/probe name | Sequence | Genome type |
|---|---|---|---|
| | Ns_1630_P3-1Primer R | ACGTTACCATTCGTCTACAG (SEQ ID NO. 277) | |
| | Ns_1630_P3-1Probe T-FAM | tt(A)caagcga 5'-Eclipse/3'-FAM (SEQ ID NO. 278) | |
| | Ns_1630_P3-1Probe C-HEX | gC(a)aaaacag 5'-Eclipse/3'-HEX (SEQ ID NO. 279) | |
| LS | 369_Ns-1Primer F | TCCCTAAACCAAGTGACTCC (SEQ ID NO. 280) | S genome |
| | 369_Ns-1Primer R | GGTATCAAGGTCATTTCCAG (SEQ ID NO. 281) | |
| | 369_Ns-1Probe T-FAM | tgT(a)agcacta 5'-Eclipse/3'-FAM (SEQ ID NO. 282) | |
| | 369_Ns-1Probe C-HEX | gC(a)agcact 5'-Eclipse/3'-HEX | |
| | L6_1145-3Primer F | AGAGGATGACAGTGGAGCAA (SEQ ID NO. 283) | T genome |
| | L6_1145-3Primer R | TAACGCCAAGAAGATATGGAA (SEQ ID NO. 284) | |
| | L6_1145-3Probe T-FAM | ggT(a)aaatcaac 5'-Eclipse/3'-FAM (SEQ ID NO. 285) | |
| | L6_1145-3Probe C-HEX | ggC(a)aaatca 5'-Eclipse/3'-HEX (SEQ ID NO. 286) | |
| | 1025_1547-3Primer F | GTTGAAAGTTCAAATGATTCAG (SEQ ID NO. 287) | T genome |
| | 1025_1547-3Primer R | GAGGAGGGTAACGATCAG (SEQ ID NO. 288) | |
| | 1025_1547-3Probe T-FAM | gcttgttA(g)tt 5'-Eclipse/3'-FAM (SEQ ID NO. 289) | |
| | 1025_1547-3Probe C-HEX | cttgttG(g)tta 5'-Eclipse/3'-HEX (SEQ ID NO. 290) | |

(c) Evaluation of Axillary Buds in Field

Cultivation in Field

In the field of Leaf Tobacco Research Center, during an ordinary cultivation period (sowing in March and planting in April), each line of the mutants was cultivated by a high-ridge, mulch-cultivation method under the following conditions. ridge length: 16 m, ridge intervals: 120 cm, planting distance: 43 cm, and the number of plan per ridge: 37. 1 ridge was assigned for cultivation of 1 line, and, one month after transplant, 10 to 15 individuals showing approximately identical growth were determined by appearance and were preliminarily selected. Then, 10 individuals from those were subjected to a subsequent examination. During the examination, no agrochemicals for suppressing axillary buds (such as Contact) was used at all.

Determination of Flowering Time

During flowering time, the number of above-ground leaves was determined. Immediately before topping, predicted flowering time was determined. By performing topping through cutting off 1 to 4 leaves below the first flower branch, the numbers of above-ground leaves were made the same among lines to be compared and evaluated.

Evaluation of Development of Axillary Buds

Over the total of 7 times on the day of topping and each week since the topping, the number of axillary buds with a stem having a length of approximately 5 mm was recorded. The axillary buds thus recorded were picked by hand from the base thereof, and the fresh weight (FW) of the axillary buds thus picked was measured. The primary axillary buds, the secondary axillary buds, and the tertiary axillary buds were individually measured and recorded. The measurement records are then put together.

Figure 6:
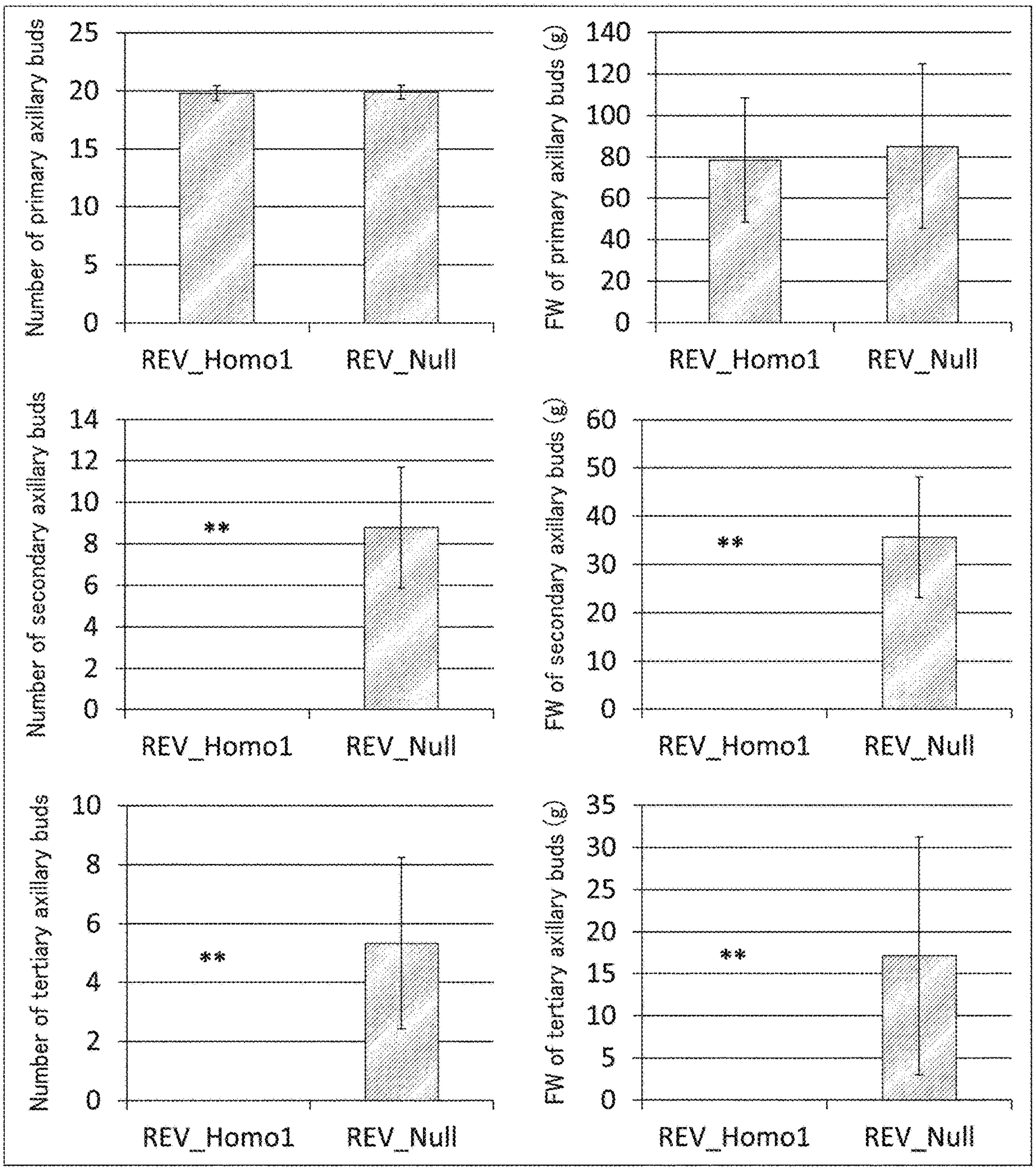
FIG. 6 is a view showing the results of the effects on the development of axillary buds by mutations introduced into NtREV genes in accordance with Examples of the present invention.

FIG. 6 shows the results of the evaluation of the development of axillary buds of mutants in which mutations were introduced into NtREV. The NtREV_Homo line ($T^{+}S^{+}$) did not produce secondary axillary buds or tertiary axillary buds. The NtREV Nul1 line ($T^{-}S^{-}$) produced secondary axillary buds and tertiary axillary buds (there is a statistically significant difference in comparison with $T^{+}S^{+}$). Meanwhile, there was no statistically significant difference found between the two lines in terms of the number and fresh weight of primary axillary buds.

Figure 7:
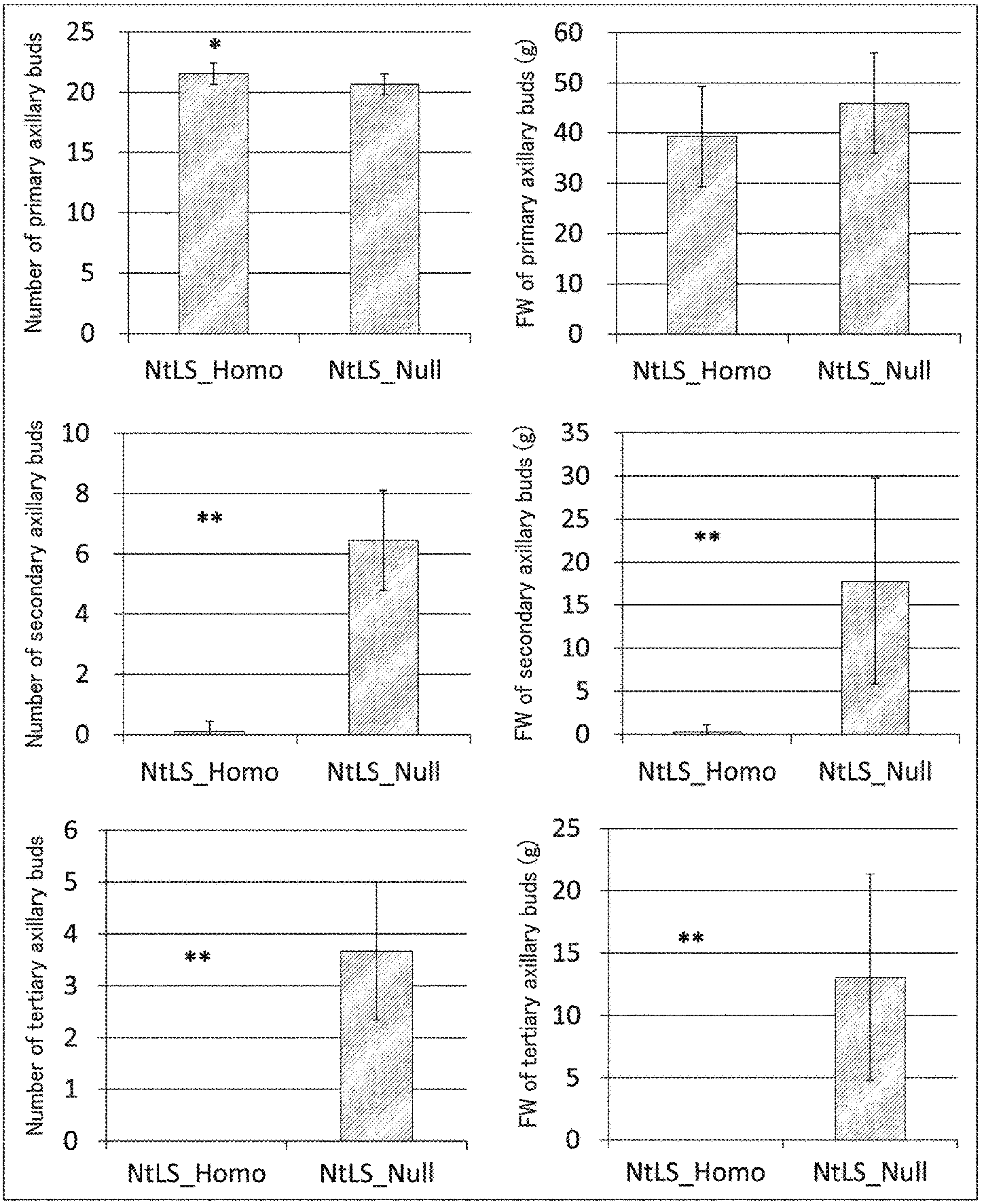
FIG. 7 is a view showing the results of the effects on the development of axillary buds by mutations introduced into NtLS genes in accordance with Examples of the present invention.

FIG. 7 shows the results of the evaluation of the development of axillary buds of mutants in which mutations were introduced into NtLS. The NtLS_Homo line ($T^{+}S^{+}$) showed that there was a statistically significant decrease in the number and fresh weight of secondary axillary buds in comparison with the NtLS_Nul1 line ($T^{-}S^{-}$). In addition, the NtLS_Homo line ($T^{+}S^{+}$) did not produce tertiary axillary buds (there is a statistically significant difference in comparison with the NtLS_Nul1 line). Meanwhile, there was no statistically significant difference found between the two lines in terms of the number and fresh weight of primary axillary buds.

The results above indicate that in the mutants of NtREV and NtLS also, the development of secondary axillary buds (and tertiary axillary buds) was selectively suppressed as in the case of suppression of gene expression.

(3-3. Mutant of NtBl1 Produced by CRISPR/Cas9 System)

(a) Preparation for Transformation

Figure 8:
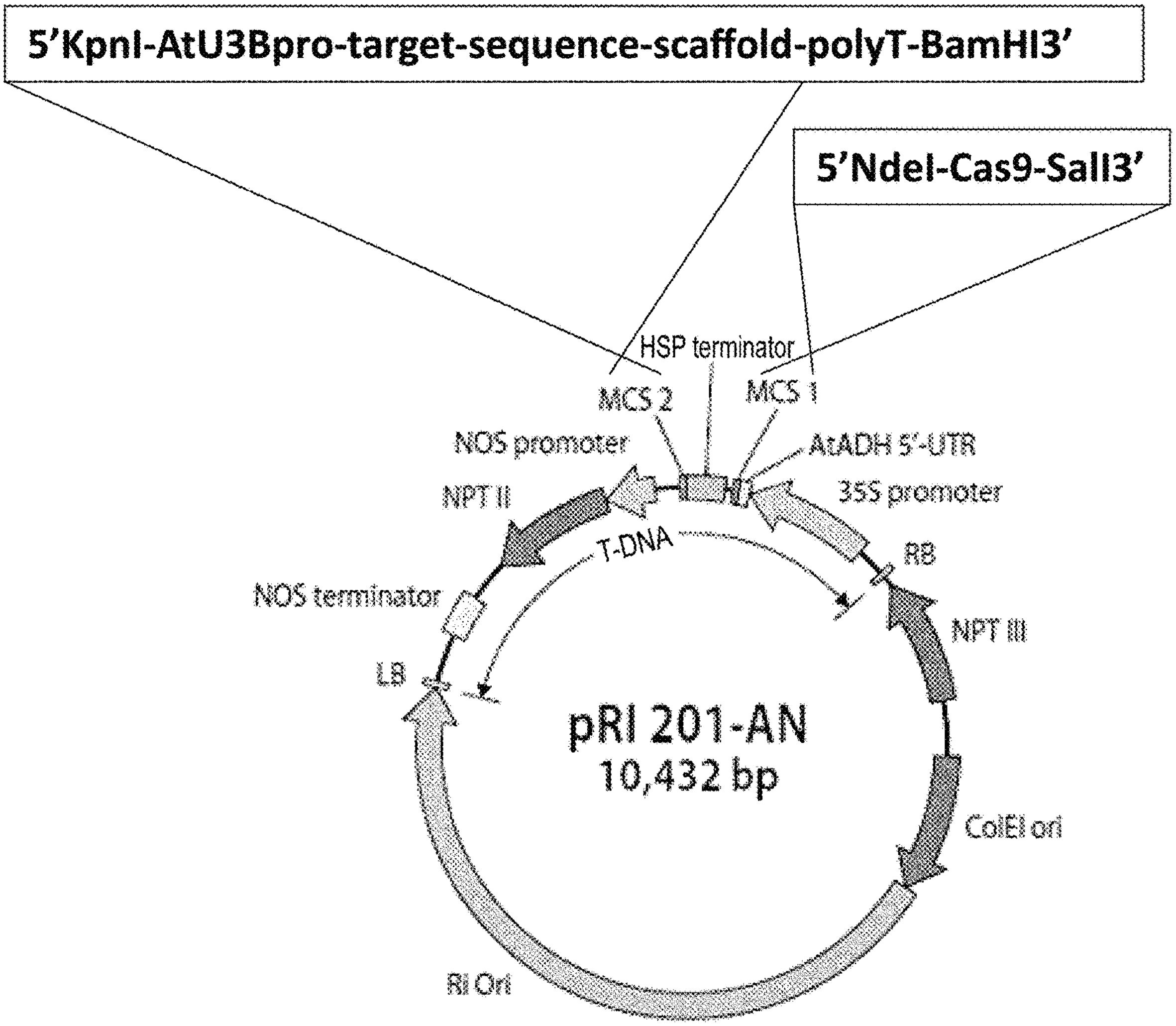
FIG. 8 is a view schematically illustrating a construction of a vector used for introducing a mutation into NtBl1 gene by CRISPR/Cas9 system.

As a vector for transforming *Agrobacterium*, a binary vector pRI-201-AN (Takara-Bio Inc.) was used. Between NdeI-SalI of pRI-201-AN, pcoCas9 (Reference 2) which had been subjected to codon optimization for plants was introduced. Between KpnI-BamHI, a sgRNA expression cassette was introduced. As a promoter for guide sequence $GN_{20}GG$, AtU6-1 (Reference 3) was used. As a promoter for guide sequence $AN_{20}GG$, AtU3B (Reference 4) was used. As a scaffold-polyT sequence, the sequence reported in Reference 2 was used. A diagram of the constructed vector is shown in FIG. 8. (In FIG. 8, the target sequence is the guide sequence described herein.) Specifically, the sgRNA expression cassette was designed so that the guide sequence excluding PAM sequence (NGG) at 3' end is inserted between the promoter and the scaffold-polyT sequence. Life Technologies Corporation was entrusted with synthesis, through GeneArt (registered trademark) Strings (trademark) DNA Fragments, of sgRNA expression cassette in which KpnI site and BamHI site are added to 5' end and 3' end, respectively (Chem. 1). Cas9, in which NdeI site and SalI are added to 5' end and 3' end, respectively, was obtained through entrusting Takara-Bio Inc. with synthesis of the Cas9 (Chems. 2 and 3).

[Chem. 1]

(SEQ ID NO. 291)

aattggtaccTTTACTTTAAATTTTTTCTTATGCAGCCTGTGATGGATAAC

TGAATCAAACAAATGGCGTCTGGGTTTAAGAAGATCTGTTTTGGCTATGTT

GGACGAAACAAGTGAACTTTTAGGATCAACTTCAGTTTATATATGGAGCTT

ATATCGAGCAATAAGATAAGTGGGCTTTTTATGTAATTTAATGGGCTATCG

TCCATAGATTCACTAATACCCATGCCCAGTACCCATGTATGCGTTTCATAT

-continued

AAGCTCCTAATTTCTCCCACATCGCTCAAATCTAAACAAATCTTGTTGTAT

ATATAACACTGAGGGAGCAACATTGGTCacaatgatatcaagaattacGTT

TTAGAGCTAGAAATAGCAAGTTAAAATAAGGCTAGTCCGTTATCAACTTGA

AAAAGTGGCACCGAGTCGGTGCTTTTTTTggatccaatt

The underlined portion indicates the guide sequence. The portion upstream to the underlined portion indicates the AtU3B promoter sequence. The portion downstream to the underlined portion indicates the scaffold-polyT sequence. The lower case letters at the terminus indicate restriction enzyme sequences of KpnI and BamHI.

[Chem. 2]
Cas9 sequence (SEQ ID NO. 292)

catATGGATTACAAGGATGATGATGATAAGGATTACAAGGATGATGATGAT

AAGATGGCTCCAAAGAAGAAGAGAAAGGTTGGAATCCACGGAGTTCCAGCT

GCTGATAAGAAGTACTCTATCGGACTTGACATCGGAACCAACTCTGTTGGA

TGGCCTGTTATCACCGATGAGTACAAGGTTCCATCTAAGAAGTTCAAGGTT

CTTGGAAACACCGATAGACACTCTATCAAGAAGAACCTTATCGGTGCTCTT

CTTTTCGATTCTGGAGAGACCGCTGAGGCTACCAGATTGAAGAGAACCGCT

AGAAGAAGATACACCAGAAGAAAGAACAGAATCTGCTACCTTCAGGAAATC

TTCTCTAACGAGATGGCTAAGGTTGATGATTCTTTCTTCCACAGACTTGAG

GAGTCTTTCCTTGTTGAGGAGGATAAGAAGCACGAGAGACACCCAATCTTC

GGAAACATCGTTGATGAGGTTGCTTACCACGAGAAGTACCCAACCATCTAC

CACCTTAGAAAGAAGTTGGTTGATTCTACCGATAAGGCTGATCTTAGACTT

ATCTACCTTGCTCTTGCTCACATGATCAAGTTCAGAGGACACTTCCTTATC

GAGGGAGACCTTAACCCAGATAACTCTGATGTTGATAAGTTGTTCATCCAG

CTTGTTCAGACCTACAACCAGCTTTTCGAGGAGAAACCCAATCAACGCTTC

TGGAGTTGATGCTAAGGCTATCCTTTCTGCTAGATTTCTAAGTCTCGTAGA

CTTGAGAACCTTATCGCTCAGCTTCCAGGAGAGAAGAAGAACGGACTTTTC

GGAAACCTTATCGCTCTTTCTCTTGGACTTACCCCAAACTTCAAGTCTAAC

TTCGATCTTGCTGAGGATGCTAAGTTGCAGCTTTCTAAGGATACCTACGAT

GATGATCTTGATAACCTTCTTGCTCAGATCGGAGATCAGTACGCTGATCTT

TTCCTTGCTGCTAAGAACCTTTCTGATGCTATCCTTCTTTCTGACATCCTT

AGAGTTAACACCGAGATCACCAAGGCTCCACTTTCTGCTTCTATGATCAAG

AGATACGATGAGCACCACCAGGATCTTACCCTTTTGAAGGCTCTTGTTAGA

CAGCAGCTTCCAGAGAAGTACAAGGAAATCTTCTTCGATCAGTCTAAGAAC

GGATACGCTGGATACATCGATGGAGGAGCTTCTCAGGAGGAGTTCTACAAG

TTCATCAAGCCAATCCTTGAGAAGATGGATGGAACCGAGGAGCTTCTTGTT

AAGTTGAACAGAGAGGATCTTCTTAGAAAGCAGAGAACCTTCGATAACGGA

TCTATCCCACACCAGATCCACCTTGGAGAGCTTCACGCTATCCTTCGTAGA

CAGGAGGATTTCTACCCATTCTTGAAGGATAACAGAGAGAAGATCGAGAAG

ATCCTTACCTTCAGAATCCCATACTACGTTGGACCACTTGCTAGAGGAAAC

TCTCGTTTCGCTTGGATGACCAGAAAGTCTGAGGAGACCATCACCCCTTGG

-continued

AACTTCGAGGAGGTAAGTTTCTGCTTCTACCTTTGATATATATATAATAAT

TATCATTAATTAGTAGTAATATAATATTTCAAATATTTTTTTCAAAATAAA

AGAATGTAGTATATAGCAATTGCTTTTCTGTAGTTTATAAGTGTGTATATT

TTAATTTATAACTTTTCTAATATATGACCAAAATTTGTTGATGTGCAGGTT

GTTGATAAGGGAGCTTCTGCTCAGTCTTTCATCGAGAGAATGACCAACTTC

GATAAGAACCTTCCAAACGAGAAGGTTCTTCCAAAGCACTCTCTTCTTTAC

GAGTACTTCACCGTTTACAACGAGCTTACCAAGGTTAAGTACGTTACCGAG

GGAATGAGAAAGCCAGCTTTCCTTTCTGGAGAGCAGAAGAAGGCTATCGTT

GATCTTCTTTTCAAGACCAACAGAAAGGTTACCGTTAAGCAGTTGAAGGAG

GATTACTTCAAGAAGATCGAGTGCTTCGATTCTGTTGAAATCTCTGGAGTT

GAGGATAGATTCAACGCTTCTCTTGGAACCTACCACGATCTTTTGAAGATC

ATCAAGGATAAGGATTTCCTTGATAACGAGGAGAACGAGGACATCCTTGAG

GACATCGTTCTTACCCTTACCCTTTTCGAGGATAGAGAGATGATCGAGGAG

AGACTCAAGACCTACGCTCACCTTTTCGATGATAAGGTTATGAAGCAGTTG

AAGAGAAGAAGATACACCGGATGGGGTAGACTTTCTCGTAAGTTGATCAAC

GGAATCAGAGATAAGCAGTCTGGAAAGACCATCCTTGATTTCTTGAAGTCT

GATGGATTCGCTAACAGAAACTTCATGCAGCTTATCCACGATGATTCTCTT

ACCTTCAAGGAGGACATCCAGAAGGCTCAGGTTTCTGGACAGGGAGATTCT

CTTCACGAGCACATCGCTAACCTTGCTGGATCTCCAGCTATCAAGAAGGGA

ATCCTTCAGACCGTTAAGGTTGTTGATGAGCTTGTTAAGGTT

The sequence continues to the next page.

[Chem. 3]

ATGGGTAGACACAAGCCAGAGAACATCGTTATCGAGATGGCTAGAGAGAAC

CAGACCACCCAGAAGGGACAGAAGAACTCTCGTGAGAGAATGAAGAGAATC

GAGGAGGGAATCAAGGAGCTTGGATCTCAAATCTTGAAGGAGCACCCAGTT

GAGAACACCCAGCTTCAGAACGAGAAGTTGTACCTTTACTACCTTCAGAAC

GGAAGAGATATGTACGTTGATCAGGAGCTTGACATCAACAGACTTTCTGAT

TACGATGTTGATCACATCGTTCCACAGTCTTTCTTGAAGGATGATTCTATC

GATAACAAGGTTCTTACCCGTTCTGATAAGAACAGAGGAAAGTCTGATAAC

GTTCCATCTGAGGAGGTTGTTAAGAAGATGAAGAACTACTGGAGACAGCTT

CTTAACGCTAAGTTGATCACCCAGAGAAAGTTCGATAACCTTACCAAGGCT

GAGAGAGGAGGACTTTCTGAGCTTGATAAGGCTGGATTCATCAAGAGACAG

CTTGTTGAGACCAGACAGATCACCAAGCACGTTGCTCAGATCCTTGATTCT

CGTATGAACACCAAGTACGATGAGAACGATAAGTTGATCAGAGAGGTTAAG

GTTATCACCTTGAAGTCTAAGTTGGTTTCTGATTTCAGAAAGGATTTCCAG

TTCTACAAGGTTAGAGAGATCAACAACTACCACCACGCTCACGATGCTTAC

CTTAACGCTGTTGTTGGAACCGCTCTTATCAAGAAGTACCCAAAGTTGGAG

TCTGAGTTCGTTTACGGAGATTACAAGGTTTACGATGTTAGAAAGATGATC

GCTAAGTCTGAGCAGGAGATCGGAAAGGCTACCGCTAAGTACTTCTTCTAC

TCTAACATCATGAACTTCTTCAAGACCGAGATCACCCTTGCTAACGGAGAG

-continued

```
ATCAGAAAGAGACCACTTATCGAGACCAACGGAGAGACCGGAGAGATCGTT

TGGGATAAGGGAAGAGATTTCGCTACCGTTAGAAAGGTTCTTTCTATGCCA

CAGGTTAACATCGTTAAGAAAACCGAGGTTCAGACCGGAGGATTCTCTAAG

GAGTCTATCCTTCCAAAGAGAAACTCTGATAAGTTGATCGCTAGAAAGAAG

GATTGGGACCCAAAGAAGTACGGAGGATTCGATTCTCCAACCGTTGCTTAC

TCTGTTCTTGTTGTTGCTAAGGTTGAGAAGGGAAAGTCTAAGAAGTTGAAG

TCTGTTAAGGAGCTTCTTGGAATCACCATCATGGAGCGTTCTTCTTTCGAG

AAGAACCCAATCGATTTCCTTGAGGCTAAGGGATACAAGGAGGTTAAGAAG

GATCTTATCATCAAGTTGCCAAAGTACTCTCTTTTCGAGCTTGAGAACGGA

AGAAAGAGAATGCTTGCTTCTGCTGGAGAGCTTCAGAAGGGAAACGAGCTT

GCTCTTCCATCTAAGTACGTTAACTTCCTTTACCTTGCTTCTCACTACGAG

AAGTTGAAGGGATCTCCAGAGGATAACGAGCAGAAGCAGCTTTTCGTTGAG

CAGCACAAGCACTACCTTGATGAGATCATCGAGCAAATCTCTGAGTTCTCT

AAGAGAGTTATCCTTGCTGATGCTAACCTTGATAAGGTTCTTTCTGCTTAC

AACAAGCACAGAGATAAGCCAATCAGAGAGCAGGCTGAGAACATCATCCAC

CTTTTCACCCTTACCAACCTTGGTGCTCCAGCTGCTTTCAAGTACTTCGAT

ACCACCATCGATAGAAAAAGATACACCTCTACCAAGGAGGTTCTTGATGCT

ACCCTTATCCACCAGTCTATCACCGGACTTTACGAGACCAGAATCGATCTT

TCTCAGCTTGCAGGAGATAAGAGACCAGCTGCTACCAAGAAGGCTGGACAG

GCTAAGAAGAAGAAGTGAgtcgac
```

In the above Cas9 sequence over 2 pages, the underlined portions indicate the NdeI sequence and the SalI sequence.

With use of pRI201-AN in which the Cas9 and the sgRNA expression cassette were introduced, *Agrobacterium* LBA4404 was transformed by electroporation. The *Agrobacterium* was grown on an AB plate containing kanamycin at 25 μg/ml. Then, *Agrobacterium* of a single colony was isolated.

(b) Transformation of Tobacco and Cultivation of a Transformant

Segments of a cotyledon collected from tobacco (variety: SR-1) 10 days after sowing were co-cultured for 3 days with the transformed *Agrobacterium* obtained as described above. Then, the *Agrobacterium* was then removed from the segments of the cotyledon by washing the segments with use of distilled water containing an antibacterial agent (cefotaxime). Then, the *Agrobacterium* was completely removed by culturing, for 4 days, the washed segments of the cotyledon in Linsmaier and Skoog medium containing an antibacterial agent. Then, the segments of the cotyledon were transferred to and cultured in Linsmaier and Skoog medium containing antibiotics (kanamycin), so that redifferentiated individuals (shoots) having kanamycin resistance were obtained. The shoots were transferred to Linsmaier and Skoog medium and then rooted. From the rooted shoots, individuals having high-level expression of Cas9 mRNA (having an expression level twice as much or higher in comparison with eukaryotic elfa which is the control) were selected, and then transplanted into and grown in a 9-cm pot containing soil for transplantation (Compost: 40 L, wild soil: 30 L, Akadama soil (small): 10 L, Akadama soil (medium): 10 L, vermiculite: 10 L, fertilizer (S625): 1000 g).

(c) Confirmation of Presence/Absence of Mutation and Mutant Sequence

PCR was performed by use of Tks Gflex (trademark) DNA polymerase (Takara-Bio Inc.) with genomic DNA as a template, which genomic DNA was extracted from a leaf of a transformant of tobacco. The reaction conditions and primers of the PCR are as follows.

(Reaction Conditions)

30 seconds at 94° C.

40 cycles while each cycle includes 10 seconds at 98° C., 15 seconds at 55° C., and 60 seconds at 68° C.

60 seconds at 68° C.

```
(Primers)
T genome
Combination of NtB11-1_2A_F1:
                                        (SEQ ID NO. 293)
AAGTATTACTACTACAAAATTCCAACG,
and

Nb_B11_2A_R1:
                                        (SEQ ID NO. 294)
CCATCTGATGAAGAACAACTTGC

S genome
Combination of NtB11-2_1A_F1:
                                        (SEQ ID NO. 295)
TTAAACACTAGAGAGTGAGAGAGTGC,
and

NtB11-2_2A_F1:
                                        (SEQ ID NO. 296)
CAGATGTTTAATTATTAAGACAAAGTTCC.
```

After the PCR reactions, denaturation and annealing were performed under the following conditions. Denaturation: 5 minutes at 95° C., annealing: 1 second at 85° C./1 second at 85° C., 1 second at 60° C., constant at 30° C. The Ramp Rate at 85° C. to 60° C. was 5% (drop rate of 0.1° C./second), and the Ramp Rate at 60° C. to 30° C. was 10% (drop rate of 0.1° C./second). The PCR products of 5 μl after the denaturation and annealing were treated in a reaction system of 10 μl with use of T7 endonuclease I (New England Biolabs) of 1 U, and then were separated by electrophoresis. Then, it was checked whether or not the PCR products were cleaved by an enzyme. Separately, the PCR products were cloned with use of Zero Blunt TOPO PCR Cloning Kit, and the nucleotide sequence of the clone was determined.

(d) Selection of a Transformant

Individuals of T0 generation having mutations (deletion or insertion of 1 or more bases) in a T genome and an S genome were selfed and collected, so that a T1 line was obtained. The presence/absence of the mutations in the individuals of the T1 line was confirmed as in (c) above. Based on the results of the confirmation, individuals of a T1 line ($T^+S^+$) having homozygous mutations in a T genome and an S genome were selected. The individuals of the T1 line ($T^+S^+$) were selfed so that individuals of a T2 line ($T^+S^+$) were obtained. The individuals of a T2 line ($T^+S^+$) were used for a test.

Mutant polypeptide in individuals of T2 line obtained 2A-1_121, 2 Å-1_126, 2 Å-133_1, 2 Å-161_17 (Bl1-1-T genome: 1b deletion)

While WT consists of 336 amino acids, polypeptides (SEQ ID NOs. 92, 94, 96, 106) are produced such that unrelated 12 amino acids (TGILNSRKSLWD (positions 108 through 119 in SEQ ID NOs. 92, 94, 96, 106)) are added in addition to up to 107 amino acids identical to those of WT.

2A-1_121, 2A-1_126 (Bl1-2-S genome: 5b deletion)

While WT consists of 337 amino acids, polypeptides (SEQ ID NOs. 91, 93) are produced such that unrelated 3 amino acids (LEY) are added in addition to up to 106 amino acids identical to those of WT.

2A-133_1 (Bl1-2-S genome: 3b deletion)

A polypeptide (SEQ ID NO. 95) of 337 amino acids in which 107th N (asparagine) is deleted from 337 amino acids constituting WT is produced.

2A-161_8, 2A-161_122 (Bl1-1-T genome: 22b deletion)

While WT consists of 336 amino acids, polypeptides (SEQ ID NOs. 104, 108) are produced such that unrelated 11 amino acids (EILNSRKSLWD (positions 102 through 112 in SEQ ID NOs. 104, 108)) are added in addition to up to 101 amino acids identical to those of WT.

2A-161_8, 2A-161_17, 2A-161_122 (Bl1-2-S genome: 2b deletion)

While WT consists of 337 amino acids, polypeptides (SEQ ID NOs. 103, 105, 107) are produced such that unrelated 4 amino acids (KLEY (positions 107 through 110 in SEQ ID NOs. 103, 105, 107)) are added in addition to up to 106 amino acids identical to those of WT.

(e) Evaluation of Axillary Buds in Greenhouse

The individuals of T2 line ($T^+S^+$) obtained in (d) above were cultivated in a greenhouse, and axillary buds were evaluated. The details of the evaluation are as described in 2-2. above.

Figure 9:
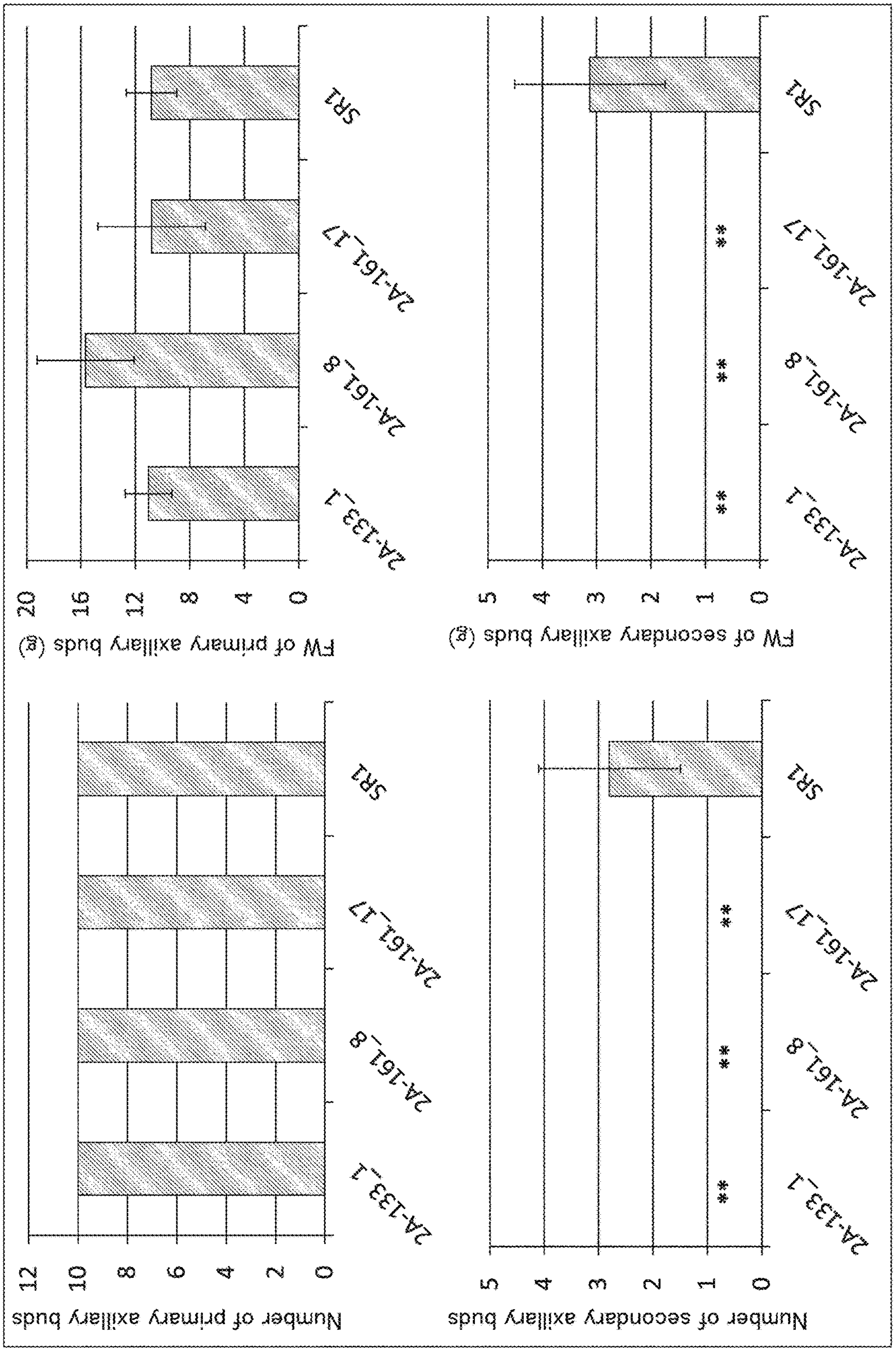
FIG. 9 is a view showing the results of the effects on the development of axillary buds by mutations introduced into NtBl1 genes in accordance with Examples of the present invention.
Figure 10:
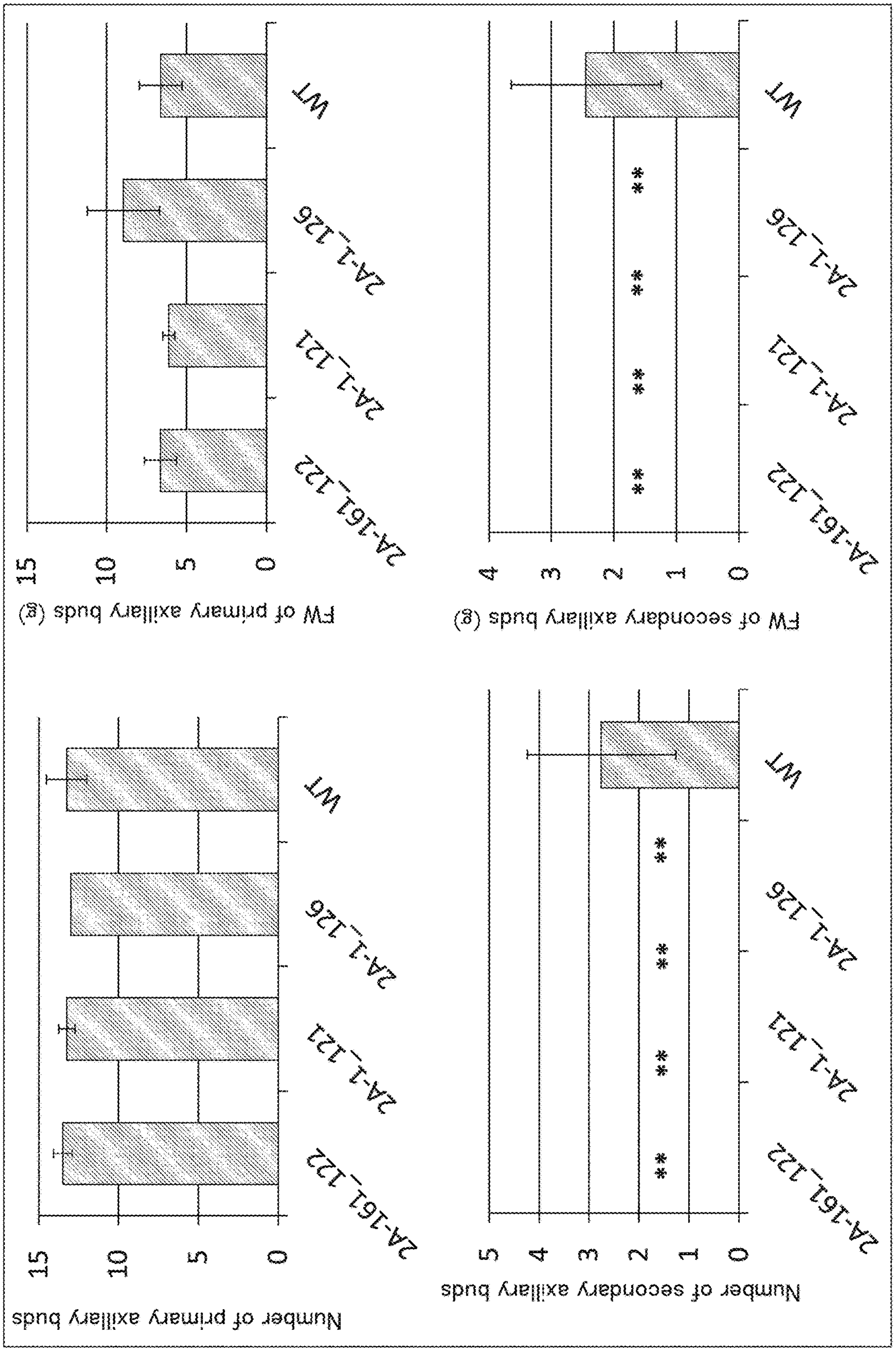
FIG. 10 is a view showing the results of the effects on the development of axillary buds by mutations introduced into NtBl1 genes in accordance with Examples of the present invention.

FIGS. 9 and 10 show the results of the evaluation of the development of axillary buds of mutants in which mutations were introduced into NtBl1. As shown in FIGS. 9 and 10, none of the individuals in which the mutations were introduced into NtBL1 gene showed any significant difference from a wild-type in terms of the number and weight of primary axillary buds, and the individuals showed a statistically significant decrease in the number and weight of secondary axillary buds in comparison with the wild-type.

The results above indicate that in the mutants of NtBl1 also, the development of secondary axillary buds was selectively suppressed as in the case of suppression of gene expression.

[4. Confirmation of Effect of Mutation Introduced into Target Gene on Position at which Axillary Buds Develop]

Figure 11:
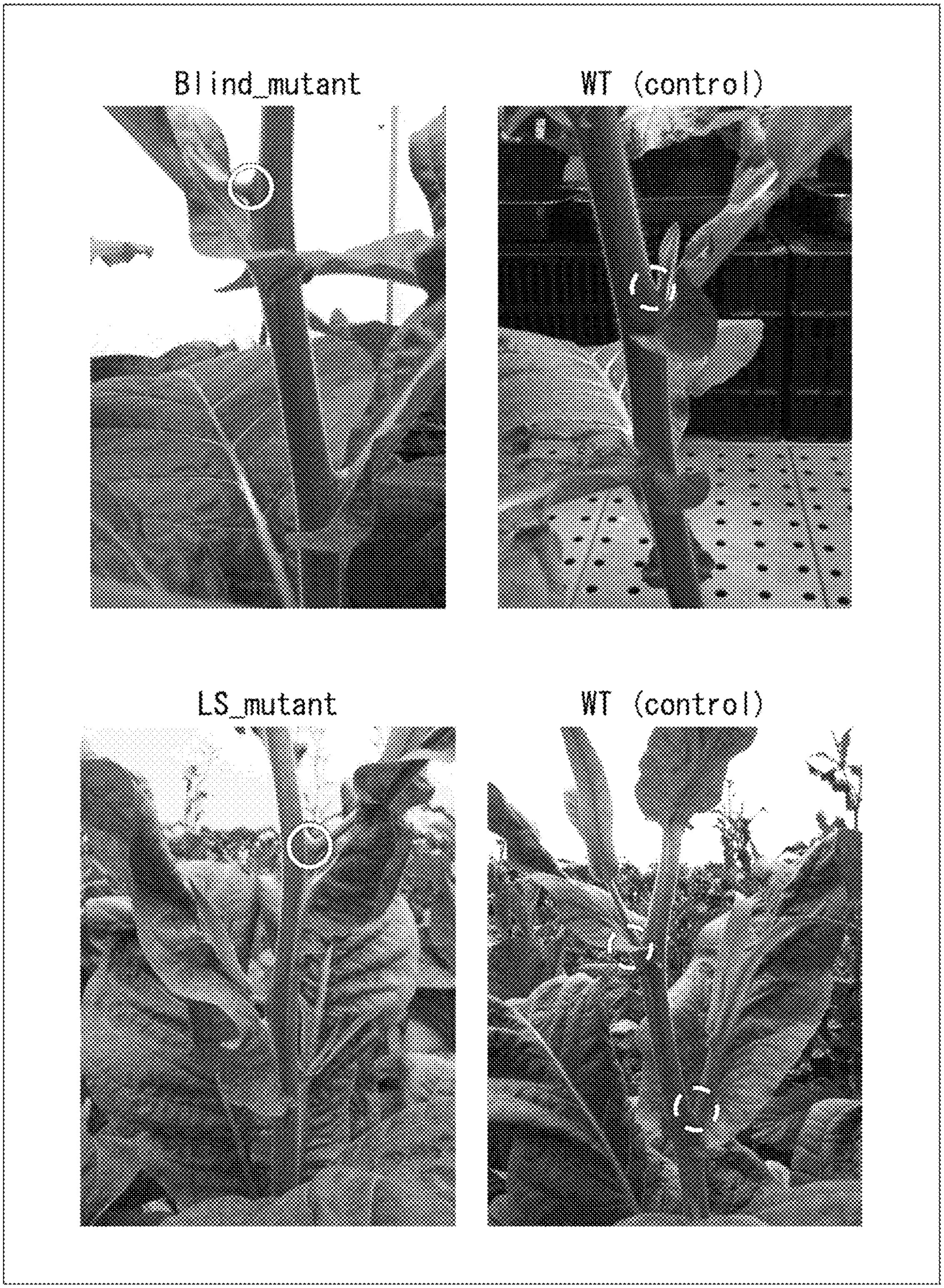
FIG. 11 is a view showing the results of the effects on the position of the developed axillary buds by mutations introduced into NtBl1 genes or NtLS genes in accordance with Examples of the present invention.

The NtBl1 mutants prepared by CRISPR/Cas9 system were cultivated in Koitotron as in the case of WT (SR-1). 1 week after topping, the positions at which primary axillary buds developed was checked (upper part of FIG. 11). Selection was made from Tsukuba No. 1 mutant panel. The NtLS mutants (Homo line) thus prepared were cultivated in the field as in the case of the NtLS mutants (Null line). 63 days after transplantation, the position at which the primary axillary buds developed was checked (lower part of FIG. 11).

As shown in FIG. 11, the two mutants showed that primary axillary buds were formed at positions shifted from the leaf axil. Therefore, it is extremely easy to pick primary axillary buds from these mutants. This is significant because picking axillary buds poses the following problems. In a case where axillary buds to be picked are formed at the leaf axil, there is a possibility that a branch where the leaf to be harvested is located may be damaged. Such damage can become a pathway through which a pathogen invades. This can have a considerable adverse effect on the yield and quality of leaves.

[5. Confirmation of Effect of Mutation Introduced into Target Gene on Growth of Tobacco Plant]

(a) Target to be tested

The effects of each gene mutation in the following lines on the growth of a plant were examined as described below: (i) the line evaluated in (c) of 3-2. and (ii) the T3 line which is a selfed progeny of Bl1_2A-1_121 evaluated in (e) of 3-3. As a comparison group, the varieties used for producing each mutant were used.

(b) Conditions

In a greenhouse (at a fixed temperature of 25° C.), each individual planted in a 9-cm pot was cultivated until budding. The composition of the rich soil is identical to that described in 2-2. At the time of budding, the plant height, fresh weight, and dry weight of each individual, and the leaf length and leaf width at each leaf position were measured. A plant height is a length from the surface of rich soil in a pot to the base of the topmost flower branch. A fresh weight is a total weight of 16 above-ground leaves (NtLS mutant, NtREV mutant) or 14 above-ground leaves (NtBl1 mutant) immediately after the leaves are harvested. A dry weight is a weight of harvested leaves (whose fresh weight has been measured) after they are dried by hot air at a temperature of 70° C. and a relative humidity of 7%. A leaf length is a length-wise distance from the petiole to the tip of a leaf. A leaf width is a maximum width of a leaf. In order to determine the leaf length and leaf width, numbers to indicate leaf positions were assigned from a bottommost leaf (1) to a topmost one in order.

(c) Results

Figure 12:
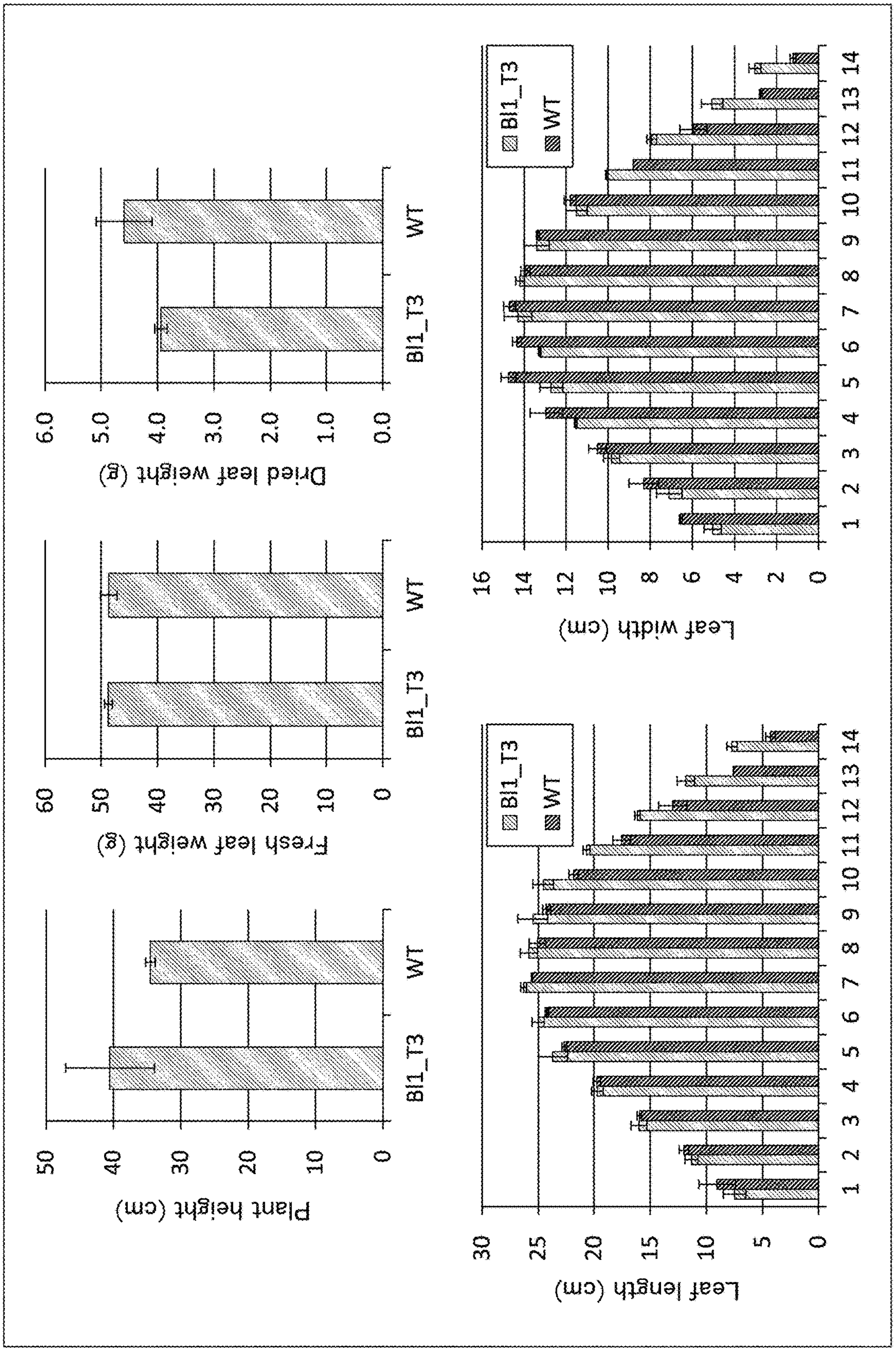
FIG. 12 is a view showing the results of the effects on the growth of tobacco plants by mutations introduced into NtBl1 genes in accordance with Examples of the present invention.
Figure 13:
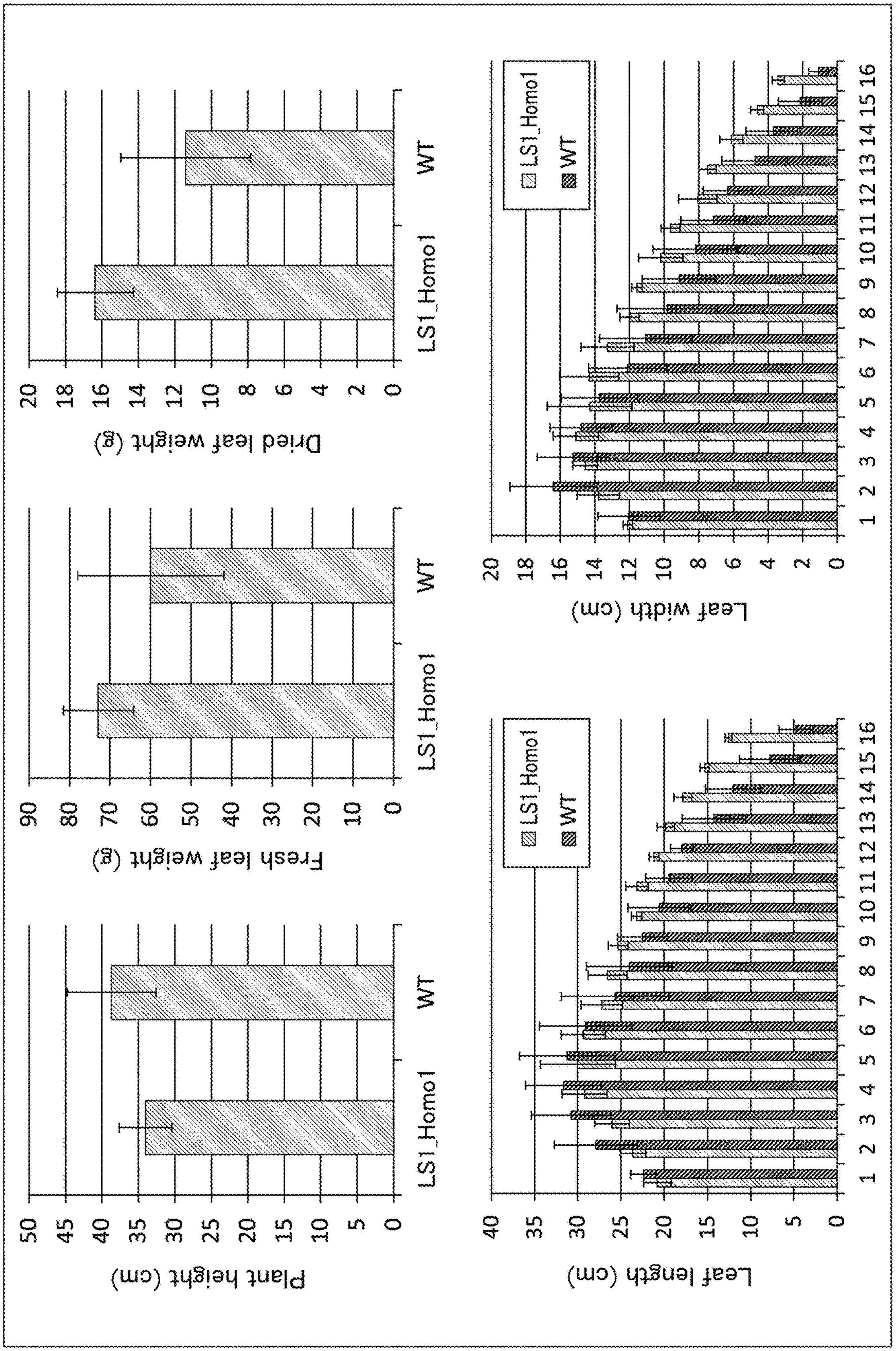
FIG. 13 is a view showing the results of the effects on the growth of tobacco plants by mutations introduced into NtLS genes in accordance with Examples of the present invention.
Figure 14:
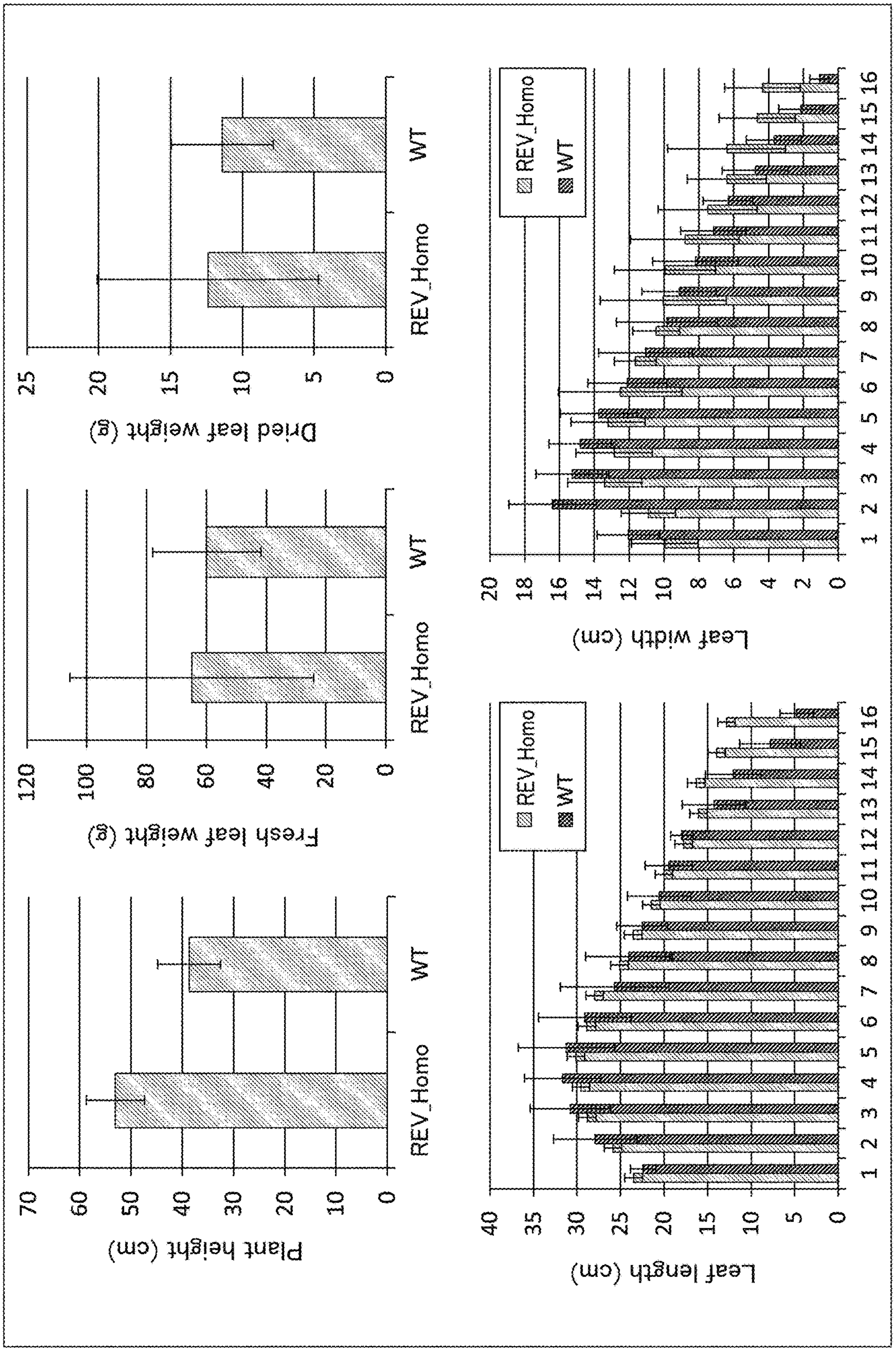
FIG. 14 is a view showing the results of the effects on the growth of tobacco plants by mutations introduced into NtREV genes.

As is clear from FIG. 12 (mutant: n=3, WT (Tsukuba No. 1): n=2), FIG. 13 (mutant and WT (Tsukuba No. 1): n=3), and FIG. 14 (mutant: n=2, WT (Tsukuba No. 1): n=3), there was no statistically significant difference found between the mutant group and the control group in terms of the plant height, fresh weight, and dry weight. In addition, as is clear from these drawings, there was also no remarkable difference found between the mutant group and the control group in terms of the leaf length and the leaf width.

The above facts indicate that each mutant shows growth and leaf yields which are substantially identical to the control group. It was therefore found that because of the following reasons (1) through (3), the mutants in accordance with these Examples are extremely useful as tobacco plants from which leaves are intended to be harvested: (1) it is easy to control axillary buds, (2) there is no decrease in yield, and (3) the plant is highly likely to survive.

[6. Confirmation of Effect of Mutation Introduced into Target Gene on Development of Axillary Buds (2)]

Mutants having profiles below were prepared, and the following of the mutants were evaluated: (i) a growth state, (ii) development of axillary buds, and (iii) development of axillary buds in a case where an agrochemical for suppressing axillary buds was used.

LS_21_Null: A mutant ($T^+S^+$) which (i) is an F3 individual obtained by causing an F1 individual, which was obtained by crossing Ns369 mutant and Nt1025 mutant, to self twice, (ii) homozygously has a mutation of the Ns369 mutant (expressing a polypeptide of SEQ ID NO. 41) in an S genome, and (iii) homozygously has a mutation of the Nt1025 mutant (expressing a polypeptide of SEQ ID NO. 40) in a T genome.

LS19_WT: A mutant ($T^-S^-$) which (i) is an F3 individual obtained by causing an F1 individual, which was obtained by crossing Ns369 mutant and Nt1025 mutant, to self twice and (ii) has no mutation of LS gene in a T genome or an S genome.

LS15_Null, LS85_Null: Mutants ($T^+S^+$) each of which (i) is an F3 individual obtained by causing an F1 individual, which was obtained by crossing Ns369 mutant and Ns1145 mutant, to self twice, (ii) homozygously has a mutation of the Ns369 mutant (expressing a polypeptide of SEQ ID NO. 41) in an S genome, and (iii) homozygously has a mutation of the Nt1145 mutant (expressing a polypeptide of SEQ ID NO. 39) in a T genome.

LS_57_WT: A mutant ($T^-S^-$) which (i) is an F3 individual obtained by causing an F1 individual, which was obtained by crossing Ns369 mutant and Ns1145 mutant, to self twice and (ii) has no mutation of LS gene in a T genome or an S genome.

REV_26_Nu-W and REV_89_Nu-W: Mutants each of which was obtained as follows. K326 was crossed with the following mutant ($T^+S^+$) so as to obtain F1: the mutant ($T^+S^+$) which (i) homozygously has a mutation of the Nt1605 mutant (expressing a polypeptide of SEQ ID NO. 37) in a T genome and (ii) homozygously has a mutation of the Ns1630 mutant (expressing a polypeptide of SEQ ID NO. 39) in an S genome. K326 was backcrossed with F1 once so as to obtain BC1F1. The BC1F1 was selfed twice so as to obtain BC1F3 individuals. Of the BC1F3 individuals, the following mutant ($T^+S^-$) was regarded as each of REV_26_Nu-W and REV_89_Nu-W: the mutant ($T^+S^-$) which (i) homozygously has a mutation of the Nt1605 mutant (expressing a polypeptide of SEQ ID NO. 37) in a T genome and (ii) has no mutation of REV gene in an S genome.

REV_26_Nu-He and REV_89 Nu-He: Mutants each of which was obtained as follows. K326 was crossed with the following mutant ($T^+S^+$) so as to obtain F1: the mutant ($T^+S^+$) which (i) homozygously has a mutation of the Nt1605 mutant (expressing a polypeptide of SEQ ID NO. 37) in a T genome and (ii) homozygously has a mutation of the Ns1630 mutant (expressing a polypeptide of SEQ ID NO. 39) in an S genome. K326 was backcrossed with F1 once so as to obtain BC1F1. The BC1F1 was selfed twice so as to obtain BC1F3 individuals. Of the BC1F3 individuals, the following mutant ($T^+S^{+/-}$) was regarded as each of REV_26_Nu-He and REV_89_Nu-He: the mutant ($T^+S^{+/-}$) which (i) homozygously has a mutation of the Nt1605 mutant (expressing a polypeptide of SEQ ID NO. 37) in a T genome and (ii) heterozygously has a mutation of the Ns1630 mutant (expressing a polypeptide of SEQ ID NO. 39) in an S genome.

REV35_WT: A mutant which was obtained as follows. K326 was crossed with the following mutant ($T^+S^+$) so as to obtain F1: the mutant ($T^+S^+$) which (i) homozygously has a mutation of the Nt1605 mutant (expressing a polypeptide of SEQ ID NO. 37) in a T genome and (ii) homozygously has a mutation of the Ns1630 mutant (expressing a polypeptide of SEQ ID NO. 39) in an S genome. K326 was backcrossed with F1 once so as to obtain BC1F1. The BC1F1 was selfed twice so as to obtain BC1F3 individuals. Of the BC1F3 individuals, the mutant ($T^+S^-$) which has no mutation of REV gene in a T genome or an S genome was regarded as REV35_WT.

REV_F3_Null: A mutant ($T^+S^+$) which (i) is an F3 individual obtained by causing an F1 individual, which was obtained by crossing Nt1605 mutant and Ns1630 mutant, to self twice, (ii) homozygously has a mutation of the Nt1605 mutant (expressing a polypeptide of SEQ ID NO. 37) in a T genome, and (iii) homozygously has a mutation of the Ns1630 mutant (expressing a polypeptide of SEQ ID NO. 39) in an S genome.

REV_F3_WT: A mutant ($T^-S^-$) which (i) is an F3 individual obtained by causing an F1 individual, which was obtained by crossing Nt1605 mutant and Ns1630 mutant, to self twice and (ii) has no mutation of REV gene in a T genome or an S genome.

(1) Evaluation of Growth

Examination was conducted using (i) 3 lines of LS mutant null lines, (ii) 2 lines which serve as controls of the mutant null lines, and (iii) Tsukuba No. 1 which is a parent variety of the mutant. As the mutant null lines, the following were used: LS_21-1_Null, LS_15_Null, and LS_85_Null. The controls of the mutant null lines were as follows. LS_19_WT, which is an F2 segregated line and has no mutation in LS, was used as the control of the mutant null line LS_21-1_Null. LS_57_WT, which is an F2 segregated line and has no mutation in LS, was used as the control of the mutant null lines LS_15_Null and LS_85_Null.

In the field of Leaf Tobacco Research Center, during a cultivation period slightly later than an ordinary cultivation period (sowing in March through April and planting in May), the individuals of each line above were cultivated by a high-ridge, mulch-cultivation method under the following conditions. Planting distance: 43 cm and ridge intervals: 120 cm. As a fertilizer, compost in an amount of 2000 kg/10 a and Agri 622 in an amount of 120 kg/10 a were used. Evaluation was made for the days of flowering, the plant height, the number of above-ground leaves, the fresh leaf weight, and the dry weight of individuals of each line cultivated. The days of flowering is herein the number of days from the date on which sowing was performed to the date on which the first flower was bloomed. The plant height refers to a height from the ground to the base of the topmost flower branch. The number of above-ground leaves refers to a total number of leaves located from the ground through leaves located immediately below the first flower branch. The fresh leaf weight was the total weight of all of the above-ground leaves before drying. The dry weight was the weight of all of the above-ground leaves after drying. 6 individuals of each line were evaluated, and an average of evaluated values and a standard deviation were calculated. It was examined whether or not there was any statistically significant difference in evaluated value between the mutant null lines and the controls.

Figure 15:
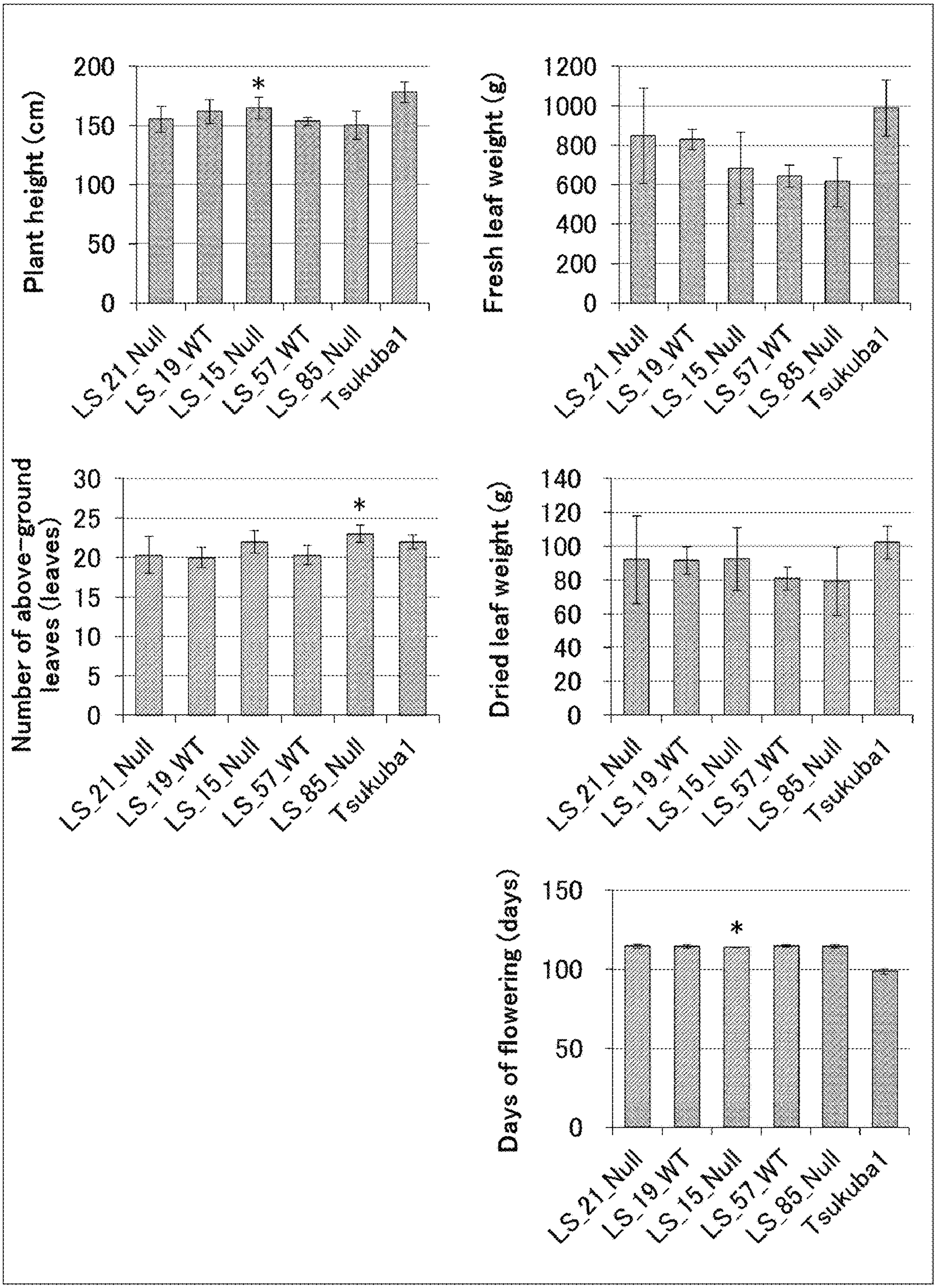
FIG. 15 is a view showing the results of the effects on the growth of tobacco plants by mutations introduced into LS genes.

The results will be described below with reference to FIG. 15. There was no significant difference in evaluated value between the controls and the mutant null lines except that (i) the plant height of LS_15_Null was significantly higher than that of the control (LS_57_WT), (ii) the days of flowering of LS_15_Null was significantly shorter than that of the control LS_57_WT, and (iii) the number of above-ground leaves of LS_85_Null was significantly larger than that of the control (LS_57_WT). The above fact indicates that the mutations of LS genes do not have large effects on growth.

(2) Evaluation of Development of Axillary Buds

Each individual was cultivated as in (1) above. LS mutants and the controls thereof were as follows. The mutant null line (LS_21) and the control thereof (LS_19_WT), and the LS null mutants (LS_15, LS_85) and the controls thereof (LS57_WT) were used for a test. LS_21 was cultivated in two ridges so as to conduct a replicated test. As REV mutants, 4 lines (REV_26_Nu-W, REV_26_Nu-He, REV89_Nu-W, REV_89_Nu-He) of BC2F3 segregated lines having been subjected to backcrossing (backcrossing parent: K326) were used. As the control of the REV mutants, the control (REV_35_WT) of the 4 lines was used. Furthermore, REV null mutant (REV_F3_Null) not having been subjected to backcrossing and the control thereof (REV_F3_WT) were also used as the REV mutant and the control thereof. Furthermore, Tsukuba No. 1, which is a parent variety of each mutant, and K326, which is a backcrossing parent of BC2F3 segregated line were also used for the test.

During flowering time, topping was performed immediately below the first flower branch. Then, axillary buds produced on above-ground leaves were examined. The first examination was conducted on the day of the topping and, on the subsequent weeks, 1 examination was conducted each week so that the total of 8 examinations were conducted. The axillary buds having a stem length of 5 mm or more were examined such that for each individual, the positions of axillary buds collected were recorded, and, after the axillary buds were collected, the weight of the axillary buds was measured. Primary axillary buds, secondary axillary bud, and tertiary axillary buds were separately examined and counted.

Figure 16:
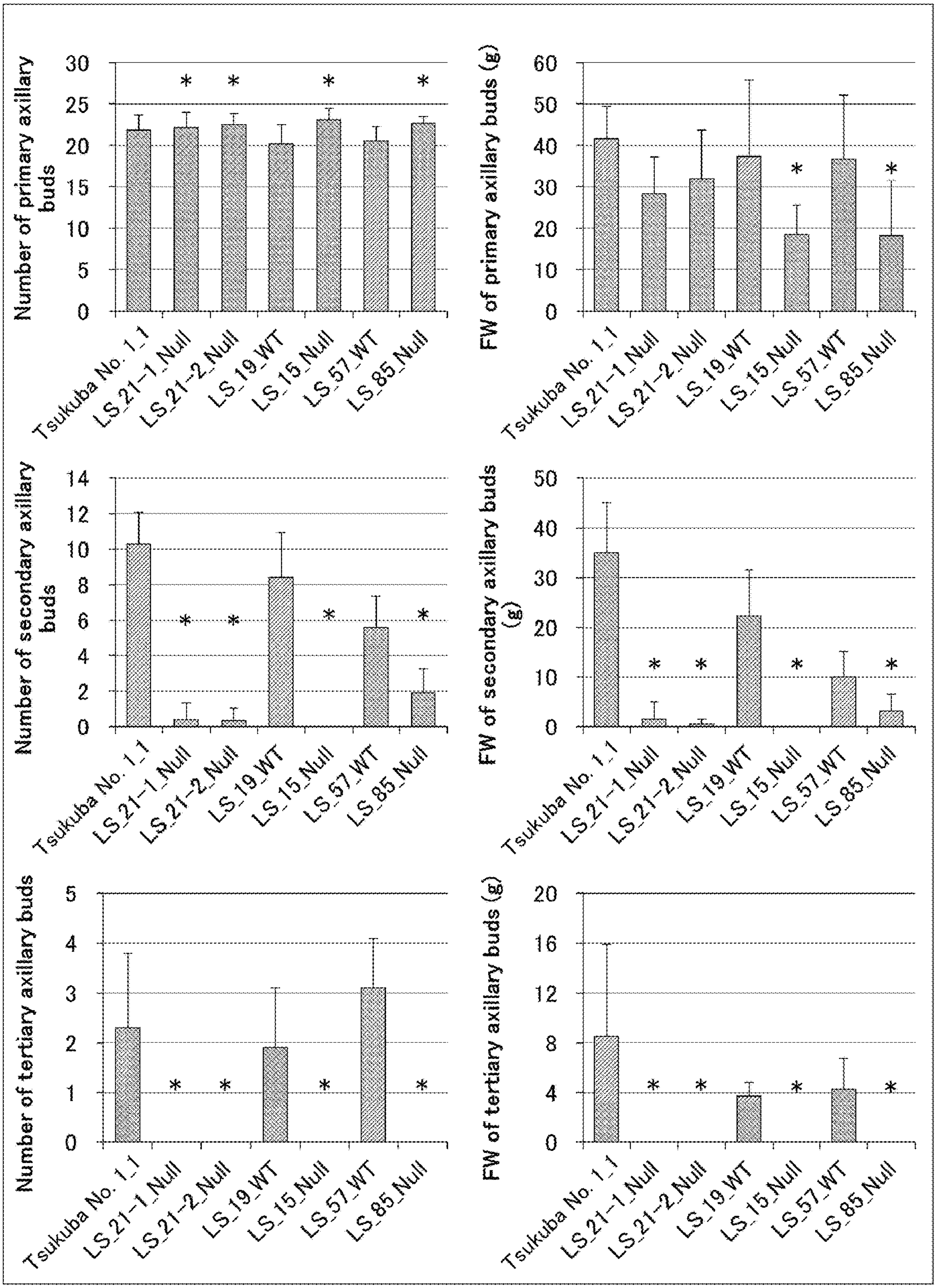
FIG. 16 is a view showing the results of the effects on the development of axillary buds by mutations introduced into LS genes.

The results will be described below with reference to FIGS. 16 and 17. FIG. 16 shows the results of evaluation of LS mutants, and FIG. 17 shows the results of evaluation of REV mutants.

As shown in FIG. 16, each of the 3 LS mutant null lines exhibited a tendency that (i) the number of primary axillary buds is larger in comparison with the control and (ii) the fresh leaf weight (FW) is lower in comparison with the control. The number of primary axillary buds of the LS mutant null lines is large, possibly because of the fact that the LS mutant null lines tend to have a larger number of above-ground leaves in comparison with the controls (FIG. 15). Meanwhile, secondary axillary buds and tertiary axillary buds were largely reduced in comparison with the controls, or were not formed at all. The results above confirmed that the formation of secondary axillary buds and subsequent axillary buds of mutants having different mutations of LS is suppressed.

Figure 17:
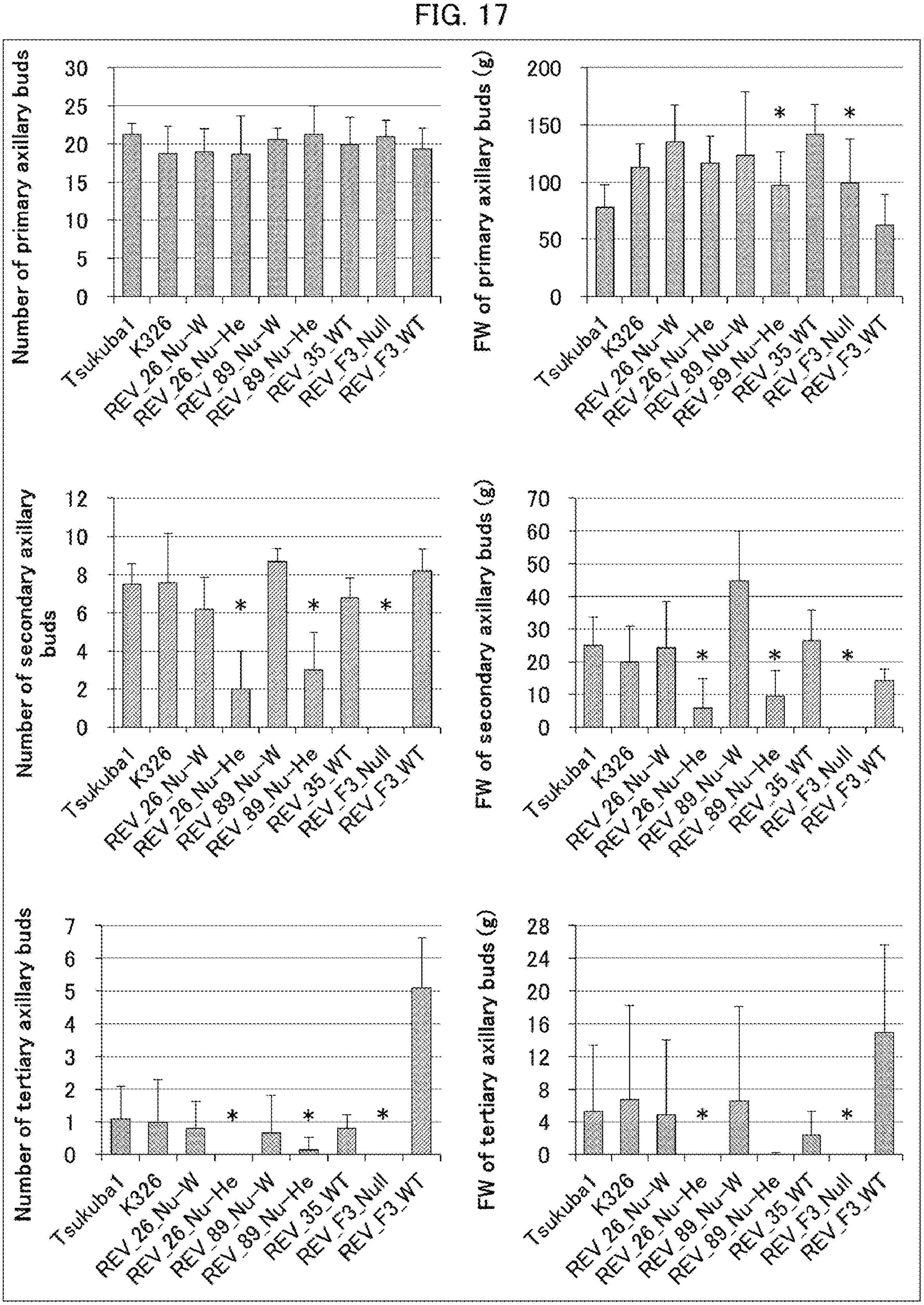
FIG. 17 is a view showing the results of the effects on the development of axillary buds by mutations introduced into REV genes.

As shown in FIG. 17, REV_F3_Nul1 in which mutations were introduced into all of alleles of REV genes exhibited that no secondary axillary buds or tertiary axillary buds were formed at all. In addition, according to 2 lines (REV_26_Nu-He, REV_89_Nu-He) in which 2 alleles in a T genome have mutations and 1 allele in an S genome has a mutation, secondary axillary buds are formed, but the number of secondary axillary buds and the fresh leaf weight were decreased to ½ or lower than those of the control (REV_35_WT). This decrease is statistically significant.

Meanwhile, according to 2 lines (REV_26_Nu-W, REV_89_Nu-W) in which 2 alleles in a T genome have mutations and no mutation has occurred in an S genome, the number of secondary axillary buds and the fresh leaf weight were equivalent to those of the control (REV_35_WT). Therefore, in terms of REV gene, it was confirmed that introduction of mutations into the total of 3 alleles produces the effect of suppressing secondary axillary buds even if the mutations are not introduced into all of alleles in a T genome and an S genome.

(3) Development of Axillary Buds in a Case where Agrochemical for Suppressing Axillary Buds is Used With use of a pot (inner diameter: 25 cm, height: 24 cm) which was filled with 5 L of rich soil, individuals were cultivated in a mesh house. The composition of the rich soil was as follows. Compost: 40 L, wild soil: 10 L, Kiryu sand: 15 L, Akadama soil (small): 15 L, Akadama soil (medium): 15 L, vermiculite: 10 L, Burley 5625 (fertilizer): 1000 g. Sowing was performed in May, and, after approximately 1.5 months passed since transplantation, 2 L of rich soil was added. During flowering time, up to 2 leaves below the first flower branch were cut off (topping), and, 3 days later, 30-fold diluted Contact (OAT Agrio Co., Ltd.) was applied in an amount of 20 ml per individual. 4 to 7 days after the application, it was checked whether or not Contact came into contact with primary axillary buds, and the primary axillary buds with which Contact was not in contact were recorded. After outgrowth, the primary axillary buds with which Contact was not in contact were removed. Thereafter, secondary axillary buds formed at sites where Contact was not in contact with the primary axillary buds were excluded from the subjects of examination. An individual had an average of 1 to 2 sites where Contact was not in contact with primary axillary buds. After the application of Contact, the occurrence of secondary axillary buds was examined once a week, over the total of 13 times. Since the average number of leaves produced per line varied between 25 and 31, comparisons were made between ratios of secondary axillary buds to the number of leaves produced. LS_15_null and LS_85_null, which are null mutants of LS, were compared with their control LS_77_wt in which no mutation occurred to LS. LS_14_null and LS24_null, which are null mutants of LS, were compared with their control LS_19_wt in which no mutation occurred to LS.

Figure 18:
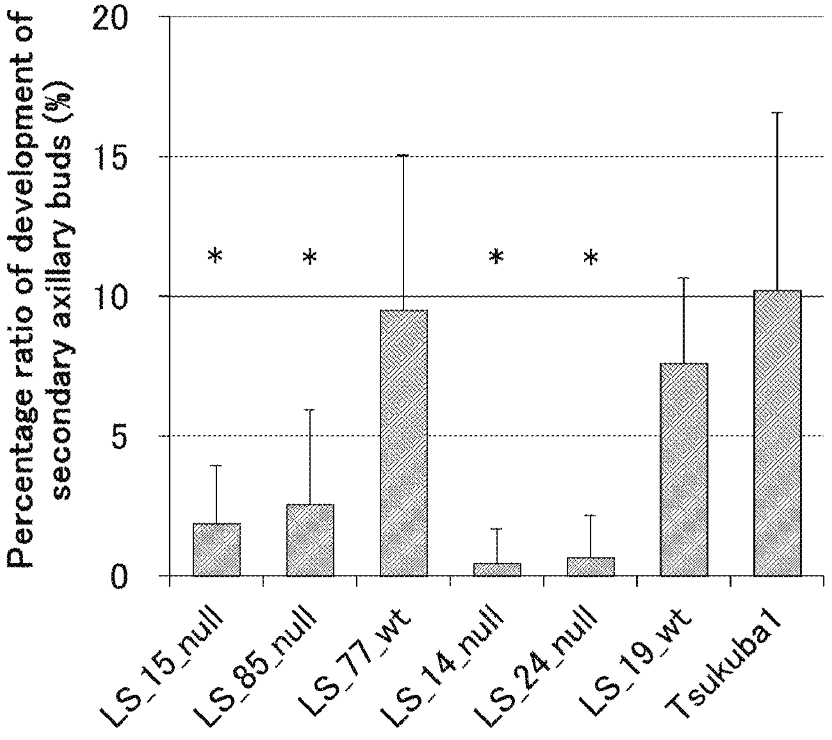
FIG. 18 is a view showing the results of the effects on the development of axillary buds by mutations introduced into LS genes.

The results will be described below with reference to FIG. 18. Due to the mutation of LS gene, there was a statistically significant and large decrease in the number of secondary axillary buds that occurred (relative to the number of leaves produced) after the application of Contact.

[7. Confirmation of Effect of Mutation Introduced into Target Gene on Development of Axillary Buds (3)]

(7-1. REV Mutant and #15360 Mutant)

With use of CRISPR/Cas9 system, new mutants were prepared, and the development of axillary buds was evaluated. Since the procedure of the preparation was in compliance with the description of 3-3., only the differences from 3-3. will be described below.

(a) Preparation for Transformation

In construction of vectors for transforming *Agrobacterium*, Life Technologies Corporation was entrusted with the synthesis of sgRNA expression cassettes. The nucleotide sequences of the sgRNA expression cassettes obtained are as follows.

[Chem. 4]

REVG2

(SEQ ID NO. 297)

```
aattggtaccAAGCTTCGTTGAACAACGGAAACTCGACTTGCCTTCCGCAC
AATACATCATTTCTTCTTAGCTTTTTTTCTTCTTCTTCGTTCATACAGTTT
TTTTTTGTTTATCAGCTTACATTTTCTTGAACCGTAGCTTTCGTTTTCTTC
TTTTTAACTTTCCATTCGGAGTTTTTGTATCTTGTTTCATAGTTTGTCCCA
GGATTAGAATGATTAGGCATCGAACCTTCAAGAATTTGATTGAATAAAACA
TCTTCATTCTTAAGATATGAAGATAATCTTCAAAAGGCCCCTGGGAATCTG
AAAGAAGAGAAGCAGGCCCATTTATATGGGAAAGAACAATAGTATTTCTTA
TATAGGCCCATTTAAGTTGAAAACAATCTTCAAAAGTCCCACATCGCTTAG
ATAAGAAAACGAAGCTGAGTTTATATACAGCTAGAGTCGAAGTAGTGATTg
agttcctttccaaggctacGTTTTAGAGCTAGAAATAGCAAGTTAAAATAA
GGCTAGTCCGTTATCAACTTGAAAAAGTGGCACCGAGTCGGTGCTTTTTTT
ggatccaatt
```

-continued

[Chem. 5]
REVG5

(SEQ ID NO. 298)
aattggtaccAAGCTTCGTTGAACAACGGAAACTCGACTTGCCTTCCGCAC
AATACATCATTTCTTCTTAGCTTTTTTTCTTCTTCTTCGTTCATACAGTTT
TTTTTTGTTTATCAGCTTACATTTTCTTGAACCGTAGCTTTCGTTTTCTTC
TTTTTAACTTTCCATTCGGAGTTTTTGTATCTTGTTTCATAGTTTGTCCCA
GGATTAGAATGATTAGGCATCGAACCTTCAAGAATTTGATTGAATAAAACA
TCTTCATTCTTAAGATATGAAGATAATCTTCAAAAGGCCCCTGGGAATCTG
AAAGAAGAGAAGCAGGCCCATTTATATGGGAAAGAACAATAGTATTTCTTA
TATAGGCCCATTTAAGTTGAAAACAATCTTCAAAAGTCCCACATCGCTTAG
ATAAGAAAACGAAGCTGAGTTTATATACAGCTAGAGTCGAAGTAGTGATTg
gagtggcagcccgagcatgGTTTTAGAGCTAGAAATAGCAAGTTAAAATAA
GGCTAGTCCGTTATCAACTTGAAAAAGTGGCACCGAGTCGGTGCTTTTTTT
ggatccaatt

[Chem. 6]
ROXG1

(SEQ ID NO. 299)
aattggtaccAAGCTTCGTTGAACAACGGAAACTCGACTTGCCTTCCGCAC
AATACATCATTTCTTCTTAGCTTTTTTTCTTCTTCTTCGTTCATACAGTTT
TTTTTTGTTTATCAGCTTACATTTTCTTGAACCGTAGCTTTCGTTTTCTTC
TTTTTAACTTTCCATTCGGAGTTTTTGTATCTTGTTTCATAGTTTGTCCCA
GGATTAGAATGATTAGGCATCGAACCTTCAAGAATTTGATTGAATAAAACA -continued TCTTCATTCTTAAGATATGAAGATAATCTTCAAAAGGCCCCTGGGAATCTG
AAAGAAGAGAAGCAGGCCCATTTATATGGGAAAGAACAATAGTATTTCTTA
TATAGGCCCATTTAAGTTGAAAACAATCTTCAAAAGTCCCACATCGCTTAG
ATAAGAAAACGAAGCTGAGTTTATATACAGCTAGAGTCGAAGTAGTGATTg
tgtagcagctcgtgaaagaGTTTTAGAGCTAGAAATAGCAAGTTAAAATAA
GGCTAGTCCGTTATCAACTTGAAAAAGTGGCACCGAGTCGGTGCTTTTTTT
ggatccaatt In each of the above three sgRNA expression cassettes, (i) the underlined portion indicates the guide sequence, (ii) the portion upstream to the underlined portion indicates the AtU6-26 promoter sequence, (iii) the portion downstream to the underlined portion indicates the scaffold-polyT sequence, and (iv) the lower case letters at the terminus indicate restriction enzyme sequences of KpnI and BamHI.

(b) Transformation of Tobacco and Cultivation of Transformant

The transformation of a tobacco plant and the cultivation of the transformant were as described in (b) of 3-3. except that selection of individuals based on Cas9 mRNA level was not performed.

(c) Confirmation of Presence/Absence of Mutation and Mutant Sequence

The following were checked as described in (c) of 3-3.: (i) the presence/absence of a mutation in the cultivated transformants and (ii) the mutant sequences. Primers for specifically amplifying a region containing a guide sequence on genomic DNA were designed. The sequences of the primers are shown in the following Table.

TABLE 3

| Primer name | Sequence | Target sample | Analyzed genome |
|---|---|---|---|
| REV_Nt_in2_F1 | AACCAATGGACAAGAAACGGATGGCA (SEQ ID NO. 260) | REVG2 | T genome |
| REV_Nt_in4_R1 | TTTAGCTATCCAGTCAAAGAGGCACG (SEQ ID NO. 261) | | |
| REV_Ns_in2_F1 | CCAATAAACAAGAAACAGATGATGG (SEQ ID NO. 253) | | S genome |
| REV_Ns_in4_R1 | GAGACATGGCAATACTGAATTTTCA (SEQ ID NO. 256) | | |
| REV_Nt_in4_F1 | AAAAAAATTCAGTATTGCCACGTGC (SEQ ID NO. 155) | REVG5 | T genome |
| REV_Nt_in6_R1 | AGCCTACGTGAAGATTGATGAGAAA (SEQ ID NO. 262) | | |
| REV_Ns_in4_F1 | GAAAATTCAGTATTGCCATGTC (SEQ ID No. 152) | | S genome |
| REV_Ns_in6_R1 | AGCCTACGTGAAGATTGATGAGAAG (SEQ ID NO. 257) | | |
| 15360-1_F1 | TGCATGGACAATCTCCTCTT (SEQ ID NO. 176) | ROXG1 | T genome |
| 15360-1_R1-2 | CAACAGGAGTTGAGTTATTCTCAT (SEQ ID NO. 178) | | |
| 15360-2_F1 | GCATGGACAATCTCATCTTCTC (SEQ ID No. 177) | | S genome |
| 15360-2_R1 | CTGGGCAATATTCCACCATT (SEQ ID NO. 181) | | |

The reaction conditions of PCR were as follows.

(REVG2)

60 seconds at 94° C.

45 cycles while each cycle includes 10 seconds at 98° C., 15 seconds at 60° C., and 50 seconds at 68° C.

(REVG5, ROXG1)

60 seconds at 94° C.

45 cycles while each cycle includes 10 seconds at 98° C., 15 seconds at 62° C., and 50 seconds at 68° C.

(d) Selection of Transformants

Individuals of T0 generation having mutations (deletion or insertion of 1 or more bases) in a T genome and an S genome were selfed and collected, so that a T1 line was obtained. The presence/absence of the mutation in the individuals of the T1 line and the sequence in the individuals of the T1 line were confirmed with use of the primers shown in Table 3. T1 individuals, in which mutations occurred to all of 4 alleles of an S genome and a T genome, were selected and used for the test. The details of the T1 individuals obtained are as follows.

REV_G2-15

T genome: 6 bases CAAGGC are deleted. While WT consists of 839 amino acids, a polypeptide (SEQ ID NO. 65) is produced such that 2 amino acids (KA) (175th and 176th amino acids) are deleted so as to constitute 837 amino acids.

S genome: 1 base A is inserted. While WT consists of 838 amino acids, a polypeptide (SEQ ID NO. 64) is produced such that unrelated 5 amino acids (YRNCC) are added in addition to an amino acid sequence in which up to 176 amino acids are identical to those of WT.

REV_G2_94

T genome: 1 base T is inserted. While WT consists of 839 amino acids, a polypeptide (SEQ ID NO. 67) is produced such that unrelated 5 amino acids (YRNCC) are added in addition to an amino acid sequence in which up to 176 amino acids are identical to those of WT.

S genome: 1 base T is inserted. While WT consists of 838 amino acids, a polypeptide (SEQ ID NO. 66) is produced such that unrelated 5 amino acids (YRNCC (positions 177 through 181 in SEQ ID NO. 66)) are added in addition to an amino acid sequence in which up to 176 amino acids are identical to those of WT.

REV_G5_18

T genome: 1 base C is inserted. While WT consists of 839 amino acids, a polypeptide (SEQ ID NO. 68) is produced such that unrelated 4 amino acids (MWSC (positions 213 through 216 in SEQ ID NO. 68)) are added in addition to an amino acid sequence in which up to 212 amino acids are identical to those of WT.

S genome: 5 bases TCGAC are inserted. While WT consists of 838 amino acids, a polypeptide (SEQ ID NO. 69) is produced such that unrelated 7 amino acids (RHVVLLV (positions 213 through 219 in SEQ ID NO. 69)) are added in addition to an amino acid sequence in which up to 212 amino acids are identical to those of WT.

REV_G5_59

T genome: 28 bases are deleted. While WT consists of 839 amino acids, a polypeptide (SEQ ID NO. 71) is produced such that unrelated 54 amino acids (QRLLRSSKIDLLGSE-IAGTLKFSQCFLQEMEQLNFCTRRYMLLPPW LLHV-IFGL (positions 212 through 265 in SEQ ID NO. 71)) are added in addition to an amino acid sequence in which up to 211 amino acids are identical to those of WT.

S genome: 3 bases GCA are deleted. While WT consists of 838 amino acids, a polypeptide (SEQ ID NO. 70) is produced such that 1 amino acid (A) (212th amino acid) is deleted so as to constitute 837 amino acids.

ROX_G1-1 (15360_G1-1), ROXG1-30 (15360_G1-30)

T genome: 1 base A is inserted. While WT consists of 165 amino acids, polypeptides (SEQ ID NOs. 123, 125) are produced such that unrelated 3 amino acids (KKA) are added in addition to an amino acid sequence in which up to 40 amino acids are identical to those of WT.

S genome: 1 base A is deleted. While WT consists of 168 amino acids, polypeptides (SEQ ID NOs. 122, 124) are produced such that unrelated 14 amino acids (EGIESVIVSRFCRV (positions 41 through 54 in SEQ ID NOs. 122, 124)) are added in addition to an amino acid sequence in which up to 40 amino acids are identical to those of WT.

ROX_G1-131 (15360_G1-131)

T genome: 1 base A is deleted. While WT consists of 165 amino acids, a polypeptide (SEQ ID NO. 129) is produced such that unrelated 14 amino acids (EGIESVIVSRFCRV (positions 41 through 54 in SEQ ID NO. 129)) are added in addition to an amino acid sequence in which up to 40 amino acids are identical to those of WT.

S genome: 39 bases and 13 bases are inserted. While WT consists of 168 amino acids, a polypeptide (SEQ ID NO. 128) is produced such that unrelated 4 amino acids (FLCG) are added in addition to an amino acid sequence in which up to 39 amino acids are identical to those of WT.

ROX_G1-46 (15360_G1-46)

T genome: 20 bases are deleted. While WT consists of 165 amino acids, a polypeptide (SEQ ID NO. 127) is produced such that unrelated 3 amino acids (ENQ) are added in addition to an amino acid sequence in which up to 36 amino acids are identical to those of WT.

S genome: 1 base G is inserted. While WT consists of 168 amino acids, a polypeptide (SEQ ID NO. 126) is produced such that unrelated 3 amino acids (EKA) are added in addition to an amino acid sequence in which up to 40 amino acids are identical to those of WT.

(e) Evaluation of Development of Axillary Buds in Greenhouse

Figure 19:
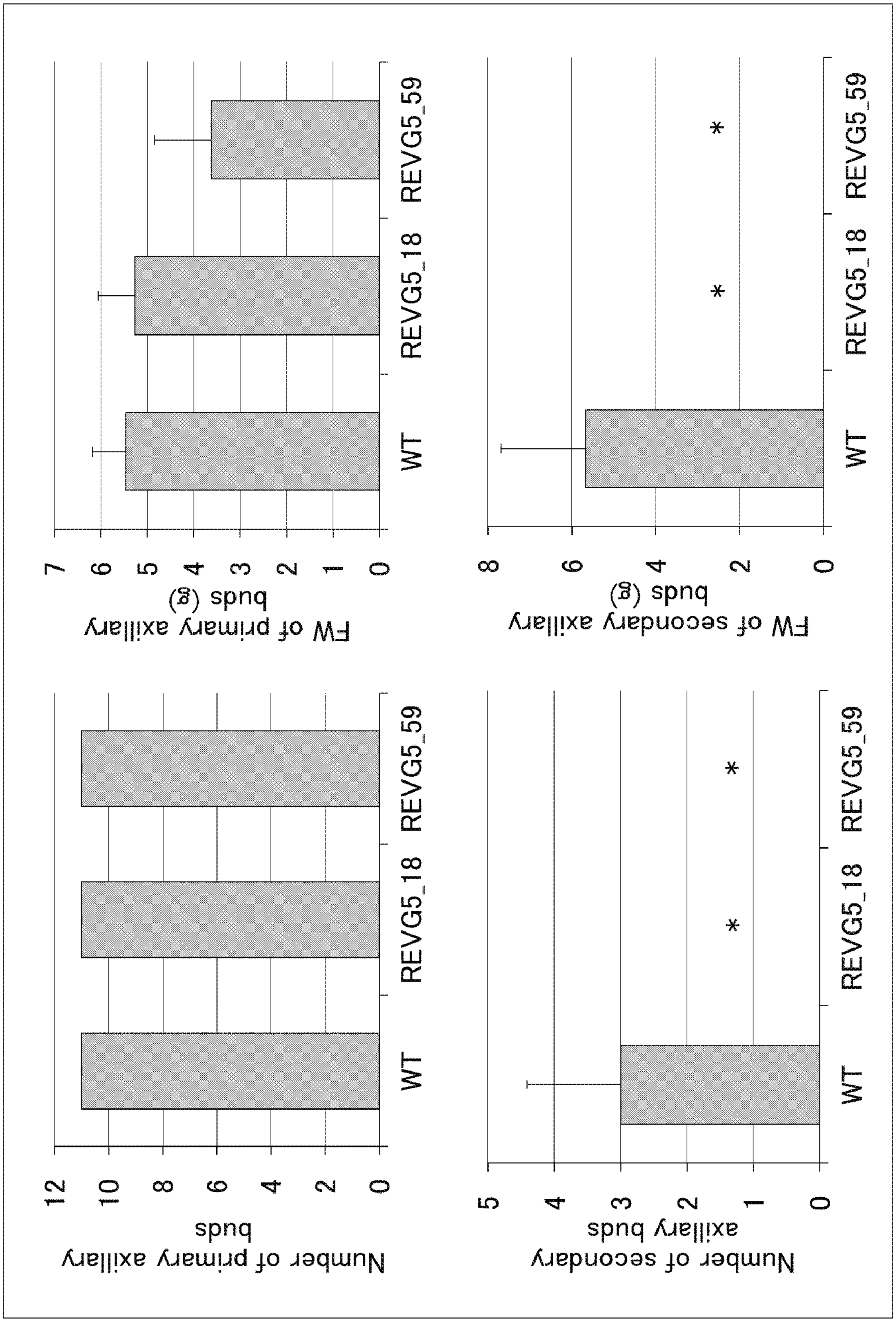
FIG. 19 is a view showing the results of the effects on the development of axillary buds by mutations introduced into REV genes.
Figure 20:
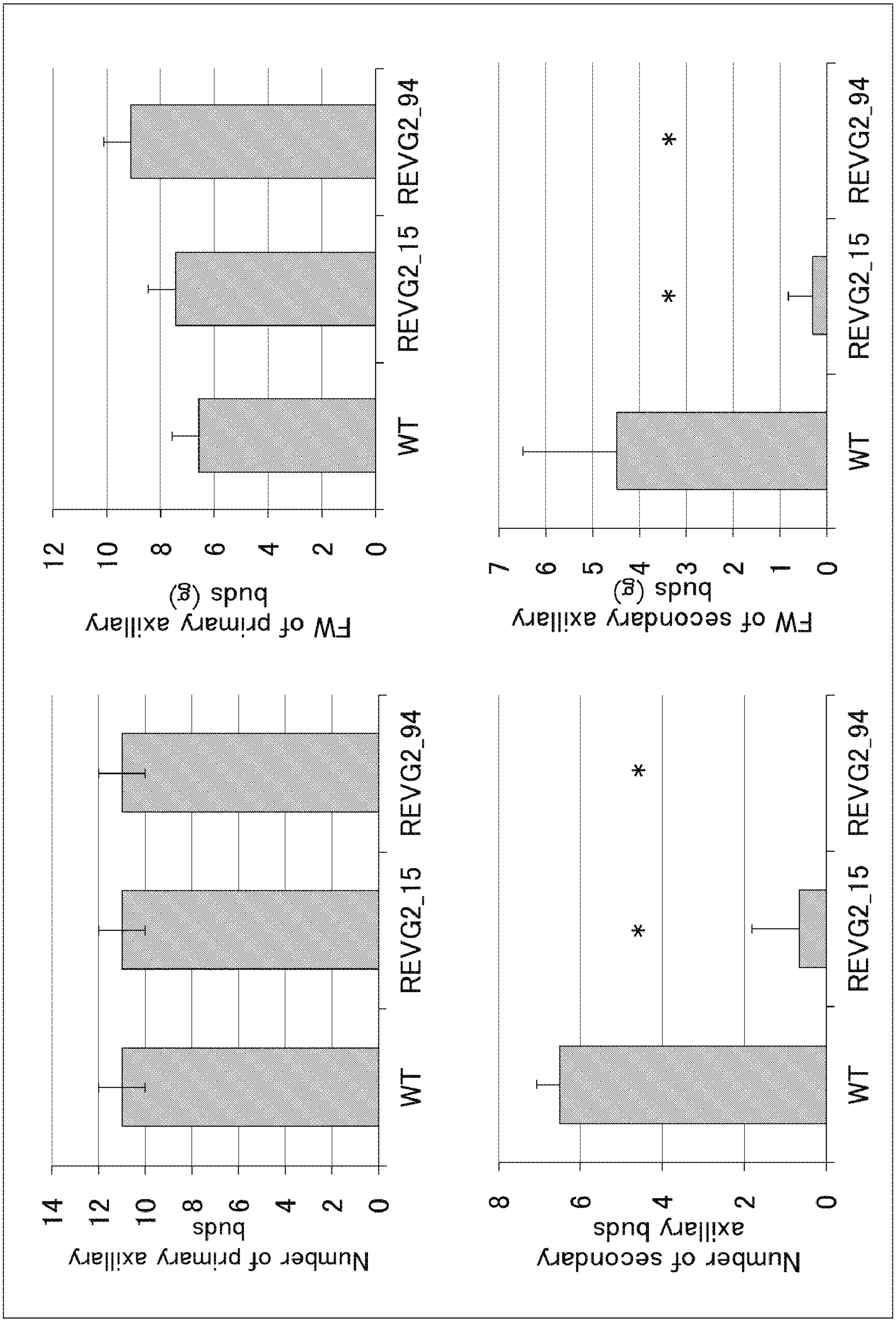
FIG. 20 is a view showing the results of the effects on the development of axillary buds by mutations introduced into REV genes.
Figure 21:
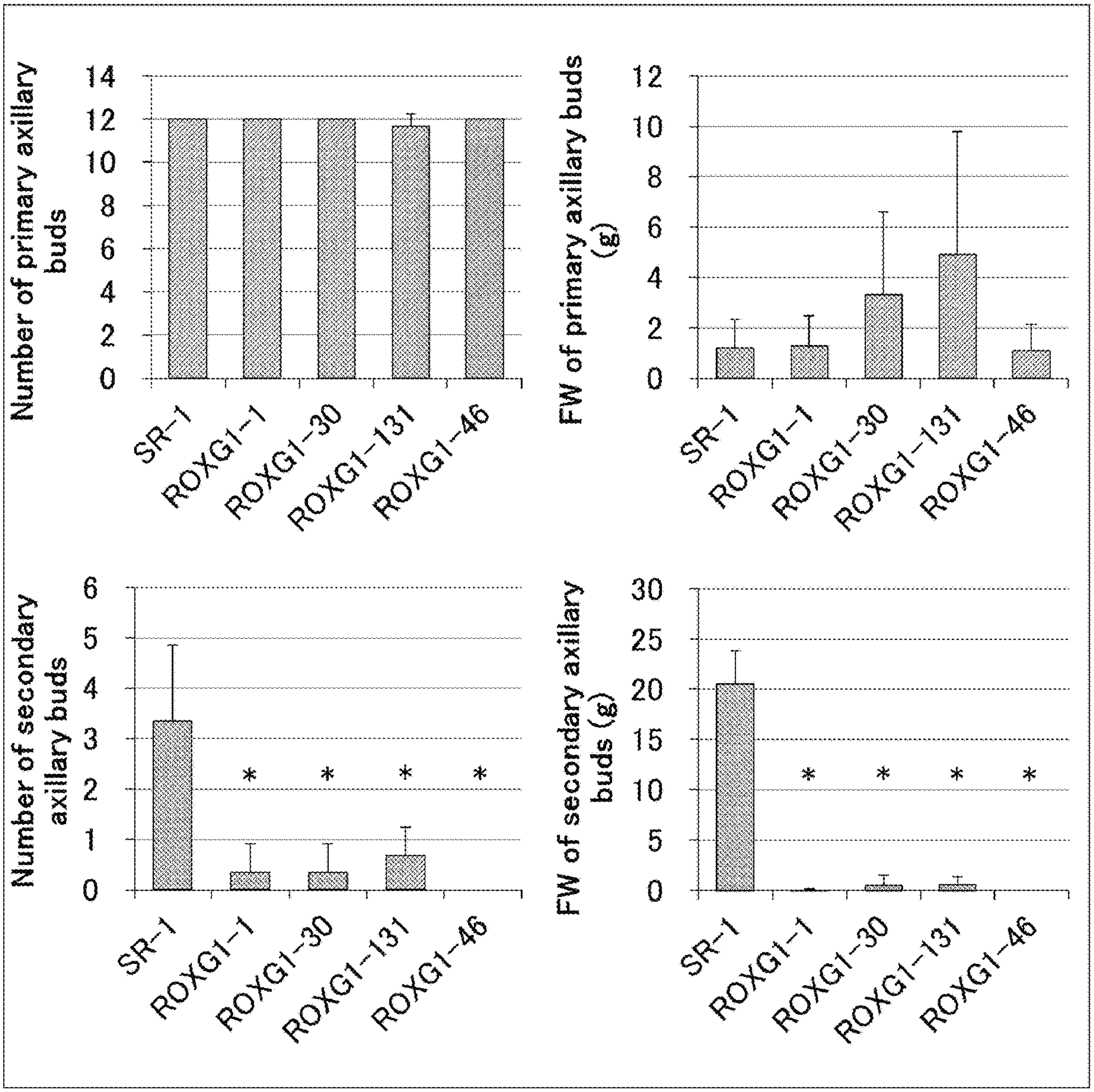
FIG. 21 is a view showing the results of the effects on the development of axillary buds by mutations introduced into #15360.

The individuals of T1 line obtained in (d) above were cultivated in a greenhouse, and evaluated according to the description of 2-2. FIGS. 19 and 20 show the results of evaluation of REV mutants, and FIG. 21 shows the results of evaluation of #15360 mutants.

As shown in FIGS. 19 and 20, none of the 4 lines in which the mutations were introduced into REV showed any significant difference from a wild-type in terms of the number and fresh weight of primary axillary buds, and the 4 lines showed a statistically significant decrease in the number and fresh weight of secondary axillary buds in comparison with the wild-type. As shown in FIG. 21, none of the 4 lines in which the mutations were introduced into #15360 showed any significant difference from a wild-type in terms of the number and fresh weight of primary axillary buds, and the 4 lines showed a statistically significant decrease in the number and fresh weight of secondary axillary buds in comparison with the wild-type. In terms of REV, the results above reveal that the development of secondary axillary buds was selectively suppressed in not only the mutants selected from TUM prepared by EMS treatment but also a plurality of different mutants prepared by CRISPR/Cas9 system. In terms of #15360, it was confirmed that the development of secondary axillary buds was selectively suppressed in a plurality of different mutants prepared by CRISPR/Cas9 system as in the case of suppression of gene expression.

(7-2. B11 Mutant and LS Mutant)

(a) Preparation for Transformation

In the construction of the vectors for transforming *Agrobacterium*, Life Technologies Corporation was entrusted with synthesis, through GeneArt (registered trademark) Strings (trademark) DNA Fragments, of sgRNA expression cassette in which KpnI site and BamHI site are added to 5' end and 3' end, respectively. The base sequences of the sgRNA expression cassettes obtained are as follows.

[Chem. 7]
2G-36_10, 2G-37_103, 2G-126_10, 2G-126_139
(SEQ ID NO. 300)
aattggtaccAGAAATCTCAAAATTCCGGCAGAACAATTTTGAATCTCGAT
CCGTAGAAACGAGACGGTCATTGTTTTAGTTCCACCACGATTATATTTGAA
ATTTACGTGAGTGTGAGTGAGACTTGCATAAGAAAATAAAATCTTTAGTTG
GGAAAAAATTCAATAATATAAATGGGCTTGAGAAGGAAGCGAGGGATAGGC
CTTTTTCTAAAATAGGCCCATTTAAGCTATTAACAATCTTCAAAAGTACCA
CAGCGCTTAGGTAAAGAAAGCAGCTGAGTTTATATATGGTTAGAGACGAAG
TAGTGATTggaagagttgtagattgagaGTTTTAGAGCTAGAAATAGCAAG
TTAAAATAAGGCTAGTCCGTTATCAACTTGAAAAAGTGGCACCGAGTCGGT
GCTTTTTTTggatccaatt In the above sequence, (i) the underlined portion indicates the guide sequence, (ii) the portion upstream to the underlined portion indicates the AtU6-1 promoter sequence, (iii) the portion downstream to the underlined portion indicates the scaffold-polyT sequence, and (iv) the lower case letters at the terminus indicate restriction enzyme sequences of KpnI and BamHI.

In addition, sgRNA expression cassettes, in which KpnI site and BamHI site are added to 5' end and 3' end, respectively, were synthesized by utilizing gene synthesis service of Eurofins Genomics K.K. The nucleotide sequences of the sgRNA expression cassettes obtained are as follows. Note that the subsequent transformation of tobacco and the cultivation of the transformant are not different from the description in 3-3. above, and therefore will not be described.

[Chem. 8]
LS_1A
(SEQ ID NO. 301)
aattggtaccTTTACTTTAAATTTTTTCTTATGCAGCCTGTGATGGATAAC
TGAATCAAACAAATGGCGTCTGGGTTTAAGAAGATCTGTTTTGGCTATGTT
GGACGAAACAAGTGAACTTTTAGGATCAACTTCAGTTTATATATGGAGCTT
ATATCGAGCAATAAGATAAGTGGGCTTTTTATGTAATTTAATGGGCTATCG
TCCATAGATTCACTAATACCCATGCCCAGTACCCATGTATGCGTTTCATAT
AAGCTCCTAATTTCTCCCACATCGCTCAAATCTAAACAAATCTTGTTGTAT
ATATAACACTGAGGGAGCAACATTGGTCactgtgtattttatcttcacGTT
TTAGAGCTAGAAATAGCAAGTTAAAATAAGGCTAGTCCGTTATCAACTTGA
AAAAGTGGCACCGAGTCGGTGCTTTTTTTggatccaatt -continued

[Chem. 9]
LS_3A
(SEQ ID NO. 302)
aattggtaccTTTACTTTAAATTTTTTCTTATGCAGCCTGTGATGGATAAC
TGAATCAAACAAATGGCGTCTGGGTTTAAGAAGATCTGTTTTGGCTATGTT
GGACGAAACAAGTGAACTTTTAGGATCAACTTCAGTTTATATATGGAGCTT
ATATCGAGCAATAAGATAAGTGGGCTTTTTATGTAATTTAATGGGCTATCG
TCCATAGATTCACTAATACCCATGCCCAGTACCCATGTATGCGTTTCATAT
AAGCTCCTAATTTCTCCCACATCGCTCAAATCTAAACAAATCTTGTTGTAT
ATATAACACTGAGGGAGCAACATTGGTCacgagtaattctttcttcttGTT
TTAGAGCTAGAAATAGCAAGTTAAAATAAGGCTAGTCCGTTATCAACTTGA
AAAAGTGGCACCGAGTCGGTGCTTTTTTTggatccaatt

[Chem. 10]
B1_4A
(SEQ ID NO. 303)
aattggtaccTTTACTTTAAATTTTTTCTTATGCAGCCTGTGATGGATAAC
TGAATCAAACAAATGGCGTCTGGGTTTAAGAAGATCTGTTTTGGCTATGTT
GGACGAAACAAGTGAACTTTTAGGATCAACTTCAGTTTATATATGGAGCTT
ATATCGAGCAATAAGATAAGTGGGCTTTTTATGTAATTTAATGGGCTATCG
TCCATAGATTCACTAATACCCATGCCCAGTACCCATGTATGCGTTTCATAT
AAGCTCCTAATTTCTCCCACATCGCTCAAATCTAAACAAATCTTGTTGTAT
ATATAACACTGAGGGAGCAACATTGGTCagctaacaagttgtaccaaGTTT
TAGAGCTAGAAATAGCAAGTTAAAATAAGGCTAGTCCGTTATCAACTTGAA
AAAGTGGCACCGAGTCGGTGCTTTTTTTggatccaatt In each of the above three sequences, (i) the underlined portion indicates the guide sequence, (ii) the portion upstream to the underlined portion indicates the AtU3B promoter sequence, (iii) the portion downstream to the underlined portion indicates the scaffold-polyT sequence, and (iv) the lower case letters at the terminus indicate restriction enzyme sequences of KpnI and BamHI.

(b) Confirmation of Presence/Absence of Mutation and Mutant Sequence

The following were checked as described in (c) of 3-3.: (i) the presence/absence of a mutation in the cultivated transformants and (ii) the mutant sequences. Primers for specifically amplifying a region containing a guide sequence on genomic DNA were designed. The sequences of the primers are as follows. In addition, as shown below, PCR was performed with only part of the conditions changed.

(2A-1_14, 2A-1_19, 2A-1_119, 2A-1_120, 2A_133_17, 2A_133_122, 2A_133_142: T genome)
Combination of NtB11-1_2A_F1:
(SEQ ID NO. 293)
AAGTATTACTACTACAAAATTCCAACG,
and -continued Nb_B11_2A_R1:

(SEQ ID NO. 294)

CCATCTGATGAAGAACAACTTGC (2A-1_14, 2A-1_19, 2A-1_119, 2A-1_120, 2A_133_17, 2A_133_122, 2A_133_142: S genome)
Combination of NtB11-2_1A_F1:

(SEQ ID NO. 295)

TTAAACACTAGAGAGTGAGAGAGTGC,
and

NtB11-2_2A_F1:

(SEQ ID NO. 296)

CAGATGTTTAATTATTAAGACAAAGTTCC (2G-35_10 2G-37_103, 2G-126_10, 2G-126_139: T genome)
NtB11-1_2G_F1:

(SEQ ID NO. 304)

ATATGTTTGAATATAGGGGGAGGG,
and

NtB11-1_2G_R1:

(SEQ ID NO. 305)

TGGTTTACAAAAGGAAAAGTTTTC (2G-35_10, 2G-37_103, 2G-126_10, 2G-126_139: S genome)
Combination of NtB11-2_2G_F1:

(SEQ ID NO. 306)

ATATGTTTGAGTATAAAGGGAGGA,
and

NtB11-2_2G_R1:

(SEQ ID NO. 307)

TTGGTTTACTAGAGAAAAAATTTCC (LS_1A-8_4, 13, LS_1A-9_32, 48: T genome)
Combination of LS_1A_F_T:

(SEQ ID NO. 308)

TACCGGTACTGGAAATGACCTC,
and

LS_1A_R_T:

(SEQ ID NO. 309)

TCCTTAACATTTCGCGGTCT (LS_1A-8_4, 13, LS_1A-9_32, 48: S genome)
Combination of LS_1A_F_S:

(SEQ ID NO. 310)

CCGGTACTGGAAATGACCTTG,
and
LS_1,2_R3:

(SEQ ID NO. 264)

GCAAAGTTGCTTCCAATGAAT (LS_3A-12, LS_3A-15, and LS_3A-30: T genome)
Combination of LS_3A_4G_F_T:

(SEQ ID NO. 311)

GTTTGGTTCGGAAGAGAAATTATAG,
and

LS_3A_4G_R_T:

(SEQ ID NO. 312)

CTTTGTCCTTCACCATGCAG (LS_3A-12, LS_3A-15, and LS_3A-30: S genome)
Combination of LS_3A_4G_F_S:

(SEQ ID NO. 313)

TTGGTTCGGGAGAGAAATAATTGA,
and

LS_3A_4G_R_S:

(SEQ ID NO. 314)

CGCCAAGAAGATATGGAAAA (B1_4A-11, B1_4A-13, B14A-16: T genome)
Combination of B1_3A_4A_F_T:

(SEQ ID NO. 315)

ATTTCTTCTGCCCACCAGC,
and

-continued

B1_3A_4A_R_ST:

(SEQ ID NO. 316)

TCTCATCATTGAACACGAACA (B1_4A-11, B1_4A-13, B14A-16: S genome)
Combination of B1_3A_4A_F_S:

(SEQ ID NO. 317)

CCTAATTTGGGTGCTACAAATAAT,
and

B1_3A_4A_R_ST:

(SEQ ID NO. 316)

TCTCATCATTGAACACGAACA (Changes in PCR conditions)

T genome of LS_1A 60 seconds at 94° C.

40 cycles while each cycle includes 10 seconds at 98° C., 15 seconds at 57° C., and 50 seconds at 68° C.

S genome of LS_1A 60 seconds at 94° C.

45 cycles while each cycle includes 10 seconds at 98° C., 15 seconds at 65° C., and 50 seconds at 68° C.

T genome of LS_3A 60 seconds at 94° C.

45 cycles while each cycle includes 10 seconds at 98° C., 15 seconds at 55° C., and 35 seconds at 68° C.

S genome of LS_3A 60 seconds at 94° C.

40 cycles while each cycle includes 10 seconds at 98° C., 15 seconds at 60° C., and 50 seconds at 68° C.

T genome and S genome of Bl_4A 60 seconds at 94° C.

40 cycles while each cycle includes 10 seconds at 98° C., 15 seconds at 60° C., and 50 seconds at 68° C.

(c) Selection of Transformants

According to the description in 3-3. above, T2 line and T1 line below were selected. First, mutant polypeptides in individuals of T2 line obtained are as follows.

2A-1_14

T genome: While WT consists of 336 amino acids, a polypeptide (SEQ ID NO. 84) is produced such that unrelated 12 amino acids (TGILNSRKSLWD (positions 108 through 119 in SEQ ID NO. 84)) are added in addition to up to 107 amino acids identical to those of WT.

S genome: While WT consists of 337 amino acids, a polypeptide identical to WT is produced, and a polypeptide (SEQ ID NO. 83) is produced such that unrelated 3 amino acids (LEY) are added in addition to up to 106 amino acids identical to those of WT.

2A-1_19

T genome: While WT consists of 336 amino acids, a polypeptide identical to WT is produced, and a polypeptide (SEQ ID NO. 86) is produced such that unrelated 12 amino acids (TGILNSRKSLWD (positions 108 through 119 in SEQ ID NO. 86)) are added in addition to up to 107 amino acids identical to those of WT.

S genome: While WT consists of 337 amino acids, a polypeptide (SEQ ID NO. 85) is produced such that unrelated 3 amino acids (LEY) are added in addition to up to 106 amino acids identical to those of WT.

2A_133_17

T genome: While WT consists of 336 amino acids, a polypeptide (SEQ ID NO. 98) is produced such that unrelated 12 amino acids (TGILNSRKSLWD (positions 108 through 119 in SEQ ID NO. 98)) are added in addition to up to 107 amino acids identical to those of WT.

S genome: A polypeptide (SEQ ID NO. 97) consisting of 337 amino acids identical to those of WT is produced.

2A_133_122

T genome: While WT consists of 336 amino acids, a polypeptide (SEQ ID NO. 100) is produced such that unrelated 12 amino acids (TGILNSRKSLWD (positions 108 through 119 in SEQ ID NO. 100)) are added in addition to up to 107 amino acids identical to those of WT.

S genome: While WT consists of 337 amino acids, a polypeptide identical to WT is produced, and a polypeptide (SEQ ID NO. 99) is produced such that 107th asparagine of WT is deleted so as to constitute 336 amino acids.

2A_133_142

T genome: While WT consists of 336 amino acids, a polypeptide (SEQ ID NO. 102) is produced such that unrelated 12 amino acids (TGILNSRKSLWD (positions 108 through 119 in SEQ ID NO. 102)) are added in addition to up to 107 amino acids identical to those of WT.

S genome: While WT consists of 337 amino acids, a polypeptide identical to WT is produced, and a polypeptide (SEQ ID NO. 101) is produced such that 107th asparagine of WT is deleted so as to constitute 336 amino acids.

2A_1_119

T genome: While WT consists of 336 amino acids, a polypeptide (SEQ ID NO. 88) is produced such that unrelated 12 amino acids (TGILNSRKSLWD (positions 108 through 119 in SEQ ID NO. 88)) are added in addition to up to 107 amino acids identical to those of WT.

S genome: A polypeptide (SEQ ID NO. 87) consisting of 337 amino acids identical to those of WT is produced.

2A_1_120

T genome: While WT consists of 336 amino acids, a polypeptide (SEQ ID NO. 90) is produced such that unrelated 12 amino acids (TGILNSRKSLWD (positions 108 through 119 in SEQ ID NO. 90)) are added in addition to up to 107 amino acids identical to those of WT.

S genome: A polypeptide (SEQ ID NO. 89) consisting of 337 amino acids identical to those of WT is produced.

2G-35_10

T genome: While WT consists of 336 amino acids, a polypeptide (SEQ ID NO. 110) is produced such that unrelated 8 amino acids (KMAKLSKA (positions 57 through 64 in SEQ ID NO. 110)) are added in addition to up to 56 amino acids identical to those of WT.

S genome: While WT consists of 337 amino acids, a polypeptide (SEQ ID NO. 109) is produced such that up to 56 amino acids are identical to those of WT.

2G-37_103

T genome: While WT consists of 336 amino acids, a polypeptide (SEQ ID NO. 112) is produced such that 2 amino acids (55th and 56th amino acids) are deleted so as to constitute 334 amino acids.

S genome: While WT consists of 337 amino acids, a polypeptide (SEQ ID NO. 111) is produced such that unrelated 7 amino acids (MAKLFKA (positions 55 through 61 in SEQ ID NO. 111)) are added in addition to up to 54 amino acids identical to those of WT.

2G-126_10

T genome: While WT consists of 336 amino acids, a polypeptide (SEQ ID NO. 114) is produced such that unrelated 2 amino acids (DG) are added in addition to up to 56 amino acids identical to those of WT.

S genome: While WT consists of 337 amino acids, a polypeptide (SEQ ID NO. 113) is produced such that up to 56 amino acids are identical to those of WT.

2G-126_139

T genome: While WT consists of 336 amino acids, a polypeptide (SEQ ID NO. 118) is produced such that unrelated 1 amino acids (I) are added in addition to up to 54 amino acids identical to those of WT.

S genome: While WT consists of 337 amino acids, a polypeptide (SEQ ID NO. 117) is produced such that unrelated 6 amino acids (AKLFKA (positions 53 through 58 in SEQ ID NO. 117)) are added in addition to up to 52 amino acids identical to those of WT.

Next, the mutant polypeptides in individuals of T1 line obtained are as follows.

LS_1A-8

T genome: While WT consists of 410 amino acids, a polypeptide (SEQ ID NO. 73) is produced such that unrelated 15 amino acids (TQALKRPRNVKDFFA (positions 248 through 262 in SEQ ID NO. 73)) are added in addition to up to 247 amino acids identical to those of WT.

S genome: While WT consists of 407 amino acids, a polypeptide (SEQ ID NO. 72) is produced such that unrelated 15 amino acids (PQALERPRKVKDFFA (positions 244 through 258 in SEQ ID NO. 72)) are added in addition to up to 243 amino acids identical to those of WT.

LS_1A-9

T genome: While WT consists of 410 amino acids, a polypeptide (SEQ ID NO. 76) is produced such that unrelated 3 amino acids (TGS) are added in addition to up to 246 amino acids identical to those of WT.

S genome: While WT consists of 407 amino acids, (i) a polypeptide (SEQ ID NO. 75) is produced such that unrelated 15 amino acids (SQALERPRKVKDFFA (positions 245 through 259 in SEQ ID NO. 75)) are added in addition to up to 244 amino acids identical to those of WT and (ii) a polypeptide (SEQ ID NO. 74) is produced such that unrelated 15 amino acids (TQALERPRKVKDFFA (positions 245 through 259 in SEQ ID NO. 74)) are added in addition to up to 244 amino acids identical to those of WT.

LS_3A-12

T genome: While WT consists of 410 amino acids, a polypeptide (SEQ ID NO. 78) is produced such that unrelated 18 amino acids (SWVGKINPFFPYLLGVKL (positions 395 through 412 in SEQ ID NO. 78)) are added in addition to up to 394 amino acids identical to those of WT.

S genome: While WT consists of 407 amino acids, a polypeptide (SEQ ID NO. 77) is produced such that unrelated 66 amino acids (SWVGKINPFFPYLLGVKFKTLKNKIFIYLHGEGQRGLQSQVLFFFFY IYILFGFKVIGLMNVLILT (positions 392 through 457 in SEQ ID NO. 77)) are added in addition to up to 391 amino acids identical to those of WT.

LS_3A-15

T genome: While WT consists of 410 amino acids, a polypeptide (SEQ ID NO. 80) is produced such that unrelated 18 amino acids (SWVGKINPFFPYLLGVKL (positions 395 through 412 in SEQ ID NO. 80)) are added in addition to up to 394 amino acids identical to those of WT.

S genome: While WT consists of 407 amino acids, a polypeptide (SEQ ID NO. 79) is produced such that unrelated 66 amino acids (SWVGKINPFFPYLLGVKFKTLKNKIFIYLHGEGQRGLQSQVLFFFFY IYILFGFKVIGLMNVLILT (positions 392 through 457 in SEQ ID NO. 79)) are added in addition to up to 391 amino acids identical to those of WT.

LS_3A-30

T genome: While WT consists of 410 amino acids, a polypeptide (SEQ ID NO. 82) is produced such that unrelated 14 amino acids (LAKSTPFFHIFLAL (positions 398 through 411 in SEQ ID NO. 82)) are added in addition to up to 397 amino acids identical to those of WT.

S genome: While WT consists of 407 amino acids, a polypeptide (SEQ ID NO. 81) is produced such that unrelated 18 amino acids (LAKSTPFFHIFLALNLKP (positions 395 through 412 in SEQ ID NO. 81)) are added in addition to up to 394 amino acids identical to those of WT.

Bl_4A-11

T genome: While WT consists of 336 amino acids, a polypeptide (SEQ ID NO. 121) is produced such that unrelated 29 amino acids (MATMAVLL-DVTTTTVCSCSMMRIITSQMR (positions 302 through 330 in SEQ ID NO. 121)) are added in addition to up to 301 amino acids identical to those of WT.

S genome: While WT consists of 337 amino acids, (i) a polypeptide (SEQ ID NO. 120) is produced such that unrelated 5 amino acids (QWQQW (positions 303 through 307 in SEQ ID NO. 120)) are added in addition to up to 302 amino acids identical to those of WT and (ii) a polypeptide (SEQ ID NO. 119) is produced such that unrelated 4 amino acids (YYWM (positions 303 through 306 in SEQ ID NO. 119)) are added in addition to likewise up to 302 amino acids identical to those of WT.

(e) Evaluation of Development of Axillary Buds in Greenhouse

Figure 22:
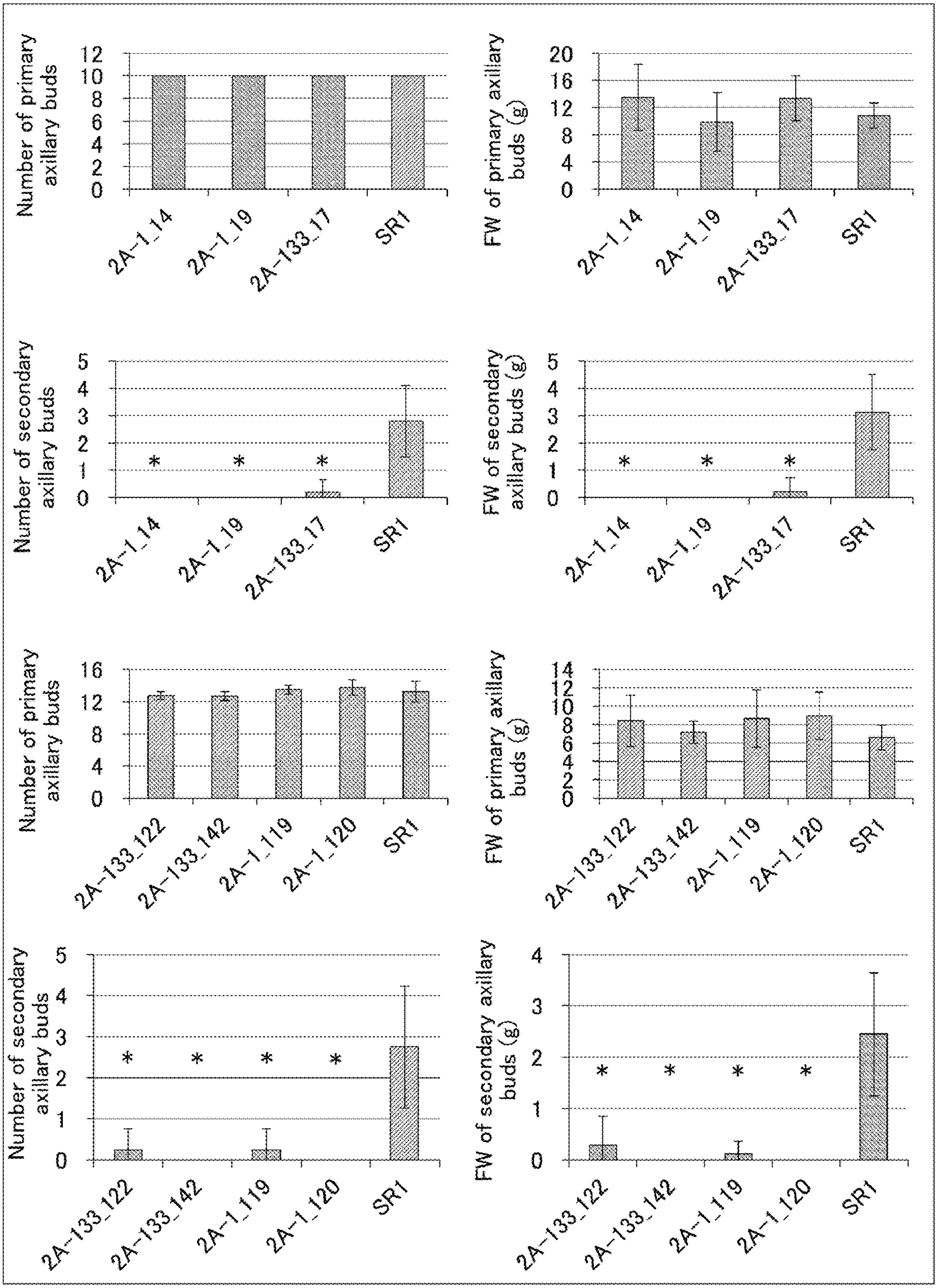
FIG. 22 is a view showing the results of the effects on the development of axillary buds by mutations introduced into Bl1 genes.

Individuals of 7 of T2 lines (2A-1_14, 2A-133_122, 2A-133_142, 2A-1_19, 2A-133_17, 2A-1_119, and 2A-1_120), in which at least one of alleles of Bl1 gene was not mutated, were cultivated in a greenhouse, and axillary buds thereof were evaluated according to the description of 3-3. above. 2A-1_14, 2A-133_122, and 2A-133_142 did not have a mutation of one of alleles of Bl1 in an S genome ($T^{+/+}S^{+/-}$). 2A-1_19 did not have a mutation of one of alleles of Bl1 in a T genome ($T^{+/-}S^{+/+}$). 2A-133_17, 2A-1_119, and 2A-1_120 did not have a mutation of any of alleles of Bl1 in an S genome ($T^{+/+}S^{-/-}$). Although none of the 7 lines evaluated did not show any difference from the control WT (SR-1) in terms of the number and weight of primary axillary buds, there was a significant decrease in the number and weight of secondary axillary buds (FIG. 22). Therefore, it was found that in order to suppress secondary axillary buds, it is unnecessary to introduce mutations into all of (4) alleles of NtBl1 gene on an S genome and a T genome, but it is only necessary to introduce mutations into 2 alleles of NtBl1 gene on the S genome and the T genome.

Figure 23:
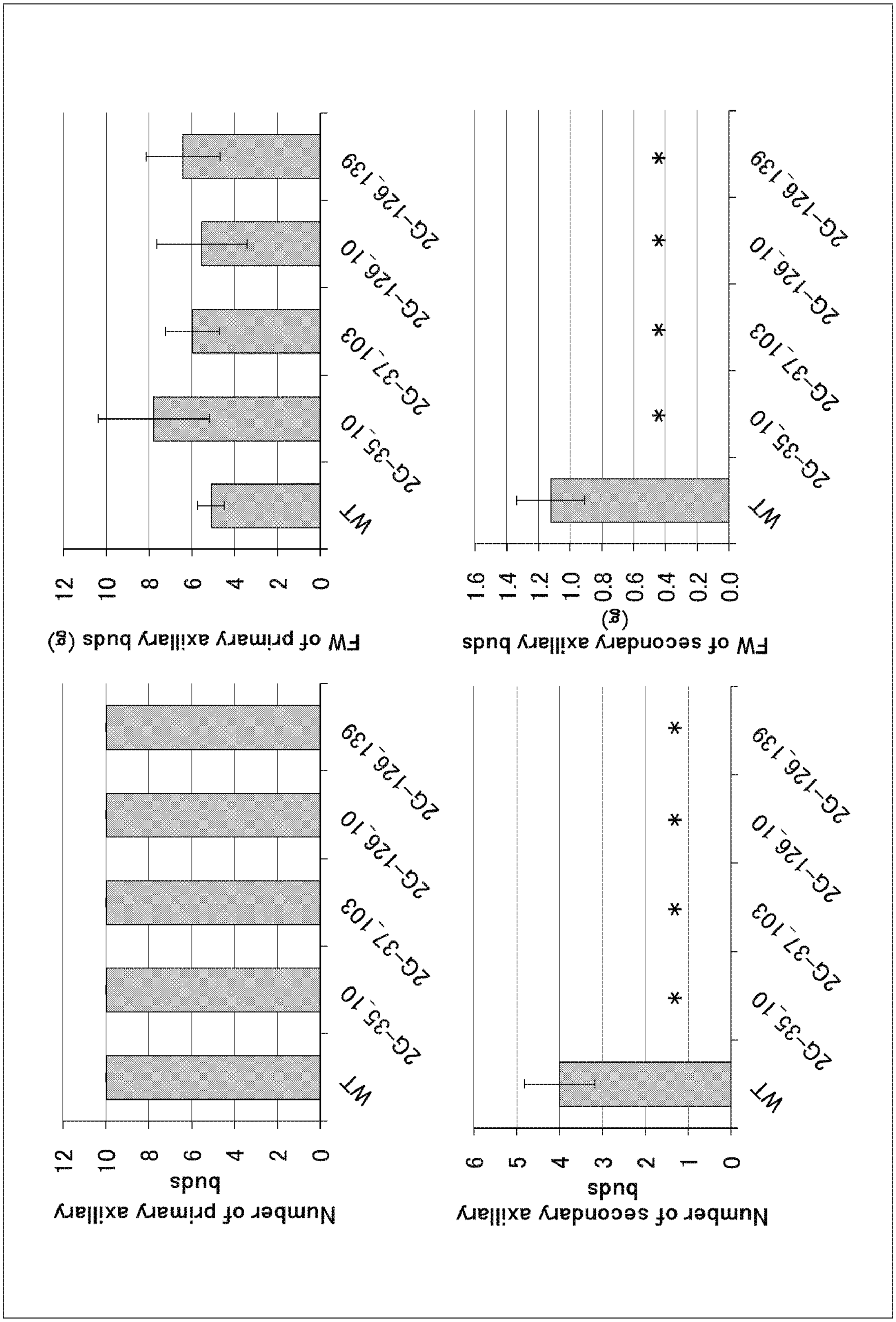
FIG. 23 is a view showing the results of the effects on the development of axillary buds by mutations introduced into Bl1 genes.
Figure 24:
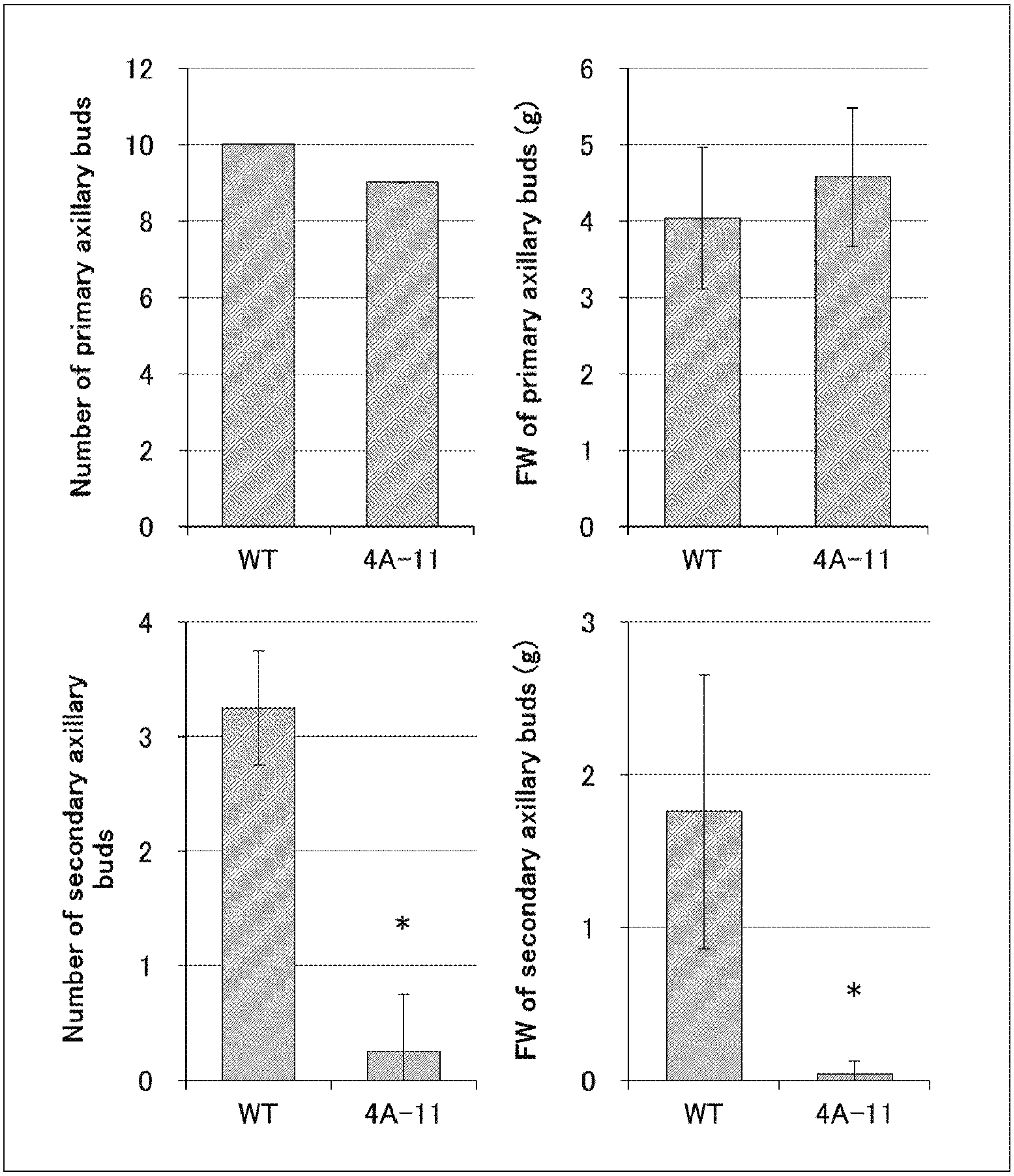
FIG. 24 is a view showing the results of the effects on the development of axillary buds by mutations introduced into Bl1 genes.

Axillary buds of 5 of T2 lines (2G-35_10, 2 G-37_103, 2 G-126_10, 2G-126_139, Bl_4A-11) were evaluated. Although these lines have mutations introduced into different genes (LS or Bl1), these lines share commonality in that the mutation causes frame shifting, so that a polypeptide shorter than a wild-type polypeptide is produced. FIG. 23 shows the results of evaluation of 2G-35_10, 2 G-37_103, 2 G-126_10, and 2G-126_139. FIG. 24 shows the results of evaluation of Bl_4A-11. FIGS. 23 and 24 summarize 3 evaluations of axillary buds performed after topping. In 4 lines of 2G and 1 line of Bl_4A in which mutations were introduced into Bl1 gene, there was no difference observed in terms of the number and weight of primary axillary buds, but a remarkable decrease in the number and weight of secondary axillary buds was shown. In particular, the 4 lines of 2G exhibited no development of secondary axillary buds. The results above reveal that a plurality of different mutants of Bl1 gene also showed selectively suppression of the development of secondary axillary buds.

Figure 25:
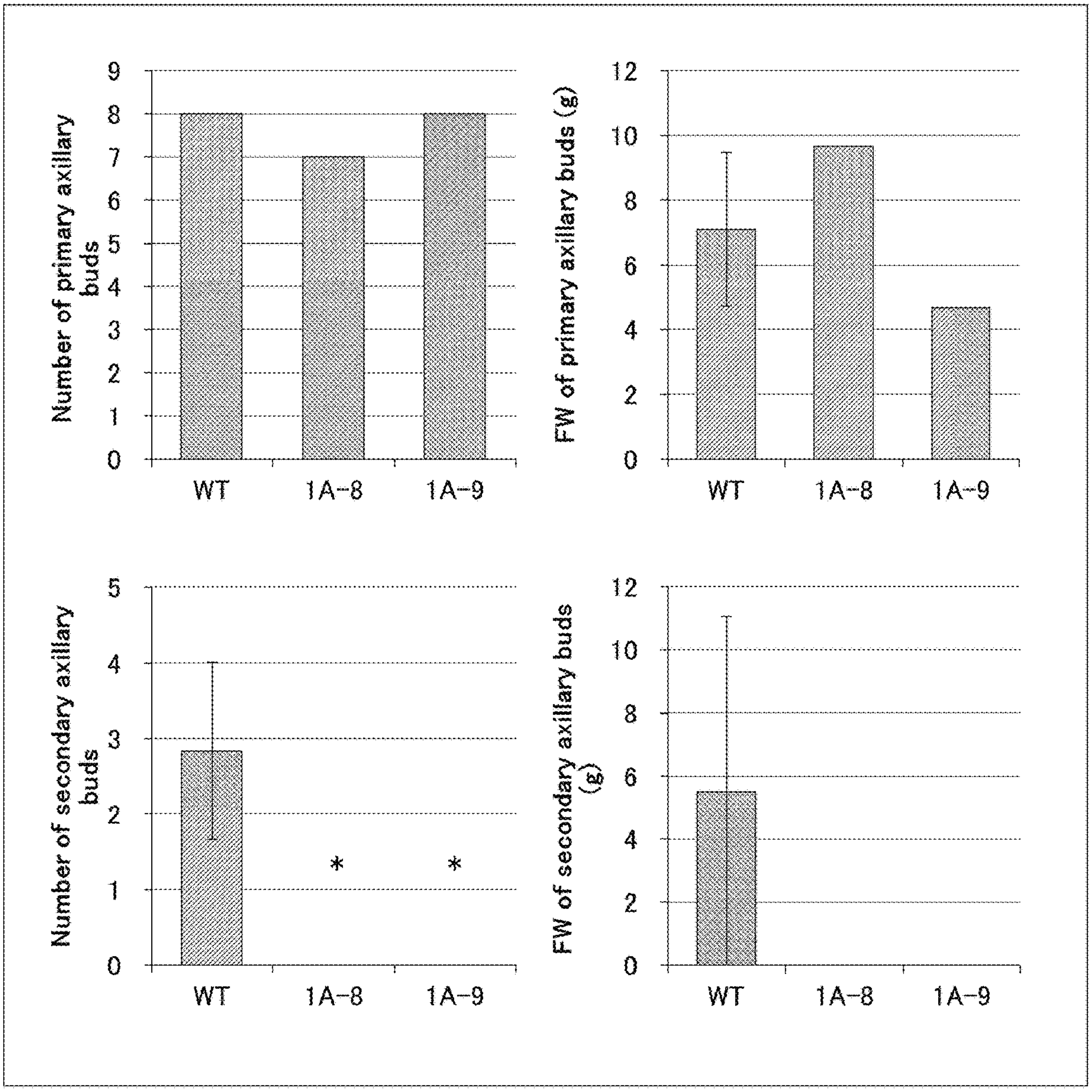
FIG. 25 is a view showing the results of the effects on the development of axillary buds by mutations introduced into LS genes.
Figure 26:
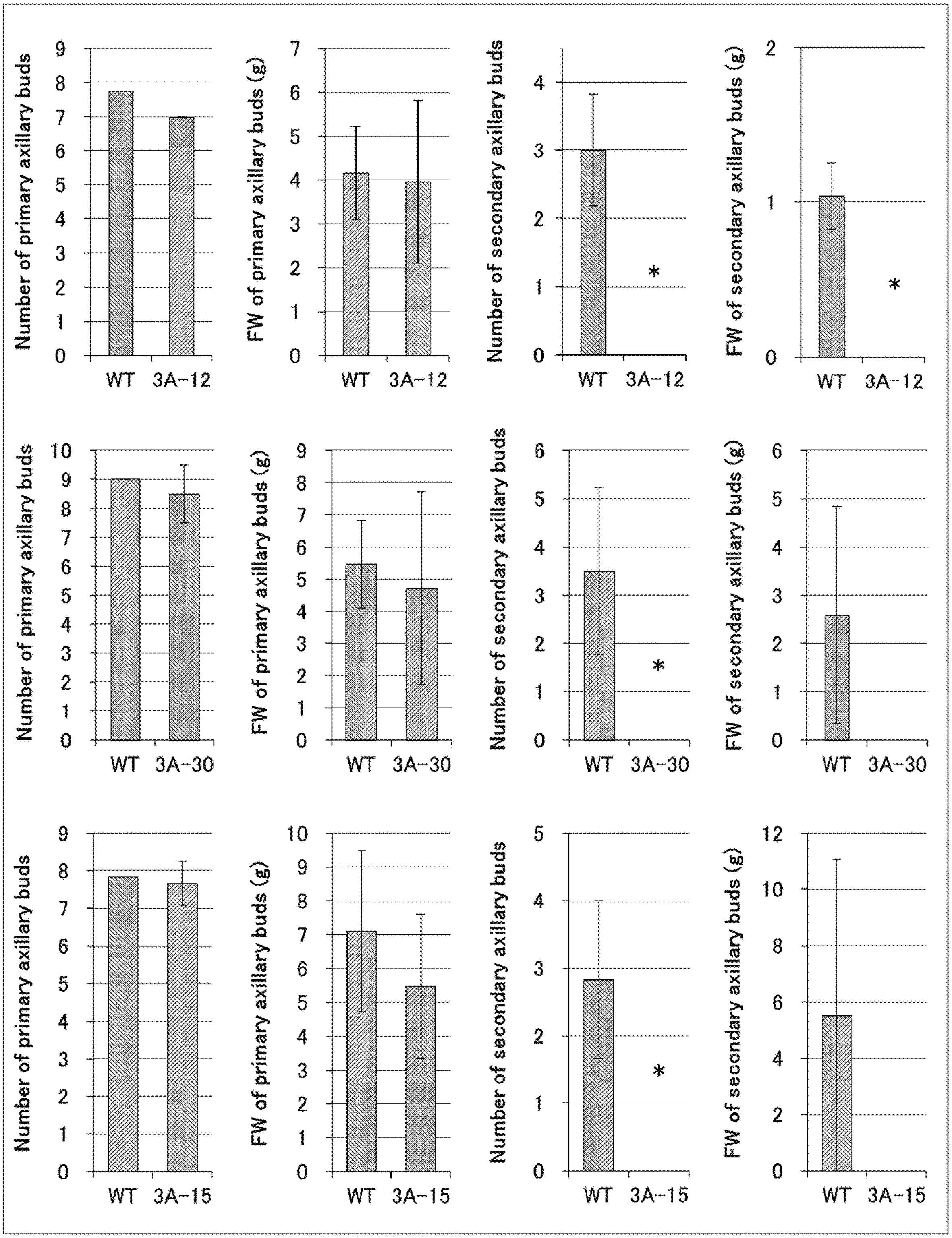
FIG. 26 is a view showing the results of the effects, on the development of axillary buds by mutations introduced into LS genes.

Next, 5 of T1 lines (LS_1A-8, LS_1A-9, LS_3A-12, LS_3A-15, LS_3A-30) were likewise evaluated. FIG. 25 shows the results of evaluation of LS_1A-8 and LS_1A-9. FIG. 26 shows the results of evaluation of LS_3A-12, LS_3A-15, and LS_3A-30. FIGS. 25 and 26 summarize 3 evaluations of axillary buds performed after topping. None of the 2 lines of LS_1 Å and 3 lines of LS_3A exhibited any difference in terms of the number and weight of primary axillary buds, and no developments of secondary axillary buds were observed at all. In terms of LS gene also, the results above reveal that, as in the case of REV gene, the development of secondary axillary buds was selectively suppressed in not only the mutants selected from TUM prepared by EMS treatment but also a plurality of different mutants prepared by CRISPR/Cas9 system.

REFERENCES

1. Takahashi H, Kamakura H, Sato Y, Shiono K, Abiko T, Tsutsumi N, Nagamura Y, Nishizawa NK, Nakazono M. (2010) A method for obtaining high quality RNA from paraffin sections of plant tissues by laser microdissection. J Plant Res 123: 807-813
2. Li J F, Norville J E, Aach J, McCormack M, Zhang D, Bush J, Church G M, Sheen J. (2013) Multiplex and homologous recombination-mediated genome editing in *Arabidopsis* and *Nicotiana benthamiana* using guide RNA and Cas9. Nat Biotechnol. 31(8), 688-91.
3. Waibel F, Filipowicz W. (1990) U6 snRNA genes of *Arabidopsis* are transcribed by RNA polymerase III but contain the same two upstream promoter elements as RNA polymerase II-transcribed U-snRNA genes. Nucleic Acids Res. 25; 18(12), 3451-8.4. Marshallsay Cl, Kiss T, Filipowicz W. (1990) Amplification of plant U3 and U6 snRNA gene sequences using primers specific for an upstream promoter element and conserved intragenic regions. Nucleic Acids Res. 25; 18(12), 3459-66.

INDUSTRIAL APPLICABILITY

With an embodiment of the present invention, it is possible to suppress the development of unnecessary axillary buds during cultivation of tobacco plant. This allows for a reduction in labor and cost during cultivation, and leads to an increase in quality of leaves to be harvested. In addition, with an embodiment of the present invention, it is possible to selectively suppress the development of secondary axillary buds. This can increase the possibility of preventing the death of a plant caused by damage due to a disaster or the like.

The invention claimed is:

1. A tobacco plant in which a mutation is introduced into a genome, which mutation causes functional suppression of:

at least one of a gene containing, as a coding region, a polynucleotide encoding a polypeptide having a sequence identity of 90% or higher with an amino acid sequence represented by SEQ ID NO. 9 and a gene containing, as a coding region, a polynucleotide encoding a polypeptide having a sequence identity of 90% or higher with an amino acid sequence represented by SEQ ID NO. 11;

the functional suppression suppressing development of, of all of axillary buds, secondary axillary buds which develop after removal of primary axillary buds, the functional suppression being a decrease in abundance of the polypeptide in comparison with a wild-type plant, the functional suppression being promotion of degradation of an mRNA transcribed from said at least one gene, the mutation is an insertion, into a region outside of a region in which said at least one gene is present, of a polynucleotide expressing a factor which promotes the degradation of the mRNA, and the factor being an antisense RNA molecule or an RNAi molecule.

2. A tobacco plant in which a mutation is introduced into a genome, which mutation causes functional suppression of at least one of a gene containing, as a coding region, a polynucleotide encoding a polypeptide having a sequence identity of 90% or higher with an amino acid sequence represented by SEQ ID NO. 9 and a gene containing, as a coding region, a polynucleotide encoding a polypeptide having a sequence identity of 90% or higher with an amino acid sequence represented by SEQ ID NO. 11;

the functional suppression suppressing development of, of all of axillary buds, secondary axillary buds which develop after removal of primary axillary buds, and the mutation being introduced into said at least one gene.

3. The tobacco plant as set forth in claim 1, wherein the functional suppression causes the number or weight of the secondary axillary buds to decrease to not more than ½ of that of a wild-type plant.

4. The tobacco plant as set forth in claim 2, wherein the functional suppression causes the number or weight of the secondary axillary buds to decrease to not more than ½ of that of a wild-type plant.

5. The tobacco plant as set forth in claim 2, wherein the functional suppression is a decrease in abundance of the polypeptide in comparison with a wild-type plant.

6. The tobacco plant as set forth in claim 4, wherein the functional suppression is a decrease in an amount of translation of the polypeptide in comparison with a wild-type plant.

7. The tobacco plant as set forth in claim 4, wherein the functional suppression is a decrease in an amount of transcription from said at least one gene to an mRNA in comparison with a wild-type plant.

8. The tobacco plant as set forth in claim 4, wherein the functional suppression is promotion of degradation of an mRNA transcribed from said at least one gene.

9. The tobacco plant as set forth in claim 2, wherein the mutation is introduced by mutagen treatment, genome editing, or gene knockout.

10. The tobacco plant as set forth in claim 1, wherein the tobacco plant belongs to *Nicotiana tabacum* or *Nicotiana rustica.*

11. The tobacco plant as set forth in claim 2, wherein the tobacco plant belongs to *Nicotiana tabacum* or *Nicotiana rustica.*

12. A method of producing a tobacco plant, comprising the step of:

(a) introducing a mutation that causes functional suppression of at least one of a gene containing, as a coding region, a polynucleotide encoding a polypeptide having a sequence identity of 90% or higher with an amino acid sequence represented by SEQ ID NO. 9 and a gene containing, as a coding region, a polynucleotide encoding a polypeptide having a sequence identity of 90% or higher with an amino acid sequence represented by SEQ ID NO. 11;

the functional suppression suppressing development of, of all of axillary buds, secondary axillary buds which develop after removal of primary axillary buds, the step (a) including inserting, into a region outside of a region in which said at least one gene is present, a polynucleotide expressing a factor which promotes degradation of an mRNA transcribed from said at least one gene, and the factor being an antisense RNA molecule or an RNAi molecule.

13. A method of producing a tobacco plant, comprising the step of:

(a) introducing a mutation that causes functional suppression of any of at least one of a gene containing, as a coding region, a polynucleotide encoding a polypeptide having a sequence identity of 90% or higher with an amino acid sequence represented by SEQ ID NO. 9 and a gene containing, as a coding region, a polynucleotide encoding a polypeptide having a sequence identity of 90% or higher with an amino acid sequence represented by SEQ ID NO. 11;

the functional suppression suppressing development of, of all of axillary buds, secondary axillary buds which develop after removal of primary axillary buds, and the step (a) including introducing the mutation into said at least one gene.

14. The method as set forth in claim 12, further comprising the step of:

(b) selecting, from individuals produced by the step (a), an individual in which development of, of all of the axillary buds, secondary axillary buds that develop after removal of primary axillary buds is suppressed.

15. The method as set forth in claim 13, further comprising the step of:

(b) selecting, from individuals produced by the step (a), an individual in which development of, of all of the axillary buds, secondary axillary buds that develop after removal of primary axillary buds is suppressed.

16. The method as set forth in claim 14, wherein in the step (b), an individual, in which the number or weight of the secondary axillary buds is decreased in comparison with that of a wild-type plant, is selected.

17. The method as set forth in claim 15, wherein in the step (b), an individual, in which the number or weight of the secondary axillary buds is decreased in comparison with that of a wild-type plant, is selected.

18. The method as set forth in claim 13, wherein the step (a) is carried out by mutagen treatment, genome editing, or gene knockout.

19. An offspring or a bred progeny, wherein:

the offspring is of a tobacco plant recited in claim 1;

the bred progeny is obtained by crossing a tobacco plant recited in claim 1; and the following (A) is satisfied:

(A)

a mutation is introduced into a genome, which mutation causes functional suppression of at least one of a gene containing, as a coding region, a polynucleotide encoding a polypeptide having a sequence identity of 90% or higher with an amino acid sequence represented by SEQ ID NO. 9 and a gene containing, as a coding region, a polynucleotide encoding a polypeptide having a sequence identity of 90% or higher with an amino acid sequence represented by SEQ ID NO. 11;

the functional suppression suppresses development of, of all of axillary buds, secondary axillary buds which develop after removal of primary axillary buds, the functional suppression is a decrease in abundance of the polypeptide in comparison with a wild-type plant, the functional suppression is promotion of degradation of an mRNA transcribed from said at least one gene, the mutation is an insertion, into a region outside of a region in which said at least one gene is present, of a polynucleotide expressing a factor which promotes the degradation of the mRNA, and the factor is an antisense RNA molecule or an RNAi molecule.

20. An offspring or a bred progeny, wherein:

the offspring is of a tobacco plant recited in claim 2;

the bred progeny is obtained by crossing a tobacco plant recited in claim 2; and the following (B) is satisfied:

(B)

a mutation is introduced into a genome, which mutation causes functional suppression of at least one of a gene containing, as a coding region, a polynucleotide encoding a polypeptide having a sequence identity of 90% or higher with an amino acid sequence represented by SEQ ID NO. 9 and a gene containing, as a coding region, a polynucleotide encoding a polypeptide having a sequence identity of 90% or higher with an amino acid sequence represented by SEQ ID NO. 11;

the functional suppression suppressing development of, of all of axillary buds, secondary axillary buds which develop after removal of primary axillary buds, and the mutation is introduced into said at least one gene.

21. An offspring or a bred progeny, wherein:

the offspring is of a tobacco plant produced by a method recited in claim 12;

the bred progeny is obtained by crossing a tobacco plant produced by a method recited in claim 12; and the following (A) is satisfied:

(A)

a mutation is introduced into a genome, which mutation causes functional suppression of at least one of a gene containing, as a coding region, a polynucleotide encoding a polypeptide having a sequence identity of 90% or higher with an amino acid sequence represented by SEQ ID NO. 9 and a gene containing, as a coding region, a polynucleotide encoding a polypeptide having a sequence identity of 90% or higher with an amino acid sequence represented by SEQ ID NO. 11;

the functional suppression suppresses development of, of all of axillary buds, secondary axillary buds which develop after removal of primary axillary buds, the functional suppression is a decrease in abundance of the polypeptide in comparison with a wild-type plant, the functional suppression is promotion of degradation of an mRNA transcribed from said at least one gene, the mutation is an insertion, into a region outside of a region in which said at least one gene is present, of a polynucleotide expressing a factor which promotes the degradation of the mRNA, and the factor is an antisense RNA molecule or an RNAi molecule.

22. An offspring or a bred progeny, wherein:

the offspring is of a tobacco plant produced by a method recited in claim 13;

the bred progeny is obtained by crossing a tobacco plant produced by a method recited in claim 13; and the following (B) is satisfied:

(B)

a mutation is introduced into a genome, which mutation causes functional suppression of at least one of a gene containing, as a coding region, a polynucleotide encoding a polypeptide having a sequence identity of 90% or higher with an amino acid sequence represented by SEQ ID NO. 9 and a gene containing, as a coding region, a polynucleotide encoding a polypeptide having a sequence identity of 90% or higher with an amino acid sequence represented by SEQ ID NO. 11;

the functional suppression suppressing development of, of all of axillary buds, secondary axillary buds which develop after removal of primary axillary buds, and the mutation is introduced into said at least one gene.

23. A leaf tobacco harvested from a tobacco plant recited in claim 1.

24. A leaf tobacco harvested from a tobacco plant recited in claim 2.

25. A leaf tobacco harvested from a tobacco plant produced by a method recited in claim 12.

26. A leaf tobacco harvested from a tobacco plant produced by a method recited in claim 13.

27. A leaf tobacco harvested from an offspring or a bred progeny recited in claim 19.

28. A leaf tobacco harvested from an offspring or a bred progeny recited in claim 20.

29. A leaf tobacco harvested from an offspring or a bred progeny recited in claim 21.

30. A leaf tobacco harvested from an offspring or a bred progeny recited in claim 22.

* * * * *